United States Patent
Kamenecka et al.

(10) Patent No.: US 11,434,236 B2
(45) Date of Patent: *Sep. 6, 2022

(54) HALO-SUBSTITUTED PIPERIDINES AS OREXIN RECEPTOR MODULATORS

(71) Applicants: ASTRAZENECA AB, Södertälje (SE); EOLAS THERAPEUTICS, INC., Carlsbad, CA (US)

(72) Inventors: Theodore M. Kamenecka, Palm Beach Gardens, FL (US); Jörg Holenz, Bolton, MA (US); Steven Wesolowski, Natick, MA (US); Yuanjun He, Palm Beach Gardens, FL (US); Roland Bürli, Hertfordshire (GB)

(73) Assignees: ASTRAZENECA AB, Södertälje (SE); EOLAS THERAPEUTICS, INC., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/116,773

(22) Filed: Dec. 9, 2020

(65) Prior Publication Data

US 2021/0214348 A1 Jul. 15, 2021

Related U.S. Application Data

(63) Continuation of application No. 16/076,818, filed as application No. PCT/US2017/017408 on Feb. 10, 2017, now Pat. No. 10,894,789.

(60) Provisional application No. 62/294,940, filed on Feb. 12, 2016, provisional application No. 62/336,102, filed on May 13, 2016.

(51) Int. Cl.
| | |
|---|---|
| A61K 31/506 | (2006.01) |
| A61K 31/4545 | (2006.01) |
| C07D 417/14 | (2006.01) |
| C07D 401/14 | (2006.01) |
| C07D 409/14 | (2006.01) |
| C07D 413/14 | (2006.01) |
| A61P 25/34 | (2006.01) |

(52) U.S. Cl.
CPC ............ *C07D 417/14* (2013.01); *A61P 25/34* (2018.01); *C07D 401/14* (2013.01); *C07D 409/14* (2013.01); *C07D 413/14* (2013.01)

(58) Field of Classification Search
CPC ..... A61K 31/506; A61K 31/4545; A61P 3/04; A61P 25/28; A61P 25/30
USPC ................................................. 514/275, 318
See application file for complete search history.

(56) References Cited

U.S. PATENT DOCUMENTS

| | | | |
|---|---|---|---|
| 5,049,578 A | 9/1991 | Varma et al. | |
| 9,440,982 B2 | 9/2016 | Kamenecka et al. | |
| 9,499,517 B2 | 11/2016 | Kamenecka et al. | |
| 9,896,452 B2 | 2/2018 | Kamenecka et al. | |
| 10,894,789 B2 * | 1/2021 | Kamenecka | C07D 409/14 |
| 2008/0132490 A1 | 6/2008 | Berqman et al. | |
| 2009/0012073 A1 | 1/2009 | Branch et al. | |
| 2009/0203736 A1 | 8/2009 | Knust et al. | |
| 2010/0168134 A1 | 7/2010 | Breslin et al. | |
| 2010/0184808 A1 | 7/2010 | Aissaoui et al. | |
| 2011/0003835 A1 | 1/2011 | Mueller et al. | |
| 2011/0263643 A1 | 10/2011 | Cox et al. | |
| 2012/0165339 A1 | 6/2012 | Terauchi et al. | |
| 2012/0295921 A1 | 11/2012 | Breslin et al. | |
| 2017/0226103 A1 | 8/2017 | Kamenecka et al. | |

FOREIGN PATENT DOCUMENTS

| | | |
|---|---|---|
| WO | 2000047576 A1 | 8/2000 |
| WO | 2000047577 A1 | 8/2000 |
| WO | 2000047580 A2 | 8/2000 |
| WO | 2000071508 A2 | 11/2000 |
| WO | 2001085693 A1 | 11/2001 |
| WO | 2001096302 A1 | 12/2001 |
| WO | 2002044172 A1 | 6/2002 |
| WO | 2002051232 A2 | 7/2002 |
| WO | 2002051838 A1 | 7/2002 |
| WO | 2002089800 A2 | 11/2002 |
| WO | 2002090355 A1 | 11/2002 |
| WO | 2003002559 A2 | 1/2003 |
| WO | 2003032991 A1 | 4/2003 |
| WO | 2003037847 A1 | 5/2003 |
| WO | 2003041711 A1 | 5/2003 |
| WO | 2003051368 A1 | 6/2003 |
| WO | 2003051872 A1 | 6/2003 |
| WO | 2003051873 A1 | 6/2003 |
| WO | 2004004733 A1 | 1/2004 |
| WO | 2004026866 A1 | 4/2004 |
| WO | 2004033418 A2 | 4/2004 |
| WO | 2004041791 A1 | 5/2004 |
| WO | 2004041807 A1 | 5/2004 |
| WO | 2004041816 A1 | 5/2004 |
| WO | 2004052876 A1 | 6/2004 |

(Continued)

OTHER PUBLICATIONS

Hughes et al; "Shape of the relapse curve and long-term abstinence among untreated smokers;" Addiction; 99:29-38 (2004).

(Continued)

*Primary Examiner* — Charanjit Aulakh

(57) ABSTRACT

The present application relates to certain halo-substituted piperidine compounds, pharmaceutical compositions containing them, and methods of using them, including methods for treating substance addiction, panic disorder, anxiety, post-traumatic stress disorder, pain, depression, seasonal affective disorder, an eating disorder, or hypertension.

32 Claims, No Drawings

(56) References Cited

FOREIGN PATENT DOCUMENTS

| | | |
|---|---|---|
| WO | 2004085403 A1 | 10/2004 |
| WO | 2004096780 A1 | 11/2004 |
| WO | 2005060959 A1 | 7/2005 |
| WO | 2005075458 A1 | 8/2005 |
| WO | 2005118548 A1 | 12/2005 |
| WO | 2006067224 A2 | 6/2006 |
| WO | 2006110626 A1 | 10/2006 |
| WO | 2006127550 A1 | 11/2006 |
| WO | 2007008276 A2 | 1/2007 |
| WO | 2007019234 A2 | 2/2007 |
| WO | 2007025069 A2 | 3/2007 |
| WO | 2007061763 A2 | 5/2007 |
| WO | 2007085178 A1 | 8/2007 |
| WO | 2007085565 A1 | 8/2007 |
| WO | 2007085718 A1 | 8/2007 |
| WO | 2007088276 A2 | 8/2007 |
| WO | 2007116374 A1 | 10/2007 |
| WO | 2007122591 A2 | 11/2007 |
| WO | 2007126934 A2 | 11/2007 |
| WO | 2007143856 A1 | 12/2007 |
| WO | 2008008517 A2 | 1/2008 |
| WO | 2008008518 A1 | 1/2008 |
| WO | 2008008551 A2 | 1/2008 |
| WO | 2008020405 A2 | 2/2008 |
| WO | 2008026149 A1 | 3/2008 |
| WO | 2008038251 A2 | 4/2008 |
| WO | 2008065626 A2 | 6/2008 |
| WO | 2008078291 A1 | 7/2008 |
| WO | 2008081399 A2 | 7/2008 |
| WO | 2008087611 A2 | 7/2008 |
| WO | 2008107335 A1 | 9/2008 |
| WO | 2008108991 A1 | 9/2008 |
| WO | 2008110488 A1 | 9/2008 |
| WO | 2008117241 A2 | 10/2008 |
| WO | 2008122513 A1 | 10/2008 |
| WO | 2008139416 A1 | 11/2008 |
| WO | 2008143856 A2 | 11/2008 |
| WO | 2008147518 A1 | 12/2008 |
| WO | 2008150364 A1 | 12/2008 |
| WO | 2009004584 A1 | 1/2009 |
| WO | 2009016087 A1 | 2/2009 |
| WO | 2009016560 A2 | 2/2009 |
| WO | 2009016564 A2 | 2/2009 |
| WO | 2009020642 A1 | 2/2009 |
| WO | 2009022311 A2 | 2/2009 |
| WO | 2009023126 A2 | 2/2009 |
| WO | 2009040730 A1 | 4/2009 |
| WO | 2009058238 A1 | 5/2009 |
| WO | 2009079637 A1 | 6/2009 |
| WO | 2009080533 A1 | 7/2009 |
| WO | 2009092642 A1 | 7/2009 |
| WO | 2009104155 A1 | 8/2009 |
| WO | 2009124956 A1 | 10/2009 |
| WO | 2009150614 A1 | 12/2009 |
| WO | 2009153180 A1 | 12/2009 |
| WO | 2009156951 A2 | 12/2009 |
| WO | 2010004507 A1 | 1/2010 |
| WO | 2010012620 A1 | 2/2010 |
| WO | 2010017260 A1 | 2/2010 |
| WO | 2010044054 A1 | 4/2010 |
| WO | 2010048010 A1 | 4/2010 |
| WO | 2010048012 A1 | 4/2010 |
| WO | 2010048013 A1 | 4/2010 |
| WO | 2010048014 A1 | 4/2010 |
| WO | 2010048016 A1 | 4/2010 |
| WO | 2010048017 A1 | 4/2010 |
| WO | 2010051236 A1 | 5/2010 |
| WO | 2010051237 A1 | 5/2010 |
| WO | 2010051238 A1 | 5/2010 |
| WO | 2010060470 A1 | 6/2010 |
| WO | 2010060471 A1 | 6/2010 |
| WO | 2010060472 A1 | 6/2010 |
| WO | 2010063662 A1 | 6/2010 |
| WO | 2010063663 A1 | 6/2010 |
| WO | 2010072722 A1 | 7/2010 |
| WO | 2010086366 A1 | 8/2010 |
| WO | 2010122151 A1 | 10/2010 |
| WO | 2011005636 A1 | 1/2011 |
| WO | 2011006960 A2 | 1/2011 |
| WO | 2011016234 A2 | 2/2011 |
| WO | 2011023578 A1 | 3/2011 |
| WO | 2011023585 A1 | 3/2011 |
| WO | 2011050198 A1 | 4/2011 |
| WO | 2011050200 A1 | 4/2011 |
| WO | 2011050202 A2 | 4/2011 |
| WO | 2011053522 A1 | 5/2011 |
| WO | 2011061318 A2 | 5/2011 |
| WO | 2011073316 A1 | 6/2011 |
| WO | 2011076744 A1 | 6/2011 |
| WO | 2011076747 A1 | 6/2011 |
| WO | 2011138265 A2 | 11/2011 |
| WO | 2011138266 A1 | 11/2011 |
| WO | 2012081692 A1 | 6/2012 |
| WO | 2012085852 A1 | 6/2012 |
| WO | 2012085857 A1 | 6/2012 |
| WO | 2012089606 A1 | 7/2012 |
| WO | 2012089607 A1 | 7/2012 |
| WO | 2012101487 A1 | 8/2012 |
| WO | 2012110986 A1 | 8/2012 |
| WO | 2012114252 A1 | 8/2012 |
| WO | 2012145581 A1 | 10/2012 |
| WO | 2012153729 A1 | 11/2012 |
| WO | 2013005755 A1 | 1/2013 |
| WO | 2013050938 A1 | 4/2013 |
| WO | 2013059163 A1 | 4/2013 |
| WO | 2013059222 A1 | 4/2013 |
| WO | 2013062857 A1 | 5/2013 |
| WO | 2013062858 A1 | 5/2013 |
| WO | 2013068935 A1 | 5/2013 |
| WO | 2013092893 A1 | 6/2013 |
| WO | 2013119639 A1 | 8/2013 |
| WO | 2013123240 A1 | 8/2013 |
| WO | 2013127913 A1 | 9/2013 |
| WO | 2013139730 A1 | 9/2013 |
| WO | 2015123355 A1 | 8/2015 |

OTHER PUBLICATIONS

N. L. Benowitz, "Pharmacology of nicotine: addiction, smoking-induced disease, and therapeutics", Annu Rev Pharmacol Toxicol 49, 57-71 (2009).

J. D. Killen, S. P. Fortmann, "Craving is associated with smoking relapse: findings from three prospective studies", Exp Clin Psychopharmacol 5(2), 137-142 (1997).

T. M. Piasecki, "Relapse to smoking", Clin Psychol Rev 26, 196-215 (2006).

R. D. Hurt et al., "Nicotine patch therapy for smoking cessation combined with physician advice and nurse follow-up", Oneyear outcome and percentage of nicotine replacement. JAMA 271, 595-600 (1994).

E. C. Westman, F. M. Behm, D. L. Simel, J. E. Rose, "Smoking behaviour on the first day of a quit attempt predicts longterm abstinence", Arch Intern Med 157, 335-340 (1997).

P. S. Hendricks, K. L. Delucchi, N. L. Benowitz, S. M. Hall, "Clinical significance of early smoking withdrawal effects and their relationships with nicotine metabolism: preliminary results from a pilot study", Nicotine Tob Res 16, 615-620 (May 2014).

J.A. Hollander, "Insular hypocrein transmission regulates nicotine reward", PNAS 105, 49, (Dec. 9, 2008).

J. A. Hollander, "Hypocretin-1 receptors regulate the reinforcing and reward-enhancing effects of cocaine: pharmacological and behavioural genetics evidence", Frontiers in Behavioral Neuroscience, 6, 47, (Jul. 24, 2012).

J. E. Fragale, "The role of orexin-1 receptor signalling in demand for the opioid fentanyl", Neuropsychopharmacology, Q1-8, (May 21, 2019).

E. M. Pich, "Orexin 1 receptor antagonists in compulsive behaviour and anxiety: possible therapeutic use", Frontiers in Neuroscience, 9, 26, (Feb. 2014).

(56) References Cited

OTHER PUBLICATIONS

A. Flores, "The hypocretin/orexin receptor-1 as a novel target to modulate cannabinoid reward", Biol Psychiatry, 75, 499-507 (2014).
K. Lei, "Nucleus accumbens shell Orexin-1 receptors are critical mediators of binge intake in excessive-drinking individuals", Frontiers in Neuroscience, 13, 88, (Feb. 13, 2019).
Response to Eurasian Office Action dated Oct. 4, 2019, in Eurasian Patent Application No. 201891714.
Damasio, A., "Alzheimer's Disease and Related Dementias," Cecil Textbook of Medicine, 20th edition, vol. 2: 1992-1996 (1996).
Di Fabio, et al. "Discovery process and pharmacological characterization of a novel dual orexin 1 and orexin 2 receptor antagonist useful for treatment of sleep disorders," Bioorganic & Medicinal Chemistry Letters 21: 5562-5567 (2011).
"FDA mulls drug to slow late-stage Alzheimer's," URL; http://www.cnn.com/2003/HEALTH/conditions/09/24/alzheimers.drug.ap/indexhtml [retrieved on Sep. 23, 2003].
Gatfield, et al., "Orexin Receptor Antagonists: A New Concept In CNS Disorders?," ChemMedChem, vol. 5: 1197-1214 (2010).
Heifetz, et al., "Study of Human Orexin-1 and -2 G-Protein-Coupled Receptors with Novel and Published Antagonists by Modeling, Molecular Dynamics Simulations, and Site-Directed Mutagenesis," Biochemistry, vol. 51: 3178-3197 (2012).
Hirose, et al., "N-Acyl 6,7-Dimethoxy-1,2,3,4-tetrahydroisoquinoline: The First Orexin-2 Receptor Selective Non-peptidic Antagonist," Bioorganic & Medicinal Chemistry Letters 13: 4497-4499 (2003).
Jiang, et al., "Disubstituted piperidines as potent orexin (hypocretin) receptor antagonists," Bioorganic & Medicinal Chemistry Letters 22: 3890-3893 (2012).
Layzer, R., "Section Five—Degenerative Diseases of the Nervous System," Cecil Textbook of Medicine, 20th edition, vol. 2: 2050-2057 (1996).
Whitman, et al., "Discovery of a Potent, CNS-Penetrant Orexin Receptor Antagonist Based on and N,N-Disubstituted-1,4-diazepane Scaffold that Promotes Sleep in Rats," ChemMedChem, vol. 4: 1069-1074 (2009).
Luyi Zhou, et al., "Orexin Receptor Targets for Anti-Relapse Medication Development in Drug Addiction" Pharmaceuticals 2011, vol. 4, pp. 804-821.
Andrea C. Haynes, et al., "Anorectic, thermogenic and anti-obesity activity of a selective orexin-1 receptor antagonist in ob/ob mice", Regulatory Peptides, v. 104, 2002, pp. 153-159.
Laura Piccoli, et al., "Role of Orexin-1 Receptor Mechanisms on Compulsive Food Consumption in a Model of Binge Eating in Female Rats", Neuropsychopharmacology, May 2012, v. 37, pp. 1999-2011.

* cited by examiner

HALO-SUBSTITUTED PIPERIDINES AS OREXIN RECEPTOR MODULATORS

RELATED APPLICATIONS

This application claims the benefit of priority to U.S. Provisional Patent Application No. 62/294,940, filed Feb. 12, 2016, and U.S. Provisional Patent Application No. 62/336,102, filed May 13, 2016, which applications are hereby incorporated by reference in their entirety.

STATEMENT OF GOVERNMENT SUPPORT

This invention was made with government support under Grant Numbers 1 P01DA033622 and 1 U01 NS083614 awarded by the National Institutes of Health. The government has certain rights in this invention.

BACKGROUND

Orexins are a family of homologous peptides including species orexin A, or OR-A, and orexin B, or OR-B. Orexin A is a 33 amino acid peptide and orexin B is a 28 amino acid peptide (Sakurai T. et al., Cell (1998), 92, 573-585). Orexins are produced in neurons of the lateral hypothalamus and bind to at least two distinct G-protein-coupled receptors, termed $OX_1$ and $OX_2$ receptors. The $OX_1$ receptor is selective for OR-A, while the $OX_2$ receptor can bind both OR-A and OR-B. Orexins are found to stimulate food consumption, regulate states of sleep and wakefulness, and may be involved in neural mechanisms of drug abuse and addiction.

Orexin receptors are suitable targets for the development of drug candidates for the treatment of a variety of Orexin-related pathologies or symptoms, such as, but not limited to, sleep/wake disorders, anxiety, and obesity. Numerous modulators of $OX_1$, $OX_2$, or both, have been developed to date [J. Med. Chem. 2016, 59(2), 504-530]. However, many of the reported Orexin receptor modulators, such as antagonist ligands, have suboptimal metabolic stabilities. This translates into short half-lives and high observed clearance in in vivo pharmacokinetic experiments (Chem Med Chem, 2012, 7, 415-424; Bioorganic & Medicinal Chemistry Letters 2012, 22, 3890-3894; Bioorganic & Medicinal Chemistry Letters, 2015, 25, 1884-1891; J. Med. Chem. 2015, 58, 5620-5636). There remains a need for small molecule modulators of Orexin receptors with desirable pharmaceutical properties.

SUMMARY OF THE APPLICATION

This application provides a compound of formula (I),

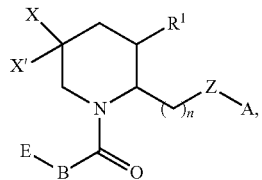

(I)

or its pharmaceutically acceptable salt hereof, wherein:
X is halogen, such as F;
X' is H or halogen, such as F;
Z is $NR^2$ or O;

A is aryl, aroyl, heteroaryl, or heteroaroyl, wherein A is optionally substituted with one or more substituents independently selected from the group consisting of alkyl, such as $C_{1-4}$alkyl (e.g., methyl, ethyl, —$CHF_2$, or —$CF_3$); cycloalkyl; halo, such as —F, —Cl, or —Br (e.g., —Cl); —OH; alkoxy, such as methoxy; —CN; —$NR^aR^b$; —$N(R^a)$C(O) alkyl; —$N(R^a)CO_2$alkyl; —$N(R^a)SO_2$alkyl; —C(O) alkyl; —$CO_2H$; —$CO_2$alkyl; —$CONR^aR^b$; —$SO_2$alkyl; and —$SO_2NR^aR^b$; wherein $R^a$ and $R^b$ are independently for each occurrence H or alkyl;

B is aryl or heteroaryl, wherein B is optionally substituted with one or more substituents independently selected from the group consisting of alkyl, such as $C_{1-4}$alkyl (e.g., methyl, ethyl, isopropyl, —$CH_2CF_3$, —$CHF_2$, or —$CF_3$); cycloalkyl; halo, such as —F, —Cl, or —Br (e.g., —F or —Cl); —OH; alkoxy, such as methoxy or isopropoxy (e.g., methoxy); —CN; —$NR^cR^d$; —$N(R^c)$C(O) alkyl; —$N(R^c)CO_2$alkyl; —$N(R^c)SO_2$alkyl; —C(O)alkyl; —$CO_2H$; —$CO_2$alkyl; —$CONR^cR^d$; —$SO_2$alkyl; and —$SO_2NR^cR^d$; wherein $R^c$ and $R^d$ are independently for each occurrence H or alkyl;

E is aryl or heteroaryl, wherein E is optionally substituted with one or more substituents independently selected from the group consisting of alkyl, such as $C_{1-4}$alkyl (e.g., methyl, ethyl, —$CHF_2$, or —$CF_3$); cycloalkyl; halo, such as —F, —Cl, or —Br (e.g., —F or —Cl); —OH; alkoxy, such as methoxy; —CN; —$NR^eR^f$; —$N(R^e)$C(O) alkyl; —$N(R^e)$ $CO_2$alkyl; —$N(R^e)SO_2$alkyl; —C(O)alkyl; —$CO_2H$; —$CO_2$alkyl; —$CONR^eR^f$; —$SO_2$alkyl; and —$SO_2NR^eR^f$; wherein $R^e$ and $R^f$ are independently for each occurrence H or alkyl;

n is 1, 2, or 3;
$R^1$ is alkyl, such as $C_{1-4}$alkyl (e.g., methyl); and
$R^2$ is H or alkyl, such as $C_{1-4}$alkyl (e.g., methyl).

In certain embodiments, A is aryl or heteroaryl, wherein A is optionally substituted with one or more substituents independently selected from the group consisting of alkyl, such as $C_{1-4}$ alkyl (e.g., methyl, ethyl, —$CHF_2$, or —$CF_3$); cycloalkyl; halo, such as —F, —Cl, or —Br (e.g., —Cl); —OH; alkoxy, such as methoxy; —CN; —$NR^aR^b$; —$N(R^a)$ C(O) alkyl; —$N(R^a)CO_2$alkyl; —$N(R^a)SO_2$alkyl; —C(O) alkyl; —$CO_2H$; —$CO_2$alkyl; —$CONR^aR^b$; —$SO_2$alkyl; and —$SO_2NR^aR^b$; wherein $R^a$ and $R^b$ are independently for each occurrence H or alkyl.

In certain embodiments, n is 1.
In certain embodiments, X' is halogen, such as F.
In certain embodiments, the compound of formula (I) can be represented by formula (Ia),

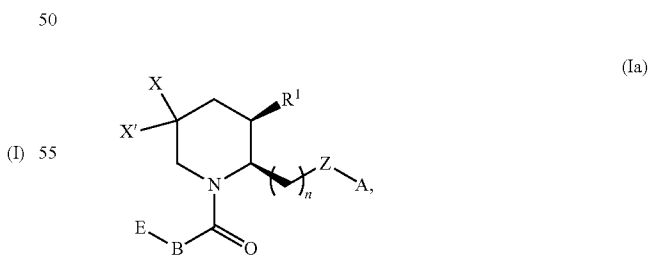

(Ia)

or a pharmaceutically acceptable salt thereof, wherein
X is halogen, such as F;
X' is H or halogen, such as F;
Z is $NR^2$ or O;
A is aryl, aroyl, heteroaryl, or heteroaroyl, wherein A is optionally substituted with one or more substituents independently selected from the group consisting of alkyl, such as $C_{1-4}$alkyl (e.g., methyl, ethyl, —$CHF_2$, or —$CF_3$); cycloalkyl; halo, such as —F, —Cl, or —Br (e.g., —Cl); —OH; alkoxy, such as methoxy; —CN; —$NR^aR^b$; —$N(R^a)$ C(O) alkyl; —$N(R^a)CO_2$alkyl; —$N(R^a)SO_2$alkyl; —C(O) alkyl; —$CO_2H$; —$CO_2$alkyl; —$CONR^aR^b$; —$SO_2$alkyl; and —$SO_2NR^aR^b$; wherein $R^a$ and $R^b$ are independently for each occurrence H or alkyl;

B is aryl or heteroaryl, wherein B is optionally substituted with one or more substituents independently selected from the group consisting of alkyl, such as $C_{1-4}$alkyl (e.g., methyl, ethyl, isopropyl, —$CH_2CF_3$, —$CHF_2$, or —$CF_3$); cycloalkyl; halo, such as —F, —Cl, or —Br (e.g., —F or —Cl); —OH; alkoxy, such as methoxy or isopropoxy (e.g., methoxy); —CN; —$NR^cR^d$; —$N(R^c)C(O)$ alkyl; —$N(R^c)$ $CO_2$alkyl; —$N(R^c)SO_2$alkyl; —C(O)alkyl; —$CO_2H$; —$CO_2$alkyl; —$CONR^cR^d$; —$SO_2$alkyl; and —$SO_2NR^cR^d$; wherein $R^c$ and $R^d$ are independently for each occurrence H or alkyl;

E is aryl or heteroaryl, wherein E is optionally substituted with one or more substituents independently selected from the group consisting of alkyl, such as $C_{1-4}$alkyl (e.g., methyl, ethyl, —$CHF_2$, or —$CF_3$); cycloalkyl; halo, such as —F, —Cl, or —Br (e.g., —F or —Cl); —OH; alkoxy, such as methoxy; —CN; —$NR^eR^f$; —$N(R^e)C(O)$ alkyl; —$N(R^e)$ $CO_2$alkyl; —$N(R^e)SO_2$alkyl; —C(O)alkyl; —$CO_2H$; —$CO_2$alkyl; —$CONR^eR^f$; —$SO_2$alkyl; and —$SO_2NR^eR^f$; wherein $R^e$ and $R^f$ are independently for each occurrence H or alkyl;

n is 1, 2, or 3;

$R^1$ is alkyl, such as $C_{1-4}$alkyl (e.g., methyl); and $R^2$ is H or alkyl, such as $C_{1-4}$alkyl (e.g., methyl).

In certain embodiments, A is aryl or heteroaryl, wherein A is optionally substituted with one or more substituents independently selected from the group consisting of alkyl, such as $C_{1-4}$ alkyl (e.g., methyl, ethyl, —$CHF_2$, or —$CF_3$); cycloalkyl; halo, such as —F, —Cl, or —Br (e.g., —Cl); —OH; alkoxy, such as methoxy; —CN; —$NR^aR^b$; —$N(R^a)$ C(O) alkyl; —$N(R^a)CO_2$alkyl; —$N(R^a)SO_2$alkyl; —C(O) alkyl; —$CO_2H$; —$CO_2$alkyl; —$CONR^aR^b$; —$SO_2$alkyl; and —$SO_2NR^aR^b$; wherein $R^a$ and $R^b$ are independently for each occurrence H or alkyl.

In certain embodiments, n is 1.

In certain embodiments, X' is halogen, such as F.

In certain embodiments, the compound of formula (I) can be represented by formula (Ib),

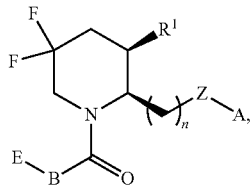

(Ib)

or a pharmaceutically acceptable salt thereof, wherein

Z is $NR^2$ or O;

A is aryl, aroyl, heteroaryl, or heteroaroyl, wherein A is optionally substituted with one or more substituents independently selected from the group consisting of alkyl, such as $C_{1-4}$alkyl (e.g., methyl, ethyl, —$CHF_2$, or —$CF_3$); cycloalkyl; halo, such as —F, —Cl, or —Br (e.g., —Cl); —OH; alkoxy, such as methoxy; —CN; —$NR^aR^b$; —$N(R^a)$ C(O) alkyl; —$N(R^a)CO_2$alkyl; —$N(R^a)SO_2$alkyl; —C(O) alkyl; —$CO_2H$; —$CO_2$alkyl; —$CONR^aR^b$; —$SO_2$alkyl; and —$SO_2NR^aR^b$; wherein $R^a$ and $R^b$ are independently for each occurrence H or alkyl;

B is aryl or heteroaryl, wherein B is optionally substituted with one or more substituents independently selected from the group consisting of alkyl, such as $C_{1-4}$alkyl (e.g., methyl, ethyl, isopropyl, —$CH_2CF_3$, —$CHF_2$, or —$CF_3$); cycloalkyl; halo, such as —F, —Cl, or —Br (e.g., —F or —Cl); —OH; alkoxy, such as methoxy or isopropoxy (e.g., methoxy); —CN; —$NR^cR^d$; —$N(R^c)C(O)$ alkyl; —$N(R^c)$ $CO_2$alkyl; —$N(R^c)SO_2$alkyl; —C(O)alkyl; —$CO_2H$; —$CO_2$alkyl; —$CONR^cR^d$; —$SO_2$alkyl; and —$SO_2NR^cR^d$; wherein $R^c$ and $R^d$ are independently for each occurrence H or alkyl;

E is aryl or heteroaryl, wherein E is optionally substituted with one or more substituents independently selected from the group consisting of alkyl, such as $C_{1-4}$alkyl (e.g., methyl, ethyl, —$CHF_2$, or —$CF_3$); cycloalkyl; halo, such as —F, —Cl, or —Br (e.g., —F or —Cl); —OH; alkoxy, such as methoxy; —CN; —$NR^eR^f$; —$N(R^e)C(O)$ alkyl; —$N(R^e)$ $CO_2$alkyl; —$N(R^e)SO_2$alkyl; —C(O)alkyl; —$CO_2H$; —$CO_2$alkyl; —$CONR^eR^f$; —$SO_2$alkyl; and —$SO_2NR^eR^f$; wherein $R^e$ and $R^f$ are independently for each occurrence H or alkyl;

n is 1, 2, or 3;

$R^1$ is alkyl, such as $C_{1-4}$alkyl (e.g., methyl); and $R^2$ is H or alkyl, such as $C_{1-4}$alkyl (e.g., methyl).

In certain embodiments, A is aryl or heteroaryl, wherein A is optionally substituted with one or more substituents independently selected from the group consisting of alkyl, such as $C_{1-4}$ alkyl (e.g., methyl, ethyl, —$CHF_2$, or —$CF_3$); cycloalkyl; halo, such as —F, —Cl, or —Br (e.g., —Cl); —OH; alkoxy, such as methoxy; —CN; —$NR^aR^b$; —$N(R^a)$ C(O) alkyl; —$N(R^a)CO_2$alkyl; —$N(R^a)SO_2$alkyl; —C(O) alkyl; —$CO_2H$; —$CO_2$alkyl; —$CONR^aR^b$; —$SO_2$alkyl; and —$SO_2NR^aR^b$; wherein $R^a$ and $R^b$ are independently for each occurrence H or alkyl.

In certain embodiments, n is 1.

In certain embodiments, the compound of formula (I) can be represented by formula (II):

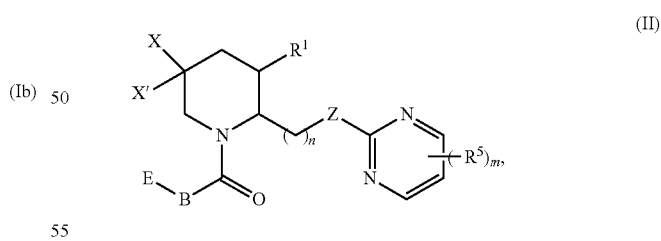

(II)

or a pharmaceutically acceptable salt thereof, wherein:

m=1, 2, or 3; and $R^5$ represents alkyl, cycloalkyl, halo, —OH, alkoxy, —CN, —$NR^jR^k$, —$N(R^j)C(O)$ alkyl, —$N(R^j)C_2$alkyl, —$N(R^j)SO_2$alkyl, —C(O)alkyl, —$CO_2H$, —$CO_2$alkyl, —$CONR^jR^k$, —$SO_2$alkyl, or —$SO_2NR^jR^k$; wherein $R^j$ and $R^k$ are independently for each occurrence H or alkyl; and X, X', Z, B, E, n, $R^1$ and $R^2$ are as defined herein.

In certain such embodiments, the compound of formula (II) can be represented by formula (IIa),

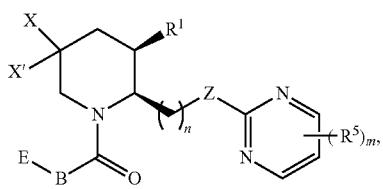

(IIa)

or a pharmaceutically acceptable salt thereof. In certain such embodiments, X and X' are both F.

In certain embodiments, the compound of formula (I) can be represented by formula (III):

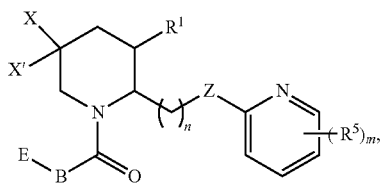

(III)

or a pharmaceutically acceptable salt thereof; wherein:
m=1, 2, 3, or 4; and
$R^5$ represents alkyl, cycloalkyl, halo, —OH, alkoxy, —CN, —$NR^jR^k$, —$N(R^j)C(O)$ alkyl, —$N(R^j)C_2$alkyl, —$N(R^j)SO_2$alkyl, —C(O)alkyl, —$CO_2H$, —$CO_2$alkyl, —$CONR^jR^k$, —$SO_2$alkyl, or —$SO_2NR^jR^k$; wherein $R^j$ and $R^k$ are independently for each occurrence H or alkyl; and
X, X', Z, B, E, n, $R^1$ and $R^2$ are as defined herein.

In certain such embodiments, the compound of formula (III) can be represented by formula (IIIa),

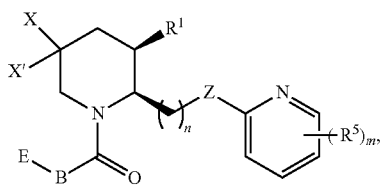

(IIIa)

or a pharmaceutically acceptable salt thereof. In certain such embodiments, X and X' are both F.

In certain embodiments, the compound of formula (I) can be represented by formula (IV):

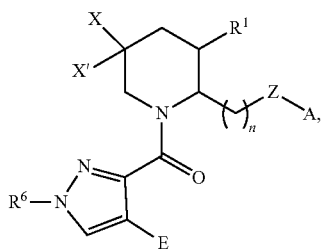

(IV)

or a pharmaceutically acceptable salt thereof; wherein:
$R^6$ represents alkyl, cycloalkyl, halo, —OH, alkoxy, —CN, —$NR^oR^p$, —$N(R^o)C(O)$ alkyl, —$N(R^p)CO_2$alkyl, —$N(R^o)SO_2$alkyl, —C(O)alkyl, —$CO_2H$, —$CO_2$alkyl, —$CONR^oR^p$, —$SO_2$alkyl, or —$SO_2NR^oR^p$; wherein $R^o$ and $R^p$ are independently for each occurrence H or alkyl; and
X, X', Z, A, E, n, $R^1$ and $R^2$ are as defined herein.

In certain such embodiments, the compound of formula (IV) can be represented by formula (IVa),

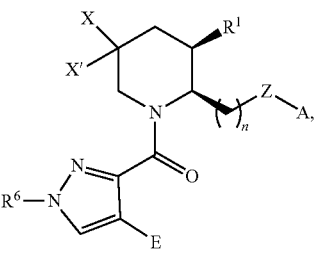

(IVa)

or a pharmaceutically acceptable salt thereof. In certain such embodiments, X and X' are both F.

In certain embodiments, the compound of formula (I) can be represented by formula (V):

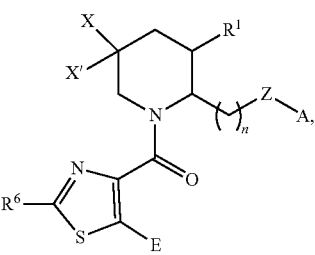

(V)

or a pharmaceutically acceptable salt thereof; wherein:
$R^6$ represents alkyl, cycloalkyl, halo, —OH, alkoxy, —CN, —$NR^oR^p$, —$N(R^o)C(O)$ alkyl, —$N(R^p)CO_2$alkyl, —$N(R^o)SO_2$alkyl, —C(O)alkyl, —$CO_2H$, —$CO_2$alkyl, —$CONR^oR^p$, —$SO_2$alkyl, or —$SO_2NR^oR^p$; wherein $R^o$ and $R^p$ are independently for each occurrence H or alkyl; and
X, X', Z, A, E, n, $R^1$ and $R^2$ are as defined herein.

In certain such embodiments, the compound of formula (V) can be represented by formula (Va),

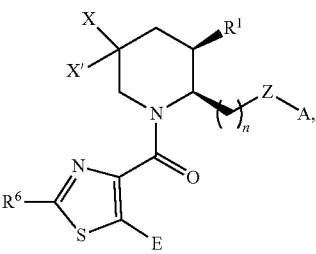

(Va)

or a pharmaceutically acceptable salt thereof. In certain such embodiments, X and X' are both F.

In certain embodiments, the compound of Formula (I), (Ia), (Ib), (II), (IIa), (III), (IIIa), (IV), (IVa), (V), or (Va) is a compound selected from those species described or exemplified in the detailed description below.

In certain embodiments, this application provides a pharmaceutical composition, comprising at least one compound of Formula (I), (Ia), (Ib), (II), (IIa), (III), (IIIa), (IV), (IVa), (V), or (Va), or a pharmaceutically acceptable salt thereof. Pharmaceutical compositions as described herein may further comprise a pharmaceutically acceptable excipient. In certain embodiments, this application also describes a compound of Formula (I), (Ia), (Ib), (II), (IIa), (III), (IIIa), (IV), (IVa), (V), or (Va) or a pharmaceutically acceptable salt thereof, or a composition comprising of any of the foregoing for use as a medicament.

In another aspect, this application provides methods of treating a disease, disorder, or medical condition mediated by orexin receptor activity a subject in need of such treatment, such as those described herein, comprising administering to the subject, such as a patient, an effective amount of at least one compound described herein or a pharmaceutically acceptable salt thereof in a dose, at a frequency, and for a duration to provide a beneficial effect to the subject. The orexin receptor can be $OX_1$, $OX_2$, or both.

In some embodiments, this application provides methods of treating a disease, disorder, or medical condition in a subject in need, such as a patient, comprising administering to the subject, such as a patient, an effective amount of at least one compound described herein or a pharmaceutically acceptable salt thereof in a dose, at a frequency, and for a duration to provide a beneficial effect to the subject.

In certain embodiments, this application provides the use of a compound described herein, or a pharmaceutically acceptable salt thereof, or a composition comprising of any of the foregoing in the preparation of a medicament for the treatment of diseases, disorders, and medical conditions regulated by orexin receptor activity, and the use of such compounds and salts for treatment of such diseases and medical conditions.

In certain embodiments, this application provides the use of a compound described herein, or a pharmaceutically acceptable salt thereof, or a composition comprising of any of the foregoing in the preparation of a medicament for the treatment of diseases, disorders, and medical conditions, and the use of such compounds and salts for treatment of such diseases, disorder, and medical conditions.

In certain embodiments, this application provides a method of treating a disease, disorder, or medical condition in a subject, such as a patient, comprising modulating an orexin receptor, wherein the modulating an orexin receptor comprises administering to the subject at least one compound of Formula (I), (Ia), (Ib), (II), (IIa), (III), (IIIa), (IV), (IVa), (V), or (Va) or a pharmaceutically acceptable salt thereof, or a composition comprising of any of the foregoing, in a dose, at a frequency, and for a duration to provide a beneficial effect to the subject patient.

In certain embodiments, the disease, disorder, or medical condition is an eating disorder, obesity, alcoholism or an alcohol-related disorder, drug abuse or addiction, a sleep disorder, a cognitive dysfunction in a psychiatric or neurologic disorder, depression, anxiety, panic disorder, schizophrenia, Alzheimer's disease, Parkinson's disease, Huntington's chorea, head ache, migraine, pain, gastrointestinal diseases, epilepsy, inflammations, immune-related diseases, ulcers, irritable bowel syndrome, diarrhea, gastroesophageal reflux, endocrine-related diseases, cancer, hypertension, behavior disorder, mood disorder, manic depression, dementia, sex disorder, psychosexual disorder, and renal disease. In certain embodiments, the disease, disorder, or medical condition is selected from the group consisting of drug abuse or addiction, a sleep disorder, a cognitive dysfunction in a psychiatric or neurologic disorder, depression, anxiety, panic disorder, post-traumatic stress disorder, seasonal affective disorder, schizophrenia, Alzheimer's disease, Parkinson's disease, Huntington's chorea, pain, behavior disorder, mood disorder, manic depression, dementia, sex disorder, and psychosexual disorder.

In certain embodiments, the disease, disorder, or medical condition is selected from the group consisting of an eating disorder, obesity, alcoholism or an alcohol-related disorder, headache, migraine, gastrointestinal diseases, inflammations, immune-related diseases, ulcers, irritable bowel syndrome, diarrhea, gastroesophageal reflux, endocrine-related diseases, cancer, hypertension, and renal disease.

In certain embodiments, drug abuse and addiction can include abuse of or addiction to cocaine, opiates, amphetamines, ethanol, cannabis/marijuana, or nicotine.

In certain embodiments, this application provides a method of modulating the activity of an orexin receptor, such as one or both of $OX_1$ or $OX_2$, comprising contacting a cell comprising the orexin receptor with an effective amount of at least one compound described herein, or a pharmaceutically acceptable salt thereof, or a composition comprising any one of the foregoing.

In certain embodiments, this application describes a method of modulating the activity of an orexin receptor, such as one or both of $OX_1$ or $OX_2$, comprising contacting a cell comprising the orexin receptor with an effective amount of at least one compound of Formula (I), (Ia), (Ib), (II), (IIa), (III), (IIIa), (IV), (IVa), (V), or (Va) or a pharmaceutically acceptable salt thereof, and/or with at least one compound or pharmaceutical composition as described herein. In certain embodiments of the foregoing, the contacting is in vitro, ex vivo, or in vivo.

Additional embodiments, features, and advantages of the invention will be apparent from the following detailed description and through practice of the embodiments described in this application.

DETAILED DESCRIPTION

The present application provides a compound of formula (I),

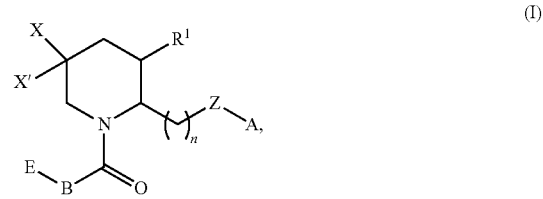

or a pharmaceutically acceptable salt thereof, wherein:

X is halogen, such as F;

X' is H or halogen, such as F;

Z is $NR^2$ or O;

A is optionally substituted aryl, aroyl, heteroaryl, or heteroaroyl;

B is optionally substituted aryl or heteroaryl;

E is optionally substituted aryl or heteroaryl;

n is 1, 2, or 3;

$R^1$ is alkyl, such as $C_{1-4}$alkyl (e.g., methyl); and $R^2$ is H or alkyl, such as $C_{1-4}$alkyl (e.g., methyl).

In certain embodiments, the compound of formula (I) can be represented by Formula (Ia):

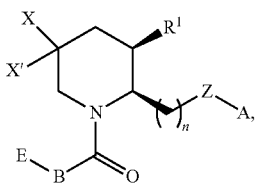

(Ia)

or a pharmaceutically acceptable salt thereof, wherein
X is halogen, such as F;
X' is H or halogen, such as F;
Z is $NR^2$ or O;
A is optionally substituted aryl, aroyl, heteroaryl, or heteroaroyl;
B is optionally substituted aryl or heteroaryl;
E is optionally substituted aryl or heteroaryl;
n=1, 2, or 3;
$R^1$ is alkyl, such as $C_{1-4}$alkyl (e.g., methyl); and
$R^2$ is H or alkyl, such as $C_{1-4}$alkyl (e.g., methyl).

In certain embodiments, the compound of formula (I) can be represented by formula (Ib),

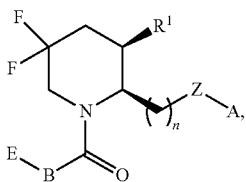

(Ib)

or a pharmaceutically acceptable salt thereof, wherein
Z is $NR^2$ or O;
A is optionally substituted aryl, aroyl, heteroaryl, or heteroaroyl;
B is optionally substituted aryl or heteroaryl;
E is optionally substituted aryl or heteroaryl;
n is 1, 2, or 3;
$R^1$ is alkyl, such as $C_{1-4}$alkyl (e.g., methyl); and
$R^2$ is H or alkyl, such as $C_{1-4}$alkyl (e.g., methyl).

In certain embodiments of the compound of formula (I), (Ia), or (Ib), A is optionally substituted with one or more substituents independently selected from the group consisting of alkyl, such as $C_{1-4}$alkyl (e.g., methyl, ethyl, —$CHF_2$, or —$CF_3$); cycloalkyl; halo, such as —F, —Cl, or —Br (e.g., —Cl); —OH; alkoxy, such as methoxy; —CN; —$NR^aR^b$; —$N(R^a)C(O)$ alkyl; —$N(R^a)CO_2$alkyl; —$N(R^a)SO_2$alkyl; —C(O)alkyl; —$CO_2H$; —$CO_2$alkyl; —$CONR^aR^b$; —$SO_2$alkyl; and —$SO_2NR^aR^b$; wherein $R^a$ and $R^b$ are independently for each occurrence H or alkyl. In certain such embodiments, A is aryl or heteroaryl.

In certain embodiments of the compound of formula (I), (Ia), or (Ib), B is optionally substituted with one or more substituents independently selected from the group consisting of alkyl, such as $C_{1-4}$alkyl, (e.g., methyl, ethyl, isopropyl, —$CH_2CF_3$, —$CHF_2$, or —$CF_3$); cycloalkyl; halo, such as —F, —Cl, or —Br (e.g., —F or —Cl); —OH; alkoxy, such as methoxy or isopropoxy (e.g., methoxy); —CN; —$NR^cR^d$; —$N(R^c)C(O)$ alkyl; —$N(R^c)CO_2$alkyl; —$N(R^c)SO_2$alkyl; —C(O)alkyl; —$CO_2H$; —$CO_2$alkyl; —$CONR^cR^d$; —$SO_2$alkyl; and —$SO_2NR^cR^d$; wherein $R^c$ and $R^d$ are independently for each occurrence H or alkyl.

In certain embodiments of the compound of formula (I), (Ia), or (Ib), E is optionally substituted with one or more substituents independently selected from the group consisting of alkyl, such as $C_{1-4}$alkyl (e.g., methyl, ethyl, —$CHF_2$, or —$CF_3$); cycloalkyl; halo, such as —F, —Cl, or —Br (e.g., —F or —Cl); —OH; alkoxy, such as methoxy; —CN; —$NR^eR^f$; —$N(R^e)C(O)$ alkyl; —$N(R^e)CO_2$alkyl; —$N(R^e)SO_2$alkyl; —C(O)alkyl; —$CO_2H$; —$CO_2$alkyl; —$CONR^eR^f$; —$SO_2$alkyl; and —$SO_2NR^eR^f$; wherein $R^e$ and $R^f$ are independently for each occurrence H or alkyl.

In certain embodiments, the compound of formula (I) can be represented by formula (II) or (IIa).

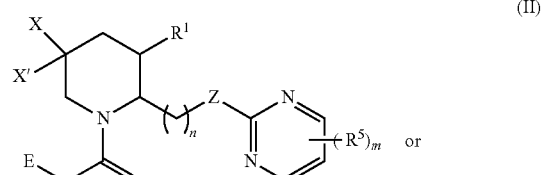

(II)

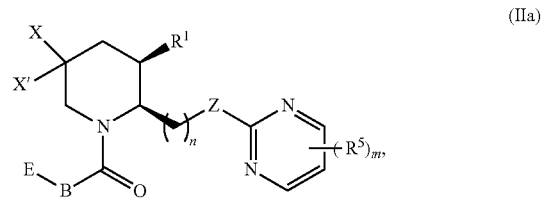

(IIa)

or a pharmaceutically acceptable salt thereof; wherein:
X is halogen, such as F;
X' is H or halogen, such as F;
Z is $NR^2$ or O;
M is 1, 2, or 3;
B is aryl or heteroaryl, wherein B is optionally substituted with one or more substituents independently selected from the group consisting of alkyl, such as $C_{1-4}$alkyl (e.g., methyl, ethyl, isopropyl, —$CH_2CF_3$, —$CHF_2$, or —$CF_3$); cycloalkyl; halo, such as —F, —Cl, or —Br (e.g., —F or —Cl); —OH; alkoxy, such as methoxy or isopropoxy (e.g., methoxy); —CN; —$NR^cR^d$; —$N(R^c)C(O)$ alkyl; —$N(R^c)CO_2$alkyl; —$N(R^c)SO_2$alkyl; —C(O)alkyl; —$CO_2H$; —$CO_2$alkyl; —$CONR^cR^d$; —$SO_2$alkyl; and —$SO_2NR^cR^d$; wherein $R^c$ and $R^d$ are independently for each occurrence H or alkyl;

E is aryl or heteroaryl, wherein E is optionally substituted with one or more substituents independently selected from the group consisting of alkyl, such as $C_{1-4}$alkyl (e.g., methyl, ethyl, —$CHF_2$, or —$CF_3$); cycloalkyl; halo, such as —F, —Cl, or —Br (e.g., —F or —Cl); —OH; alkoxy, such as methoxy; —CN; —$NR^aR^b$; —$N(R^b)C(O)$ alkyl; —$N(R^b)CO_2$alkyl; —$N(R^b)SO_2$alkyl; —C(O)alkyl; —$CO_2H$; —$CO_2$alkyl; —$CONR^eR^f$; —$SO_2$alkyl; and —$SO_2NR^eR^f$; wherein $R^e$ and $R^f$ are independently for each occurrence H or alkyl;

n is 1, 2, or 3;
$R^1$ is alkyl, such as $C_{1-4}$alkyl (e.g., methyl);
$R^2$ is H or alkyl, such as $C_{1-4}$alkyl (e.g., methyl); and
$R^5$ represents alkyl, cycloalkyl, halo, —OH, alkoxy, —CN, —$NR^jR^k$, —$N(R^j)C(O)$ alkyl, —$N(R^j)CO_2$alkyl, —$N(R^j)SO_2$alkyl, —C(O)alkyl, —$CO_2H$, —$CO_2$alkyl, —$CONR^jR^k$, —$SO_2$alkyl, or —$SO_2NR^jR^k$; wherein $R^j$ and $R^k$ are independently for each occurrence H or alkyl.

In certain embodiments, the compound of formula (I) can be represented by formula (III) or (IIIa):

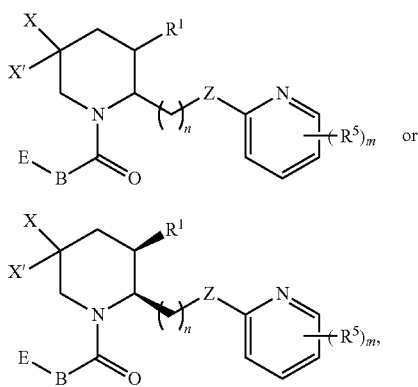

(III)

(IIIa)

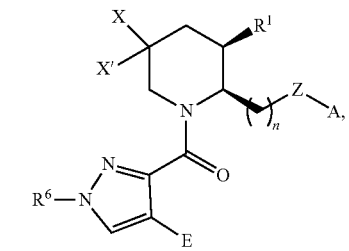

or a pharmaceutically acceptable salt thereof; wherein:
X is halogen, such as F;
X' is H or halogen, such as F;
Z is NR$^2$ or O;
m is 1, 2, 3, or 4;
B is aryl or heteroaryl, wherein B is optionally substituted with one or more substituents independently selected from the group consisting of alkyl, such as $C_{1-4}$alkyl (e.g., methyl, ethyl, isopropyl, —CH$_2$CF$_3$, —CHF$_2$, or —CF$_3$); cycloalkyl; halo, such as —F, —Cl, or —Br (e.g., —F or —Cl); —OH; alkoxy, such as methoxy or isopropoxy (e.g., methoxy); —CN; —NR$^c$R$^d$; —N(R$^c$)C(O) alkyl; —N(R$^c$)CO$_2$alkyl; —N(R$^c$)SO$_2$alkyl; —C(O)alkyl; —CO$_2$H; —CO$_2$alkyl; —CONR$^c$R$^d$; —SO$_2$alkyl; and —SO$_2$NR$^c$R$^d$; wherein R$^c$ and R$^d$ are independently for each occurrence H or alkyl;
E is aryl or heteroaryl, wherein E is optionally substituted with one or more substituents independently selected from the group consisting of alkyl, such as $C_{1-4}$alkyl (e.g., methyl, ethyl, —CHF$_2$, or —CF$_3$); cycloalkyl; halo, such as —F, —Cl, or —Br (e.g., —F or —Cl); —OH; alkoxy, such as methoxy; —CN; —NR$^e$R$^f$; —N(R$^e$)C(O) alkyl; —N(R$^e$) CO$_2$alkyl; —N(R$^e$)SO$_2$alkyl; —C(O)alkyl; —CO$_2$H; —CO$_2$alkyl; —CONR$^e$R$^f$; —SO$_2$alkyl; and —SO$_2$NR$^e$R$^f$; wherein R$^e$ and R$^f$ are independently for each occurrence H or alkyl;
n is 1, 2, or 3;
R$^1$ is alkyl, such as $C_{1-4}$alkyl (e.g., methyl);
R$^2$ is H or alkyl, such as $C_{1-4}$alkyl (e.g., methyl); and
R$^5$ represents alkyl, cycloalkyl, halo, —OH, alkoxy, —CN, —NR$^j$R$^k$, —N(R$^j$)C(O) alkyl, —N(R$^j$)C$_2$alkyl, —N(R$^j$)SO$_2$alkyl, —C(O)alkyl, —CO$_2$H, —CO$_2$alkyl, —CONR$^j$R$^k$, —SO$_2$alkyl, or —SO$_2$NR$^j$R$^k$; wherein R$^j$ and R$^k$ are independently for each occurrence H or alkyl.

In certain embodiments, the compound of formula (I) can be represented by formula (IV) or (IVa):

(IV)

(IVa)

or a pharmaceutically acceptable salt thereof, wherein:
X is halogen, such as F;
X' is H or halogen, such as F;
Z is NR$^2$ or O;
A is aryl, aroyl, heteroaryl, or heteroaroyl, wherein A is optionally substituted with one or more substituents independently selected from the group consisting of alkyl, such as $C_{1-4}$alkyl (e.g., methyl, ethyl, —CHF$_2$, or —CF$_3$); cycloalkyl; halo, such as —F, —Cl, or —Br (e.g., —Cl); —OH; alkoxy, such as methoxy; —CN; —NR$^a$R$^b$; —N(R$^a$) C(O) alkyl; —N(R$^a$)CO$_2$alkyl; —N(R$^a$)SO$_2$alkyl; —C(O) alkyl; —CO$_2$H; —CO$_2$alkyl; —CONR$^a$R$^b$; —SO$_2$alkyl; and —SO$_2$NR$^a$R$^b$; wherein R$^a$ and R$^b$ are independently for each occurrence H or alkyl;
E is aryl or heteroaryl, wherein E is optionally substituted with one or more substituents independently selected from the group consisting of alkyl, such as $C_{1-4}$alkyl (e.g., methyl, ethyl, —CHF$_2$, or —CF$_3$); cycloalkyl; halo, such as —F, —Cl, or —Br (e.g., —F or —Cl); —OH; alkoxy, such as methoxy; —CN; —NR$^e$R$^f$; —N(R$^e$)C(O) alkyl; —N(R$^e$) CO$_2$alkyl; —N(R$^e$)SO$_2$alkyl; —C(O)alkyl; —CO$_2$H; —CO$_2$alkyl; —CONR$^e$R$^f$; —SO$_2$alkyl; and —SO$_2$NR$^e$R$^f$; wherein R$^e$ and R$^f$ are independently for each occurrence H or alkyl;
n is 1, 2, or 3;
R$^1$ is alkyl, such as $C_{1-4}$alkyl (e.g., methyl);
R$^2$ is H or alkyl, such as $C_{1-4}$alkyl (e.g., methyl);
R$^6$ represents alkyl, cycloalkyl, halo, —OH, alkoxy, —CN, —NR$^o$R$^p$, —N(R$^o$)C(O) alkyl, —N(R$^p$)CO$_2$alkyl, —N(R$^o$)SO$_2$alkyl, —C(O)alkyl, —CO$_2$H, —CO$_2$alkyl, —CONR$^o$R$^p$, —SO$_2$alkyl, or —SO$_2$NR$^o$R$^p$; wherein R$^o$ and R$^p$ are independently for each occurrence H or alkyl.

In certain embodiments, the compound of formula (I) can be represented by formula (V) or (Va):

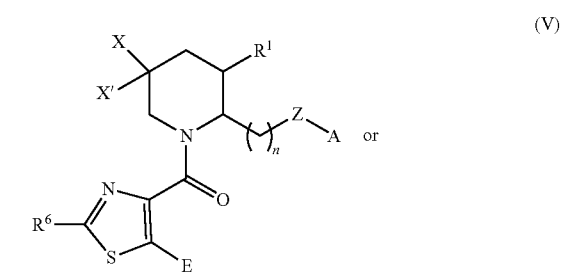

(V)

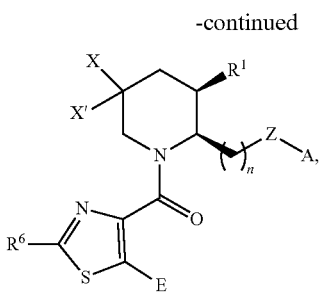

(Va)

or a pharmaceutically acceptable salt thereof; wherein:
X is halogen, such as F;
X' is H or halogen, such as F;
Z is $NR^2$ or O;
A is aryl, aroyl, heteroaryl, or heteroaroyl, wherein A is optionally substituted with one or more substituents independently selected from the group consisting of alkyl, such as $C_{1-4}$alkyl (e.g., methyl, ethyl, —$CHF_2$, or —$CF_3$); cycloalkyl; halo, such as —F, —Cl, or —Br (e.g., —Cl); —OH; alkoxy, such as methoxy; —CN; —$NR^aR^b$; —$N(R^a)$C(O) alkyl; —$N(R^a)CO_2$alkyl; —$N(R^a)SO_2$alkyl; —C(O)alkyl; —$CO_2H$; —$CO_2$alkyl; —$CONR^aR^b$; —$SO_2$alkyl; and —$SO_2NR^aR^b$; wherein $R^a$ and $R^b$ are independently for each occurrence H or alkyl;
E is aryl or heteroaryl, wherein E is optionally substituted with one or more substituents independently selected from the group consisting of alkyl, such as $C_{1-4}$alkyl (e.g., methyl, ethyl, —$CHF_2$, or —$CF_3$); cycloalkyl; halo, such as —F, —Cl, or —Br (e.g., —F or —Cl); —OH; alkoxy, such as methoxy; —CN; —$NR^eR^f$; —$N(R^e)$C(O) alkyl; —$N(R^e)CO_2$alkyl; —$N(R^e)SO_2$alkyl; —C(O)alkyl; —$CO_2H$; —$CO_2$alkyl; —$CONR^eR^f$; —$SO_2$alkyl; and —$SO_2NR^eR^f$; wherein $R^e$ and $R^f$ are independently for each occurrence H or alkyl;
n is 1, 2, or 3;
$R^1$ is alkyl, such as $C_{1-4}$alkyl (e.g., methyl);
$R^2$ is H or alkyl, such as $C_{1-4}$alkyl (e.g., methyl); and
$R^6$ represents alkyl, cycloalkyl, halo, —OH, alkoxy, —CN, —$NR^oR^p$, —$N(R^o)$C(O) alkyl, —$N(R^p)CO_2$alkyl, —$N(R^o)SO_2$alkyl, —C(O)alkyl, —$CO_2H$, —$CO_2$alkyl, —$CONR^oR^p$, —$SO_2$alkyl, or —$SO_2NR^oR^p$; wherein $R^o$ and $R^p$ are independently for each occurrence H or alkyl.

In certain embodiments, compounds of formula (I), (Ia), (Ib), (II), (IIa), (III), (IIIa), (IV), (IVa), (V), or (Va), or pharmaceutically acceptable salts thereof, are further characterized as follows.

In certain embodiments, A is aryl or heteroaryl.
In certain embodiments, n is 1.
In certain embodiments, X' is halogen, such as F.
In certain embodiments, Z is $NR^2$.
In certain embodiments, $R^2$ is hydrogen.
In certain other embodiments, $R^2$ is methyl.
In certain embodiments, each occurrence of X is —F.
In certain embodiments, $R^1$ is $C_{1-4}$alkyl, such as methyl.
In certain embodiments, A is an optionally substituted monocyclic or bicyclic heteroaryl.
In certain such embodiments, A is selected from the list consisting of pyridinyl, pyrimidinyl, pyrazinyl, pyridazinyl, and benzoxazolyl. In certain embodiments, A is pyridinyl. In certain embodiments, A is pyrimidinyl. In certain embodiments, A is pyrazinyl. In certain embodiments, A is pyridazinyl.
In certain embodiments, A is unsubstituted. In other embodiments, A is optionally substituted with one or more alkyl, such as ethyl, —$CHF_2$, or —$CF_3$; alkoxy, such as methoxy; or halo, such as —Cl. In certain such embodiments, A is optionally substituted with one or more substituents independently selected from the list consisting of —F, —Br, —Cl, —$CHF_2$, —$CF_3$, methyl, ethyl, and methoxy. In other embodiments, A is optionally substituted with one or more substituents independently selected from the list consisting of —F, —Br, —Cl, —$CF_3$, methyl, ethyl, and methoxy.

In certain embodiments, A is monosubstituted. In certain such embodiments, A is substituted with —$CHF_2$ or —$CF_3$, such as —$CF_3$.

In certain embodiments, B is an optionally substituted aryl, such as phenyl.
In certain embodiments, B is an optionally substituted monocyclic heteroaryl or bicyclic heteroaryl. In certain such embodiments, B selected from the list consisting of pyridinyl, pyrimidinyl, pyrazinyl, pyridazinyl, oxazolyl, isoxazolyl, imidazolyl, triazolyl, thiazolyl, thiophenyl, pyrazolyl, and benzoimidazolyl, such as pyridinyl, thiophenyl, oxazolyl, thiazolyl, pyrazolyl, triazolyl or benzoimidazolyl. In certain embodiments, B is pyridinyl. In certain embodiments, B is thiophenyl. In certain embodiments, B is oxazolyl. In certain embodiments, B is thiazolyl. In certain embodiments, B is pyrazolyl. In certain embodiments, B is triazolyl.

In certain embodiments, B is benzoimidazolyl.
In certain embodiments, B is optionally substituted with one or more substituents independently selected from the group consisting of an alkyl, such as methyl, ethyl, isopropyl, —$CHF_2$, —$CF_3$, or —$CH_2CF_3$; halo, such as —F or —Cl; alkoxy, such as methoxy; and —CN. In certain embodiments, B is optionally substituted with one or more substituents independently selected from the list consisting of —F, —Cl, —Br, —CN, methyl, ethyl, isopropyl, —$CF_3$, —$CHF_2$, —$CH_2CF_3$, isopropoxy, and methoxy. In other embodiments, B is optionally substituted with one or more substituents independently selected from the list consisting of —F, —Cl, —Br, —CN, methyl, ethyl, isopropyl, —$CF_3$, —$CH_2CF_3$, isopropoxy, and methoxy. In certain such embodiments, B is optionally substituted with one or more alkyl, such as methyl.

In certain embodiments, B is monosubstituted. In certain such embodiments, B is substituted with an alkyl, such as methyl.

In certain embodiments, E is an optionally substituted phenyl.
In certain embodiments, E is an optionally substituted monocyclic heteroaryl, such as triazoyl, tetrazolyl, pyrazolyl, pyridinyl, oxadiazolyl, pyrazinyl, or pyrimidinyl. In certain embodiments, E is triazoyl. In certain embodiments, E is tetrazolyl. In certain embodiments, E is pyrazolyl. In certain embodiments, E is pyridinyl. In certain embodiments, E is oxadiazolyl. In certain embodiments, E is pyrimidinyl. In certain embodiments, E is pyrazinyl.

In certain embodiments, E is optionally substituted with one or more substituents independently selected from the group consisting of alkyl, such as methyl, ethyl, —$ClF_2$, or —$CF_3$, e.g., methyl, halo, such as —F, —Br, or —Cl, e.g., —F or —Cl; and alkoxy, such as methoxy. In other embodiments, E is optionally substituted with one or more substituents independently selected from the group consisting of alkyl, such as methyl, ethyl, or —$CF_3$, e.g., methyl, halo, such as —F, —Br, or —Cl, e.g., —F or —Cl; and alkoxy, such as methoxy. In further such embodiments, E is optionally substituted with one or more substituent independently selected from methyl or —F.

In certain embodiments, E is monosubstituted. In other embodiments, E is unsubstituted.

In certain embodiments, the fragment —B-E in the compound of formula (I), (Ia), (Ib), (II), (IIa), (III), or (IIIa) can be represented by

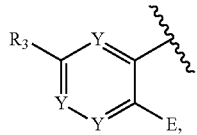

wherein:

Y, independently for each occurrence, represents CH or N; and $R^3$ represents alkyl, such as $C_{1-4}$alkyl(e.g., methyl, ethyl, isopropyl, —CH$_2$CF$_3$, or —CF$_3$); cycloalkyl; halo, such as —F, —Cl, or —Br (e.g., —F or —Cl); —OH; alkoxy, such as methoxy or isopropoxy (e.g., methoxy); —CN; —NR$^g$R$^h$; —N(R$^g$)C(O) alkyl; —N(R$^g$)CO$_2$alkyl; —N(R$^g$)SO$_2$alkyl; —C(O)alkyl; —CO$_2$H; —C$_2$alkyl; —CONR$^g$R$^h$; —SO$_2$alkyl; or —SO$_2$NR$^g$R$^h$; wherein R$^g$ and R$^h$ are each independently for each occurrence H or alkyl.

In certain such embodiments, the structure

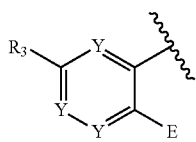

is selected from the following:

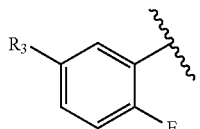 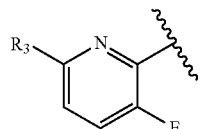

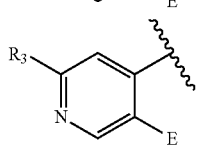 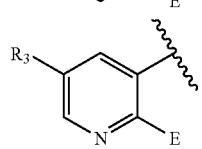

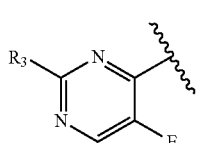 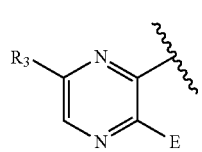

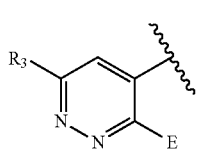

For example, in certain embodiments, the fragment —B-E is

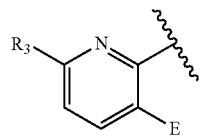

In certain such embodiments, $R^3$ is alkyl, such as —CH$_3$ or —CF$_3$; or alkoxy, such as methoxy.

In other embodiments, the fragment —B-E is

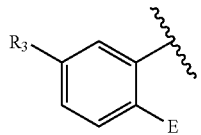

In certain such embodiments, $R^3$ is halo, such as —F or —Cl; or alkyl, such as methyl; or —CN.

In certain embodiments, the fragment —B-E in the compound of formula (I), (Ia), (Ib), (II), (IIa), (III), or (IIIa) forms a hetero-aromatic ring structure of

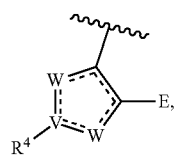

wherein: ══════, independently for each occurrence, represents a single or double bond;

W, independently for each occurrence, represents N, S, O, or CH;

V represents N or C; and $R^4$ represents alkyl, such as $C_{1-4}$alkyl(e.g., methyl, ethyl, isopropyl, —CH$_2$CF$_3$, or —CF$_3$); cycloalkyl; halo, such as —F, —Cl, or —Br (e.g., —F or —Cl); —OH; alkoxy, such as methoxy or isopropoxy (e.g., methoxy); —CN; —NR$^i$R$^j$, —N(R$^i$)C(O) alkyl, —N(R$^i$)CO$_2$alkyl, —N(R$^i$)SO$_2$alkyl, —C(O)alkyl, —CO$_2$H, —CO$_2$alkyl, —CONR$^i$R$^j$, —SO$_2$alkyl, or —SO$_2$NR$^i$R$^j$; wherein R$^i$ and R$^j$ are independently for each occurrence H or alkyl.

In certain such embodiments, the structure

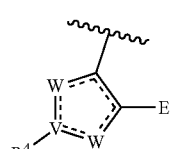

is selected from the following:

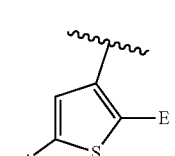 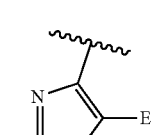 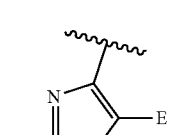

-continued

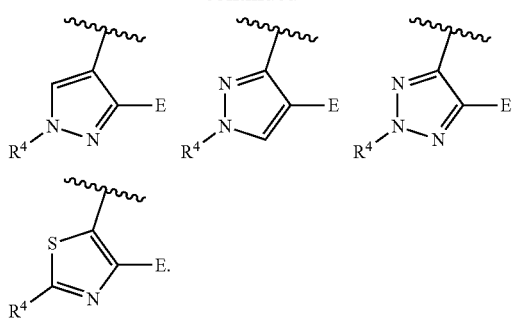

In certain embodiments, the structure

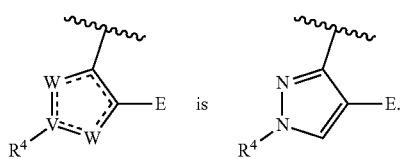 is 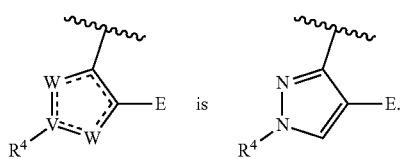

In certain such embodiments, $R^4$ is $C_{1-4}$alkyl, such as methyl. In certain other embodiments, the structure

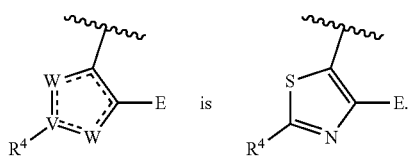 is 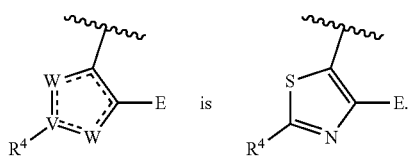

In certain such embodiments, $R^4$ is $C_{1-4}$alkyl, such as methyl.

In certain embodiments, Z is O. In other embodiments, Z is $NR^2$.

In certain embodiments, n=1.

In certain embodiments, the compound of formula (I) is selected from the compounds provided in Table 1, and pharmaceutically acceptable salts thereof.

TABLE 1

Halo-Substituted Piperidine Derivatives as Orexin Antagonists

| Compound # | Compound |
| --- | --- |
| 1 | 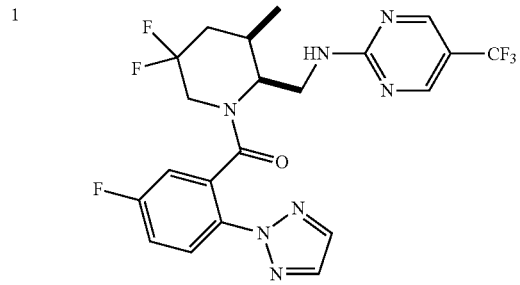 |
| 2 | 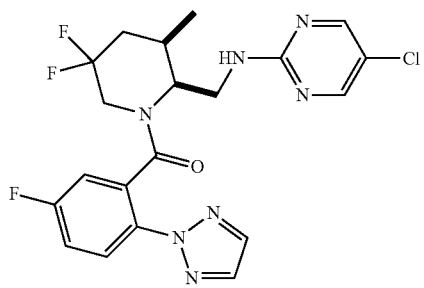 [SMILES: C[C@@H]1CC(F)(F)CN(C(=O)c2cc(F)ccc2-n2nccn2)[C@@H]1CNc1ncc(Cl)cn1] |
| 3 | 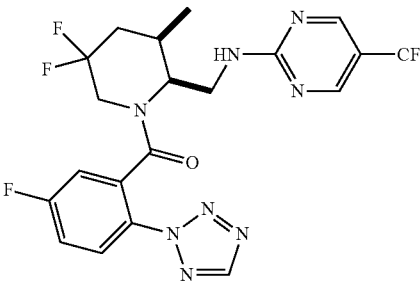 [SMILES: Cc1ccc(-n2nccn2)c(C(=O)N2CC(F)(F)C[C@@H](C)[C@H]2CNc2ncc(Cl)cn2)c1] |
| 4 | 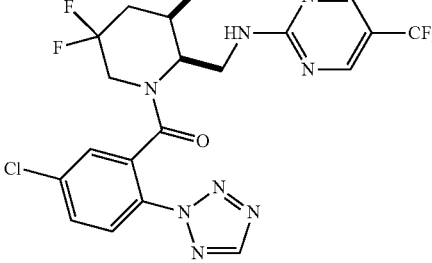 |
| 5 | 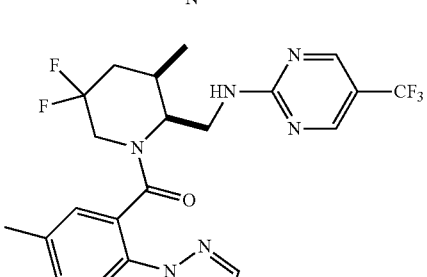 |
| 6 | 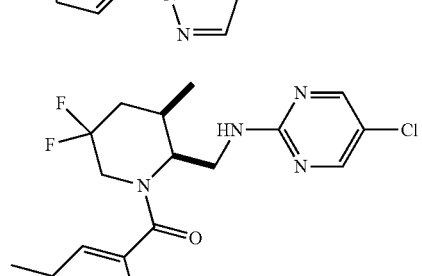 |

TABLE 1-continued

Halo-Substituted Piperidine Derivatives as Orexin Antagonists

| Compound # | Compound |
|---|---|
| 7 | (structure) |
| 8 | (structure) |
| 9 | (structure) |
| 10 | (structure) |
| 11 | (structure) |
| 12 | (structure) |
| 13 | (structure) |
| 14 | (structure) |
| 15 | (structure) |
| 16 | (structure) |

TABLE 1-continued

Halo-Substituted Piperidine Derivatives as Orexin Antagonists

| Compound # | Compound |
|---|---|
| 17 | (structure) |
| 18 | (structure) |
| 19 | (structure) |
| 20 | (structure) |
| 21 | (structure) |
| 22 | (structure) |
| 23 | (structure) |
| 24 | (structure) |
| 25 | (structure) |

TABLE 1-continued

Halo-Substituted Piperidine Derivatives as Orexin Antagonists

| Compound # | Compound |
|---|---|
| 26 | (structure) |
| 27 | (structure) |
| 28 | (structure) |
| 29 | (structure) |
| 30 | (structure) |
| 31 | (structure) |
| 32 | (structure) |
| 33 | (structure) |
| 34 | (structure) |

TABLE 1-continued

Halo-Substituted Piperidine Derivatives as Orexin Antagonists

| Compound # | Compound |
|---|---|
| 35 | (structure) |
| 36 | (structure) |
| 37 | (structure) |
| 38 | (structure) |
| 39 | (structure) |
| 40 | (structure) |
| 41 | (structure) |
| 42 | (structure) |
| 43 | (structure) |
| 44 | (structure) |

TABLE 1-continued

Halo-Substituted Piperidine Derivatives as Orexin Antagonists

| Compound # | Compound |
|---|---|
| 45 | (structure) |
| 46 | (structure) |
| 47 | (structure) |
| 48 | (structure) |
| 49 | (structure) |
| 50 | (structure) |
| 51 | (structure) |
| 52 | (structure) |
| 53 | (structure) |
| 54 | (structure) |

TABLE 1-continued

Halo-Substituted Piperidine Derivatives as Orexin Antagonists

| Compound # | Compound |
|---|---|
| 55 | (structure) |
| 56 | (structure) |
| 57 | (structure) |
| 58 | (structure) |
| 59 | (structure) |
| 60 | (structure) |
| 61 | (structure) |
| 62 | (structure) |
| 63 | (structure) |

TABLE 1-continued

Halo-Substituted Piperidine Derivatives as Orexin Antagonists

| Compound # | Compound |
|---|---|
| 64 | (structure) |
| 65 | (structure) |
| 66 | (structure) |
| 67 | (structure) |
| 68 | (structure) |
| 69 | (structure) |
| 70 | (structure) |
| 71 | (structure) |
| 72 | (structure) |
| 73 | (structure) |

TABLE 1-continued

Halo-Substituted Piperidine Derivatives as Orexin Antagonists

| Compound # | Compound |
|---|---|
| 74 | (structure) |
| 75 | (structure) |
| 76 | (structure) |
| 77 | (structure) |
| 78 | (structure) |
| 79 | (structure) |
| 80 | (structure) |
| 81 | (structure) |
| 82 | (structure) |
| 83 | (structure) |

TABLE 1-continued

Halo-Substituted Piperidine Derivatives as Orexin Antagonists

| Compound # | Compound |
|---|---|
| 84 | |
| 85 | |
| 86 | |
| 87 | |
| 88 | |
| 89 | |
| 90 | |
| 91 | |
| 92 | |
| 93 | |

TABLE 1-continued
Halo-Substituted Piperidine Derivatives as Orexin Antagonists
| Compound # | Compound |
|---|---|
| 94 | 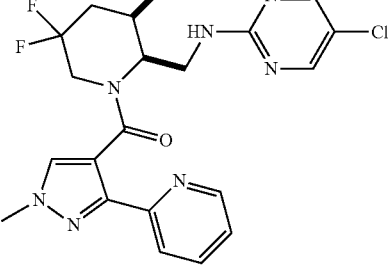 |
| 95 | 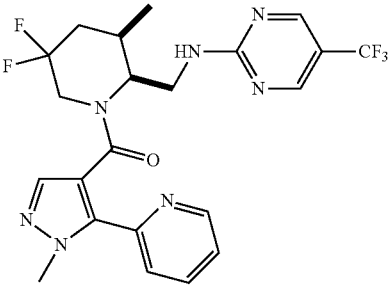 |
| 96 | 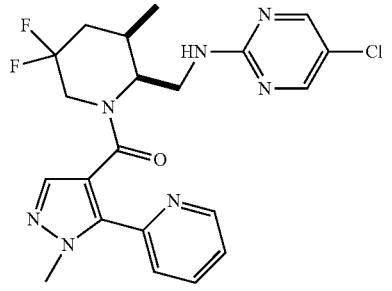 |
| 97 | 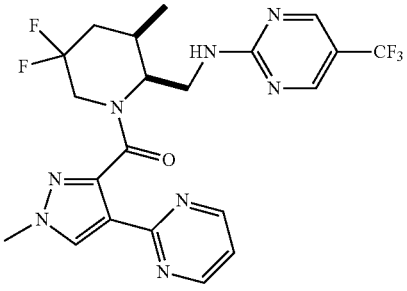 |
| 98 | 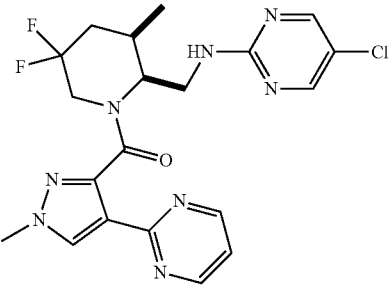 [SMILES: C[C@@H]1CC(F)(F)CN(C(=O)c2nn(C)cc2-c2ccccn2)[C@@H]1CNc1ncc(Cl)cn1] |
| 99 | 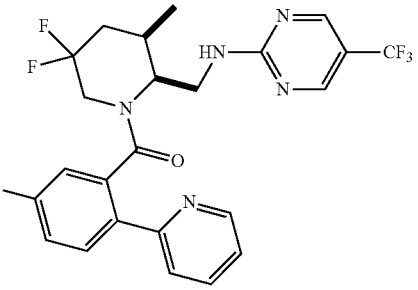 |
| 102 | 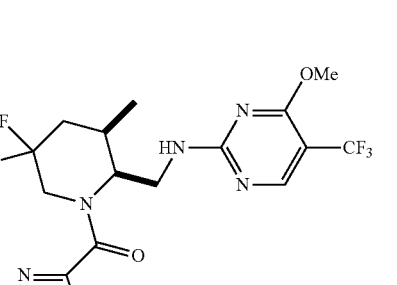 |
| 103 | 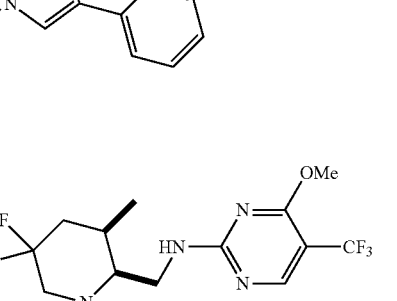 |
| 104 | 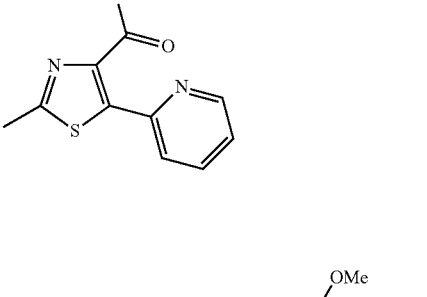 |

TABLE 1-continued

Halo-Substituted Piperidine Derivatives as Orexin Antagonists

| Compound # | Compound |
|---|---|
| 105 | |
| 106 | |
| 107 | |
| 108 | |
| 109 | |
| 110 | |
| 111 | |
| 112 | |

TABLE 1-continued

Halo-Substituted Piperidine Derivatives as Orexin Antagonists

| Compound # | Compound |
|---|---|
| 113 | (structure) |
| 114 | (structure) |
| 115 | (structure) |
| 116 | (structure) |
| 117 | (structure) |
| 118 | (structure) |
| 119 | (structure) |
| 120 | (structure) |

TABLE 1-continued

Halo-Substituted Piperidine Derivatives as Orexin Antagonists

| Compound # | Compound |
|---|---|
| 121 | [structure: 5,5-difluoro-3-methylpiperidine with CH2-NH-pyrazine-CF3 and N-acyl-(1-methyl-4-(4-fluorophenyl)pyrazole-3-carbonyl)] |
| 122 | [structure: 5,5-difluoro-3-methylpiperidine with CH2-NH-pyrazine-CF3 and N-acyl-(1-methyl-4-(4-methylphenyl)pyrazole-3-carbonyl)] |
| 123 | [structure: 5,5-difluoro-3-methylpiperidine with CH2-NH-pyrazine-CF3 and N-acyl-(1-methyl-4-(3-methylphenyl)pyrazole-3-carbonyl)] |
| 124 | [structure: 5,5-difluoro-3-methylpiperidine with CH2-NH-pyrazine-CF3 and N-acyl-(1-methyl-4-(3-methoxyphenyl)pyrazole-3-carbonyl)] |
| 125 | [structure: 5,5-difluoro-3-methylpiperidine with CH2-NH-pyrazine-CF3 and N-acyl-(1-methyl-4-(4-methoxyphenyl)pyrazole-3-carbonyl)] |
| 126 | [structure: 5,5-difluoro-3-methylpiperidine with CH2-NH-pyrazine-CF3 and N-acyl-(1-methyl-4-(2-fluorophenyl)pyrazole-3-carbonyl)] |
| 127 | [structure: 5,5-difluoro-3-methylpiperidine with CH2-NH-pyrazine-CF3 and N-acyl-(1-methyl-4-(3-fluorophenyl)pyrazole-3-carbonyl)] |
| 128 | [structure: 5,5-difluoro-3-methylpiperidine with CH2-NH-pyrazine-CF3 and N-acyl-(1-methyl-4-(3-chlorophenyl)pyrazole-3-carbonyl)] |
| 129 | [structure: 5,5-difluoro-3-methylpiperidine with CH2-NH-pyrazine-CF3 and N-acyl-(1-methyl-4-(4-chlorophenyl)pyrazole-3-carbonyl)] |
| 130 | [structure: 5,5-difluoro-3-methylpiperidine with CH2-NH-pyrazine-CF3 and N-acyl-(1-methyl-4-(2-pyridyl)pyrazole-3-carbonyl)] |

TABLE 1-continued

Halo-Substituted Piperidine Derivatives as Orexin Antagonists

| Compound # | Compound |
|---|---|
| 131 | (structure) |
| 132 | (structure) |
| 133 | (structure) |
| 134 | (structure) |
| 135 | (structure) |
| 136 | (structure) |
| 137 | (structure) |
| 138 | (structure) |
| 139 | (structure) |
| 140 | (structure) |

TABLE 1-continued

Halo-Substituted Piperidine Derivatives as Orexin Antagonists

| Compound # | Compound |
|---|---|
| 141 | (structure) |
| 142 | (structure) |
| 143 | (structure) |
| 144 | (structure) |
| 145 | (structure) |
| 146 | (structure) |
| 147 | (structure) |
| 148 | (structure) |
| 149 | (structure) |

TABLE 1-continued

Halo-Substituted Piperidine Derivatives as Orexin Antagonists

| Compound # | Compound |
|---|---|
| 150 | |
| 151 | |
| 152 | |
| 153 | |
| 154 | |
| 155 | |
| 156 | |
| 157 | |
| 158 | |
| 159 | |

TABLE 1-continued
Halo-Substituted Piperidine Derivatives as Orexin Antagonists
| Compound # | Compound |
|---|---|
| 160 | 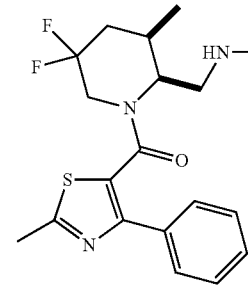 |
| 161 | 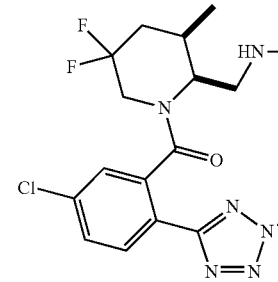 |
| 162 | 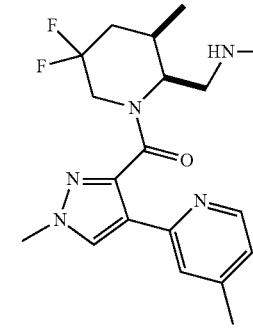 |
| 163 | 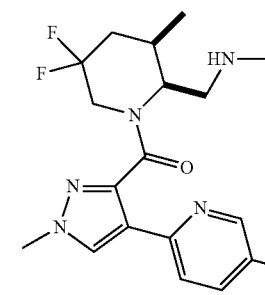 |
| 164 | 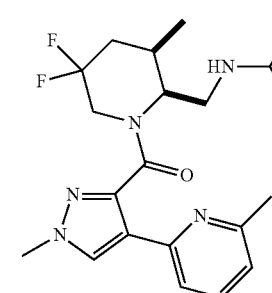 |
| 165 | 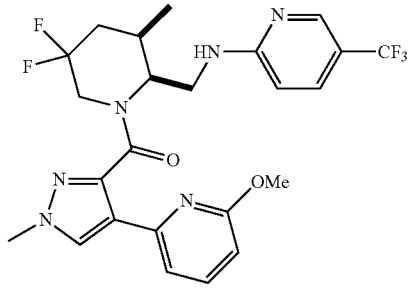 [SMILES: COc1cccc(-c2cn(C)nc2C(=O)N2CC(F)(F)C[C@@H](C)[C@H]2CNc2ncc(C(F)(F)F)cn2)n1] |
| 166 | 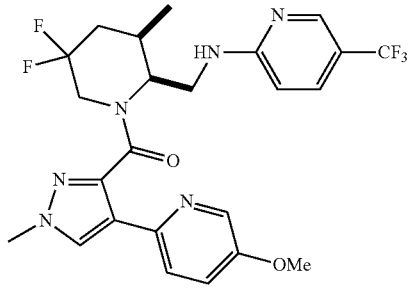 [SMILES: COc1ccc(-c2cn(C)nc2C(=O)N2CC(F)(F)C[C@@H](C)[C@H]2CNc2ccc(C(F)(F)F)cn2)cc1] |
| 167 | 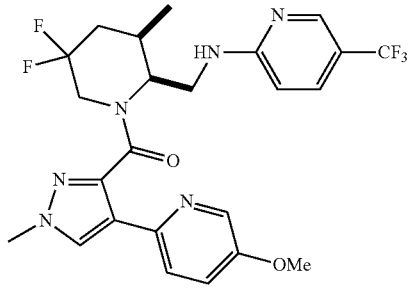 [SMILES: COc1ccc(-c2cn(C)nc2C(=O)N2CC(F)(F)C[C@@H](C)[C@H]2CNc2ccc(C(F)(F)F)cn2)cc1] |
| 168 | 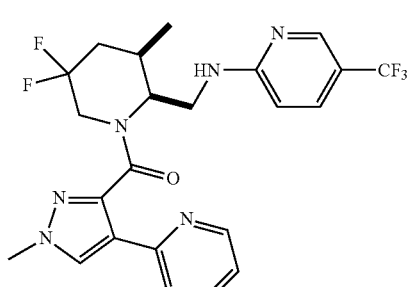 |
| 169 | 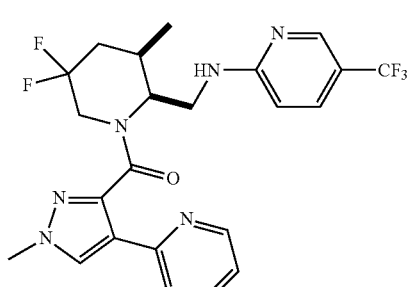 |

TABLE 1-continued

Halo-Substituted Piperidine Derivatives as Orexin Antagonists

| Compound # | Compound |
|---|---|
| 170 | (structure) |
| 171 | (structure) |
| 172 | (structure) |
| 173 | (structure) |
| 174 | (structure) |
| 175 | (structure) |
| 176 | (structure) |
| 177 | (structure) |
| 178 | (structure) |
| 179 | (structure) |

TABLE 1-continued

Halo-Substituted Piperidine Derivatives as Orexin Antagonists

| Compound # | Compound |
|---|---|
| 180 | |
| 181 | |
| 182 | |
| 183 | |
| 184 | |
| 185 | |
| 186 | |
| 187 | |
| 188 | |
| 189 | |

TABLE 1-continued

Halo-Substituted Piperidine Derivatives as Orexin Antagonists

| Compound # | Compound |
|---|---|
| 190 | |
| 191 | |
| 192 | |
| 193 | |
| 194 | |
| 195 | |
| 196 | |
| 197 | |
| 198 | |
| 199 | |

TABLE 1-continued
Halo-Substituted Piperidine Derivatives as Orexin Antagonists
| Compound # | Compound |
|---|---|
| 200 | 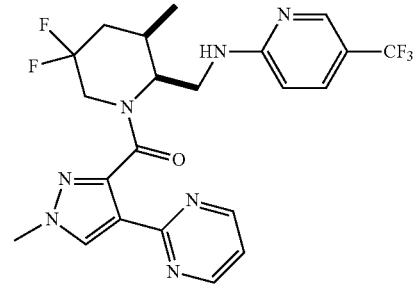 [SMILES: C[C@@H]1CC(F)(F)CN(C(=O)c2nn(C)cc2-c2ncccn2)[C@@H]1CNc1ccc(C(F)(F)F)cn1] |
| 201 | |
| 202 | |
| 203 | |
| 204 | |
| 205 | 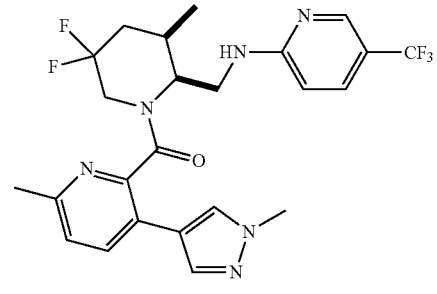 [SMILES: Cc1ccc(-c2cnn(C)c2)c(C(=O)N2CC(F)(F)C[C@@H](C)[C@H]2CNc2ccc(C(F)(F)F)cn2)n1] |
| 206 | |
| 207 | |
| 208 | |
| 209 | |

TABLE 1-continued
Halo-Substituted Piperidine Derivatives as Orexin Antagonists
| Compound # | Compound |
|---|---|
| 210 | 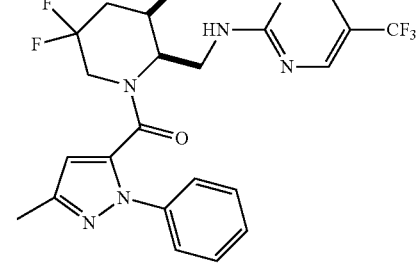 |
| 211 | |
| 212 | |
| 213 | |
| 214 | |
| 215 | 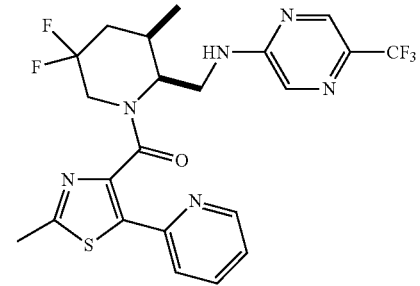 |
| 216 | |
| 217 | |
| 218 | |

TABLE 1-continued

Halo-Substituted Piperidine Derivatives as Orexin Antagonists

| Compound # | Compound |
|---|---|
| 219 | |
| 220 | |
| 221 | |
| 222 | |
| 223 | |
| 224 | |
| 225 | |
| 226 | |

TABLE 1-continued

Halo-Substituted Piperidine Derivatives as Orexin Antagonists

| Compound # | Compound |
|---|---|
| 227 | |
| 228 | |
| 229 | |
| 230 | |
| 231 | |
| 232 | |
| 233 | |
| 234 | |
| 235 | |

TABLE 1-continued

Halo-Substituted Piperidine Derivatives as Orexin Antagonists

| Compound # | Compound |
|---|---|
| 236 | |
| 237 | |
| 238 | |
| 239 | |
| 240 | |
| 241 | |
| 242 | |
| 243 | |
| 244 | |

TABLE 1-continued

Halo-Substituted Piperidine Derivatives as Orexin Antagonists

| Compound # | Compound |
|---|---|
| 245 | |
| 246 | |
| 247 | |
| 248 | |
| 249 | |
| 250 | |
| 251 | |
| 252 | |

TABLE 1-continued

Halo-Substituted Piperidine Derivatives as Orexin Antagonists

| Compound # | Compound |
|---|---|
| 253 | |
| 254 | |
| 255 | |
| 256 | |
| 257 | |
| 258 | |
| 259 | |
| 260 | |
| 261 | |
| 262 | |

TABLE 1-continued

Halo-Substituted Piperidine Derivatives as Orexin Antagonists

| Compound # | Compound |
|---|---|
| 263 | 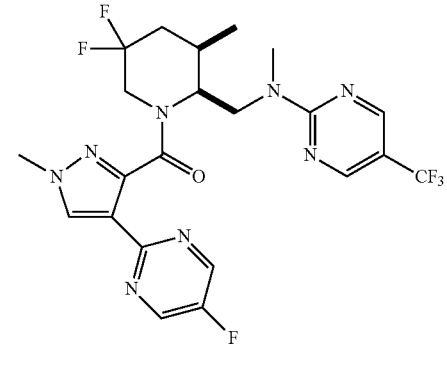 [SMILES: C[C@@H]1CC(F)(F)CN(C(=O)c2nn(C)cc2-c2ncc(F)cn2)[C@@H]1CN(C)c1ncc(C(F)(F)F)cn1] |
| 264 | |
| 265 | |
| 266 | |
| 267 | 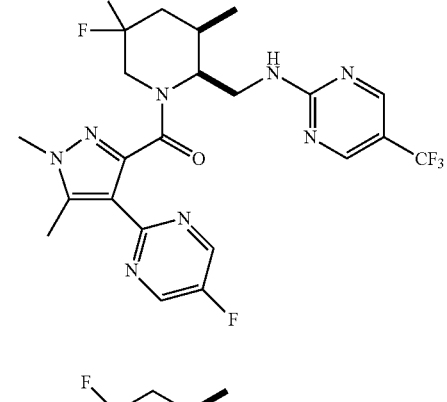 |
| 268 | |
| 269 | |

In certain embodiments, this application relates to a pharmaceutical composition comprising (a) a compound of formula (I), (Ia), (Ib), (II), (IIa), (III), (IIIa), (IV), (IVa), (V), or (Va), or a pharmaceutically acceptable salt thereof, and (b) a pharmaceutically acceptable excipient.

In certain embodiments, this application relates to a compound of formula (I), (Ia), (Ib), (II), (IIa), (III), (IIa), (IV), (IVa), (V), or (Va), or a pharmaceutically acceptable salt thereof, or a pharmaceutical composition comprising any one of the foregoing, for use as a medicament.

In certain embodiments, this application relates to a method of treating a disease, disorder, or medical condition mediated by orexin receptor activity in a subject in need of such treatment, comprising administering to the subject an effective amount of at least one compound according to formula (I), (Ia), (Ib), (II), (Ia), (III), (IIIa), (IV), (IVa), (V), or (Va), or a pharmaceutically acceptable salt thereof, or a pharmaceutical composition comprising any one of the foregoing.

In certain embodiments, this application relates to a method of treating a disease, disorder, or medical condition in a subject in need of such treatment, comprising administering to the subject an effective amount of at least one compound according to formula (I), (Ia), (Ib), (II), (IIa), (III), (IIIa), (IV), (IVa), (V), or (Va), or a pharmaceutically acceptable salt thereof, or a pharmaceutical composition comprising any one of the foregoing. In certain such embodiments, the disease, disorder or medical condition mediated by orexin receptor activity is eating disorder, obesity, alcoholism or an alcohol-related disorder, drug abuse or addiction, a sleep disorder, a cognitive dysfunction in a psychiatric or neurologic disorder, depression, anxiety, panic disorder, post-traumatic stress disorder, seasonal affective disorder, schizophrenia, Alzheimer's disease, Parkinson's disease, Huntington's chorea, headache, migraine, pain, gastrointestinal diseases, epilepsy, inflammations, immune-related diseases, ulcers, irritable bowel syndrome, diarrhea, gastroesophageal reflux, endocrine-related diseases, cancer, hypertension, behavior disorder, mood disorder, manic depression, dementia, sex disorder, psychosexual disorder, and renal disease. In certain such embodiments, the drug abuse or addiction is selected from abuse of or addiction to cocaine, opiates, amphetamines, ethanol, cannabis/marijuana, or nicotine.

In certain embodiments, this application relates to the use of a compound of formula (I), (Ia), (Ib), (II), (IIa), (III), (IIIa), (IV), (IVa), (V), or (Va), or a pharmaceutically acceptable salt thereof, or a pharmaceutical composition of any one of the foregoing, in the preparation of a medicament for the treatment of diseases, disorders, and medical conditions regulated by orexin receptor activity, and the use of such compounds for treatment of such diseases and medical conditions.

In certain embodiments, this application relates to the use of a compound of formula (I), (Ia), (Ib), (II), (IIa), (III), (IIIa), (IV), (IVa), (V), or (Va), or a pharmaceutically acceptable salt thereof, or a pharmaceutical composition of any one of the foregoing, in the preparation of a medicament for the treatment of diseases, disorders, and medical conditions, and the use of such compounds for treatment of such diseases, disorder, and medical conditions. In certain such embodiments, the disease, disorder, or medical condition is an eating disorder, obesity, alcoholism or an alcohol-related disorder, drug abuse or addiction, a sleep disorder, a cognitive dysfunction in a psychiatric or neurologic disorder, depression, anxiety, panic disorder, post-traumatic stress disorder, seasonal affective disorder, schizophrenia, Alzheimer's disease, Parkinson's disease, Huntington's chorea, headache, migraine, pain, gastrointestinal diseases, epilepsy, inflammations, immune-related diseases, ulcers, irritable bowel syndrome, diarrhea, gastroesophageal reflux, endocrine-related diseases, cancer, hypertension, behavior disorder, mood disorder, manic depression, dementia, sex disorder, psychosexual disorder, and renal disease. In certain such embodiments, the drug abuse or addiction is selected from abuse of or addiction to cocaine, opiates, amphetamines, ethanol, cannabis/marijuana, or nicotine. In certain such embodiments, the disease, disorder, or medical condition is selected from the group consisting of drug abuse or addiction, a sleep disorder, a cognitive dysfunction in a psychiatric or neurologic disorder, depression, anxiety, panic disorder, post-traumatic stress disorder, seasonal affective disorder, schizophrenia, Alzheimer's disease, Parkinson's disease, Huntington's chorea, pain, behavior disorder, mood disorder, manic depression, dementia, sex disorder, and psychosexual disorder. In certain embodiments, the disease, disorder, or medical condition is selected from the group consisting of an eating disorder, obesity, alcoholism or an alcohol-related disorder, headache, migraine, gastrointestinal diseases, inflammations, immune-related diseases, ulcers, irritable bowel syndrome, diarrhea, gastroesophageal reflux, endocrine-related diseases, cancer, hypertension, and renal disease.

As discussed above, there is a need in the field for compounds with more favorable metabolic stability and half lives. Certain embodiments of this application provide compounds found to have such advantages.

In certain embodiments, this application relates to a method of modulating the activity of an orexin receptor $OX_1$, $OX_2$, or both, comprising contacting a cell comprising the orexin receptor with an effective amount of at least one compound of formula (I), (Ia), (Ib), (II), (IIa), (III), (IIIa), (IV), (IVa), (V), or (Va), or a pharmaceutically acceptable salt thereof, or a pharmaceutical composition of any one of the foregoing. In certain such embodiments, the contacting is in vitro, ex vivo, or in vivo.

In certain embodiments, this application relates to a method of treating a disease or disorder in a subject, (e.g., a patient) in need thereof, comprising administering a compound of formula (I), (Ia), (Ib), (II), (IIa), (III), (IIIa), (IV), (IVa), (V), or (Va), or a pharmaceutically acceptable salt thereof, or a pharmaceutical composition of any one of the foregoing, wherein the disease or disorder is selected from the group consisting of an eating disorder, obesity, alcoholism or an alcohol-related disorder, drug abuse or addiction, a sleep disorder, a cognitive dysfunction in a psychiatric or neurologic disorder, depression, anxiety, panic disorder, post-traumatic stress disorder, seasonal affective disorder, schizophrenia, Alzheimer's disease, Parkinson's disease, Huntington's chorea, headache, migraine, pain, gastrointestinal diseases, epilepsy, inflammations, immune-related diseases, ulcers, irritable bowel syndrome, diarrhea, gastroesophageal reflux, endocrine-related diseases, cancer, hypertension, behavior disorder, mood disorder, manic depression, dementia, sex disorder, psychosexual disorder, and renal disease. In certain such embodiments, the disease, disorder, or medical condition is selected from the group consisting of drug abuse or addiction, a sleep disorder, a cognitive dysfunction in a psychiatric or neurologic disorder, depression, anxiety, panic disorder, post-traumatic stress disorder, seasonal affective disorder, schizophrenia, Alzheimer's disease, Parkinson's disease, Huntington's chorea, pain, behavior disorder, mood disorder, manic depression, dementia, sex disorder, and psychosexual disorder. In certain such embodiments, the disease, disorder, or medical condition is selected from the group consisting of an eating disorder, obesity, alcoholism or an alcohol-related disorder, headache, migraine, gastrointestinal diseases, inflammations, immune-related diseases, ulcers, irritable bowel syndrome, diarrhea, gastroesophageal reflux, endocrine-related diseases, cancer, hypertension, and renal disease.

In certain such embodiments, disease or disorder is selected from the group consisting of drug abuse or addiction, panic disorder, anxiety, post-traumatic stress disorder, pain, depression, seasonal affective disorder, an eating disorder, and hypertension. In certain such embodiments, the drug abuse or addiction is selected from abuse of or addiction to cocaine, opiates, amphetamines, ethanol, cannabis/marijuana, or nicotine.

Those skilled in the art will recognize that the species listed or illustrated herein are not exhaustive, and that additional species within the scope of these defined terms may also be selected.

The application also includes pharmaceutically acceptable prodrugs, salts, solvates, such as hydrates, of the compounds represented by Formula (I), (Ia), (Ib), (II), (IIa), (III), (IIIa), (IV), (IVa), (V), or (Va), preferably of those described above and of the specific compounds exemplified herein, and pharmaceutical compositions comprising such prodrugs, salts, or solvates, such as hydrates, and methods of using such salts or hydrates.

The present application also relates to pharmaceutically active metabolites of compounds described herein, and uses of such metabolites in the methods of the application.

Definitions

The definitions set forth in this application are intended to clarify terms used throughout this application.

Unless defined otherwise, all technical and scientific terms used herein have the same meaning as is commonly understood by one of ordinary skill in the art to which this invention belongs. All patents, applications, published applications and other publications referred to herein are incorporated by reference in their entireties to disclose and describe the methods and/or materials in connection with which the publications are cited. If a definition set forth in this section is contrary to or otherwise inconsistent with a definition set forth in a patent, application, or other publication that is herein incorporated by reference, the definition set forth in this section prevails over the definition incorporated herein by reference. Although any methods and materials similar or equivalent to those described herein can also be used in the practice or testing of the embodiments in present application, the preferred methods and materials are now described.

To provide a more concise description, some of the quantitative expressions given herein are not qualified with the term "about." It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

Except as otherwise noted, the methods and techniques of the present embodiments are generally performed according to conventional methods well known in the art and as described in various general and more specific references that are cited and discussed throughout the present specification. See, e.g., Loudon, Organic Chemistry, Fourth Edition, New York: Oxford University Press, 2002, pp. 360-361, 1084-1085; Smith and March, March's Advanced Organic Chemistry: Reactions, Mechanisms, and Structure, Fifth Edition, Wiley-Interscience, 2001.

The nomenclature used herein to name the subject compounds is illustrated in the Examples herein. This nomenclature has generally been derived using the commercially-available ChemBioDraw Ultra software (Cambridgesoft/Perkin Elmer), Version 12.0.

It is to be understood that the present description is not limited to particular embodiments described, as such may, of course, vary. It is also to be understood that the terminology used herein is for the purpose of describing particular embodiments only, and is not intended to be limiting, since the scope of the present application will be limited only by the appended claims.

It is appreciated that certain features of the application, which are, for clarity, described in the context of separate embodiments, may also be provided in combination in a single embodiment. Conversely, various features of the application, which are, for brevity, described in the context of a single embodiment, may also be provided separately or in any suitable subcombination. All combinations of the embodiments pertaining to the chemical groups represented by the variables are specifically embraced by the present application and are disclosed herein just as if each and every combination was individually and explicitly disclosed, to the extent that such combinations embrace compounds that are stable compounds (i.e., compounds that can be isolated, characterized, and tested for biological activity). In addition, all subcombinations of the chemical groups listed in the embodiments describing such variables are also specifically embraced by the present application and are disclosed herein just as if each and every such sub-combination of chemical groups was individually and explicitly disclosed herein.

Any formula depicted herein is intended to represent a compound of that structural formula as well as certain variations or forms. For example, a formula given herein is intended to include a racemic form, or one or more enantiomeric, diastereomeric, or geometric isomers, or tautomeric forms, or a mixture thereof. Additionally, any formula given herein is intended to refer also to a solvate, such as a hydrate, solvate, or polymorph of such a compound, or a mixture thereof. Any formula given herein is intended to refer to amorphous and/or crystalline physical forms of the compound. The compounds described herein may be analytically pure, or a mixture in which the compound comprises at least 50%, at least 70%, at least 80%, at least 90%, at least 95%, or at least 98% by weight of the mixture.

In addition, where features or aspects of the embodiments of this application are described in terms of Markush groups, those skilled in the art will recognize that embodiments described herein is also thereby described in terms of any individual member or subgroup of members of the Markush group. For example, if X is described as selected from the group consisting of bromine, chlorine, and iodine, claims for X being bromine and claims for X being bromine and chlorine are fully described.

The term "herein" refers to the entire application.

As used herein, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As used herein, the terms "including," "containing," and "comprising" are used in their open, non-limiting sense.

As used herein, "subject" (as in the subject of the treatment) refers to both mammals and non-mammals. Mammals include, for example, humans; non-human primates, e.g. apes and monkeys; and non-primates, e.g. mice, rats, rabbits, dogs, cats, cattle, horses, sheep, and goats. Non-mammals include, for example, worms, fish and birds. In some embodiments, the subject is a human.

"Substantially" as the term is used herein refers to being completely or almost completely; for example, a composition that is "substantially free" of a component either has none of the component or contains such a trace amount that any relevant functional property of the composition is unaffected by the presence of the trace amount, or a compound is "substantially pure" is there are only negligible traces of impurities present.

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group, preferably a lower alkyl group, having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

The term "alkynyl", as used herein, refers to an aliphatic group containing at least one triple bond and is intended to include both "unsubstituted alkynyls" and "substituted alkynyls", the latter of which refers to alkynyl moieties having substituents replacing one or more hydrogens on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

An "alkyl" group or "alkane" is a straight chained or branched non-aromatic hydrocarbon which is completely saturated. Typically, a straight chained or branched alkyl group has from 1 to about 20 carbon atoms, such as from 1 to 12 carbon atoms, preferably from 1 to about 10, more preferably from 1 to 4, unless otherwise defined. Examples of straight chained and branched alkyl groups include methyl, ethyl, n-propyl, isopropyl, n-butyl, isobutyl, sec-butyl, tert-butyl, pentyl, isopentyl, tert-pentyl, hexyl, isohexyl, pentyl and octyl. A $C_1$-$C_6$ straight chained or branched alkyl group is also referred to as a "lower alkyl" group.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen or more hydrogens on one or more carbons of the hydrocarbon backbone. Such substituents, if not otherwise specified, can include, for example, a halogen (such as F, Cl, Br, or I), a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), haloalkyls (such as —$CF_3$, —$CHF_2$, —$CH_2F$), —CN, and the like. Exemplary substituted alkyls are described below. Cycloalkyls can be further substituted with alkyls, alkenyls, alkoxys, alkylthios, aminoalkyls, carbonyl-substituted alkyls, haloalkyls (such as —$CF_3$, —$CHF_2$, —$CH_2F$), —CN, and the like.

The term "$(ATOM)_{i-j}$" with j>i, when used in conjunction with a chemical moiety, such as, acyl, acyloxy, alkyl, alkenyl, alkynyl, or alkoxy is meant to include groups that contain from i to j (including i and j) atoms. For example, the term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as —$CF_3$, —$CHF_2$, —$CH_2F$, or 2,2,2-trifluoroethyl, etc. $C_0$ alkyl refers to a hydrogen atom where the group is in a terminal position, a bond if internal. Similarly, for example, $C_{3-6}$cycloalkyl refers to a cycloalkyl as defined herein that has 3 to 6 carbon ring atoms. The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond respectively.

The term "alkylamino", as used herein, refers to an amino group substituted with at least one alkyl group.

The term "alkylthio", as used herein, refers to a thiol group substituted with an alkyl group and may be represented by the general formula alkylS—.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocyclyl, alkyl, alkenyl, alkynyl, and combinations thereof.

The terms "amine" and "amino" are art-recognized and refer to both unsubstituted and substituted amines and salts thereof, e.g., a moiety that can be represented by

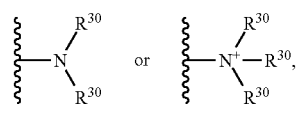

wherein each R³⁰ independently represents a hydrogen or a hydrocarbyl group, or two R³⁰ are taken together with the N atom to which they are attached complete a heterocycle having from 4 to 8 atoms in the ring structure.

The term "aminoalkyl", as used herein, refers to an alkyl group substituted with an amino group.

The term "amide", as used herein, refers to a group:

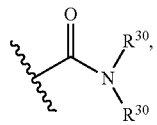

wherein each R³⁰ independently represent a hydrogen or hydrocarbyl group, or two R³⁰ are taken together with the N atom to which they are attached complete a heterocycle having from 4 to 8 atoms in the ring structure.

The term "carbamate" is art-recognized and refers to a group

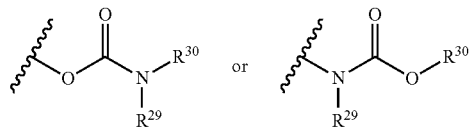

wherein R²⁹ and R³⁰ independently represent hydrogen or a hydrocarbyl group, such as an alkyl group, or R²⁹ and R³⁰ taken together with the intervening atom(s) complete a heterocycle having from 4 to 8 atoms in the ring structure.

The term "halogen," or "halide" represents chlorine, fluorine, bromine, or iodine. The term "halo" represents fluoro, chloro, bromo, or iodo.

The term "haloalkyl", as used herein, refers to an alkyl group with one or more halo substituents, or one, two, or three halo substituents. Examples of haloalkyl groups include —CF₃, —CH₂F, —CHF₂, —CH₂Br, —CH₂CF₃, and —CH₂CH₂F.

The term "heteroatom", as used herein, refers to an atom of any element other than carbon or hydrogen. Exemplary heteroatoms include but are not limited to nitrogen, oxygen, and sulfur.

The term "heteroalkyl", as used herein, refers to a saturated or unsaturated chain of carbon atoms and at least one heteroatom, wherein no two heteroatoms are adjacent.

The term "aryl", as used herein, includes substituted or unsubstituted monocyclic aromatic rings in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "aralkyl", as used herein, refers to an alkyl group substituted with an aryl group.

An "aroyl" group, as the term is used herein, refers to an aryl group bonded via an exocyclic carbonyl group, such as a benzoyl group.

The term "heteroaryl", as used herein, includes substituted or unsubstituted monocyclic aromatic ring system, preferably 5- to 7-membered aromatic rings, more preferably 5- to 6-membered rings, whose ring structures include at least one heteroatom, preferably one to four heteroatoms, more preferably one to two heteroatoms. For example, a 5-membered heteroaryl is furan, thiophene, pyrrole, oxazole, isoxazole, thiazole, isothiazole, pyrazole, imidazole, oxadiazole, thiadiazole, triazole, or tetrazole. In another example, a 6-membered heteroaryl is pyridine, pyrazine, pyrimidine, pyridazine, or triazine. The term "heteroaryl" also include substituted or unsubstituted "polycyclic" ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls.

Illustrative examples of heteroaryl groups include but are not limited to the following entities, in the form of properly bonded moieties:

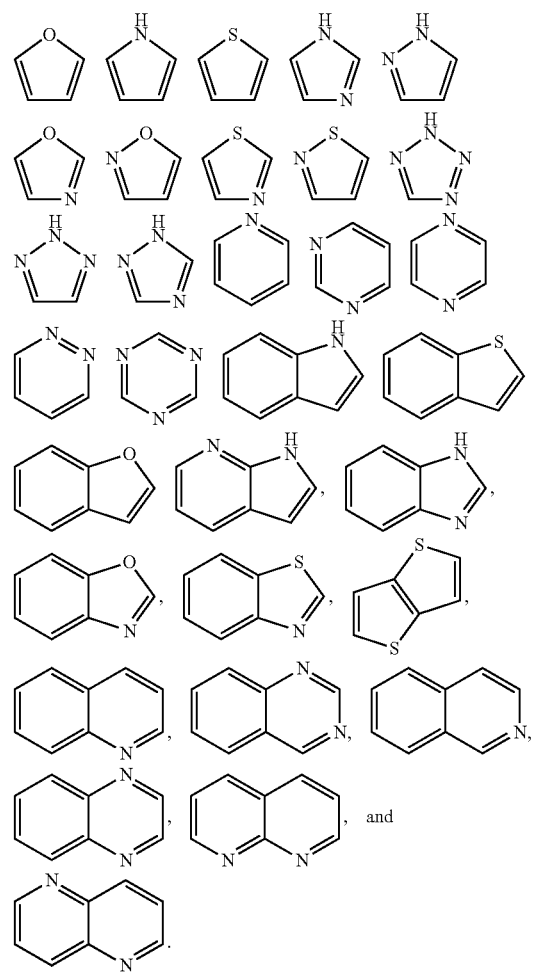

The term "heteroaralkyl" or "hetaralkyl", as used herein, refers to an alkyl group substituted with a heteroaryl group.

A "heteroaroyl" group, as the term is used herein, refers to a heteroaryl group bonded via an exocyclic carbonyl group, analogous to a benzoyl group but wherein the phenyl ring of the benzoyl group is replaced by a heteroaryl group.

The terms "heterocyclyl", "heterocycle", and "heterocyclic", as used herein, refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include substituted or unsubstituted polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "heterocyclylalkyl", as used herein, refers to an alkyl group substituted with a heterocycle group which is optionally substituted.

The terms "carbocycle", and "carbocyclic", as used herein, refers to a saturated or unsaturated ring in which each atom of the ring is carbon. The term carbocycle includes both aromatic carbocycles and non-aromatic carbocycles. Non-aromatic carbocycles include both cycloalkane rings, in which all carbon atoms are saturated, and cycloalkene rings, which contain at least one double bond. "Carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0] octane, 4,5,6,7-tetrahydro-1H-indene and bicyclo[4.1.0] hept-3-ene. "Carbocycles" may be substituted at any one or more positions capable of bearing a hydrogen atom.

A "cycloalkyl" group, as used herein, refers to a cyclic hydrocarbon which is completely saturated. "Cycloalkyl" includes monocyclic and bicyclic rings. Typically, a monocyclic cycloalkyl group has from 3 to about 10 carbon atoms, more typically 3 to 8 carbon atoms unless otherwise defined. The second ring of a bicyclic cycloalkyl may be selected from saturated, unsaturated and aromatic rings. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring.

The second ring of a fused bicyclic cycloalkyl may be selected from saturated, unsaturated and aromatic rings.

The term "carbocyclylalkyl", as used herein, refers to an alkyl group substituted with a carbocycle group.

A "cycloalkenyl" group, as used herein, refers to a cyclic hydrocarbon containing one or more double bonds. A "cycloalkynyl" group is a cyclic hydrocarbon containing one or more triple bonds.

The terms "polycyclyl", "polycycle", and "polycyclic", as used herein, refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "carbonate" is art-recognized and refers to a group —OCO$_2$—R$^{30}$, wherein R$^{30}$ represents a hydrocarbyl group.

The term "carboxy", as used herein, refers to a group represented by the formula —CO$_2$H.

The term "ester", as used herein, refers to a group —C(O)OR$^{30}$ wherein R$^{30}$ represents a hydrocarbyl group.

The term "ether," as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The term "sulfate" is art-recognized and refers to the group —OSO$_3$H, or a pharmaceutically acceptable salt thereof.

The term "sulfonamide" is art-recognized and refers to the group represented by the general formulae

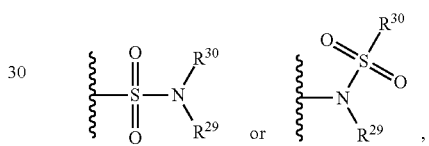

wherein R$^{29}$ and R$^{30}$ independently represents hydrogen or hydrocarbyl, such as alkyl, or R$^{29}$ and R$^{30}$ taken together with the intervening atom(s) complete a heterocycle having from 4 to 8 atoms in the ring structure.

The term "sulfoxide" is art-recognized and refers to the group —S(O)—R$^{30}$, wherein R$^{30}$ represents a hydrocarbyl.

The term "sulfonate" is art-recognized and refers to the group SO$_3$H, or a pharmaceutically acceptable salt thereof.

The term "sulfone" is art-recognized and refers to the group —S(O)$_2$—R$^{30}$, wherein R$^{30}$ represents a hydrocarbyl.

The term "thioalkyl", as used herein, refers to an alkyl group substituted with a thiol group.

The term "thioester", as used herein, refers to a group —C(O)SR$^{30}$ or —SC(O)R$^{30}$ wherein R$^{30}$ represents a hydrocarbyl.

The term "thioether", as used herein, is equivalent to an ether, wherein the oxygen is replaced with a sulfur.

The term "urea" is art-recognized and may be represented by the general formula

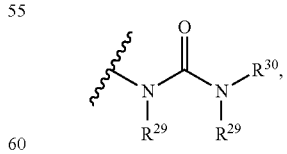

wherein R$^{29}$ and R$^{30}$ independently represent hydrogen or a hydrocarbyl, such as alkyl, or either occurrence of R$^{29}$ taken together with R$^{30}$ and the intervening atom(s) complete a heterocycle having from 4 to 8 atoms in the ring structure.

The term "substituted", as used herein, refers to moieties having substituents replacing one or more hydrogens on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this application, the heteroatoms such as nitrogen may have hydrogen substituents and/or any permissible substituents of organic compounds described herein which satisfy the valences of the heteroatoms. In some embodiments, "substituted" means that the specified group or moiety bears one, two, or three substituents. In other embodiments, "substituted" means that the specified group or moiety bears one or two substituents. In still other embodiments, "substituted" refers to the specified group or moiety bears one substituent.

Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that substituents can themselves be substituted, if appropriate.

Unless specifically stated as "unsubstituted," references to chemical moieties herein are understood to include substituted variants. For example, reference to an "aryl" group or moiety implicitly includes both substituted and unsubstituted variants. The term "unsubstituted" refers to that the specified group bears no substituents.

The term "optionally substituted", as used herein, means that substitution is optional and therefore it is possible for the designated atom or moiety to be unsubstituted.

Any disubstituent referred to herein is meant to encompass the various attachment possibilities when more than one of such possibilities are allowed. For example, reference to disubstituent -A-B—, where A≠B, refers herein to such disubstituent with A attached to a first substituted member and B attached to a second substituted member, and it also refers to such disubstituent with A attached to the second substituted member and B attached to the first substituted member.

"Protecting group", as used herein, refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, 3$^{rd}$ Ed., 1999, John Wiley & Sons, NY and Harrison et al., *Compendium of Synthetic Organic Methods*, Vols. 1-8, 1971-1996, John Wiley & Sons, NY. Representative nitrogen protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxylprotecting groups include, but are not limited to, those where the hydroxyl group is either acylated (esterified) or alkylated such as benzyl and trityl ethers, as well as alkyl ethers, tetrahydropyranyl ethers, trialkylsilyl ethers (e.g., TMS or TIPS groups), glycol ethers, such as ethylene glycol and propylene glycol derivatives and allyl ethers.

The term "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

A "pharmaceutically acceptable salt" is intended to mean a salt of a free acid or base of a compound represented herein that is non-toxic, biologically tolerable, or otherwise biologically suitable for administration to the subject. See, generally, S. M. Berge, et al., "Pharmaceutical Salts," J. Pharm. Sci., 1977, 66, 1-19. Preferred pharmaceutically acceptable salts are those that are pharmacologically effective and suitable for contact with the tissues of subjects without undue toxicity, irritation, or allergic response. A compound described herein may possess a sufficiently acidic group, a sufficiently basic group, both types of functional groups, or more than one of each type, and accordingly react with a number of inorganic or organic bases, and inorganic and organic acids, to form a pharmaceutically acceptable salt.

For a compound described herein that contains a basic group, such as an amine, a pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, or ethanesulfonic acid, or any compatible mixture of acids such as those given as examples herein, and any other acid and mixture thereof that are regarded as equivalents or acceptable substitutes in light of the ordinary level of skill in this technology.

For a compound described herein that contains an acidic group, such as a carboxylic acid group, base addition salts can be prepared by any suitable method available in the art, for example, treatment of such compound with a sufficient amount of the desired the desired base, either neat or in a suitable inert solvent. Examples of pharmaceutically acceptable base addition salts include, but are not limited to, lithium, sodium, potassium, calcium, ammonium, zinc, or magnesium salt, or other metal salts; organic amino salts, such as, alkyl, dialkyl, trialkyl, or tetra-alkyl ammonium salts.

Other examples of pharmaceutically acceptable salts include, but are not limited to, camsylate, sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, γ-hydroxybutyrates, glycolates, tartrates, and mandelates. Lists of other suitable pharmaceutically acceptable salts are found in Remington's Pharmaceutical Sciences, $17^{th}$ Edition, Mack Publishing Company, Easton, Pa., 1985.

The neutral forms of the compounds are preferably regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present application.

The term "prodrug" is intended to encompass compounds which, under physiologic conditions, are converted into the therapeutically active agents of the present application, e.g., a compound of described herein. A common method for making a prodrug is to include one or more selected moieties which are hydrolyzed under physiologic conditions to yield the desired molecule. In certain embodiments, the prodrug is converted by an enzymatic activity of the host animal. For example, a prodrug with a nitro group on an aromatic ring could be reduced by reductase to generate the desired amino group of the corresponding active compound in vivo. In another example, functional groups such as a hydroxyl, carbonate, or carboxylic acid in the parent compound are presented as an ester, which could be cleaved by esterases. Additionally, amine groups in the parent compounds are presented in, but not limited to, carbamate, N-alkylated or N-acylated forms (Simplicio et al, "Prodrugs for Amines," Molecules, (2008), 13:519-547). In certain embodiments, some or all of the compounds of described herein in a formulation represented above can be replaced with the corresponding suitable prodrug.

A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, for example, in "Design of Prodrugs", ed. H. Bundgaard, Elsevier, 1985.

A "pharmaceutically active metabolite" or "metabolite" refers to a pharmacologically active product of metabolism/biochemical modification of a compound described herein, e.g., a compound of Formula (I), (Ia), or (Ib) or salt thereof, under physiological conditions, e.g., through certain enzymatic pathway. For example, an oxidative metabolite is formed by oxidation of the parent compound during metabolism, such as the oxidation of a pyridine ring to pyridine-N-oxide. In another example, an oxidative metabolite is formed by demethylation of a methoxy group to result in a hydroxyl group.

Prodrugs and active metabolites of a compound may be determined using routine techniques known or available in the art. See, e.g., Bertolini et al., *J. Med. Chem.* 1997, 40, 2011-2016; Shan et al., *J. Pharm. Sci.* 1997, 86 (7), 765-767; Bagshawe, *Drug Dev. Res.* 1995, 34, 220-230; Bodor, *Adv. Drug Res.* 1984, 13, 255-331; Bundgaard, *Design of Prodrugs* (Elsevier Press, 1985); and Larsen, Design and Application of Prodrugs, Drug Design and Development (Krogsgaard-Larsen et al., eds., Harwood Academic Publishers, 1991).

Compounds of formulae (I), (Ia), (Ib), (II), (IIa), (III), (IIIa), (IV), (IVa), (V), and (Va), as disclosed herein, can also exist as various "solvates" or "hydrates." A "hydrate" is a compound that exists in a composition with water molecules. The composition can include water in stoichiometric quantities, such as a monohydrate or a dihydrate, or can include water in random amounts. A "solvate" is a similar composition except that a solvent other that water, such as with methanol, ethanol, dimethylformamide, diethyl ether and the like replaces the water. For example, methanol or ethanol can form an "alcoholate," " which can again be stoichiometric or non-stoichiometric. Mixtures of such solvates or hydrates can also be prepared. The source of such solvate or hydrate can be from the solvent of crystallization, inherent in the solvent of preparation or crystallization, or adventitious to such solvent.

The compounds of the application, including their pharmaceutically acceptable salts and prodrugs, can exist as various polymorphs, pseudo-polymorphs, or in amorphous state. The term "polymorph", as used herein, refers to different crystalline forms of the same compound and other solid state molecular forms including pseudo-polymorphs, such as hydrates, solvates, or salts of the same compound. Different crystalline polymorphs have different crystal structures due to a different packing of molecules in the lattice, as a result of changes in temperature, pressure, or variations in the crystallization process. Polymorphs differ from each other in their physical properties, such as x-ray diffraction characteristics, stability, melting points, solubility, or rates of dissolution in certain solvents. Thus crystalline polymorphic forms are important aspects in the development of suitable dosage forms in pharmaceutical industry.

The present application further embraces isolated compounds according to formula (I), (Ia), (Ib), (II), (IIa), (III), (IIIa), (IV), (IVa), (V), or (Va). The term "isolated compound" refers to a preparation of a compound of formula (I), (Ia), (Ib), (II), (IIa), (III), (IIIa), (IV), (IVa), (V), or (Va), or a mixture of compounds according to formula (I), (Ia), (Ib), (II), (IIa), (III), (IIIa), (IV), (IVa), (V), or (Va), wherein the isolated compound has been separated from the reagents used, and/or byproducts formed, in the synthesis of the compound or compounds. "Isolated" does not mean that the preparation is technically pure (homogeneous), but it is sufficiently pure to compound in a form in which it can be used therapeutically. Preferably an "isolated compound" refers to a preparation of a compound of formula (I), (Ia), (Ib), (II), (IIa), (III), (IIIa), (IV), (IVa), (V), or (Va) or a mixture of compounds according to formula (I), (Ia), (Ib), (II), (IIa), (III), (IIIa), (IV), (IVa), (V), or (Va), which contains the named compound or mixture of compounds according to formula (I), (Ia), (Ib), (II), (IIa), (III), (IIIa), (IV), (IVa), (V), or (Va) in an amount of at least 10 percent by weight of the total weight. Preferably the preparation contains the named compound or mixture of compounds in an amount of at least 50% by weight of the total weight; more preferably at least 80% by weight of the total weight; and most preferably at least 90%, at least 95% or at least 98% by weight of the total weight of the preparation.

The compounds of the application and intermediates may be isolated from their reaction mixtures and purified by standard techniques such as filtration, liquid-liquid extraction, solid phase extraction, distillation, recrystallization or chromatography, including flash column chromatography, or HPLC.

Isomerism and Tautomerism in Described Compounds
Tautomerism

Within the present application it is to be understood that a compound described herein or a salt thereof may exhibit the phenomenon of tautomerism whereby two chemical compounds that are capable of facile interconversion by exchanging a hydrogen atom between two atoms, to either of which it forms a covalent bond. Since the tautomeric compounds exist in mobile equilibrium with each other they may be regarded as different isomeric forms of the same compound. It is to be understood that the formulae drawings within this specification can represent only one of the possible tautomeric forms. However, it is also to be understood that the application encompasses any tautomeric form, and is not to be limited merely to any one tautomeric form utilized within the formulae drawings. The formulae drawings within this specification can represent only one of the possible tautomeric forms and it is to be understood that the specification encompasses all possible tautomeric forms of the compounds drawn not just those forms which it has been convenient to show graphically herein. For example, tautomerism may be exhibited by a pyrazolyl group bonded as indicated by the wavy line. While both substituents would be termed a 4-pyrazolyl group, it is evident that a different nitrogen atom bears the hydrogen atom in each structure.

Such tautomerism can also occur with substituted pyrazoles such as 3-methyl, 5-methyl, or 3,5-dimethylpyrazoles, and the like. Another example of tautomerism is amido-imido (lactam-lactim when cyclic) tautomerism, such as is seen in heterocyclic compounds bearing a ring oxygen atom adjacent to a ring nitrogen atom. For example, the equilibrium:

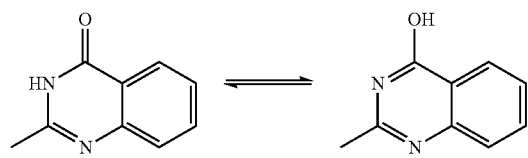

is an example of tautomerism. Accordingly, a structure depicted herein as one tautomer is intended to also include the other tautomer.

Optical Isomerism

It will be understood that when compounds of the present application contain one or more chiral centers, the compounds may exist in, and may be isolated as pure enantiomeric or diastereomeric forms or as racemic mixtures. The present application therefore includes any possible enantiomers, diastereomers, racemates in their pure forms or mixtures thereof, and salts thereof, of the compounds of the application.

The isomers resulting from the presence of a chiral center comprise a pair of non-superimposable isomers that are called "enantiomers." Single enantiomers of a pure compound are optically active, i.e., they are capable of rotating the plane of plane polarized light. Single enantiomers are designated according to the Cahn-Ingold-Prelog system. The priority of substituents is ranked based on atomic weights, a higher atomic weight, as determined by the systematic procedure, having a higher priority ranking. Once the priority ranking of the four groups is determined, the molecule is oriented so that the lowest ranking group is pointed away from the viewer. Then, if the descending rank order of the other groups proceeds clockwise, the molecule is designated (R) and if the descending rank of the other groups proceeds counterclockwise, the molecule is designated (S). In the example in Scheme 14, the Cahn-Ingold-Prelog ranking is A>B>C>D. The lowest ranking atom, D is oriented away from the viewer.

In certain embodiments, the therapeutic preparation may be enriched to provide predominantly one enantiomer of a compound (e.g., of formula (I), (Ia), or (Ib)). An enantiomerically enriched mixture may comprise, for example, at least 60 mol percent of one enantiomer, or more preferably at least 75, 90, 95, or even 99 mol percent. In certain embodiments, a compound of the invention may have greater than 30% ee, 40% ee, 50% ee, 60% ee, 70% ee, 80% ee, 90% ee, or even 95% or greater ee. In certain embodiments, the compound enriched in one enantiomer is substantially free of the other enantiomer, wherein substantially free means that the substance in question makes up less than 10%, or less than 5%, or less than 4%, or less than 3%, or less than 2%, or less than 1% as compared to the amount of the other enantiomer, e.g., in the composition or compound mixture. For example, if a composition or compound mixture contains 98 grams of a first enantiomer and 2 grams of a second enantiomer, it would be said to contain 98 mol percent of the first enantiomer and only 2% of the second enantiomer.

In certain embodiments, compounds of the application may have more than one stereocenter. In certain such embodiments, compounds of the application may be enriched in one or more diastereomer. For example, a compound of the application may have greater than 30% de, 40% de, 50% de, 60% de, 70% de, 80% de, 90% de, or even 95% or greater de.

Isolated optical isomers may be purified from racemic mixtures by well-known chiral separation techniques, such as but not limited to, normal and reverse phase chromatography, and crystallization. According to one such method, a racemic mixture of a compound of the application, or a chiral intermediate thereof, is separated using a chiral salt or carried out on a Chiralcell OD column. The column is operated according to the manufacturer's instructions.

Isolated optical isomers (enantiomerically pure compounds) can also be prepared by the use of chiral intermediates or catalysts in synthesis. When a chiral synthetic intermediate is used, the optical center (chiral center) can be preserved without racemization throughout the remainder of the preparative procedure, as is well known in the art. Chiral catalyst can be used to impart at least some degree of enantiomeric purity to products of reactions catalyzed by the chiral catalyst. And, in some cases, compounds having at least some degree of enantiomeric enrichment can be obtained by physical processes such as selective crystallization of salts or complexes formed with chiral adjuvants.

A variety of compounds in the present application may exist in particular geometric or stereoisomeric forms. The present application takes into account all such compounds, including tautomers, cis- and trans-isomers, R- and S-enantiomers, diastereomers, (D)-isomers, (L)-isomers, the racemic mixtures thereof, and other mixtures thereof, as being covered within the scope of this application. All tautomeric forms are encompassed in the present application. Additional asymmetric carbon atoms may be present in a substituent such as an alkyl group. All such isomers, as well as mixtures thereof, are intended to be included in this application, unless the stereochemistry or isomeric form is specifically indicated.

Rotational Isomerism

It is understood that due to chemical properties (i.e., resonance lending some double bond character to the C—N bond) of restricted rotation about the amide bond linkage (as illustrated below) it is possible to observe separate rotamer species and even, under some circumstances, to isolate such species (see below). It is further understood that certain structural elements, including steric bulk or substituents on the amide nitrogen, may enhance the stability of a rotamer to the extent that a compound may be isolated as, and exist indefinitely, as a single stable rotamer. The present application therefore includes any possible stable rotamers of formula (I) which are biologically active in the treatment of cancer or other proliferative disease states.

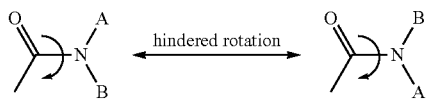

Regioisomerism

The preferred compounds of the present application have a particular spatial arrangement of substituents on the aromatic rings, which are related to the structure activity relationship demonstrated by the compound class. Often such substitution arrangement is denoted by a numbering system; however, numbering systems are often not consistent between different ring systems. In six-membered aromatic systems, the spatial arrangements are specified by the common nomenclature "para" for 1,4-substitution, "meta" for 1,3-substitution and "ortho" for 1,2-substitution as shown below.

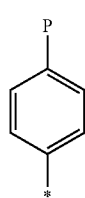
"para-"

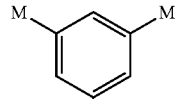
"meta-"

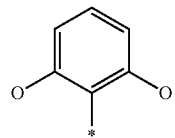
"ortho-"

Isotopical Labeling in Described Compounds

The present application further includes all pharmaceutically acceptable isotopically labeled compound [e.g., of formula (I), (Ia), (Ib), (II), (IIa), (III), (IIIa), (IV), (IVa), (V), or (Va)]. An "isotopically" or "radio-labeled" compound is a compound where one or more atoms are replaced or substituted by an atom having an atomic mass or mass number different from the atomic mass or mass number typically found in nature (i.e., naturally occurring). For example, in certain embodiments, in compounds [e.g., of formula (I), (Ia), (Ib), (II), (IIa), (III), (IIIa), (IV), (IVa), (V), or (Va)], hydrogen atoms are replaced or substituted by one or more deuterium or tritium (e.g., hydrogen atoms on a $C_{1-6}$ alkyl or a $C_{1-6}$ alkoxy are replaced with deuterium, such as $d_3$-methoxy or 1,1,2,2-$d_4$-3-methylbutyl).

Certain isotopically labeled compounds [e.g., compounds of formula (I), (Ia), (Ib), (II), (IIa), (III), (IIIa), (IV), (IVa), (V), or (Va)], for example, those incorporating a radioactive isotope, are useful in drug and/or substrate tissue distribution studies. The radioactive isotopes tritium, i.e., $^3H$, and carbon 14, i.e., $^{14}C$, are particularly useful for this purpose in view of their ease of incorporation and ready means of detection.

Such isotopically labeled compounds are useful in metabolic studies (preferably with $^{14}C$), reaction kinetic studies (with, for example $^2H$ or $^3H$), detection or imaging techniques [such as positron emission tomography (PET) or single-photon emission computed tomography (SPECT)] including drug or substrate tissue distribution assays, or in radioactive treatment of patients. Further, substitution with heavier isotopes such as deuterium (i.e., 2H) may afford certain therapeutic advantages resulting from greater metabolic stability, for example increased in vivo half-life or reduced dosage requirements.

Substitution with positron emitting isotopes, such as $^{11}C$, $^{18}F$, $^{15}O$, and $^{13}N$, can be useful in Positron Emission Topography (PET) studies for examining substrate receptor occupancy.

Isotopically labeled compounds [e.g., of formula (I), (Ia), or (Ib)] or their corresponding prodrugs can generally be prepared by conventional techniques known to those skilled in the art or by processes analogous to those described in the accompanying examples using an appropriate isotopically labeled reagent in place of the non-labeled reagent previously employed. Suitable isotopes that may be incorporated in compounds of the present application include but are not limited to isotopes of hydrogen, carbon, nitrogen, oxygen, phosphorous, fluorine, chlorine, and iodine, such as $^2H$ (also written as D for deuterium), $^3H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$, $^{131}I$, $^{31}P$, and $^{32}P$.

Isotopically labeled compounds of this application and prodrugs thereof can generally be prepared by carrying out the procedures disclosed in the schemes or in the examples and preparations described below by substituting a readily available isotopically labeled reagent for a non-isotopically labeled reagent.

Provisos may apply to any of the disclosed categories or embodiments such that specific embodiments or species may be excluded from such categories or embodiments.

In various embodiments, the compound or set of compounds, such as are used in the inventive methods, can be any one of any of the combinations and/or sub-combinations of the above-listed embodiments.

Pharmaceutical Compositions

The compositions and methods of the present application may be utilized to treat a subject, such as a mammal, e.g., human, or a non-human mammal, in need thereof. When administered to an animal, such as a human, the composition or the compound is preferably administered as a pharmaceutical composition comprising, for example, a compound of the application and a pharmaceutically acceptable carrier. In certain embodiments, the application relates to a pharmaceutical composition comprising as active ingredient a therapeutically effective amount of a compound according to formula (I), (Ia), (Ib), (II), (IIa), (III), (IIIa), (IV), (IVa), (V), or (Va), or a pharmaceutically acceptable salt, solvate, or prodrug thereof, in association with at least one pharmaceutically acceptable carrier, excipient, or diluent.

The term "pharmaceutically acceptable carrier", as used herein, refers to a pharmaceutically acceptable material, composition or vehicle, such as a liquid or solid filler, diluent, excipient, solvent or encapsulating material, which can act, for example, to stabilize, increase solubility or to increase the absorption of a compound such as a compound of the application. Each carrier must be "acceptable" in the sense of being compatible with the other ingredients of the formulation and not injurious to the patient.

Pharmaceutically acceptable carriers are well known in the art. For example, some examples of materials which can serve as pharmaceutically acceptable carriers include, but are not limited to: (1) sugars, such as lactose, glucose, sucrose or dextrans; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as glycerol or propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; (21) antioxidants, such as ascorbic acid or glutathione; and (22) other non-toxic compatible substances employed in pharmaceutical formulations, such as chelating agents, low molecular weight proteins or other stabilizers or excipients.

The choice of a pharmaceutically acceptable carrier, including a physiologically acceptable agent, depends, for example, on the route of administration of the composition. The pharmaceutical composition can be a self-emulsifying or a self-microemulsifying drug delivery system. The pharmaceutical composition also can be a liposome or other polymer matrix, which can have incorporated therein. Liposomes, for example, which comprise phospholipids or other lipids, are nontoxic, physiologically acceptable and metabolizable carriers that are relatively simple to make and administer.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

A pharmaceutical composition can be administered to a subject by any of a number of routes of administration including, but not limited to, for example, orally [for example, drenches as in aqueous or non-aqueous solutions or suspensions, tablets, pills, capsules (including sprinkle capsules and gelatin capsules), boluses, powders, granules, pastes for application to the tongue]; absorption through the oral mucosa (e.g., sublingually); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin, or as an eye drop). The composition or compound may also be formulated for inhalation. In certain embodiments, the composition or compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein. Sterile compositions are also contemplated by the application, including compositions that are in accord with national and local regulations governing such compositions. Preferably, the compositions are formulated for intravenous or oral administration.

For oral administration, the compounds the application may be provided in a solid form, such as a tablet, pills, dragees, powers, granules, or capsule, or as a solution, emulsion, or suspension. To prepare the oral compositions, the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof, (10) complexing agents, such as, modified and unmodified cyclodextrins; (11) coloring agents; (12) emulsifying and suspending agents, such as, ethoxylated isostearyl alcohols, polyoxyethylene sorbitol, sorbitan esters, microcrystalline cellulose, aluminum metahydroxide, bentonite, agar, and tragacanth; and (13) other non-toxic compatible substances employed in pharmaceutical formulations, such as, without limitation, buffering agents, perfuming and preservative agents, sweetening agents, flavoring agents.

Oral tablets may be made by compression or molding, optionally with one or more accessory ingredients, such as diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are exemplary disintegrating agents. Binding agents may include hydroxypropylmethyl cellulose, starch and gelatin. The lubricating agent, if present, may be magnesium stearate, stearic acid, or talc. If desired, the tablets may be coated with a material such as glyceryl monostearate or glyceryl distearate to delay absorption in the gastrointestinal tract, or may be coated with an enteric coating.

Other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. For example, to prepare hard gelatin capsules, active ingredient(s) may be mixed with a solid, semi-solid, or liquid diluent. Soft gelatin capsules may be prepared by mixing the active ingredient with water, oil such as peanut oil or olive oil, liquid paraffin, a mixture of mono and di-glycerides of short chain fatty acids, polyethylene glycol 400, or propylene glycol.

The pharmaceutical compositions may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs, or may be lyophilized or presented as a dry product for reconstitution with water or other suitable vehicle before use. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

In addition, formulations of the pharmaceutical compositions for administration to the mouth may be presented as a mouthwash, or an oral spray, or an oral ointment.

The phrases "parenteral administration" and "administered parenterally", as used herein, means modes of administration other than enteral and topical administration, usually by injection, and includes, without limitation, intravenous, intramuscular, intraarterial, intrathecal, intracapsular, intraorbital, intracardiac, intradermal, intranasal, intraperitoneal, transtracheal, subcutaneous, subcuticular, intraarticular, subcapsular, subarachnoid, intraspinal, and intrasternal injection and infusion.

For parenteral use, the agents of the application may be provided in sterile aqueous solutions or suspensions, buffered to an appropriate pH and isotonicity or in parenterally acceptable oil. Suitable aqueous vehicles include Ringer's solution and isotonic sodium chloride. Such forms may be presented in unit-dose form such as ampoules or disposable injection devices, in multi-dose forms such as vials from which the appropriate dose may be withdrawn, or in a solid form or pre-concentrate that can be reconstituted into a sterile injectable formulation, such as solutions or dispersions just prior to use, which may contain antioxidants, buffers, bacteriostats, solutes which render the formulation isotonic with the blood of the intended recipient or suspending or thickening agents. Illustrative infusion doses range from about 1 to 1000 µg/kg/minute of agent admixed with a pharmaceutical carrier over a period ranging from several minutes to several days.

Examples of suitable aqueous and nonaqueous carriers that may be employed in the pharmaceutical compositions of the application include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

In a preferred embodiment, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs.

For rectal, vaginal, or urethral administration, formulations of the pharmaceutical compositions may be presented as a suppository, which may be prepared by mixing one or more active compounds with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound. Formulations which are suitable for vaginal administration also include pessaries, tampons, creams, gels, pastes, foams or spray formulations containing such carriers as are known in the art to be appropriate.

For topical applications or transdermal administration, the active compounds of the present application may be mixed under sterile conditions with a pharmaceutically acceptable carrier, and with any preservatives, buffers, excipients, or propellants, such as animal and vegetable fats, oils, waxes, paraffins, starch, tragacanth, cellulose derivatives, polyethylene glycols, silicones, bentonites, silicic acid, talc and zinc oxide, or mixtures thereof. Dosage forms for the topical include powders, sprays, ointments, pastes, creams, lotions, gels, solutions, patches and inhalants.

The active compounds may be mixed with a pharmaceutical carrier at a concentration of about 0.1% to about 10% of drug to vehicle.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present application to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this application. Exemplary ophthalmic formulations are described in U.S. Publication Nos. 2005/0080056, 2005/0059744, 2005/0031697 and 2005/004074 and U.S. Pat. No. 6,583,124, the contents of which are incorporated herein by reference. If desired, liquid ophthalmic formulations have properties similar to that of lacrimal fluids, aqueous humor or vitreous humor or are compatible with such fluids. A preferred route of administration is local administration (e.g., topical administration, such as eye drops, or administration via an implant).

Alternatively or additionally, compositions can be formulated for delivery via a catheter, stent, wire, or other intraluminal device. Delivery via such devices may be especially useful for delivery to the bladder, urethra, ureter, rectum, or intestine.

Methods of introduction may also be provided by rechargeable or biodegradable devices. Various slow release polymeric devices have been developed and tested in vivo in recent years for the controlled delivery of drugs, including proteinacious biopharmaceuticals. A variety of biocompatible polymers (including hydrogels), including both biodegradable and non-degradable polymers, can be used to form an implant for the sustained release of a compound at a particular target site.

A physician or veterinarian having ordinary skill in the art can readily determine and prescribe the therapeutically effective amount of the pharmaceutical composition required. The term "therapeutically effective amount" or "dose", or "dosage", as used herein, refers to an amount or dose sufficient to generally bring about the desired therapeutic benefit or an amount sufficient to modulate the biological activity of the target receptor in subjects needing such treatment.

Effective amounts or dosages of the compounds of the application may be ascertained by routine methods, such as modeling, dose escalation, or clinical trials, taking into account routine factors. Actual dosage levels of the active ingredients in the pharmaceutical compositions may be varied. In general, a suitable daily dose of an active compound used in the compositions and methods of the application will be that amount of the compound that is the lowest dose effective to produce a therapeutic effect.

The selected dosage level will depend upon a variety of factors including the activity of the particular compound or combination of compounds employed, or the salts, solvate, and prodrug thereof, the route of administration, the time of administration, the rate of excretion of the particular compound(s) being employed, the duration of the treatment, other drugs, compounds and/or materials used in combination with particular compound(s) employed, age, sex, weight, condition, general health, prior medical history of the patient being treated, and the preference and experience of the physician or veterinarian in charge, and like factors well known in the medical arts.

For example, in choosing a regimen for a subject, such as a patient, it can frequently be necessary to begin with a higher dosage and when the condition is under control to reduce the dosage. In another example, it is also possible to start at a dosage of the pharmaceutical composition for compound at levels lower than that required in order to achieve the desired therapeutic effect and gradually increase the dosage until the desired effect is achieved.

The compounds of the application are effective over a wide dosage range. For example, in the treatment of adult humans, dosages from about 0.05 to about 5000 mg, preferably from about 1 to about 2000 mg, and more preferably between about 2 and about 2000 mg per day can be used. A typical dosage is about 10 mg to about 1000 mg per day, or 25 to 200 mg per day, or 50 to 100 mg per day, or less than 100 mg per day.

In some embodiments, the compounds of the application are dispensed in unit dosage form including from about 0.05 mg to about 1000 mg of active ingredient together with a pharmaceutically acceptable carrier per unit dosage. In other embodiments, a unit dosage form includes from about 10 to about 200 mg of active ingredient. In other embodiments, dosage forms suitable for oral, nasal, pulmonal or transdermal administration include from about 125 µg to about 1250 mg, preferably from about 250 µg to about 500 mg, and more preferably from about 2.5 mg to about 250 mg, of the compounds admixed with a pharmaceutically acceptable carrier or diluent. Methods to determine efficacy and dosage are known to those skilled in the art (Isselbacher et al. (1996) Harrison's Principles of Internal Medicine $13^{ed}$., 1814-1882, herein incorporated by reference).

Dosage forms can be administered daily or more than once a day, such as twice or thrice daily. Alternatively dosage forms can be administered less frequently than daily, such as every other day, or weekly, if found to be advisable by a prescribing physician. A larger dosage can be delivered by multiple administrations of the agent. In some embodiments, dosage forms are administered once, twice, or thrice daily. In preferred embodiments, the active compound will be administered once daily. Once improvement of the patient's disease has occurred, the dose may be adjusted for maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms. Patients may also require chronic treatment on a long-term basis.

Methods and Uses

In various embodiments, compounds of the application can be used to modulate, such as to activate (agonist), or to block activation of (antagonist), an orexin receptor. Accordingly, in various embodiments, the application provides a method of modulating an orexin receptor comprising contacting the receptor with an effective amount or concentration of a compound of the application. The orexin receptor can be $OX_1$ or $OX_2$. In various embodiments, the compound of the application is an antagonist of an orexin receptor such as $OX_1$ or $OX_2$, or both, and can be a selective inhibitor of one or the other. In various embodiments, contacting can take place in vivo within tissues of a patient, such as a human patient. In various embodiments, modulation of an orexin receptor, for example, antagonism of orexin-1, by a compound of the application can be used to treat a disease, disorder, or medical condition in a patient, as described herein.

In various embodiments, the application provides a method of treating a disease, disorder, or medical condition in a patient, such as treating a disease, disorder, or medical condition in which modulation of an orexin receptor is medically indicating, comprising administering to the subject, such as a patient, a compound of the application in a dose, at a frequency, and for duration to provide a beneficial effect to the subject. Modulation, such as agonism or antagonism, of an orexin receptor can be medically indicated in treatment of a disease, disorder, or medical condition wherein the orexin receptor plays a metabolic or regulatory role. Certain such conditions can be treated by selective modulation of a single class of orexin receptor, such as modulation of $OX_1$ while $OX_2$ is not influenced by administration of the compound of the application at the dose provided. In various embodiments, compounds of the application can be orexin-1 antagonists, and some of those are selective orexin-1 antagonists with respect to orexin-2. By "selective" is meant that one receptor is modulated at concentrations of the compound at least 10 times lower than the concentrations at which the comparative receptor is modulated by that compound. Accordingly, in various embodiments, the compound of the application can be a selective modulator, e.g., an antagonist, of orexin receptor $OX_1$. In other embodiments, the compound of the application can be a selective modulator (e.g., antagonist) of an orexin receptor $OX_2$. In further embodiments, the compound of the application can further modulate other types or classes of receptors having affinity for one or more forms of the orexin class of natural peptidic ligands.

In various embodiments, the application provides a use of a compound of the application for treatment of a disease, disorder, or medical condition in a patient. For example, a compound of the application can be used in the preparation of a medicament for administration to a patient suffering from a disease, disorder, or medical condition. More specifically, the disease, disorder, or medical condition can comprise an eating disorder, obesity, alcoholism or an alcohol-related disorder, drug abuse or addiction, a sleep disorder, a cognitive dysfunction in a psychiatric or neurologic disorder, depression, anxiety, panic disorder, schizophrenia, Alzheimer's disease, aggression associated with neurological disorders such as Alzheimer's disease, and aggression associated with neurodevelopmental disorders such as autism, Parkinson's disease, Huntington's chorea, headache, migraine, pain, gastrointestinal diseases, epilepsy, inflammations, immune-related diseases, endocrine-related diseases, cancer, hypertension, behavior disorder, mood disorder, manic depression, dementia, sex disorder, psychosexual disorder, and renal disease. Drug or substance abuse or addiction includes relapse. These may include abuse of or addiction to cocaine, opiates, amphetamines, nicotine, alcohol, cannabis, heroin, and/or any other drug of abuse.

In other embodiments, the disease, disorder, or medical condition is narcolepsy, insomnia, learning disorders, memory disorders, depression, anxiety, addiction, obsessive compulsive disorder, affective neurosis, depressive neurosis, anxiety neurosis, dysthymic disorder, behavior disorder, mood disorder, sexual dysfunction, psychosexual dysfunction, sex disorder, schizophrenia, manic depression, delirium, dementia, severe mental retardation or dyskinesias (such as Huntington's Disease or Tourette Syndrome), eating disorders (such as anorexia, bulimia, cachexia, or obesity), addictive feeding behaviors, binge/purge feeding behaviors, cardiovascular diseases, diabetes, appetite/taste disorders, emesis, vomiting, nausea, asthma, cancer, Parkinson's Disease, Cushing's Syndrome/Disease, basophile adenoma, prolactinoma, hyperprolactinemia, hypophysis tumor/adenoma, hypothalamic diseases, inflammatory bowel disease, gastric dyskinesia, gastric ulcers, Froehlich's Syndrome, adrenohypophysis disease, hypophysis diseases, adrenohypophysis hypofunction, adrenohypophysis hyperfunction, hypothalamic hypogonadism, Kallman's syndrome (anosmia, hyposmia), functional or psychogenic amenorrhea, hypopituitarism, hypothalamic hypothyroidism, hypothalamic-adrenal dysfunction, idiopathic hyperprolactinemia, hypothalamic disorders of growth hormone deficiency, idiopathic growth deficiency, dwarfism, gigantism, acromegaly, disturbed biological and circadian rhythms, sleep disturbances associated with disease such as neurological disorders, neuropathic pain, diabetic neuropathy, and restless leg syndrome, heart and lung diseases, acute and congestive heart failure, hypotension, hypertension, urinary retention, osteoporosis, angina pectoris, myocardial infarction, ischemic or hemorrhagic stroke, subsrachnoic hemorrhage, ulcers, allergies, benign prostatic hypertrophy, chronic renal failure, renal disease, impaired glucose tolerance, migraine, episodic migraine, headache disorders (such as tension-type headache, cluster headache, other trigeminal autonomic cephalalgias, other primary headaches such as hemicranias continua, secondary headaches, cranial neuralgia, or central or primary facial pain), hyperalgesia, pain, enhanced or exaggerated sensitivity to pain such as hyperalgesia, causalgia, or allodynia, acute pain, burn pain, atypical facial pain, neuropathic pain, back pain, complex regional pain syndrome I or II, arthritic pain, sports injury pain, pain related to infection (e.g., HIV), post-chemotherapy pain, post-stroke pain, post-operative pain, neuralgia, emesis, nausea, vomiting, conditions associated with visceral pain (such as irritable bowel syndrome or angina), urinary bladder incontinence (e.g., urge incontinence), tolerance to narcotics or withdrawal from narcotics, sleep disorders, sleep apnea, parasomnia, jet lag syndrome, neurodegenerative disorders, disinhibition-dementia-parkinsonism-amyotrophy complex, pallido-ponto-nigral degeneration, epilepsy, seizure disorders, or other diseases related to general orexin system dysfunction.

In still other embodiments, the compounds described herein are useful in a method of treating disorders including, but not limited to, sleep disorders, sleep disturbances, including enhancing sleep quality, improving sleep quality, increasing sleep efficiency, augmenting sleep maintenance; increasing the ratio of the time that a subject sleeps relative to the time that a subject is attempting to sleep; improving sleep initiation; decreasing sleep latency or onset (the time it takes to fall asleep); decreasing difficulties in falling asleep; increasing sleep continuity; decreasing the number of awakenings during sleep; decreasing intermittent wakings during sleep; decreasing nocturnal arousals; decreasing the time spent awake following the initial onset of sleep; increasing the total amount of sleep; reducing the fragmentation of sleep; altering the timing, frequency, or duration of REM sleep bouts; altering the timing, frequency, or duration of slow wave (such as stages 3 or 4) sleep bouts; increasing the amount and percentage of stage 2 sleep; promoting slow wave sleep; enhancing EEG-delta activity during sleep; decreasing nocturnal arousals, especially early morning awakenings; increasing daytime alertness; reducing daytime drowsiness; treating or reducing excessive daytime sleepiness; increasing satisfaction with the intensity of sleep; increasing sleep maintenance; idiopathic insomnia; sleep problems; insomnia, hypersomnia, idiopathic hypersomnia, repeatability hypersomnia, intrinsic hypersomnia, narcolepsy, interrupted sleep, sleep apnea, wakefulness, nocturnal myoclonus, REM sleep interruptions, jet-lag, shift workers' sleep disturbances, dyssomnias, night terror, insomnias associated with depression, emotional/mood disorders, Alzheimer's disease, or cognitive impairment, as well as sleep walking and enuresis, and sleep disorders that accompany aging; Alzheimer's sundowning; conditions associated with circadian rhythmicity as well as mental and physical disorders associated with travel across time zones and with rotating shift-work schedules, conditions due to drugs that cause reductions in REM sleep as a side effect; fibromyalgia; syndromes that are manifested by non-restorative sleep and muscle pain; sleep apnea that is associated with respiratory disturbances during sleep; conditions that result from a diminished quality of sleep; increasing learning; augmenting memory; increasing retention of memory; eating disorders associated with excessive food intake and complications associated therewith, compulsive eating disorders, obesity (due to any cause, whether genetic or environmental), obesity-related disorders including overeating and bulimia nervosa, hypertension, diabetes, elevated plasma insulin concentrations and insulin resistance, dyslipidemias, hyperlipidemia, endometrial, breast, prostate and colon cancer, osteoarthritis, obstructive sleep apnea, cholelithiasis, gallstones, heart disease, abnormal heart rhythms and arrythmias, myocardial infarction, congestive heart failure, coronary heart disease, sudden death, stroke, polycystic ovary disease, craniopharyngioma, the Prader-Willi Syndrome, Frohlich's syndrome, GH-deficient subjects, normal variant short stature, Turner's syndrome, and other pathological conditions showing reduced metabolic activity or a decrease in resting energy expenditure as a percentage of total fat-free mass, e.g., children with acute lymphoblastic leukemia, metabolic syndrome, also known as syndrome X, insulin resistance syndrome, reproductive hormone abnormalities, sexual and reproductive dysfunction, such as impaired fertility, infertility, hypogonadism in males and hirsutism in females, fetal defects associated with maternal obesity, gastrointestinal motility disorders, such as obesity-related gastroesophageal reflux, respiratory disorders, such as obesity-hypoventilation syndrome (Pickwickian syndrome), breathlessness, cardiovascular disorders, inflammation, such as systemic inflammation of the vasculature, arteriosclerosis, hypercholesterolemia, hyperuricaemia, lower back pain, gallbladder disease, gout, kidney cancer, increased anesthetic risk, reducing the risk of secondary outcomes of obesity, such as reducing the risk of left ventricular hypertrophy; diseases or disorders where abnormal oscillatory activity occurs in the brain, including depression, migraine, neuropathic pain, Parkinson's disease, psychosis, or schizophrenia, as well as diseases or disorders where there is abnormal coupling of activity, particularly through the thalamus; enhancing cognitive function; enhancing memory; increasing memory retention; increasing immune response; increasing immune function; hot flashes; night sweats; extending life span; schizophrenia; muscle-related disorders that are controlled by the excitation/relaxation rhythms imposed by the neural system such as cardiac rhythm and other disorders of the cardiovascular system; conditions related to proliferation of cells such as vasodilation or vasorestriction and blood pressure; cancer; cardiac arrhythmia; hypertension; congestive heart failure; conditions of the genital/urinary system; disorders of sexual function and fertility; adequacy of renal function; responsivity to anesthetics; mood disorders, such as depression or more particularly depressive disorders, for example, single episodic or recurrent major depressive disorders and dysthymic disorders, or bipolar disorders, for example, bipolar I disorder, bipolar II disorder, and cyclothymic disorder, mood disorders due to a general medical condition, and substance-induced mood disorders; anxiety disorders including acute stress disorder, agoraphobia, generalized anxiety disorder, obsessive-compulsive disorder, panic attack, panic disorder, post-traumatic stress disorder, separation anxiety disorder, social phobia, specific phobia, substance-induced mood disorders; anxiety disorders including acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition; acute neurological and psychiatric disorders such as cerebral deficits subsequent to cardiac bypass surgery and grafting, stroke, ischemic stroke, cerebral ischemia, spinal cord trauma, head trauma, perinatal hypoxia, cardiac arrest, hypoglycemic neuronal damage; Huntington's Chorea; amyotrophic lateral sclerosis; multiple sclerosis; ocular damage; retinopathy; cognitive disorders; idiopathic and drug-induced Parkinson's disease; muscular spasms and disorders associated with muscular spasticity including tremors, epilepsy, convulsions; cognitive disorders including dementia (associated with Alzheimer's disease, ischemia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders or age related cognitive decline; schizophrenia or psychosis including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced psychotic disorder; substance-related disorders and addictive behaviors (including substance-induced delirium, persisting dementia, persisting amnestic disorder, psychotic disorder or anxiety disorder; tolerance, addictive feeding, dependence or withdrawal from substances including alcohol, amphetamines, cannabis, cocaine, hallucinogens, inhalants, nicotine, opioids, phencyclidine, sedatives, hypnotics, or anxiolytics); movement disorders, including akinesias and akinetic-rigid syndromes (including Parkinson's disease, drug-induced parkinsonism, postencephalitic parkinsonism, progressive supranuclear palsy, multiple system atrophy, corticobasal degeneration, parkinsonism-ALS dementia complex and basal ganglia calcification), chronic fatigue syndrome, fatigue, including Parkinson's fatigue, multiple sclerosis fatigue, fatigue caused by a sleep disorder or a circadian rhythm disorder, medication-induced parkinsonism (such as neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Gilles de la Tourette's syndrome, epilepsy, and dyskinesias including tremor (such as rest tremor, essential tremor, postural tremor and intention tremor), chorea (such as Sydenham's chorea, Huntington's disease, benign hereditary chorea, neuroacanthocytosis, symptomatic chorea, drug-induced chorea and hemiballism), myoclonus (including generalised myoclonus and focal myoclonus), tics (including simple tics, complex tics and symptomatic tics), restless leg syndrome and dystonia (including generalized dystonia such as iodiopathic dystonia, drug-induced dystonia, symptomatic dystonia and paroxymal dystonia, and focal dystonia such as blepharospasm, oromandibular dystonia, spasmodic dysphonia, spasmodic torticollis, axial dystonia, dystonic writer's cramp and hemiplegic dystonia); attention deficit/hyperactivity disorder (ADHD); conduct disorder; migraine (including migraine headache); urinary incontinence; substance tolerance, substance withdrawal (including, substances such as opiates, nicotine, tobacco products, alcohol, benzodiazepines, cocaine, sedatives, hypnotics, etc.); psychosis; schizophrenia; anxiety (including generalized anxiety disorder, panic disorder, and obsessive compulsive disorder); mood disorders (including depression, mania, bipolar disorders); trigeminal neuralgia; hearing loss; tinnitus; neuronal damage including ocular damage; retinopathy; macular degeneration of the eye; emesis; brain edema; pain, including acute and chronic pain states, severe pain, intractable pain, inflammatory pain, neuropathic pain, post-traumatic pain, bone and joint pain (osteoarthritis), repetitive motion pain, dental pain, cancer pain, myofascial pain (muscular injury, fibromyalgia), perioperative pain (general surgery, gynecological), chronic pain, neuropathic pain, post-traumatic pain, trigeminal neuralgia, migraine and migraine headache.

In other embodiments, the disease, disorder, or medical condition is an eating disorder, obesity, alcoholism or an alcohol-related disorder, drug abuse or addiction, a sleep disorder, a cognitive dysfunction in a psychiatric or neurologic disorder, depression, anxiety, panic disorder, schizophrenia, Alzheimer's disease, Parkinson's disease, Huntington's chorea, head ache, migraine, pain, gastrointestinal diseases, epilepsy, inflammations, immune-related diseases, ulcers, irritable bowel syndrome, diarrhea, gastroesophageal reflux, endocrine-related diseases, cancer, hypertension, behavior disorder, mood disorder, manic depression, dementia, sex disorder, psychosexual disorder, and renal disease.

In still other embodiments, the disease, disorder, or medical condition is substance addiction (including relapse), panic disorder, anxiety, post-traumatic stress disorder, pain, depression, seasonal affective disorder, an eating disorder, or hypertension.

Thus, in specific embodiments the present application provides methods for: enhancing the quality of sleep; augmenting sleep maintenance; increasing REM sleep; increasing stage 2 sleep; decreasing fragmentation of sleep patterns; treating insomnia; enhancing cognition; increasing memory retention; treating or controlling obesity; treating or controlling depression; treating, controlling, ameliorating or reducing the risk of epilepsy, including absence epilepsy; treating or controlling pain, including neuropathic pain; treating or controlling Parkinson's disease; treating or controlling psychosis; or treating, controlling, ameliorating or reducing the risk of schizophrenia, in a subject in need thereof which comprises administering to the patient a therapeutically effective amount of a compound of the present application.

It is believed that antagonism of orexin-1 is medically indicated for the treatment of the above-listed conditions. By antagonism is meant blocking a receptor, in this case an orexin receptor, without causing it to transduce a signal. That is, antagonism results in blocking an endogenous or exogenous ligand from activating, or causing antagonism, of the receptor.

It is within ordinary skill to evaluate any compound disclosed and claimed herein for effectiveness in modulation of an orexin receptor and in the various cellular assays using the procedures described above or found in the scientific literature. Accordingly, the person of ordinary skill can prepare and evaluate any of the claimed compounds without undue experimentation. Any compound found to be an effective modulator, agonist or antagonist, can likewise be tested in animal models and in human clinical studies using the skill and experience of the investigator to guide the selection of dosages and treatment regimens.

In certain embodiments, the application comprises a method for conducting a pharmaceutical business, by determining an appropriate formulation and dosage of a compound of the application for treating or preventing any of the diseases or conditions as described herein, conducting therapeutic profiling of identified formulations for efficacy and toxicity in animals, and providing a distribution network for selling an identified preparation as having an acceptable therapeutic profile. In certain embodiments, the method further includes providing a sales group for marketing the preparation to healthcare providers.

In certain embodiments, the application relates to a method for conducting a pharmaceutical business by determining an appropriate formulation and dosage of a compound of the application for treating or preventing any of the disease or conditions as described herein, and licensing, to a third party, the rights for further development and sale of the formulation.

The term "healthcare providers" refers to individuals or organizations that provide healthcare services to a person, community, etc. Examples of "healthcare providers" include doctors, hospitals, continuing care retirement communities, skilled nursing facilities, subacute care facilities, clinics, multispecialty clinics, freestanding ambulatory centers, home health agencies, and HMO's.

Drug Combinations

The compounds of the present application may be used in pharmaceutical compositions or methods in combination with one or more additional active ingredients in the treatment of the diseases and disorders described herein. Further additional active ingredients include other therapeutics or agents that mitigate adverse effects of therapies for the intended disease targets. Such combinations may serve to increase efficacy, ameliorate other disease symptoms, decrease one or more side effects, or decrease the required dose of an inventive compound. In certain embodiments, such combination provides an additive effect, wherein an additive effect refers to the sum of each of the effects of individual administration of the compound of the application and one or more additional therapeutic agent(s). In other embodiments, such combination provides a synergistic effect, in which the therapeutic effect exceeds the sum of each of the effects of individual administration of the compound of the application and one or more additional therapeutic agent(s).

The additional active ingredients may be administered in a separate pharmaceutical composition from a compound of the present application or may be included with a compound of the present application in a single pharmaceutical composition. The additional active ingredients may be administered simultaneously with, prior to, or after administration of a compound of the present application. Actual dosage levels of the active ingredients in the pharmaceutical compositions may be varied so as to obtain an amount of the active ingredient that is effective to achieve the desired therapeutic response for a particular subject, such as a patient, composition, and mode of administration, without being toxic to the subject.

Combination agents include additional active ingredients are those that are known or discovered to be effective in treating the diseases and disorders described herein, including those active against another target associated with the disease. For example, compositions and formulations of the application, as well as methods of treatment, can further comprise other drugs or pharmaceuticals, e.g., other active agents useful for treating or palliative for the target diseases or related symptoms or conditions. For example, additional active ingredients include those that are known to be useful for enhancing sleep quality and preventing and treating sleep disorders and sleep disturbances, anti-diabetic agents, cardiovascular therapies, anti-obesity agents, other orexin receptor antagonists, pain medications, anti-depressants, anti-anxiety agents, cognition-enhancing agents, anti-Alzheimer's Disease therapies, and other active ingredients. Exemplary active pharmaceutical ingredients and other therapies that are suitable for combination with the presently described compounds include those listed in PCT Publ. No. WO2008/147518 at pages 23-29, which is hereby incorporated by reference. The pharmaceutical compositions of the any compound described herein may additional comprise one or more of such active agents, and methods of treatment may additionally comprise administering an effective amount of one or more of such active agents.

EXAMPLES

The following examples are offered to illustrate but not to limit the application. One of skill in the art will recognize that the following synthetic reactions and schemes may be modified by choice of suitable starting materials and reagents in order to access other compounds of Formula (I), (Ia), (Ib), (II), (IIa), (III), (IIIa), (IV), (IVa), (V), or (Va), or a pharmaceutically acceptable salt thereof.

Example 1: Synthetic Protocols

Exemplary chemical entities useful in methods of the application will now be described by reference to illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Furthermore, one of skill in the art will recognize that the transformations shown in the schemes below may be performed in any order that is compatible with the functionality of the particular pendant groups. Each of the reactions depicted in the general schemes is preferably run at a temperature from about 0° C. to the reflux temperature of the organic solvent used. Unless otherwise specified, the variables are as defined above in reference to Formula (I), (Ia), (Ib), (II), (IIa), (III), (IIIa), (IV), (IVa), (V), or (Va). Isotopically labeled compounds as described herein are prepared according to the methods described below, using suitably labeled starting materials. Such materials are generally available from commercial suppliers of radiolabeled chemical reagents.

TERMS AND ABBREVIATIONS

ACN acetonitrile;
aq aqueous;
Atm atmospheric pressure;
Boc t-butoxycarbonyl;
Borax di-sodium tetraborate or sodium borate or sodium tetraborate;
Cbz benzyloxycarbonyl;
CDI 1,1'-carbonyldiimidazole;
DAST Diethylaminosulfur trifluoride
dba dibenzylideneacetone;
DCM dichloromethane;
DEA diethylamine;
DIBAL-H diisobutylaluminium hydride;
DIPEA diisopropylethylamine;
DME 1,2-dimethoxyethane;
DMF N,N-dimethyl formamide;
DMSO dimethyl sulfoxide;
$Et_2O$ diethyl ether;

EtOAc ethyl acetate;
EtOH ethanol;
eq. or equiv. equivalent;
h hour(s);
HATU 2-(7-aza-1H-benzotriazole-1-yl)-1,1,3,3-tetramethyluronium hexafluorophosphate;
HBTU O-benzotriazole-N,N,N',N'-tetramethyluronium hexafluorophosphate
HPLC high performance liquid chromatography;
LCMS liquid chromatography mass spectrometry;
LDA lithium diisopropylamide;
LiHMDS lithium bis(trimethylsilyl)amide;
MeOH methanol;
min minute(s);
MS mass spectrometry;
MW microwave(s);
NH₄OAc ammonium acetate;
NMR nuclear magnetic resonance;
ox oxidation;
Psi pounds per square inch;
quant. quantitative;
RCM ring closing metathesis;
r.t. room temperature;
sat. saturated;
SFC supercritical fluid chromatography;
T3P propylphosphonic anhydride;
TFA trifluoroacetic acid;
THF tetrahydrofuran;
TLC thin layer chromatography;
TMEDA tetramethylethylenediamine;
UPLC ultra performance liquid chromatography.

General Synthetic Scheme

In some embodiments, compounds of formula (I), (Ia), (Ib), (II), (IIa), (III), (IIIa), (IV), (IVa), (V), or (Va) of the application, wherein both X and X' are F and Z is NR², can be prepared according to the general synthetic scheme shown in Scheme 1.

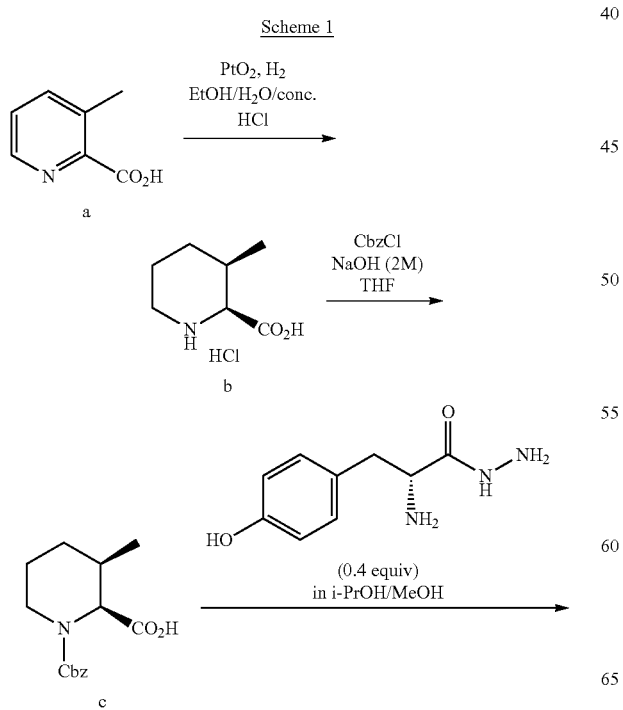

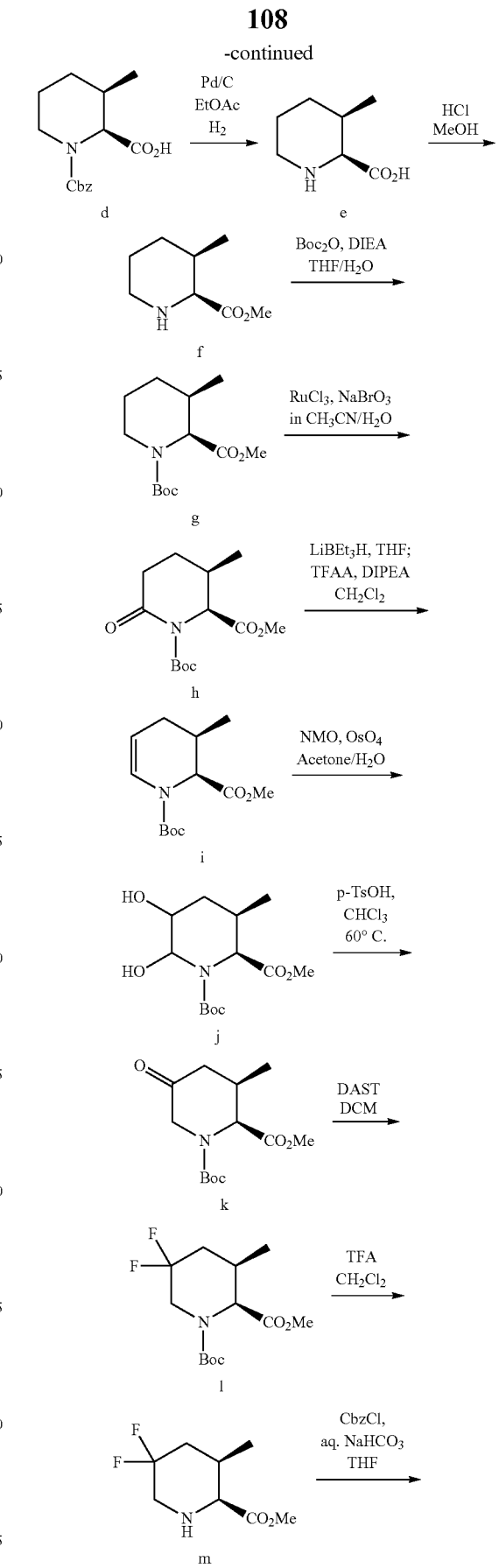

-continued
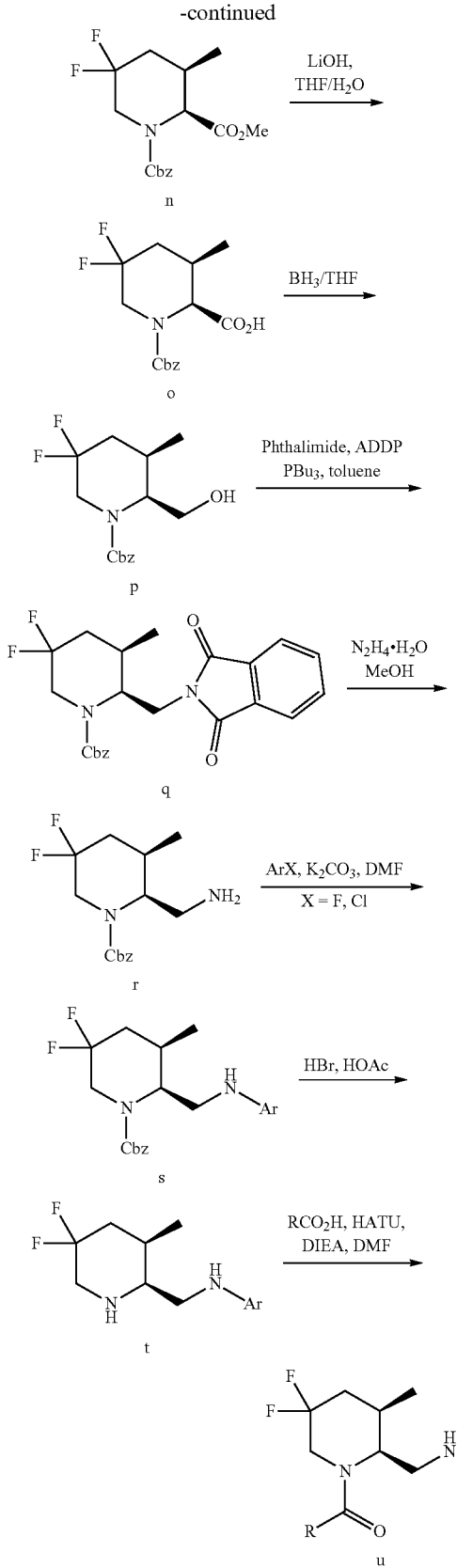
application, wherein X is F, X' is H and Z is NR², can be prepared according to the general synthetic scheme shown in Scheme 2.
Scheme 2
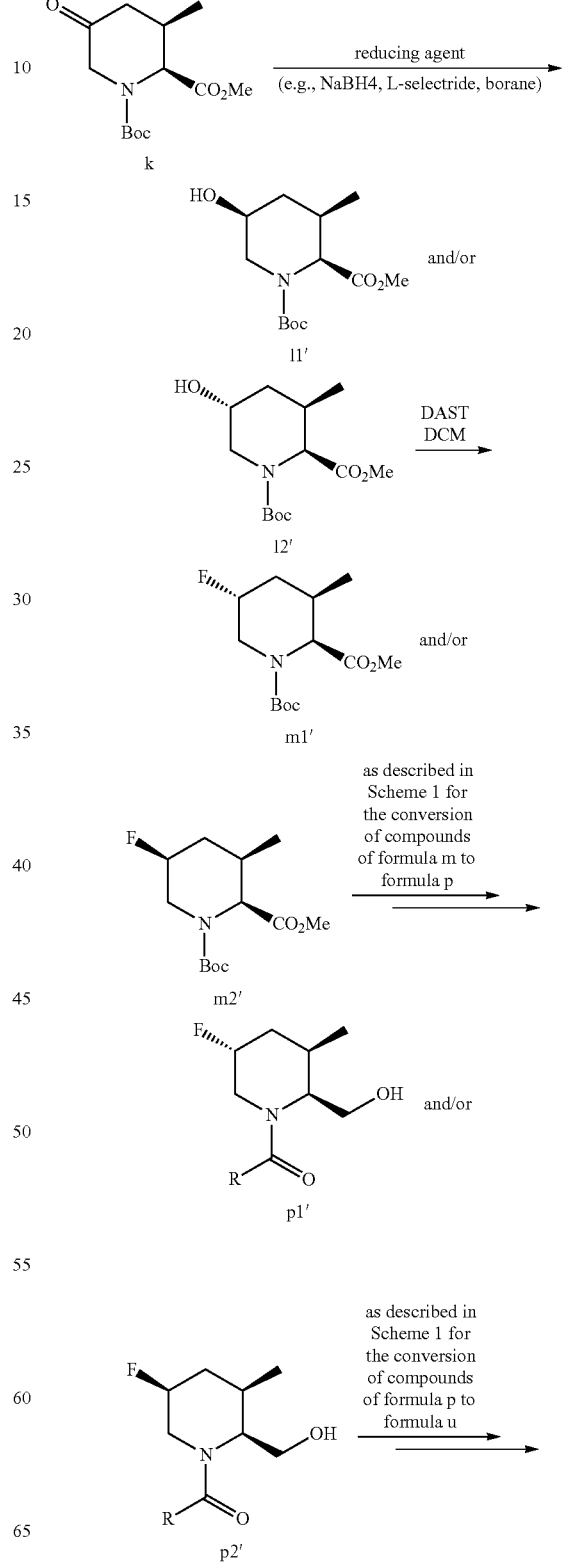
In some embodiments, compounds of formula (I), (Ia), (II), (IIa), (III), (IIIa), (IV), (IVa), (V), or (Va) of the

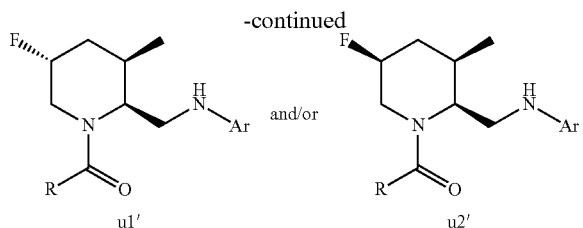

In some embodiments, compounds of formula (I), (Ia), (Ib), (II), (IIa), (III), (IIIa), (IV), (IVa), (V), or (Va) of the application, wherein X is F, X' is H or halogen, such as F, and Z is O, can be prepared according to the general synthetic scheme shown in Scheme 3.

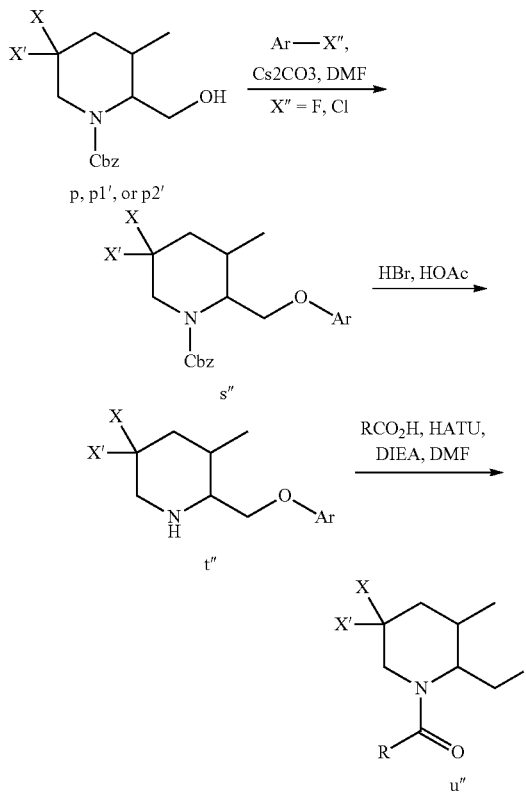

Synthesis of Compounds (b)-(u)

3-Methylpiperidine-2-carboxylic acid hydrochloride (b)

$PtO_2$ (10 g, 44.0 mol) was added to the mixture of 3-Methylpicolinic acid (100 g, 730 mmol) in 2 L of EtOH/$H_2O$ (1/1) with 200 mL of conc. HCl (36% wt). The reaction was stirred at RT under a hydrogen atmosphere at 3 MPa for 25 h, $^1$H-NMR indicated completion of reaction. The reaction was filtered through diatomaceous earth (ca. 1 cm) and concentrated to yield the title compound as a white solid (131 g, 730 mmol, 100%), which was used for next step without further purification. $^1$H NMR (MeOD, 400 MHz) δ 4.13-4.11 (m, 1H), 3.40-3.33 (m, 1H), 3.05-2.99 (m, 1H), 2.61-2.58 (m, 1H), 1.92-1.72 (m, 4H), 1.09 (d, J 7.0 Hz, 3H).

1-(Benzyloxycarbonyl)-3-methylpiperidine-2-carboxylic acid (c)

Compound b (79 g, 0.44 mol) was dissolved in 2 M NaOH/THF (1/1 v/v, 1500 mL) and cooled to 0° C. Benzyl chloroformate (113 g, 0.67 mol) was then added dropwise and the reaction was stirred at RT for 48 h. The reaction was concentrated to remove the THF, and then extracted with toluene (3×100 mL) to remove excess CbzCl and benzyl alcohol. The organic layer was discarded. The aqueous layer was acidified (pH~2) with conc. HCl and the product was extracted with EtOAc (150 mL×4), dried over $MgSO_4$, filtered, and concentrated in vacuo. The resulting colorless oil slowly solidified (103 g, 84%) and was used in the next step without further purification. $^1$H NMR (CDCl$_3$, 400 MHz) δ 7.40-7.37 (m, 5H), 5.19 (m, 2H), 4.95-4.72 (m, 1H), 4.14-4.03 (m, 1H), 3.36-3.25 (m, 1H), 1.93-1.53 (m, 5H), 1.20-1.05 (m, 3H). ESI-MS (m/z): 263.93 [M+1]$^+$.

(2S,3R)-1-(Benzyloxycarbonyl)-3-methylpiperidine-2-carboxylic acid (d)

Compound c (55 g, 0.20 mmol) was dissolved in i-PrOH (400 mL). D-Tyrosine Hydrazide (23 g, 0.12 mol) was added to give a heterogenous mixture which was heated to reflux. MeOH was added in 100 mL portions until a homogenous solution was formed. The reaction was stirred for 1 h at this temperature evaporating off some of the MeOH in the process. When the reaction just becomes cloudy, heating was turned off, and the reaction was allowed to cool to rt with vigorous stirring which yielded a thick slurry. The reaction mixture was filtered and washed with i-PrOH (100 mL) to yield a colorless solid (~40 g, ee ~94%). Recrystallization from IPA/MeOH afforded a colorless solid (36 g, >99% ee, 38%).

The colorless solid was dissolved in EtOAc (400 mL) and washed with 1 M HCl (100 mL×3), brine (100 mL) and dried over $MgSO_4$. Removal of solvent under reduced pressure afforded a colorless oil as compound d (>99.% ee, 21 g) which slowly solidified.

(2S,3R)-3-methylpiperidine-2-carboxylic acid (e)

To a solution of compound d (51 g, 0.18 mol) in EtOAc under argon was added cat. 10% Pd/C. The reaction was evacuated and purged with hydrogen (2×) from a balloon, and then stirred under a balloon of $H_2$ until starting material was consumed as judged by reverse-phase analytical HPLC (~30 h). The reaction mixture was filtered through celite. The celite was washed well with hot MeOH. The combined filtrates were concentrated in vacuo to yield the title compound e as a near colorless solid (25.5 g, 99%) which was used without further purification. $^1$H NMR (MeOD, 400 MHz) δ 3.58 (d, 1H), 3.3 (m, 1H), 2.95-2.85 (m, 1H), 2.60-2.50 (m, 1H), 1.91-1.62 (m, 4H), 1.16 (d, 3H).

(2S,3R)-methyl 3-methylpiperidine-2-carboxylate, chloride salt (f)

Excess HCl in MeOH (from AcCl and MeOH) was added to the crude amino acid compound e (25.5 g) from the previous step and the solution was warmed to reflux until starting material was consumed. An aliquot was removed after 12 h and concentrated in vacuo-crude $^1$H-NMR indicated complete conversion. The reaction was then concentrated in vacuo to afford the title compound as a pale yellow solid (34 g, 100% yield) which was used without further purification. ¹H NMR (MeOD, 400 MHz) δ 4.22 (m, 1H), 3.9 (s, 3H), 3.42-3.38 (m, 1H), 3.10-3.0 (m, 1H), 2.63-2.55 (m, 1H), 1.97-1.70 (m, 4H), 1.03 (d, 3H).

(2S,3R)-1-tert-Butyl 2-methyl 3-methylpiperidine-1,2-dicarboxylate (g)

To a solution of the crude salt compound f (34 g, 0.176 mol) from the previous step in THF (350 mL)/H₂O (250 mL) at 0° C. was added DIEA (92 mL, 3 eq) followed by BOC₂O (76 g, 2 eq). The reaction was allowed to warm to rt O/N and stirred for ~24 h. The reaction was then concentrated to remove the THF, and then diluted with EtOAc, and washed with 1M HCl (3×), NaHCO₃ (1×), brine, dried (MgSO₄) and concentrated. The resulting crude colorless oil was contaminated with BOC₂, but was used without further purification. 1H NMR (CDCl3, 400 MHz) δ 4.65 (br s, 1.0H), 4.0-3.9 (m, 1.0H), 3.69 (s, 3.0H), 3.3-3.15 (m, 1.0H), 1.9-1.8 (m, 1.0H), 1.8-1.65 (m, 1.0H), 1.65-1.5 (m, 3.0H), 1.44 (s, 9.0H), 1.01 (d, 3.0H) ppm; ESI-MS (m/z): 280.89 [M+Na]+.

(2S,3R)-1-tert-Butyl 2-methyl 3-methyl-6-oxopiperidine-1,2-dicarboxylate (h)

To a 0° C. solution of the crude carbamate compound g from the previous step and RuCl₃ (400 mg, 1 mol %) in CH₃CN (150 mL) was added dropwise a solution of NaBrO₃ (42 g, 0.28 mol) in water (250 mL). The reaction was stirred at rt for 6 h, and was then diluted with EtOAc and water. The layers were separated and the aqueous phase was extracted with EtOAc (2×). The combined organics were washed with sat aq. NaHSO₃, brine, dried (MgSO₄), and concentrated in vacuo. The crude oil was purified by chromatography on SiO₂ (EtOAc/hex) to afford the title compound as a colorless solid (39.2 g, 79% from e). ¹H NMR (MeOD, 400 MHz) δ 4.45 (d, 1H), 3.7 (s, 3H), 2.6-2.5 (m, 1H), 2.41-2.23 (m, 2H), 1.7-1.62 (m, 1H), 1.55-1.45 (m, 1H), 1.42 (s, 9H), 0.96 (d, 3H).

(2S,3R)-1-tert-Butyl 2-methyl 3-methyl-3,4-dihydropyridine-1,2(2H)-dicarboxylate (i)

To the solution of compound h (39.2 g, 0.145 mol) in THF (400 mL) at −78° C. was added LiBEt₃H (1.0 M in THF, 1.1 eq) dropwise. The reaction was stirred at −78° C. for 2 h, and then quenched with sat. aq NH₄Cl and warmed to rt and diluted with EtOAc. The layers were separated, and the aqueous layer was extracted with EtOAc (2×). The combined organics were washed with brine, dried (MgSO₄), and concentrated.

To a solution of the resulting crude colorless oil in CH₂C₂ (1 L) at −78° C. was added DIEA (101 mL, 4 eq) followed by the dropwise addition of TFAA (41 mL, 2 eq). The reaction was stirred at −78° C. for 3 h, and then slowly warmed to rt and monitored for disappearance of sm by tlc analysis. When the reaction was judged complete, it was cooled to 0° C. and quenched with sat. aq NaHCO₃. The layers were separated. The organic layer was washed with NaHCO₃, brine, dried (MgSO₄) and concentrated in vacuo. Purification on SiO₂ (EtOAc/hex) afforded the title compound as a near colorless oil which solidified (33 g, 89%). ¹H NMR (D₆-DMSO, 400 MHz) δ 6.7 (br dd, 1H), 4.85 (dt, 1H), 4.52 (dd, 1H), 3.67 (s, 1.6H), 3.63 (s, 1.4H), 2.15-2.06 (m, 1H), 2.02-1.94 (m, 1H), 1.7-1.6 (m, 1H), 1.45 (s, 4.5H), 1.4 (s, 4.5H), 1.05 (dd, 3H).

(2S,3R)-1-tert-Butyl 2-methyl 5,6-dihydroxy-3-methylpiperidine-1,2-dicarboxylate (j)

To a 0° C. solution of enamide compound i (33 g, 0.13 mol) and NMO (23 g, 0.19 mol) in acetone (300 mL) and H₂O (200 mL) was added OsO₄ (4% wt in H₂O, 1 mol %). The reaction was allowed to warm to rt O/N whereupon the reaction was judged complete by tlc analysis. The reaction was quenched with sat aq NaHSO₃ and diluted with EtOAc. The layers were separated. The aqueous layer was extracted with EtOAc (2×). The combined organics were washed with sat aq NaHSO₃, brine, dried (MgSO₄), and concentrated to give crude diol as a near colorless solid which was used without further purification (35.9 g). 1H NMR (DMSO-d6, 400 MHz) δ 5.86 (br s, 1.0H), 5.37 (br s, 1.0H), 4.67 (d, 1.0H), 4.05 (d, 1.0H), 3.90-3.83 (m, 1.0H), 3.62 (s, 3.0H), 2.67 (br s, 1.0H), 1.58-1.51 (m, 1.0H), 1.41-1.36 (m, 1.0H), 1.35 (s, 9.0H), 0.88 (d, 3.0H) ppm; ESI-MS (m/z): 312.90 [M+Na]+.

(2S,3R)-1-tert-Butyl 2-methyl 3-methyl-5-oxopiperidine-1,2-dicarboxylate (k)

To a solution of crude diol compound j in CHCl₃ (0.8 L) was added p-TsOH (200 mg). The reaction was warmed to 60° C. and monitored for disappearance of sm by tlc analysis (1-3 h). The reaction was cooled to rt, and washed with sat aq NaHCO₃ (2×), dried (MgSO₄), and concentrated in vacuo. The crude ketone was purified by chromatography on SiO₂ (EtOAc/hex) to give the title compound as a pale yellow oil (31.1 g, 88% for 2 steps). ¹H NMR (CDC₃, 400 MHz) δ 4.8 (br s, 0.6H), 4.6 (br s, 0.4H), 4.20-4.10 (m, 2H), 3.83 (s, 3H), 2.60-2.3 (m, 3H), 1.48 (br s, 9H). 1.12 (br s, 3H).

(2S,3R)-1-tert-Butyl 2-methyl 5,5-difluoro-3-methylpiperidine-1,2-dicarboxylate (l)

DAST (64 g, 0.4 mol) was added to a solution of compound k (31.1 g, 0.11 mol) in CH₂Cl₂ (110 mL) at 0° C. After stirring overnight at RT, the reaction was carefully quenched into a 0° C. mixture of CH₂Cl₂/sat aq NaHCO₃ and then warmed to rt. The layers were separated and the organic layer was washed with sat aq NaHCO₃, dried (MgSO₄), and concentrated. The crude residue was purified by chromatography on SiO₂ (EtOAc/hex) to give the title compound as a near colorless oil (26.8 g, 79%). ¹H NMR (CDCl₃, 400 MHz) δ 4.9 (br s, 0.6H), 4.65 (br s, 0.4H), 4.33-4.18 (m, 1H), 3.75 (s, 3H), 3.7-3.55 (m, 1H), 2.283 (br s, 1H), 2.1-1.86 (m, 2H), 1.49 (s, 9H). 1.2 (d, 3H).

(2S,3R)-Methyl 5,5-difluoro-3-methylpiperidine-2-carboxylate (m)

To a solution of compound 1 (10 g, 0.034 mol) in CH₂Cl₂ (150 mL) at 0° C. was added TFA (50 mL). The reaction was allowed to warm to rt and monitored for disappearance of sm by tlc analysis (3-4 h). When complete, the reaction was concentrated in vacuo to give an oil which was used without further purification. ¹H NMR (MeOD, 400 MHz) δ 4.22 (m, 1H), 3.9 (s, 3H), 3.42-3.38 (m, 1H), 3.10-3.0 (m, 1H), 2.63-2.55 (m, 1H), 1.97-1.70 (m, 4H), 1.03 (d, 3H).

(2S,3R)-1-Benzyl 2-methyl 5,5-difluoro-3-methylpiperidine-1,2-dicarboxylate (n)

To a 0° C. solution of crude compound m in THF/sat aq NaHCO₃ (400 mL, 1:1 v/v) was added CbzCl (14.6 g, 0.085 mol). The reaction was allowed to warm to rt O/N, and was then diluted with EtOAc. The layers were separated. The aqueous layer was extracted with EtOAc (2×). The combined organics were washed with brine, dried (MgSO$_4$) and concentrated. The crude residue was purified by chromatography on SiO$_2$ (EtOAc/hex) to give the title compound as a near colorless oil (10.7 g, 96% 2 steps). 1H NMR (CDCl3, 400 MHz) δ 7.5-7.3 (m, 5H), 5.3-5.1 (m, 2H), 5.0-4.9 (m, 0.6H), 4.85-4.75 (m, 0.4H, 4.5-4.35 (m, 1H), 3.8-3.8 (m, 3H), 3.7-3.5 (m, 1H), 2.4-2.25 (m, 1H), 2.2-1.9 (m, 2H), 1.15-1.0 (m, 3H).

(2S,3R)-1-(Benzyloxycarbonyl)-5,5-difluoro-3-methylpiperidine-2-carboxylic acid (o)

To a 0° C. solution of compound n (10.7 g) in THF (150 mL) was added 1M LiOH (100 mL). The reaction was allowed to warm to rt O/N. The reaction was diluted with EtOAc, and acidified with 1M HCl until pH ~3. The layers were separated, and the organic phase was washed with brine, dried (MgSO$_4$) and concentrated in vacuo to give a near colorless oil. The crude acid (9.8 g, 96%) was used without further purification. $^1$H NMR (MeOD, 400 MHz) δ 7.4-7.3 (m, 5H), 5.3-5.1 (m, 2H), 4.85-4.75 (m, 1H), 4.3-4.2 (m, 1H), 3.78-3.5 (m, 1H), 2.35-2.2 (m, 1H), 2.15-2.02 (m, 1H), 2.0-1.85 (m, 1H), 1.15 (t, 3H).

(2S,3R)-benzyl 5,5-difluoro-2-(hydroxymethyl)-3-methylpiperidine-1-carboxylate (p)

To a 0° C. solution of compound o (9.8 g, 0.031 mol) in THF (100 mL) was added BH$_3$/THF (1.0 M, 47 mL). The reaction was allowed to warm to rt and monitored by reverse-phase HPLC. Additional BH$_3$/THF (15 mL) was added. After an additional 6 h, sm was consumed by HPLC. The reaction was quenched with MeOH, and concentrated in vacuo. The crude colorless oil was taken up in EtOAc and washed with 1M HCl (2×), brine, dried (MgSO$_4$) and concentrated to give the title compound (8.8 g, 94%) as a colorless oil, which was used without further purification. ESI-MS (m/z): 300.29 [M+1]$^+$. 1H NMR (D6-DMSO, 400 MHz) δ 7.4-7.3 (m, 5H), 5.2-5.1 (q, 2H), 4.85-4.7 (m, 1H), 4.5 (d, 0.36H), 4.25-4.1 (m, 1.64H), 3.8-3.7 (m, 1H), 3.6-3.5 (m, 1H), 3.5-3.2 (m, 1H), 2.1-1.9 (m, 2H), 1.0 (br s, 3H).

(2S,3R)-benzyl 2-((1,3-dioxoisoindolin-2-yl)methyl)-5,5-difluoro-3-methylpiperidine-1-carboxylate (q)

To a solution of crude compound p (8.8 g, 0.03 mol) in dry toluene (100 mL) was added ADDP (14.9 g, 0.059 mol) followed by PBu$_3$ (17.9 g, 0.089 mol). After stirring at rt for 45 min, phthalimide (6.5 g, 0.044 mol) was added and the reaction mixture was warmed to 80° C. O/N. After 12 h, starting alcohol compound p was consumed as judged by reverse-phase analytical HPLC analysis. The reaction mixture was cooled to rt, filtered through a SiO$_2$ pad (washing with toluene), and concentrated in vacuo. The resulting crude oil was purified by chromatography on SiO$_2$ (EtOAc/hex) to afford the title compound (11 g, ~87%) contaminated by phthalimide. [The phthalimide could be removed by dissolving in EtOAc and washing with 1M NaOH, but it is also removed in the next step.] ESI-MS (m/z): 429.40 [M+1]$^+$. H NMR (D$_6$-DMSO, 400 MHz) δ 7.9-7.8 (m, 4H), 7.35-7.2 (m, 2H), 7.18-7.1 (m, 1H), 7.1-7.0 (m, 1H), 6.9 (d, 1H), 4.85-4.7 (m, 1.5H), 4.5 (d, 1H), 4.48-4.35 (m, 0.5H), 4.25-4.1 (m, 2H), 3.7-3.45 (m, 2H), 2.25-2.0 (m, 3H), 1.1 (t, 3H).

(2S,3R)-Benzyl 2-(aminomethyl)-5,5-difluoro-3-methylpiperidine-1-carboxylate (r)

Hydrazine (6.2 mL, 5 eq) was added to a solution of compound q (11 g, 23 mmol) in MeOH (150 mL). The reaction was warmed to 80° C. for 2 h wherein sm was consumed as judged by reverse-phase analytical HPLC analysis. The reaction mixture was cooled and concentrated in vacuo. The crude residue was taken up in EtOAc and washed with sat aq NaHCO$_3$ (4×), brine, dried (MgSO$_4$), and concentrated in vacuo to give the title compound (6.9 g, 90%) as a pale yellow oil which was used without further purification. %). ESI-MS (m/z): 299.3 [M+1]$^+$.

(2S,3R)-benzyl 5,5-difluoro-3-methyl-2-(((5-(trifluoromethyl)pyrimidin-2-yl)amino)methyl)piperidine-1-carboxylate (s)

(Synthetic procedure is given for the compound in which ArX is 2-Cl-5-CF$_3$-pyrimidine.) To a mixture of the crude amine compound r (2.2 g, 7.4 mmol) and K$_2$CO$_3$ (2 g, 14.8 mmol) in DMF (20 mL) was added 2-Cl-5-CF$_3$-pyrimidine (2 g, 11.1 mmol). The reaction was warmed to 80° C. for 2 h wherein the starting material was judged consumed as indicated by reverse-phase analytical HPLC. The reaction was cooled, and diluted with EtOAc, and water. The layers were separated, and the organic phase was washed with water (3×), brine, dried (MgSO$_4$) and concentrated. The crude residue was purified by chromatography on SiO$_2$ (EtOAc/hex) to give the title compound as a pale yellow solid (2.4 g, 75%). ESI-MS (m/z): 445.4 [M+1]$^+$.

(2S,3R)-5,5-difluoro-3-methyl-2-(((5-(trifluoromethyl)pyrimidin-2-yl)amino)methyl)piperidin-1-ium bromide (t)

(Synthetic procedure is given for the compound in which Ar is 5-CF$_3$-pyrimidine.) Carbamate compound s (2.4 g, 5.4 mmol) was added to 30% HBr in HOAc (15 mL). The reaction was stirred at rt (1-3 h) until sm was consumed as judged by HPLC analysis. The reaction was concentrated in vacuo to give the title compound as a pale yellow foam (2.1 g, ~100%) and was used without purification. $^1$H NMR (D$_6$-DMSO, 400 MHz) δ 9.7 (br s, 1H), 9.15 (br s, 1H), 8.7 (s, 2H), 8.15 (t, 1H), 3.92-3.7 (m, 1H), 3.7-3.5 (m, 4H), 2.4-2.05 (m, 3H), 1.1 (d, 3H).

Compound (u)

To a solution of compound t, HATU (1.5 eq), and a carboxylic acid (1.2 eq) in DMF was added DIEA (3 eq). When the starting amine was consumed as judged by HPLC (anywhere from 30 min to 24 h depending on the acid used), the reaction was diluted with EtOAc, and washed with sat aq NaHCO$_3$, brine, dried (MgSO$_4$), and concentrated. The crude residue was purified by chromatography on SiO₂ (EtOAc/hex) to give the desired compound.
Exemplary carboxylic acids include compounds aa-cv.

Compound aa: 4-(5-fluoropyrimidin-2-yl)-1-methyl-1H-pyrazole-3-carboxylic acid

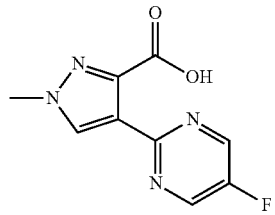 [SMILES: Cn1cc(-c2ncc(F)cn2)c(C(=O)O)n1]

Step 1: ethyl 4-iodo-1H-pyrazole-3-carboxylate

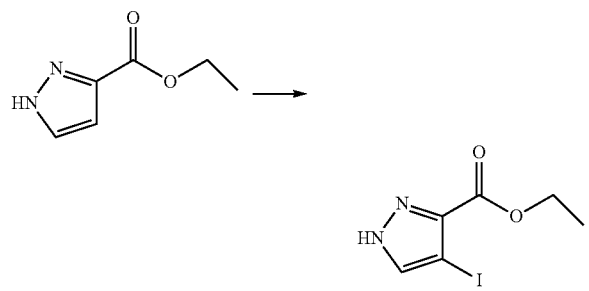

To a solution of ethyl 1H-pyrazole-3-carboxylate (2 g, 14.3 mol, 1.0 eq) and I₂ (3.6 g, 14.3 mmol, 1.0 eq) in ACN (14 mL) was added CAN (1.6 g, 2.86 mmol, 0.2 eq) at RT. The reaction mixture was stirred at RT overnight, and was monitored by reverse-phase analytical HPLC. When starting material was consumed, the reaction mixture was concentrated in vacuo to afford a crude solid which was slowly poured into a saturated Na₂S₂O₃ solution and H₂O (1:1) with stirring. The light-yellow suspension was filtered and the filter cake was washed with H₂O. The resulting near colorless solid was dried under vacuum and used without further purification. ¹H NMR (400 MHz, CDCl₃) δ 7.86 (s, 1H), 4.46 (q, J=7.2 Hz, 2H), 1.45 (t, J=7.2 Hz, 3H).

Step 2: 4-iodo-1-methyl-1H-pyrazole-3-carboxylic acid

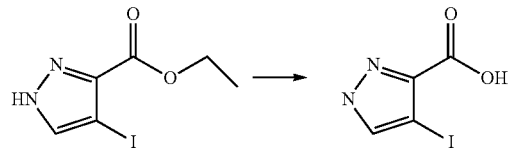

NaH (60% dispersion in mineral oil, 0.72 g, 18 mmol, 1.2 eq) was added in portions to a mixture of ethyl 4-iodo-1H-pyrazole-3-carboxylate (4.2 g, 15 mmol, 1.0 eq) and anhydrous THF (15 mL) at 0° C. Once addition of NaH was complete, the mixture was stirred for an additional 30 min at 0° C. and 1 h at RT. The mixture was re-cooled to 0° C. and then MeI (1.0 mL, 16.5 mmol, 1.1 eq) was added. When the reaction mixture solidified, the cold bath was removed and the mixture was maintained at RT for 1 h. When the starting material was consumed as judged by analytical HPLC, H₂O (0.5 mL) was added slowly to quench the reaction and then NaOH solution (2 M, 1.0 eq) was added slowly with stirring. The mixture was stirred at rt until hydrolysis of the ester was complete (~1-2 h). The light-yellow suspension was filtered and the resulting yellow solid was collected. The filtrate was concentrated in vacuo and then washed with hexanes to remove the mineral oil. The resulting aqueous layer and solid were combined and acidified with 6N HCl to pH 1~2. The aqueous was extracted with EtOAc (3×). The combined organics were washed with brine, dried (Na₂SO₄), and concentrated to afford the title acid as a pale yellow solid that was used without further purification.

Step 3: tert-butyl 4-iodo-1-methyl-1H-pyrazole-3-carboxylate

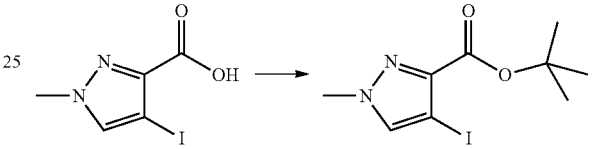

To a mixture of crude 4-iodo-1-methyl-1H-pyrazole-3-carboxylic acid (3.1 g, 12.5 mmol) and THF (15 mL) was added tert-BuOH (1.2 mL, 12.5 mol, 1.0 eq) and DMAP (0.30 g, 2.5 mmol, 0.2 eq) followed by (Boc)₂O (3.5 g, 16.2 mol, 1.3 eq) in portions. The mixture was stirred overnight at RT, and the reaction was monitored by analytical HPLC. When the acid was consumed, the reaction was concentrated in vacuo to afford a crude solid which was dissolved in EtOAc. The resulting organic solution was washed with 2N HCl (3×), H₂O, brine and dried (Na₂SO₄). The solvent was removed in vacuo to obtain the title compound as a pale yellow solid which was used without further purification. ¹H NMR (400 MHz, CDCl₃) δ 7.50 (s, 1H), 3.96 (s, 3H), 1.65 (s, 9H).

Step 4: (3-(tert-butoxycarbonyl)-1-methyl-1H-pyrazol-4-yl)boronic acid

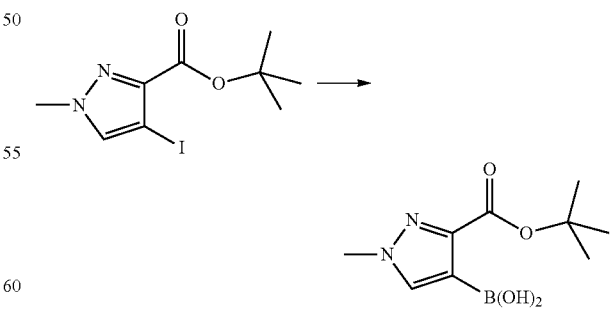

To a solution of crude tert-butyl 4-iodo-1-methyl-1H-pyrazole-3-carboxylate (1.6 g, 5.1 mmol, 1.0 eq) and B(Oi-Pr)₃ (1.8 mL, 7.7 mmol, 1.5 eq) in anhydrous THF (6 mL) at −78° C. under argon, was added n-BuLi (2.5M, 3.6 mL, 9.2 mmol) dropwise. The reaction was stirred at −78° C. and monitored by analytical HPLC for disappearance of starting material. When complete (1-2 h), H₂O (5 mL) was added slowly to quench the reaction and the resulting mixture was slowly warmed to RT. The mixture was then slowly poured into 2N HCl solution to bring the pH 2~3. The reaction mixture was diluted with EtOAc and the layers were separated. The aqueous layer was extracted with EtOAc (2×). The combined organic extracts were washed with brine, dried (Na₂SO₄) and concentrated to provide the crude boronic acid as a brown solid that was used without further purification.

Step 5: tert-butyl 4-(5-fluoropyrimidin-2-yl)-1-methyl-1H-pyrazole-3-carboxylate

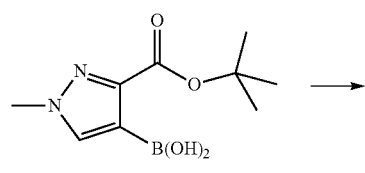

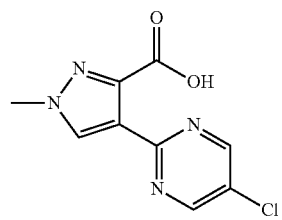 [SMILES: Cn1cc(-c2ncc(Cl)cn2)c(C(=O)O)n1]

To the crude boronic acid obtained from previous step was added DMF/H₂O (5:1, 9 mL), K₂CO₃ (1.0 g, 7.7 mmol, 1.5 eq) and 2-chloro-5-fluoropyrimidine (0.76 mL, 6.1 mmol, 1.2 eq). The mixture was degassed, and then Pd(PPh₃)₄ (0.18 g, 0.13 mmol, 0.025 eq) was added. The mixture was degassed and then heated overnight in an 80° C. oil bath under argon. The completion of the reaction was monitored by analytical HPLC. When complete, the reaction mixture was cooled to RT, and filtered through a celite pad to remove K₂CO₃ and Pd. The filter cake was washed with toluene. The filtrate was diluted with toluene was washed with H₂O and the layers were separated. The aqueous layer was extracted with toluene (2×). The combined organic layers were dried (Na₂SO₄) and concentrated to provide the crude as an amber oil that was used without further purification. ESI-MS (m/z): 278.58 [M+1]⁺.

Step 6: 4-(5-fluoropyrimidin-2-yl)-1-methyl-1H-pyrazole-3-carboxylic acid

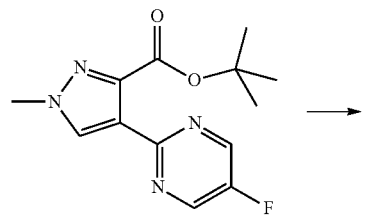

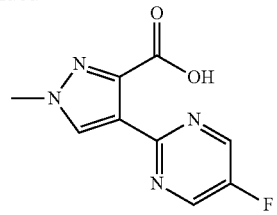

To a solution of the crude tert-butyl ester obtained from the previous step in DCM (2 mL) was added TFA (1.5 mL). The reaction mixture was stirred at RT monitoring by analytical HPLC for disappearance of starting material (3-4 h). When complete, the reaction was concentrated in vacuo to obtain the crude as a dark oil. Toluene was added and the reaction was concentrated in vacuo to remove residual TFA. The crude oil was cooled to 0° C. and MeOH was added with stirring. A suspension quickly formed and was stirred for an additional 1 h. The suspension was filtered and washed with cold MeOH to give the title compound as a near colorless solid. ¹H NMR (400 MHz, d-DMSO) δ 14.80 (broad, 1H), 9.10 (s, 2H), 8.55 (s, 1H), 4.00 (s, 3H); ESI-MS (m/z): 222.79 [M+1]⁺.

Compound ab: 4-(5-chloropyrimidin-2-yl)-1-methyl-1H-pyrazole-3-carboxylic acid

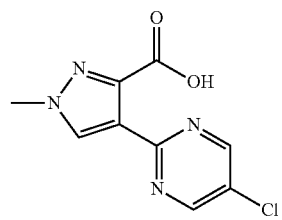 [SMILES: Cn1cc(-c2ncc(Cl)cn2)c(C(=O)O)n1]

Step 1: methyl 4-bromo-1-methyl-1H-pyrazole-3-carboxylate

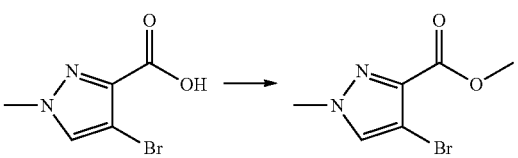

NaH (60% dispersion in mineral oil, 11.3 g, 282 mmol, 3.0 eq) was added in portions to a mixture of 4-bromo-1H-pyrazole-3-carboxylic acid (18 g, 94.2 mmol, 1.0 eq) in) anhydrous DMF (200 mL) at 0° C. under argon protection. Once addition of NaH was complete, the mixture was stirred for an additional 30 min at 0° C. and 1 h at RT. The mixture was re-cooled to 0° C. and then MeI (24 mL, 377 mmol, 4.0 eq) was added. The reaction mixture was diluted with EtOAc and washed with Sat'd NaHCO₃, brine and dried over Na₂SO₄. The organic layers were concentrated to provide the crude as solid that was used without further purification. ¹H NMR (400 MHz, CDCl₃) δ 7.87 (s, 1H), 3.96 (s, 3H), 3.88 (s, 3H).

Step 2: (3-(methoxycarbonyl)-1-methyl-1H-pyrazol-4-yl)boronic acid

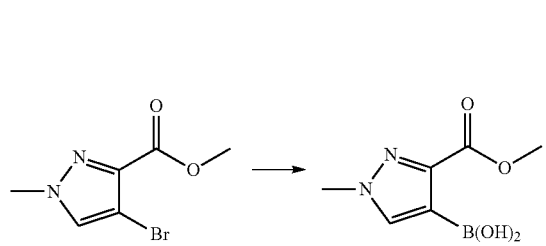

(3-(methoxycarbonyl)-1-methyl-1H-pyrazol-4-yl)boronic acid was prepared following the same general protocol as described for (3-(tert-butoxycarbonyl)-1-methyl-1H-pyrazol-4-yl)boronic acid using methyl 4-bromo-1-methyl-1H-pyrazole-3-carboxylate.

Step 3: methyl 4-(5-chloropyrimidin-2-yl)-1-methyl-1H-pyrazole-3-carboxylate

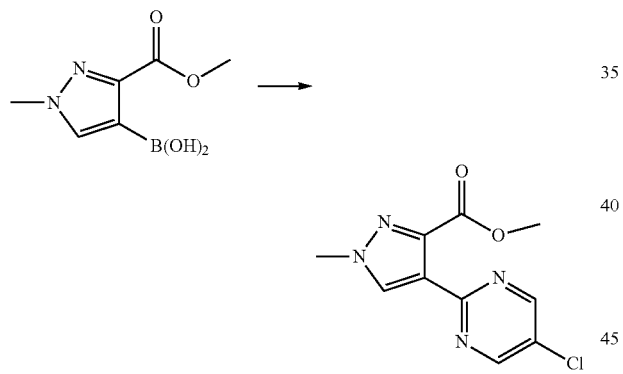

To the crude boronic acid (0.86 g, 4.14 mmol) obtained from previous step was added dioxane/H₂O (4:1, 42 mL), K₂CO₃ (1.714 g, 12.41 mmol, 3.0 eq) and 2,5-dichloropyrimidine (0.74 g, 4.14 mmol, 1.2 eq). The mixture was degassed, and then Pd(PPh₃)₄ (0.48 g, 0.41 mmol, 0.1 eq) was added. The mixture was degassed and then heated overnight in an 80° C. oil bath under argon. The completion of the reaction was monitored by analytical HPLC. When complete, the reaction mixture was cooled to RT, and filtered through a celite pad to remove K₂CO₃ and Pd. The filter cake was washed with EtOAc. The filtrate was diluted with EtOAc and washed with H₂O and the layers were separated. The aqueous layer was extracted with EtOAc (2×). The combined organic layers were concentrated to provide the crude which was purified by column chromatography on silica gel to obtain the desired product. ESI-MS (m/z): 252.97 [M+1]⁺.

Step 4: 4-(5-chloropyrimidin-2-yl)-1-methyl-1H-pyrazole-3-carboxylic acid

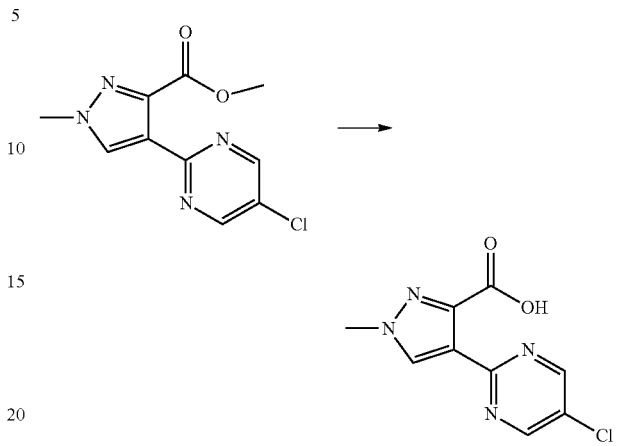

Methyl 4-(5-chloropyrimidin-2-yl)-1-methyl-1H-pyrazole-3-carboxylate (0.22 g, 0.873 mmol) in THF (5 mL) was added NaOH (1.0 M, 4 mL, 5.0 eq). The completion of the reaction was monitored by analytical HPLC. When complete, the reaction mixture was acidified to pH~2. The solvent was removed in vacuo. The crude was extracted with MeOH. The solvent was removed and the obtained acid was dried in vacuum for next step with no further purification. ESI-MS (m/z): 239.03 [M+1]⁺.

Compound ac: 1-methyl-4-(4-methylpyrimidin-2-yl)-1H-pyrazole-3-carboxylic acid

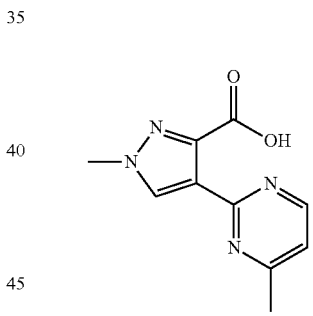

The title compound was synthesized following the same general protocol as described for 4-(5-chloropyrimidin-2-yl)-1-methyl-1H-pyrazole-3-carboxylic acid using (3-(methoxycarbonyl)-1-methyl-1H-pyrazol-4-yl)boronic acid and 2-chloro-4-methylpyrimidine. ESI-MS (m/z): 219.0 [M+1]⁺.

Compound ad: 1-methyl-4-(5-methylpyrimidin-2-yl)-1H-pyrazole-3-carboxylic acid

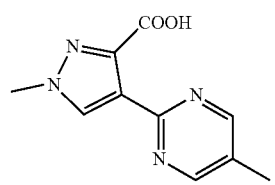

The title compound was synthesized following the same general protocol as described for 4-(5-chloropyrimidin-2-yl)-1-methyl-1H-pyrazole-3-carboxylic acid using (3-(methoxycarbonyl)-1-methyl-1H-pyrazol-4-yl)boronic acid and 2-chloro-5-methylpyrimidine. ESI-MS (m/z): 219.0 [M+1]⁺.

Compound ae: 1-methyl-4-(5-(trifluoromethyl)pyrimidin-2-yl)-1H-pyrazole-3-carboxylic acid

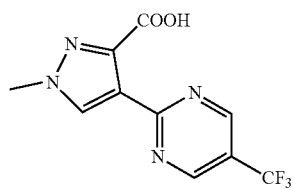 [SMILES: Cn1cc(-c2ncc(C(F)(F)F)cn2)c(C(=O)O)n1]

The title compound was synthesized following the same general protocol as described for 4-(5-chloropyrimidin-2-yl)-1-methyl-1H-pyrazole-3-carboxylic acid using (3-(methoxycarbonyl)-1-methyl-1H-pyrazol-4-yl)boronic acid and 2-chloro-5-(trifluoromethyl)pyrimidine. ESI-MS (m/z): 272.95 [M+1]⁺.

Compound af: 1-methyl-4-(pyrimidin-2-yl)-1H-pyrazole-3-carboxylic acid

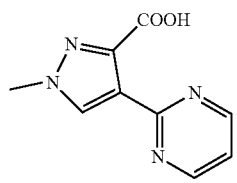

Step 1: methyl 1-methyl-4-(pyrimidin-2-yl)-1H-pyrazole-3-carboxylate

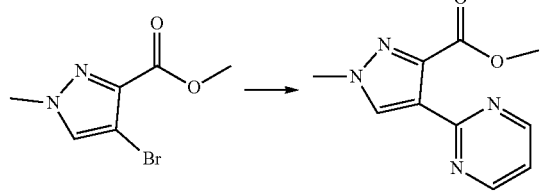

A mixture of methyl 4-bromo-1-methyl-1H-pyrazole-3-carboxylate (1.5 g, 6.84 mmol, 1.0 eq), 2-(tributylstannyl)pyrimidine (2.4 mL, 7.52 mmol, 1.1 eq), CsF (2.1 g, 13.67 mmol, 2.0 eq), Pd(PPh₃)₄ (0.79 g, 0.68 mmol, 0.1 eq) and CuI (0.13 g, 0.68 mmol, 0.1 eq) in DMF (120 mL) was degassed for 10 min and then heated overnight at oil bath at 110° C. The completion of the reaction was monitored by analytical HPLC. When complete, the mixture was cooled and concentrated. The crude was dissolved with EtOAc and washed with Sat'd NaHCO₃ and brine. The solvent was removed to obtain the crude, which was purified by silica gel to obtain the desired product. ESI-MS (m/z): 218.99 [M+1]⁺.

Step 2: 1-methyl-4-(pyrimidin-2-yl)-1H-pyrazole-3-carboxylic acid

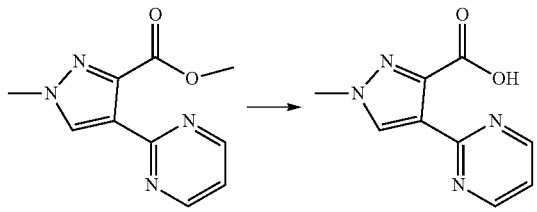

The acid was prepared following the same general protocol as described for 4-(5-chloropyrimidin-2-yl)-1-methyl-1H-pyrazole-3-carboxylic acid using methyl 1-methyl-4-(pyrimidin-2-yl)-1H-pyrazole-3-carboxylate. ESI-MS (m/z): 204.96 [M+1]⁺.

Compound a2: 1-methyl-4-(pyridin-2-yl)-1H-pyrazole-3-carboxylic acid

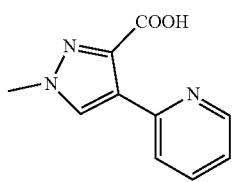

The title compound was made following the same general protocol as described for Compound af using methyl 4-bromo-1-methyl-1H-pyrazole-3-carboxylate and 2-(tributylstannyl)pyridine. ESI-MS (m/z): 203.93 [M+1]⁺.

Compound ah: 4-(5-fluoropyridin-2-yl)-1-methyl-1H-pyrazole-3-carboxylic acid

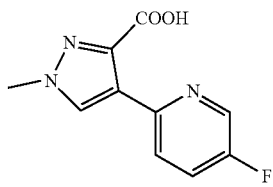 [SMILES: Cn1cc(-c2ccc(F)cn2)c(C(=O)O)n1]

Step 1: General Procedure for stannane synthesis: 5-fluoro-2-(tributylstannyl)pyridine

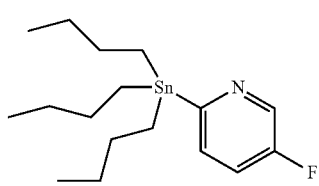 [SMILES: CCC[CH2][Sn]([CH2]CCC)([CH2]CCC)[c]1ccc(F)cn1]

To a solution of 2-bromo-5-fluoropyridine (2.42 g, 13.75 mmol, 1.0 eq) in THF (30 mL) was added n-BuLi (2.5 M in hexane, 5.5 mL, 13.75 mmol, 1.0 eq) and the mixture was stirred at −78° C. for 30 min under nitrogen atmosphere. n-Bu$_3$SnCl (4 mL, 14.58 mmol, 1.05 eq) was added and the mixture was stirred at the same temperature for another 2 h. Saturated ammonium chloride solution (150 mL) was added to the solution and extracted with ethyl acetate (150 mL×3). The combined organic layers were dried over Na$_2$SO$_4$, filtered and concentrated in vacuo. The crude 5-fluoro-2-(tributylstannyl)pyridine as a yellow oil was used without further purification.

Step 2: 4-(5-fluoropyridin-2-yl)-1-methyl-1H-pyrazole-3-carboxylic acid

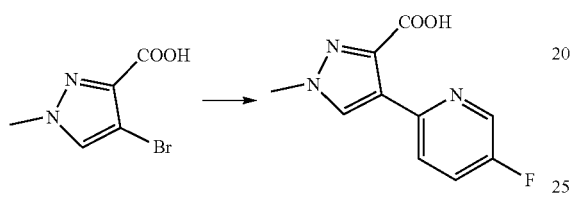

The title compound was made following the same general protocol as described for Compound af using methyl 4-bromo-1-methyl-1H-pyrazole-3-carboxylate and 5-fluoro-2-(tributylstannyl)pyridine. ESI-MS (m/z): 221.95 [M+1]$^+$.

Compound ai: 4-(3-fluoropyridin-2-yl)-1-methyl-1H-pyrazole-3-carboxylic acid

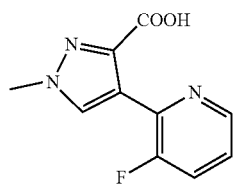 [SMILES: Cn1cc(-c2ncccc2F)c(C(=O)O)n1]

The title compound was made following the same general protocol as described for Compound af using methyl 4-bromo-1-methyl-1H-pyrazole-3-carboxylate and 3-fluoro-2-(tributylstannyl)pyridine ESI-MS (m/z): 221.95 [M+1]$^+$.

Compound aj: 1-methyl-4-(3-methylpyridin-2-yl)-1H-pyrazole-3-carboxylic acid

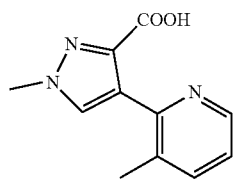 [SMILES: Cc1cccnc1-c1cn(C)nc1C(=O)O]

The title compound was made following the same general protocol as described for Compound af using methyl 4-bromo-1-methyl-1H-pyrazole-3-carboxylate and 3-methyl-2-(tributylstannyl)pyridine. ESI-MS (m/z): 217.92 [M+1]$^+$.

Compound ak: 1-methyl-4-(4-methylpyridin-2-yl)-1H-pyrazole-3-carboxylic acid

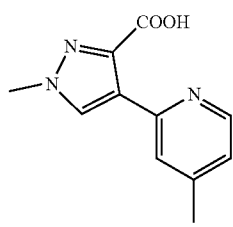 [SMILES: Cc1ccnc(-c2cn(C)nc2C(=O)O)c1]

The title compound was made following the same general protocol as described for Compound af using methyl 4-bromo-1-methyl-1H-pyrazole-3-carboxylate and 4-methyl-2-(tributylstannyl)pyridine. ESI-MS (m/z): 217.92 [M+1]$^+$.

Compound ak: 1-methyl-4-(5-methylpyridin-2-yl)-1H-pyrazole-3-carboxylic acid

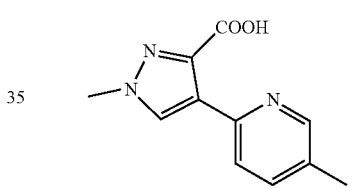

The title compound was made following the same general protocol as described for Compound af using methyl 4-bromo-1-methyl-1H-pyrazole-3-carboxylate and 5-methyl-2-(tributylstannyl)pyridine. ESI-MS (m/z): 217.92 [M+1]$^+$.

Compound am: 1-methyl-4-(6-methylpyridin-2-yl)-1H-pyrazole-3-carboxylic acid

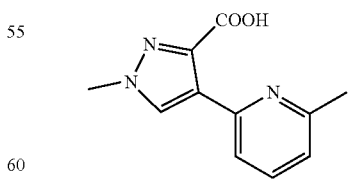

The title compound was made following the same general protocol as described for Compound af using methyl 4-bromo-1-methyl-1H-pyrazole-3-carboxylate and 2-methyl-6-(tributylstannyl)pyridine. ESI-MS (m/z): 217.92 [M+1]$^+$.

Compound an: 4-(6-methoxypyridin-2-yl)-1-methyl-1H-pyrazole-3-carboxylic acid

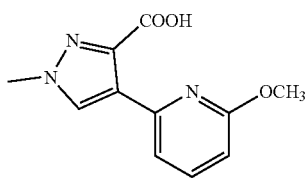 [SMILES: COc1cccc(-c2cn(C)nc2C(=O)O)n1]

The title compound was made following the same general protocol as described for Compound af using methyl 4-bromo-1-methyl-1H-pyrazole-3-carboxylate and 2-methoxy-6-(tributylstannyl)pyridine. ESI-MS (m/z): 233.94 [M+1]$^+$.

Compound ao: 1-methyl-4-(pyridin-3-yl)-1H-pyrazole-3-carboxylic acid

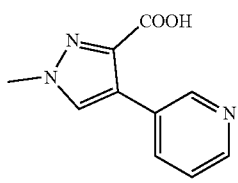

Step 1: methyl 1-methyl-4-(pyridin-3-yl)-1H-pyrazole-3-carboxylate

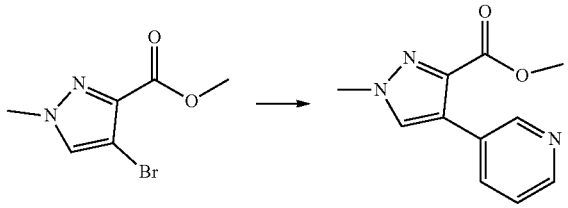

The mixture of methyl 4-bromo-1-methyl-1H-pyrazole-3-carboxylate (0.15 g, 0.684 mmol, 1.0 eq), pyridin-3-ylboronic acid (0.11 g, 0.89 mmol, 1.3 eq) and K$_2$CO$_3$ (0.28 g, 2.05 mmol, 3.0 eq) in dioxane/H$_2$O (4:1, 3 mL was degassed, and then Pd(PPh$_3$)$_4$ (0.08 g, 0.07 mmol, 0.1 eq) was added. The mixture was degassed and then heated for 30 min at 120° C. in a microwave reactor. The completion of the reaction was monitored by analytical HPLC. When complete, the reaction mixture was cooled to RT and diluted with EtOAc and washed with H$_2$O and the layers were separated. The aqueous layer was extracted with EtOAc (2×). The combined organic layers were concentrated to provide the crude which was purified by column chromatography on silica gel to obtain the desired product. ESI-MS (m/z): 218.08 [M+1]$^+$.

Step 2: 1-methyl-4-(pyridin-3-yl)-1H-pyrazole-3-carboxylic acid

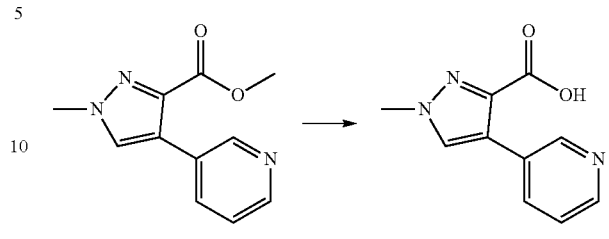

The acid was prepared following the same general protocol as described for 4-(5-chloropyrimidin-2-yl)-1-methyl-1H-pyrazole-3-carboxylic acid using methyl 1-methyl-4-(pyrimidin-2-yl)-1H-pyrazole-3-carboxylate. ESI-MS (m/z): 203.93 [M+1]$^+$.

Compound ap: 4-(2-fluorophenyl)-1-methyl-1H-pyrazole-3-carboxylic acid

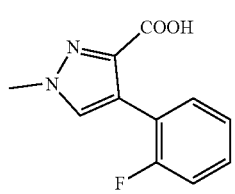 [SMILES: Cn1cc(-c2ccccc2F)c(C(=O)O)n1]

The title compound was made following the same general protocol as described for Compound ao using methyl 4-bromo-1-methyl-1H-pyrazole-3-carboxylate and (2-fluorophenyl)boronic acid ESI-MS (m/z): 220.84 [M+1]$^+$.

Compound aq: 4-(3-fluorophenyl)-1-methyl-1H-pyrazole-3-carboxylic acid

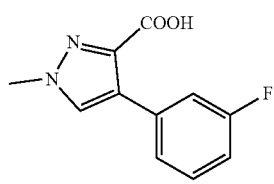 [SMILES: Cn1cc(-c2cccc(F)c2)c(C(=O)O)n1]

The title compound was made following the same general protocol as described for Compound ao using methyl 4-bromo-1-methyl-1H-pyrazole-3-carboxylate and (3-fluorophenyl)boronic acid. ESI-MS (m/z): 220.84 [M+1]$^+$.

Compound ar: 1-methyl-4-(p-tolyl)-1H-pyrazole-3-carboxylic acid

The title compound was made following the same general protocol as described for Compound ao using methyl 4-bromo-1-methyl-1H-pyrazole-3-carboxylate and p-tolyl-boronic acid. ESI-MS (m/z): 216.83 [M+1]$^+$.

Compound as:
1-methyl-4-(o-tolyl)-1H-pyrazole-3-carboxylic acid

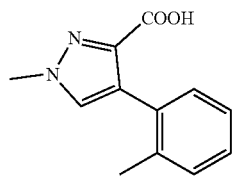 [SMILES: Cc1ccccc1-c1cn(C)nc1C(=O)O]

The title compound was made following the same general protocol as described for Compound ao using methyl 4-bromo-1-methyl-1H-pyrazole-3-carboxylate and o-tolyl-boronic acid ESI-MS (m/z): 216.83 [M+1]$^+$.

Compound at:
1-methyl-4-(m-tolyl)-1H-pyrazole-3-carboxylic acid

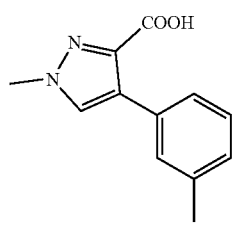 [SMILES: Cc1cccc(-c2cn(C)nc2C(=O)O)c1]

The title compound was made following the same general protocol as described for Compound ao using methyl 4-bromo-1-methyl-1H-pyrazole-3-carboxylate and m-tolyl-boronic acid. ESI-MS (m/z): 216.83 [M+1]$^+$.

Compound au: 4-(3-methoxyphenyl)-1-methyl-1H-pyrazole-3-carboxylic acid

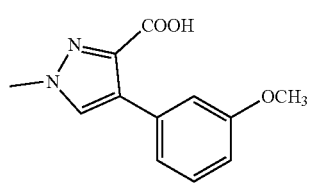 [SMILES: COc1cccc(-c2cn(C)nc2C(=O)O)c1]

The title compound was made following the same general protocol as described for Compound ao using methyl 4-bromo-1-methyl-1H-pyrazole-3-carboxylate and (3-methoxyphenyl)boronic acid. ESI-MS (m/z): 232.84 [M+1]$^+$.

Compound av: 4-(4-methoxyphenyl)-1-methyl-1H-pyrazole-3-carboxylic acid

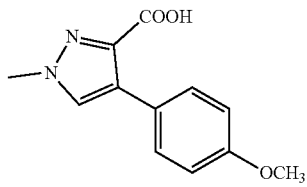 [SMILES: COc1ccc(-c2cn(C)nc2C(=O)O)cc1]

The title compound was made following the same general protocol as described for Compound ao using methyl 4-bromo-1-methyl-1H-pyrazole-3-carboxylate and (4-methoxyphenyl)boronic acid. ESI-MS (m/z): 232.84 [M+1]$^+$.

Compound aw: 4-(4-chlorophenyl)-1-methyl-1H-pyrazole-3-carboxylic acid

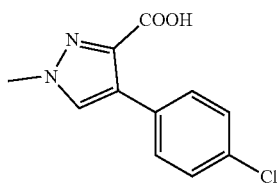 [SMILES: Cn1cc(-c2ccc(Cl)cc2)c(C(=O)O)n1]

The title compound was made following the same general protocol as described for Compound ao using methyl 4-bromo-1-methyl-1H-pyrazole-3-carboxylate and (4-chlorophenyl)boronic acid. ESI-MS (m/z): 236.86 [M+1]$^+$.

Compound ax: 1-methyl-4-(6-methylpyridin-3-yl)-1H-pyrazole-3-carboxylic acid

The title compound was made following the same general protocol as described for Compound ao using methyl 4-bromo-1-methyl-1H-pyrazole-3-carboxylate and (6-methylpyridin-3-yl)boronic acid. ESI-MS (m/z): 217.92 [M+1]$^+$.

Compound av: 1,5-dimethyl-4-(pyrimidin-2-yl)-1H-pyrazole-3-carboxylic acid

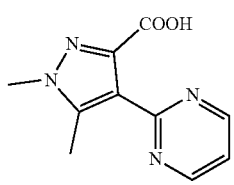 [SMILES: Cc1c(-c2ncccn2)c(C(=O)O)nn1C]

131

Step 1: tert-butyl 4-bromo-1,5-dimethyl-1H-pyrazole-3-carboxylate

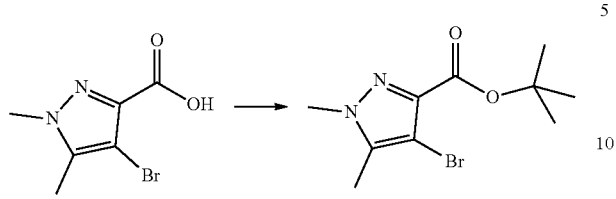

To a mixture of 4-bromo-1,5-dimethyl-1H-pyrazole-3-carboxylic acid (1.0 g, 4.56 mmol, 1.0 eq) and t-BuOH (0.87 mL, 9.12 mmol, 2.0 eq) in DCM (15 mL) was added DMAP (0.11 g, 0.91 mmol, 0.2 eq) and DCC (1.13 g, 5.47 mmol, 1.2 eq). The completion of the reaction was monitored by analytical HPLC. When complete, the reaction mixture was diluted with DCM and washed with 0.5 N HCl, water, Sat'd NaHCO$_3$ and brine. The combined organic layers were concentrated to provide the crude which was purified by column chromatography on silica gel to obtain the desired product. $^1$H NMR (400 MHz, CDCl$_3$) δ 3.95 (s, 3H), 2.27 (s, 3H), 1.65 (s, 9H).

Step 2: tert-butyl 1,5-dimethyl-4-(pyrimidin-2-yl)-1H-pyrazole-3-carboxylate

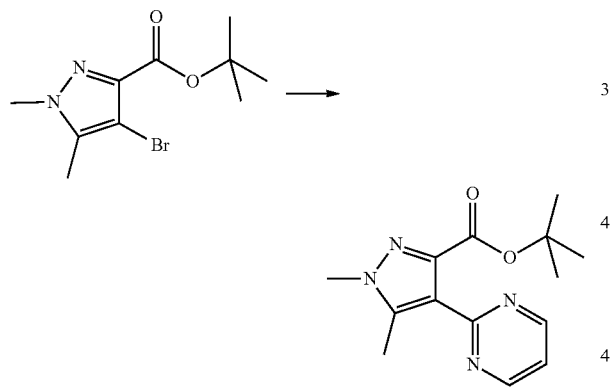

The title compound was prepared following the same general protocol as described for Compound sg using tert-butyl 4-bromo-1,5-dimethyl-1H-pyrazole-3-carboxylate and 2-(tributylstannyl)pyrimidine. ESI-MS (m/z): 274.99 [M+1]$^+$.

Step 3: 1,5-dimethyl-4-(pyrimidin-2-yl)-1H-pyrazole-3-carboxylic acid

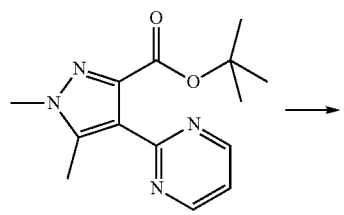

132

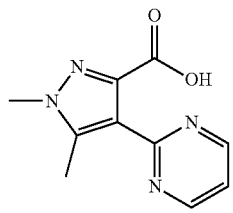

The acid was prepared following the same general protocol as described for Compound af using tert-butyl 1,5-dimethyl-4-(pyrimidin-2-yl)-1H-pyrazole-3-carboxylate. ESI-MS (m/z): 218.84 [M+1]$^+$.

Compound az: 5-(5-fluoropyridin-2-yl)-2-methylthiazole-4-carboxylic acid

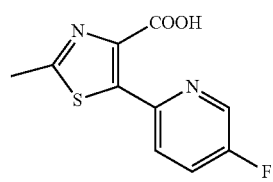 [SMILES: Cc1nc(C(=O)O)c(-c2ccc(F)cn2)s1]

Step 1: 5-fluoro-2-(tributylstannyl)pyridine

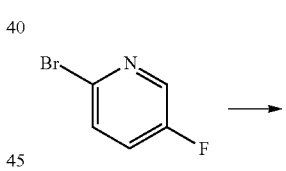

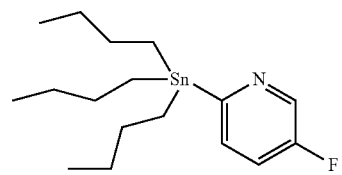

To a solution of 2-bromo-5-fluoropyridine (2.42 g, 13.75 mmol, 1.0 eq) in THF (30 mL) was added n-BuLi (2.5 M in hexane, 5.5 mL, 13.75 mmol, 1.0 eq) and the mixture was stirred at −78° C. for 30 min under nitrogen atmosphere. n-Bu$_3$SnCl (4 mL, 14.58 mmol, 1.05 eq) was added and the mixture was stirred at the same temperature for another 2 h. Saturated ammonium chloride solution (150 mL) was added to the solution and extracted with ethyl acetate (150 mL×3). The combined organic layers were dried over Na$_2$SO$_4$, filtered and concentrated in vacuo. The crude 5-fluoro-2-(tributylstannyl)pyridine as a yellow oil was used without further purification.

Step 2: methyl 5-(5-fluoropyridin-2-yl)-2-methylthiazole-4-carboxylate

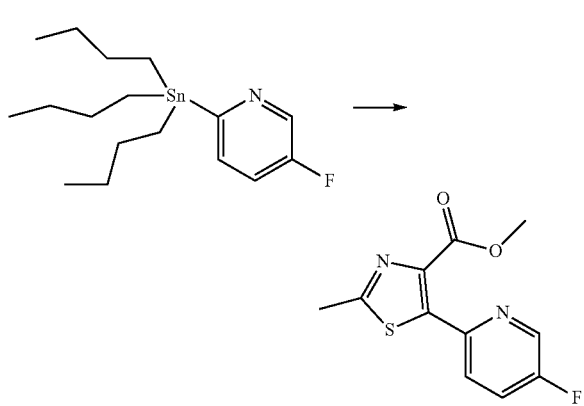

A mixture of methyl methyl 5-bromo-2-methylthiazole-4-carboxylate (0.15 g, 0.635 mmol, 1.0 eq), 5-fluoro-2-(tributylstannyl)pyridine (0.368 g, 0.95 mmol, 1.5 eq), CsF (0.193 g, 13.67 mmol, 2.0 eq), Pd(PPh$_3$)$_4$ (0.073 g, 0.064 mmol, 0.1 eq) and CuI (0.012 g, 0.064 mmol, 0.1 eq) in DMF (4 mL) was degassed for 5 min and then heated for 1 h at 120° C. in a microwave reactor. The completion of the reaction was monitored by analytical HPLC. When complete, the mixture was cooled and concentrated. The crude was dissolved with EtOAc and washed with Sat'd NaHCO$_3$ and brine. The solvent was removed to obtain the crude, which was purified by silica gel to obtain the desired product. ESI-MS (m/z): 253.07 [M+1]$^+$.

Step 3: 5-(5-fluoropyridin-2-yl)-2-methylthiazole-4-carboxylic acid

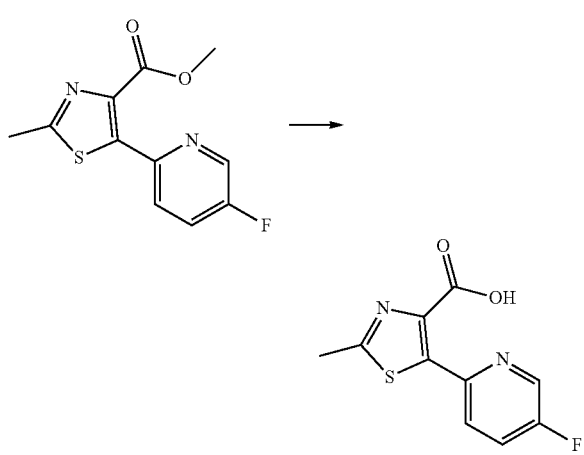

methyl 5-(5-fluoropyridin-2-yl)-2-methylthiazole-4-carboxylate (0.16 g, 0.64 mmol, 1.0 eq) in THE (5 mL) was added NaOH (1M, 3 mL, 5.0 eq). The mixture was heat for 2 h at 100° C. at oil bath. The completion of the reaction was monitored by analytical HPLC. When complete, the reaction mixture was acidified to pH-2. The solvent was removed in vacuo. The crude was purified by silica gel to obtain the desired acid. ESI-MS (m/z): 238.82 [M+1]$^+$.

Compound ba: 5-(4-fluoropyridin-2-yl)-2-methylthiazole-4-carboxylic acid

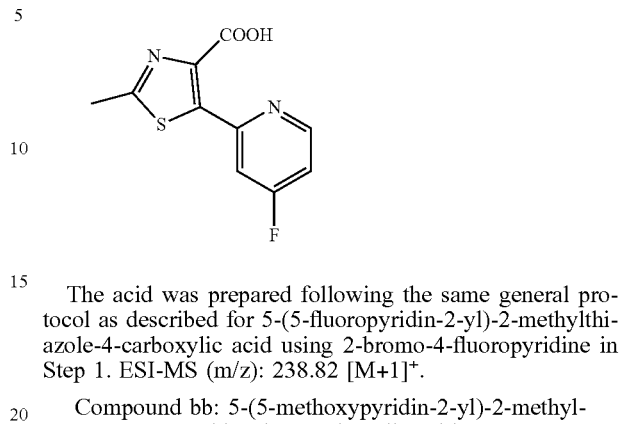

The acid was prepared following the same general protocol as described for 5-(5-fluoropyridin-2-yl)-2-methylthiazole-4-carboxylic acid using 2-bromo-4-fluoropyridine in Step 1. ESI-MS (m/z): 238.82 [M+1]$^+$.

Compound bb: 5-(5-methoxypyridin-2-yl)-2-methylthiazole-4-carboxylic acid

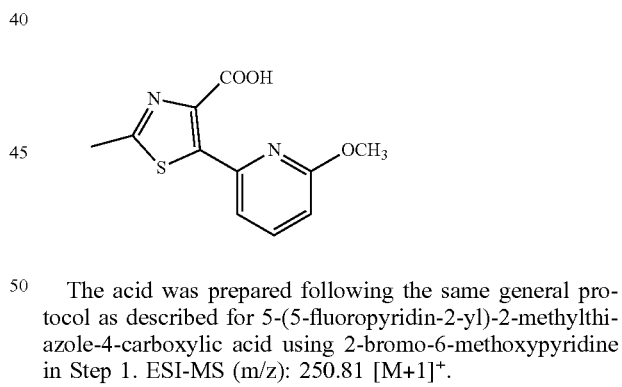

The acid was prepared following the same general protocol as described for 5-(5-fluoropyridin-2-yl)-2-methylthiazole-4-carboxylic acid using 2-bromo-5-methoxypyridine in Step 1. ESI-MS (m/z): 250.81 [M+1]$^+$.

Compound bc: 5-(6-methoxypyridin-2-yl)-2-methylthiazole-4-carboxylic acid

The acid was prepared following the same general protocol as described for 5-(5-fluoropyridin-2-yl)-2-methylthiazole-4-carboxylic acid using 2-bromo-6-methoxypyridine in Step 1. ESI-MS (m/z): 250.81 [M+1]$^+$.

Compound bd: 2-methyl-5-(3-methylpyridin-2-yl)thiazole-4-carboxylic acid

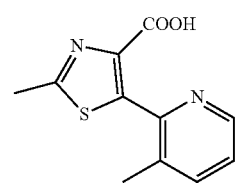 [SMILES: Cc1nc(C(=O)O)c(-c2ncccc2C)s1]

The acid was prepared following the same general protocol as described for 5-(5-fluoropyridin-2-yl)-2-methylthiazole-4-carboxylic acid using 2-bromo-3-methylpyridine in Step 1. ESI-MS (m/z): 234.79 [M+1]$^+$.

Compound be: 2-methyl-5-(5-methylpyridin-2-yl)thiazole-4-carboxylic acid

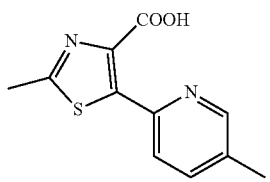

The acid was prepared following the same general protocol as described for 5-(5-fluoropyridin-2-yl)-2-methylthiazole-4-carboxylic acid using 2-bromo-5-methylpyridine in Step 1. ESI-MS (m/z): 234.79 [M+1]$^+$.

Compound bf: 2-methyl-5-(6-methylpyridin-2-yl)thiazole-4-carboxylic acid

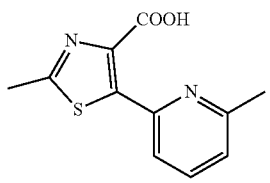

The acid was prepared following the same general protocol as described for 5-(5-fluoropyridin-2-yl)-2-methylthiazole-4-carboxylic acid using 2-bromo-6-methylpyridine in Step 1. ESI-MS (m/z): 234.79 [M+1]$^+$.

Compound b2: 2-methyl-5-(4-methylpyridin-2-yl)thiazole-4-carboxylic acid

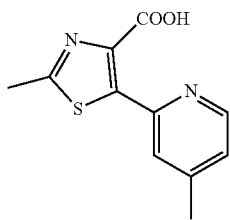 [SMILES: Cc1ccnc(-c2sc(C)nc2C(=O)O)c1]

The acid was prepared following the same general protocol as described for 5-(5-fluoropyridin-2-yl)-2-methylthiazole-4-carboxylic acid using 2-bromo-4-methylpyridine in Step 1. ESI-MS (m/z): 234.79 [M+1]$^+$.

Compound bh: 2-methyl-5-(pyridin-2-yl)thiazole-4-carboxylic acid

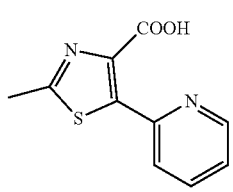

The acid was prepared following the same general protocol as described for 5-(5-fluoropyridin-2-yl)-2-methylthiazole-4-carboxylic acid using 2-(tributylstannyl)pyridine in Step 2. ESI-MS (m/z): 220.82 [M+1]$^+$.

Compound bi: 2-methyl-5-(pyrimidin-2-yl)thiazole-4-carboxylic acid

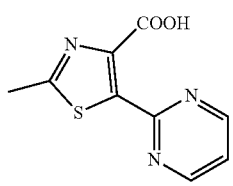

The acid was prepared following the same general protocol as described for 5-(5-fluoropyridin-2-yl)-2-methylthiazole-4-carboxylic acid using 2-(tributylstannyl)pyrimidine in Step 1. ESI-MS (m/z): 221.26 [M+1]$^+$.

Compound bj: 5-methyl-2-(pyridin-2-yl)thiophene-3-carboxylic acid

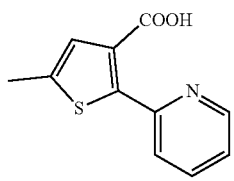

The acid was prepared following the same general protocol as described for 5-(5-fluoropyridin-2-yl)-2-methylthiazole-4-carboxylic acid in Compound az using 2-(tributylstannyl)pyridine and ethyl 2-bromo-5-methylthiophene-3-carboxylate in Step 2. ESI-MS (m/z): 219.94 [M+1]$^+$.

Compound bk: 2-methyl-5-(pyridin-2-yl)oxazole-4-carboxylic acid

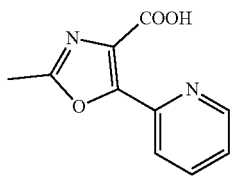

Step 1: ethyl 5-bromo-2-methyloxazole-4-carboxylate

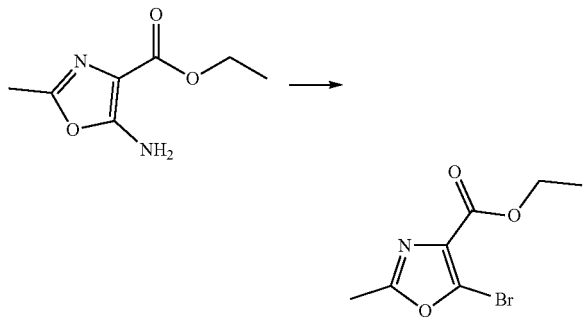

A mixture of tert-butyl nitrite (1.25 mL, 10.50 mmol, 2.0 eq) and CuBr$_2$ (1.76 g, 7.87 mmol, 1.5 eq) in acetonitrile (15 mL) was stirred at 0° C. and a solution of ethyl 5-amino-2-methyloxazole-4-carboxylate (0.89 g, 5.248 mmol, 1.0 eq) in acetonitrile (20 mL) was added dropwise. The reaction mixture was stirred overnight at RT. The mixture was diluted with EtOAc, washed with water and brine, and concentrated in vacuo. The crude was purified by chromatography on silica gel to obtain the desired product.

Step 2: 2-methyl-5-(pyridin-2-yl)oxazole-4-carboxylic acid

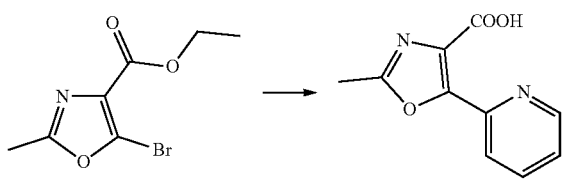

The acid was prepared following the same general protocol as described for 5-(5-fluoropyridin-2-yl)-2-methylthiazole-4-carboxylic acid in Compound az using 2-(tributylstannyl)pyridine and ethyl 5-bromo-2-methyloxazole-4-carboxylate in Step 1. ESI-MS (m/z): 204.93 [M+1]$^+$.

Compound bl: 1-methyl-3-(pyridin-2-yl)-1H-pyrazole-4-carboxylic acid

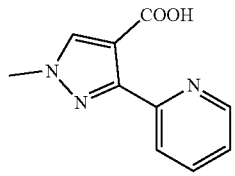

The acid was prepared following the same general protocol as described for 5-(5-fluoropyridin-2-yl)-2-methylthiazole-4-carboxylic acid in Compound az using 2-(tributylstannyl)pyridine and ethyl 3-bromo-1-methyl-1H-pyrazole-4-carboxylate in Step 1. ESI-MS (m/z): 203.93 [M+1]$^+$.

Compound bm: 1-methyl-5-(pyridin-2-yl)-1H-pyrazole-4-carboxylic acid

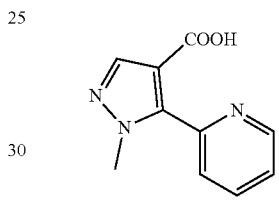

The acid was prepared following the same general protocol as described for 5-(5-fluoropyridin-2-yl)-2-methylthiazole-4-carboxylic acid in Compound az using 2-(tributylstannyl)pyridine and ethyl 5-bromo-1-methyl-1H-pyrazole-4-carboxylate in Step 1. ESI-MS (m/z): 203.93 [M+1]$^+$.

Compound bn: 4-cyano-4'-fluoro-[1,1'-biphenyl]-2-carboxylic acid

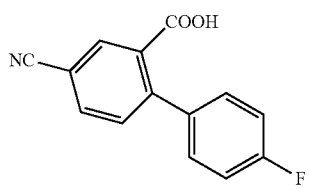 [SMILES: N#Cc1ccc(-c2ccc(F)cc2)c(C(=O)O)c1]

The mixture of 2-bromo-5-cyanobenzoic acid (0.2 g, 0.89 mmol, 1.0 eq), 2-(4-fluorophenyl)-4,4,5,5-tetramethyl-1,3,2-dioxaborolane (0.39 g, 1.77 mmol, 2.0 eq) and K$_2$CO$_3$ (0.37 g, 2.655 mmol, 3.0 eq) in DMF (4.5 Ml) was degassed, and then Pd(dppf)Cl$_2$ (0.07 g, 0.09 mmol, 0.1 eq) was added. The mixture was degassed and then heated for 2 h at 120° C. in a microwave reactor. The completion of the reaction was monitored by analytical HPLC. When complete, the reaction mixture was cooled to RT and acidified to pH5. The mixture was concentrated to provide the crude which was purified by column chromatography on silica gel to obtain the desired product. $^1$H NMR (400 MHz, CDCl$_3$) δ 8.16 (d, J=1.6 Hz, 1H), 7.91 (dd, J=8.2 Hz, 1.6 Hz, 1H), 7.57 (d, J=7.6 Hz, 1H), 7.39 (m, 2H), 7.17 (m, 2H).

Compound bo: 5-fluoro-2-(2H-tetrazol-2-yl)benzoic acid

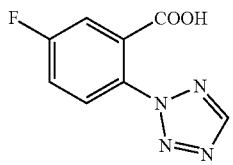

To a 20 mL microwave tube was added 2-bromo-5-fluorobenzoic acid (1.08 g, 4.93 mmol, 1.0 eq), Cs$_2$CO$_3$ (3 g, 9.86 mmol, 2.0 eq), CuI (0.09 g, 0.49 mmol, 0.1 eq) and DMF (10 mL). N, N'-dimethylglycine (0.09 g, 0.99 mmol, 0.2 eq) was added and the mixture was irradiated at 120° C. for 1 h. The reaction mixture was cooled to RT and acidified to pH5. The mixture was concentrated to provide the crude which was purified by column chromatography on silica gel to obtain the desired product. ESI-MS (m/z): 208.88 [M+1]$^+$.

Compound bp: 5-chloro-2-(2H-tetrazol-2-yl)benzoic acid

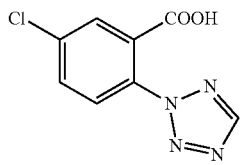 [SMILES: O=C(O)c1cc(Cl)ccc1-n1ncnn1]

The acid was prepared following the same general protocol as described 5-fluoro-2-(2H-tetrazol-2-yl)benzoic acid using 5-chloro-2-iodobenzoic acid. H NMR (400 MHz, CDCl$_3$) δ 9.30 (s, 1H), 8.06 (d, J=1.6 Hz, 1H), 7.96 (d, J=8.2 Hz, 1.6 Hz, 1H), 7.92 (d, J=8.2 Hz, 1H). ESI-MS (m/z): 224.88 [M+1]$^+$.

Compound bq: 5-chloro-2-(2-methyl-2H-tetrazol-5-yl)benzoic acid

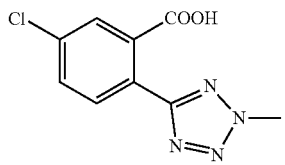 [SMILES: Cn1nnc(-c2ccc(Cl)cc2C(=O)O)n1]

Step 1: methyl 2-bromo-5-chlorobenzoate

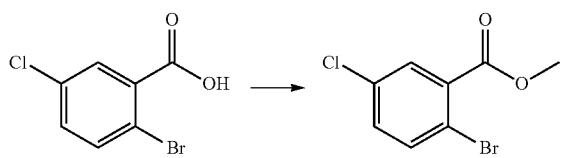

To a mixture of 2-bromo-5-chlorobenzoic acid (10.4 g, 44.16 mmol, 1.0 eq) in MeOH (250 mL) at ice bath was added slowly SOCl$_2$ (4.8 mL, 66.24 mmol, 1.5 eq). The reaction mixture was warm to RT and heated at 80° C. oil bath overnight. The completion of the reaction was monitored by analytical HPLC. When complete, the reaction mixture was cooled to RT and concentrated. The crude was dissolved with EtOAc and washed with Sat'd NaHCO$_3$, brine and dried over Na$_2$SO$_4$. The organic layer was concentrated to obtain the desired product for the next step with no further purification.

Step 2: methyl 5-chloro-2-cyanobenzoate

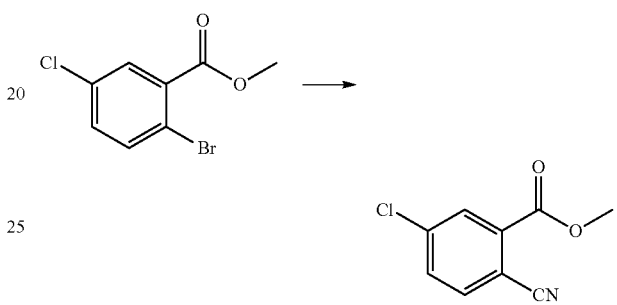

A mixture of methyl 2-bromo-5-chlorobenzoate (8.275 g, 33.17 mmol, 1.0 eq) and ZnCN (2.03 g, 17.25 mmol, 0.52 eq) in DMF (40 mL) was degassed, and then Pd(PPh$_3$)$_4$ (0.767 g, 0.66 mmol, 0.02 eq) was added. The mixture was heated overnight at 90° C. at oil bath. The completion of the reaction was monitored by analytical HPLC. When complete, the reaction mixture was cooled to RT and concentrated to provide the crude which was purified by column chromatography on silica gel to obtain the desired product.

Step 3: methyl 5-chloro-2-(2H-tetrazol-5-yl)benzoate

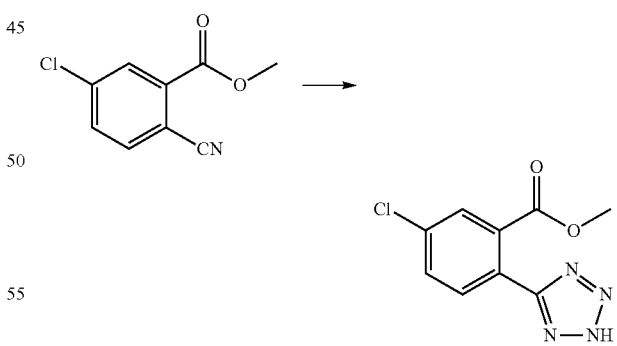

A mixture of methyl 5-chloro-2-cyanobenzoate (5.31 g, 26.11 mmol, 1.0 eq), NaN$_3$ (5.1 g, 78.33 mmol, 3.0 eq) and triethylamine hydrochloride (10.8 g, 78.33 mmol, 3.0 eq) in toluene (100 mL) was heated overnight at 100° C. oil bath. The completion of the reaction was monitored by analytical HPLC. When complete, the reaction mixture was cooled to RT and concentrated to provide the crude which was purified by column chromatography on silica gel to obtain the desired product. ESI-MS (m/z): 238.98 [M+1]$^+$.

Step 4: methyl
5-chloro-2-(2-methyl-2H-tetrazol-5-yl)benzoate

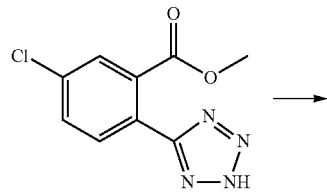

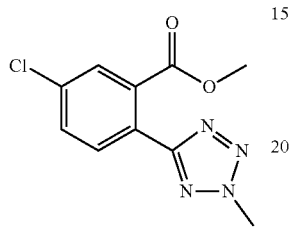

To a mixture of methyl 5-chloro-2-(2H-tetrazol-5-yl)benzoate (1.411 g, 5.91 mmol, 1.0 eq) and K₂CO₃ (1.23 g, 8.87 mmol, 1.5 eq) in DMF (20 mL) was added MeI (0.55 mL, 8.87 mmol, 1.5 eq). The mixture was stirred overnight at 50° C. oil bath. The completion of the reaction was monitored by analytical HPLC. When complete, the reaction mixture was cooled to RT and concentrated to provide the crude, which was dissolved with EtOAc, washed with water, sat'd NaHCO₃ and brine. The organic layer was concentrated to obtain the crude which was purified by column chromatography on silica gel to obtain the major fraction which is the desired product. ESI-MS (m/z): 252.92 [M+1]⁺.

Step 5:
5-chloro-2-(2-methyl-2H-tetrazol-5-yl)benzoic acid

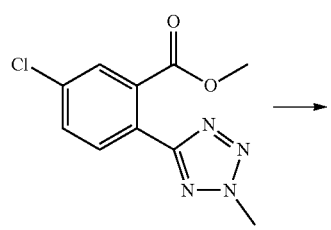

The acid was prepared following the same general protocol as described for 5-(5-fluoropyridin-2-yl)-2-methylthiazole-4-carboxylic acid in Compound az in Step 2 using methyl 5-chloro-2-(2-methyl-2H-tetrazol-5-yl)benzoate. ESI-MS (m/z): 238.90 [M+1]⁺.

Compound br:
5-methyl-2-(2-methyl-2H-tetrazol-5-yl)benzoic acid

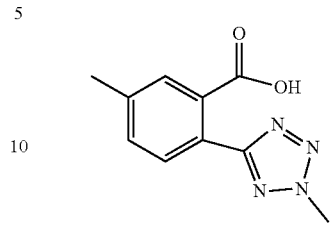

The acid was prepared following the same general protocol as described for 5-chloro-2-(2-methyl-2H-tetrazol-5-yl)benzoic acid in Compound bq using methyl 2-cyano-5-methylbenzoate. ESI-MS (m/z): 218.90 [M+1]⁺.

Compound bs: 5:
5-methyl-2-(1-methyl-1H-tetrazol-5-yl)benzoic acid

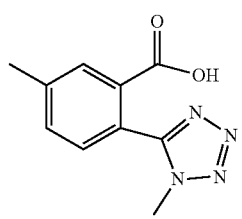 [SMILES: Cc1ccc(-c2nnnn2C)c(C(=O)O)c1]

The acid was prepared following the same general protocol as described for 5-chloro-2-(2-methyl-2H-tetrazol-5-yl)benzoic acid in Compound bq using methyl 2-cyano-5-methylbenzoate and was the minor isomer isolated from the reaction. ESI-MS (m/z): 218.9 [M+1]⁺.

Compound bt:
5-chloro-2-(3-methyl-1,2,4-oxadiazol-5-yl)benzoic acid

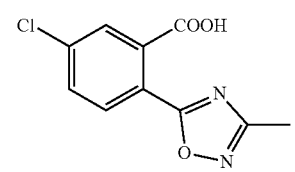 [SMILES: Cc1noc(-c2ccc(Cl)cc2C(=O)O)n1]

Step 1: methyl 5-chloro-2-methylbenzoate

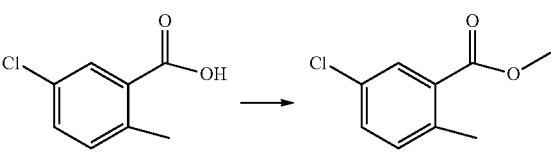

The acid was prepared following the same general protocol as described 5-chloro-2-(2-methyl-2H-tetrazol-5-yl)benzoic acid in step 1, using 5-chloro-2-methylbenzoic acid.

Step 2: methyl 2-(bromomethyl)-5-chlorobenzoate

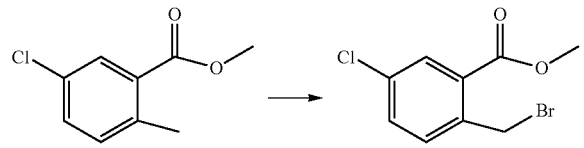

A solution of compound 2 (6.95 g, 37.63, 1.0 eq mmol), N-bromosuccinimide (7.03 g, 39.51 mmol, 1.05 eq) and benzoyl peroxide (0.55 g, 2.26 mmol, 0.06 eq) in carbon tetrachloride (50 mL) was heated to reflux for overnight. The completion of the reaction was monitored by analytical HPLC. When complete, the reaction mixture was cooled to RT and concentrated to provide the crude, which was dissolved with EtOAc, washed with sat'd NaHCO$_3$, dried over sodium sulfate, concentrated and purified by flash column chromatography to afford the desired product.

Step 3: methyl 5-chloro-2-formylbenzoate

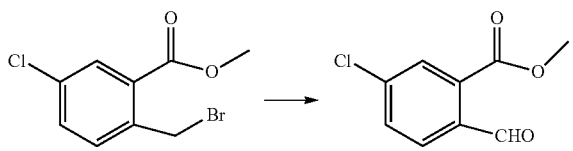

A mixture of methyl 2-(bromomethyl)-5-chlorobenzoate (9.9 g, 37.63 mmol, 1.0 eq) and N-methylmorpholine oxide (10.0 g, 94.08 mmol, 2.5 eq) in DMSO (40 mL) was stirred overnight at RT. The completion of the reaction was monitored by analytical HPLC. When complete, the mixture was diluted with EtOAc, washed with sat'd NaHCO$_3$, dried over sodium sulfate, concentrated and purified by flash column chromatography to afford the desired product.

Step 4: 4-chloro-2-(methoxycarbonyl)benzoic acid

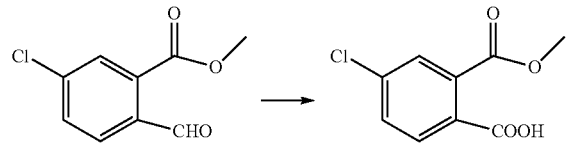

methyl 5-chloro-2-formylbenzoate (3.3 g, 16.60 mmol, 1.0 eq) was dissolved in t-BuOH (160 mL) and water (16 mL). Then 2-methyl-2-butene (8.8 mL, 83.0 mmol, 5 eq) and NaH$_2$PO$_4$ (2.0 g, 16.60 mmol, 1.0 eq) were added. To the stirred suspension was portionwise added NaClO$_2$ (3.8 g, 33.2 mmol, 2 eq.) at rt. After 1 hr at rt, the mixture was diluted with AcOEt and water, then acidified with aqueous KHSO$_4$ solution to approximately pH 4. The organic extract was washed with brine, dried over Na$_2$SO$_4$, filtered and concentrated to give crude which was used for next step without purification.

Step 5: methyl (Z)-2-((((1-aminoethylidene)amino)oxy)carbonyl)-5-chlorobenzoate 4-chloro-2-(methoxycarbonyl)benzoate

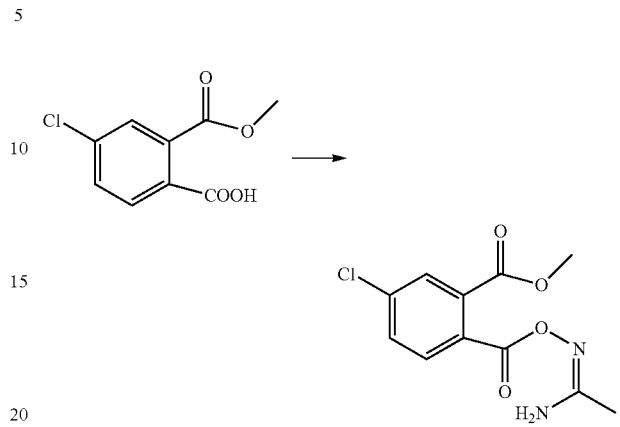

To a mixture of 4-chloro-2-(methoxycarbonyl)benzoic acid (0.414 g, 1.93 mmol, 1.0 eq) and DMF (1 drop) in DCM (10 mL) at 0° C. was added oxalyl chloride (0.18 mL, 2.10 mmol, 1.1 eq) dropwise. Gas evolution commenced immediately and after 5 min the ice bath was removed. When gas evolution had ceased and the mixture was stirred at RT for another hour and then concentrated. The crude was dissolved in fresh DCM (10 mL) and treated with N-hydroxyacetamidine (0.17 g, 2.31 mmol, 1.2 eq) in several portions followed by TEA (0.8 mL, 5.79 mmol, 3.0 eq). The mixture was stirred overnight at RT and then concentrated in vacuo to obtain the crude, which was purified by flash column chromatography to afford mixture of (Z)-isomer and (E)-isomer. ESI-MS (m/z): 270.92 [M+1]$^+$.

Step 6: methyl 5-chloro-2-(3-methyl-1,2,4-oxadiazol-5-yl)benzoate

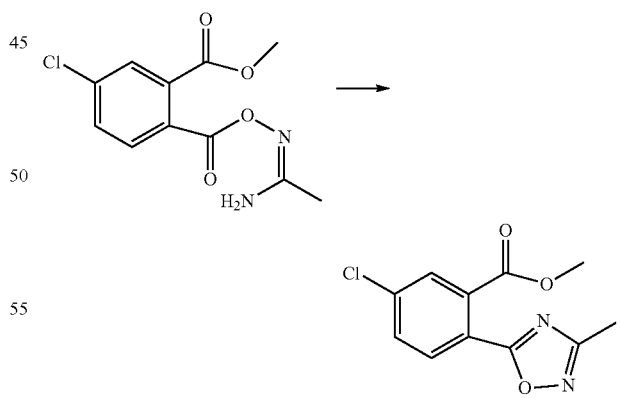

The mixture (obtained from the above step) in Toluene (10 mL) was refluxed overnight. The completion of the reaction was monitored by analytical HPLC. When complete, the mixture was diluted with EtOAc, washed with sat'd NaHCO$_3$, dried over sodium sulfate, concentrated and purified by flash column chromatography to afford the desired product. ESI-MS (m/z): 252.94 [M+1]$^+$.

Step 7: 5-chloro-2-(3-methyl-1,2,4-oxadiazol-5-yl)benzoic acid

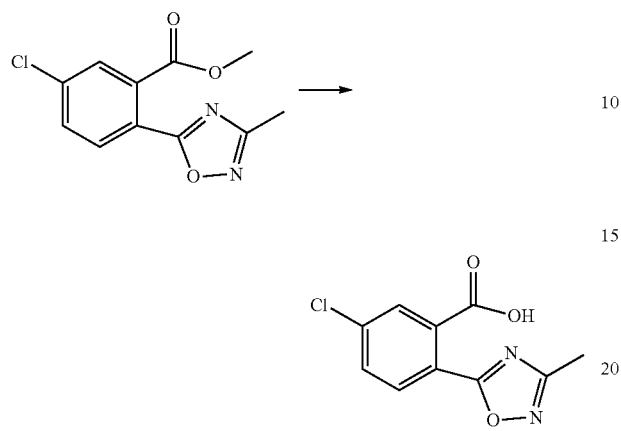

The acid was prepared following the same general protocol as described for 5-(5-fluoropyridin-2-yl)-2-methylthiazole-4-carboxylic acid Compound az in Step 2 using methyl 5-chloro-2-(3-methyl-1,2,4-oxadiazol-5-yl)benzoate. ESI-MS (m/z): 238.94 [M+1]⁺.

Compound bu: 1-ethyl-4-(pyrimidin-2-yl)-1H-pyrazole-3-carboxylic acid

Step 1: methyl 4-bromo-1-ethyl-1H-pyrazole-3-carboxylate

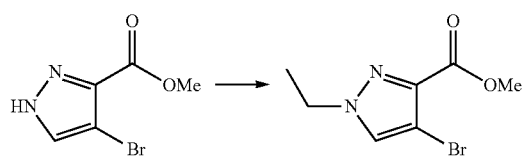

A solution of methyl 4-bromo-1H-pyrazole-3-carboxylate (1 eq), EtI (1.4 eq) and triethylamine (3 eq) in dichloromethane (10 mL) was stirred at room temperature overnight. After removal of solvent under reduced pressure, the residue was dissolved in ethyl acetate (10 mL) and washed with 1 M HCl (5 mL), brine (5 mL), dried over Na$_2$SO$_4$. Removal of solvent under reduced pressure afforded the title compound as a colorless oil. ESI-MS (m/z): 232.62 [M+H]⁺

Step 2: methyl 1-ethyl-4-(4,4,5,5-tetramethyl-1,3,2-dioxaborolan-2-yl)-1H-pyrazole-3-carboxylate

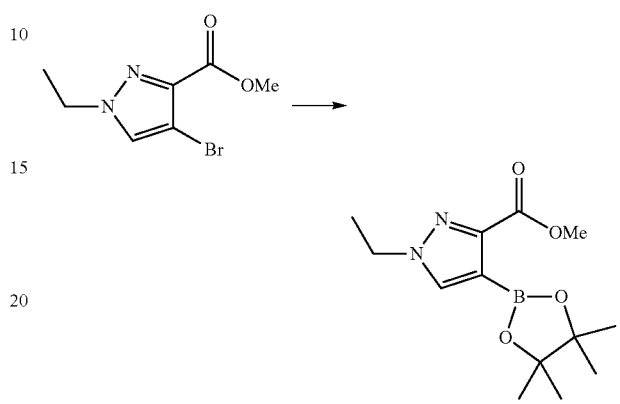

A mixture of methyl 4-bromo-1-ethyl-1H-pyrazole-3-carboxylate (1 eq), 4,4,4',4',5,5,5',5'-octamethyl-2,2'-bi(1,3,2-dioxaborolane) (1 eq), KOAc (2 eq) and Pd(dppf)Cl$_2$ (5 mol %) in 1,4-dioxane (10 mL) was stirred at 100° C. overnight. The precipitate was removed by filtration and the filtrate was used for next step without further purification. ESI-MS (m/z): 281.64 [M+H]⁺

Step 3: 1-ethyl-4-(pyrimidin-2-yl)-1H-pyrazole-3-carboxylic acid

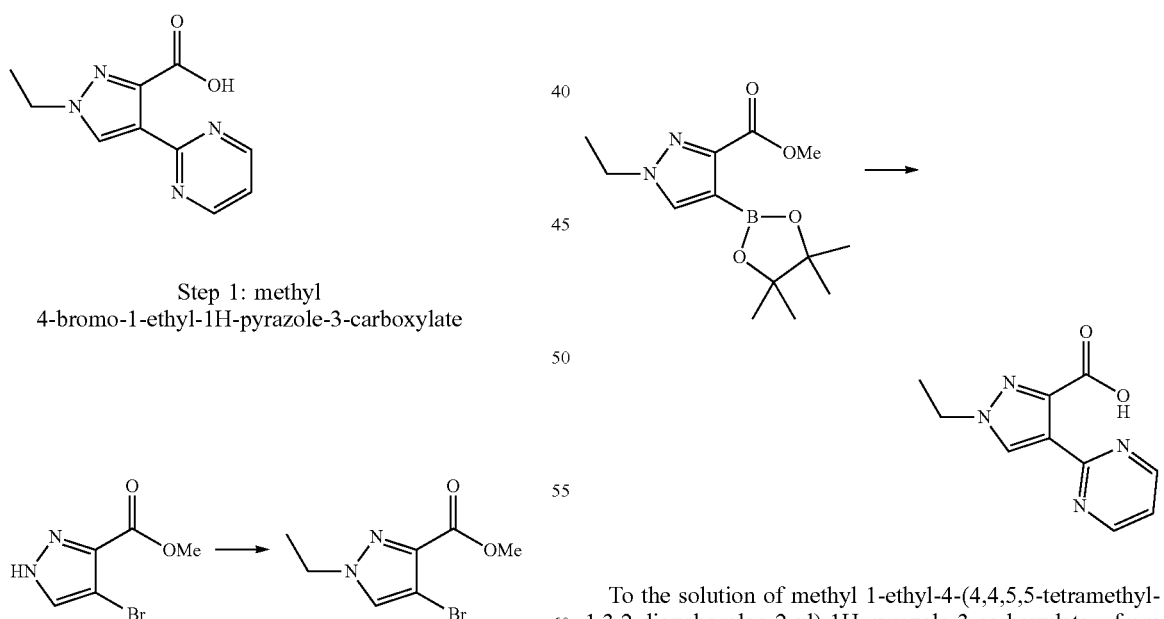

To the solution of methyl 1-ethyl-4-(4,4,5,5-tetramethyl-1,3,2-dioxaborolan-2-yl)-1H-pyrazole-3-carboxylate from the last step were added 2-bromopyrimidine (1.1 eq), Na$_2$CO$_3$ (2 eq), Pd(PPh$_3$)$_4$ (10 mol %), 1,4-dioxane (20 mL) and H$_2$O (5 mL). The mixture was stirred at 100° C. overnight. After removal of solvents under reduced pressure, the residue was purified by prep-HPLC to afford the title compound as a colorless solid. ESI-MS (m/z): 219.18 [M+H]⁺

Compound bv: 1-isopropyl-4-(pyrimidin-2-yl)-1H-pyrazole-3-carboxylic acid

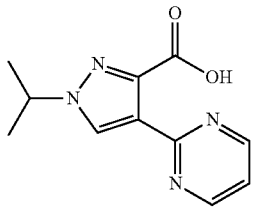 [SMILES: CC(C)n1cc(-c2ncccn2)c(C(=O)O)n1]

The title compound was synthesized as a colorless solid following the same general protocol as described for 1-ethyl-4-(pyrimidin-2-yl)-1H-pyrazole-3-carboxylic acid using methyl 4-bromo-1H-pyrazole-3-carboxylate and 2-iodopropane. ESI-MS (m/z): 232.81 [M+H]$^+$

Compound bw: 4-(pyrimidin-2-yl)-1-(2,2,2-trifluoroethyl)-1H-pyrazole-3-carboxylic acid

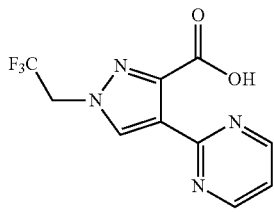 [SMILES: O=C(O)c1nn(CC(F)(F)F)cc1-c1ncccn1]

The title compound was synthesized as a colorless solid following the same general protocol as described for 1-ethyl-4-(pyrimidin-2-yl)-1H-pyrazole-3-carboxylic acid using methyl 4-bromo-1H-pyrazole-3-carboxylate and 2,2,2-trifluoroethyl trifluoromethanesulfonate. ESI-MS (m/z): 272.88 [M+H]$^+$

Compound bx: 5-fluoro-2-(2-methyl-2H-tetrazol-5-yl)benzoic acid

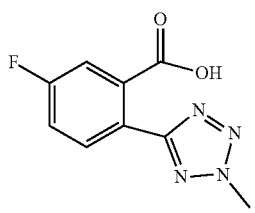 [SMILES: Cn1nnc(-c2ccc(F)cc2C(=O)O)n1]

The acid was prepared following the same general protocol as described for 5-chloro-2-(2-methyl-2H-tetrazol-5-yl)benzoic acid in Compound bq using methyl 2-cyano-5-fluorobenzoate. ESI-MS (m/z): 222.90 [M+1]$^+$.

Compound by: 4-(5-chloropyridin-2-yl)-1-methyl-1H-pyrazole-3-carboxylic acid

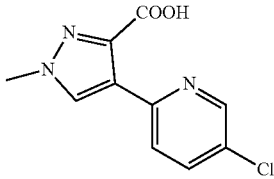 [SMILES: Cn1cc(-c2ccc(Cl)cn2)c(C(=O)O)n1]

The title compound was made following the same general protocol as described for Compound af using methyl 4-bromo-1-methyl-1H-pyrazole-3-carboxylate and 5-chloro-2-(tributylstannyl)pyridine. ESI-MS (m/z): 237.78 [M+1]$^+$.

Compound bz: 4-(4-chloropyridin-2-yl)-1-methyl-1H-pyrazole-3-carboxylic acid

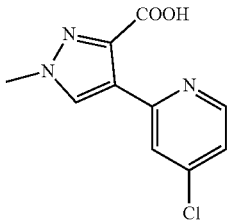 [SMILES: Cn1cc(-c2cc(Cl)ccn2)c(C(=O)O)n1]

The title compound was made following the same general protocol as described for Compound af using methyl 4-bromo-1-methyl-1H-pyrazole-3-carboxylate and 4-chloro-2-(tributylstannyl)pyridine. ESI-MS (m/z): 237.78 [M+1]$^+$.

Compound ca: 4-(5-methoxypyridin-2-yl)-1-methyl-1H-pyrazole-3-carboxylic acid

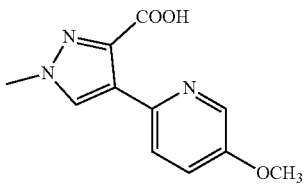 [SMILES: COc1ccc(-c2cn(C)nc2C(=O)O)nc1]

The title compound was made following the same general protocol as described for Compound af using methyl 4-bromo-1-methyl-1H-pyrazole-3-carboxylate and 4-methoxy-2-(tributylstannyl)pyridine. ESI-MS (m/z): 233.94 [M+1]$^+$.

Compound cb:
1-methyl-4-phenyl-1H-pyrazole-3-carboxylic acid

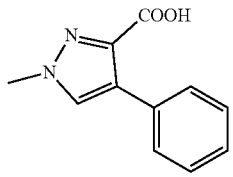

The title compound was made following the same general protocol as described for Compound ao using methyl 4-bromo-1-methyl-1H-pyrazole-3-carboxylate and phenylboronic acid. ESI-MS (m/z): 202.86 [M+1]$^+$.

Compound cc: 4-(4-fluorophenyl)-1-methyl-1H-pyrazole-3-carboxylic acid

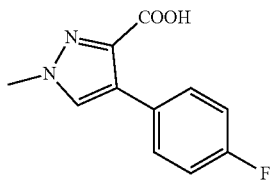 [SMILES: Cn1cc(-c2ccc(F)cc2)c(C(=O)O)n1]

The title compound was made following the same general protocol as described for Compound ao using methyl 4-bromo-1-methyl-1H-pyrazole-3-carboxylate and (4-fluorophenyl)boronic acid ESI-MS (m/z): 220.84 [M+1]$^+$.

Compound cd: 4-(3-chlorophenyl)-1-methyl-1H-pyrazole-3-carboxylic acid

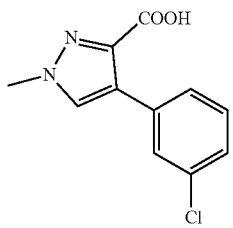 [SMILES: Cn1cc(-c2cccc(Cl)c2)c(C(=O)O)n1]

The title compound was made following the same general protocol as described for Compound ao using methyl 4-bromo-1-methyl-H-pyrazole-3-carboxylate and (3-chlorophenyl)boronic acid ESI-MS (m/z): 236.86 [M+1]$^+$.

Compound ce:
5-(4-fluorophenyl)-2-methyloxazole-4-carboxylic acid

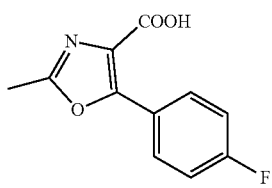 [SMILES: Cc1nc(C(=O)O)c(-c2ccc(F)cc2)o1]

The title compound was made following the same general protocol as described for Compound ao using ethyl 5-bromo-2-methyloxazole-4-carboxylate and (4-fluorophenyl)boronic acid. ESI-MS (m/z): 221.86 [M+1]$^+$.

Compound cf:
2-methyl-5-phenyloxazole-4-carboxylic acid

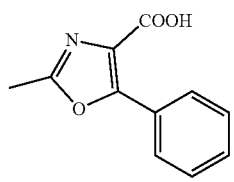

The title compound was made following the same general protocol as described for Compound ao using ethyl 5-bromo-2-methyloxazole-4-carboxylate and phenylboronic acid. ESI-MS (m/z): 203.87 [M+1]$^+$.

Compound cg:
2-methyl-5-(pyridin-3-yl)oxazole-4-carboxylic acid

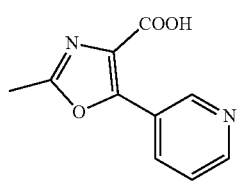

The title compound was made following the same general protocol as described for Compound ao using ethyl 5-bromo-2-methyloxazole-4-carboxylate and 3-pyridylboronic acid. ESI-MS (m/z): 204.93 [M+1]$^+$.

Compound ch: 2-methyl-5-(pyridin-2-yl)-2H-1,2,3-triazole-4-carboxylic acid

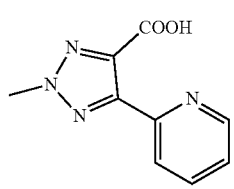

The acid was prepared following the same general protocol as described for 5-(5-fluoropyridin-2-yl)-2-methylthiazole-4-carboxylic acid in Compound az using 2-(tributylstannyl)pyridine and methyl 5-bromo-2-methyl-2H-1,2,3-triazole-4-carboxylate in Step 2. ESI-MS (m/z): 204.97 [M+1]$^+$.

Compound ci:
2-methyl-5-phenyl-2H-1,2,3-triazole-4-carboxylic acid

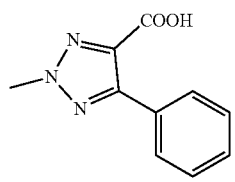

The title compound was made following the same general protocol as described for Compound ao using methyl 5-bromo-2-methyl-2H-1,2,3-triazole-4-carboxylate and phenylboronic acid. ESI-MS (m/z): 203.20 [M+1]$^+$.

Compound cj: 5-(4-fluorophenyl)-2-methyl-2H-1,2,3-triazole-4-carboxylic acid

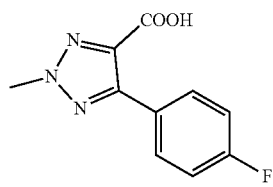 [SMILES: Cn1nc(C(=O)O)c(-c2ccc(F)cc2)n1]

The title compound was made following the same general protocol as described for Compound ao using methyl 5-bromo-2-methyl-2H-1,2,3-triazole-4-carboxylate and (4-fluorophenyl)boronic acid ESI-MS (m/z): 221.19 [M+1]$^+$.

Compound ck: 5-(5-chloropyridin-2-yl)-2-methyl-2H-1,2,3-triazole-4-carboxylic acid

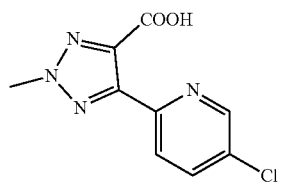 [SMILES: Cn1nc(C(=O)O)c(-c2ccc(Cl)cn2)n1]

The acid was prepared following the same general protocol as described for 4-(5-fluoropyrimidin-2-yl)-1-methyl-1H-pyrazole-3-carboxylic acid in Compound aa using 5-bromo-2-methyl-2H-1,2,3-triazole-4-carboxylic acid. ESI-MS (m/z): 238.81 [M+1]$^+$.

Compound cl:
6-methoxy-3-(2H-1,2,3-triazol-2-yl)picolinic acid

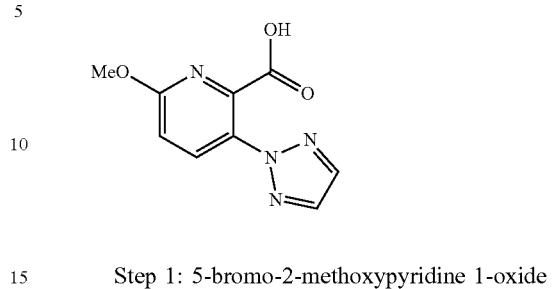

Step 1: 5-bromo-2-methoxypyridine 1-oxide

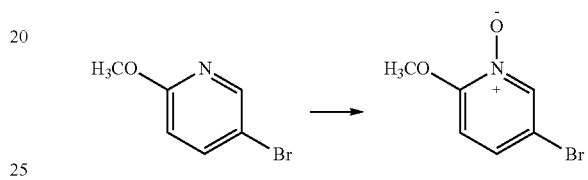

To a solution of 5-bromo-2-methoxypyridine (1 eq) in CHCl$_3$ was added MCPBA (4 eq). The reaction was warmed to 100° C. for 2 h, and then cooled to room temperature. The reaction was cooled to 0° C. and quenched with aqueous Na$_2$S$_2$O$_3$ solution and saturated aqueous NaHCO$_3$. The layers were separated, and the organic layer was washed with sat. aq. NaHCO$_3$, brine, dried (MgSO$_4$) and concentrated to give the title compound which was used without further purification.

Step 2: 3-bromo-6-methoxypicolinonitrile

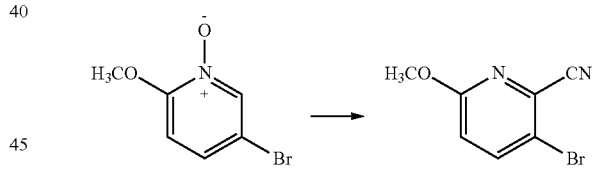

To a solution of 5-bromo-2-methoxypyridine 1-oxide (1 eq) in CH$_3$CN was added TEA (3 eq) followed by TMSCN (4 eq). The reaction was warmed to 100° C. for 14 h, and then cooled and quenched with saturated aqueous NaHCO$_3$ and diluted with EtOAc. The layers were separated, and the organic layer was washed with sat. aq. NaHCO$_3$, brine, dried (MgSO$_4$) and concentrated in vacuo to give the title compound which was purified by chromatography on SiO$_2$ (EtOAc/hex) to give the title compound. ESI-MS (m/z): 213.19 [M+1]$^+$.

Step 3: 3-bromo-6-methoxypicolinic acid

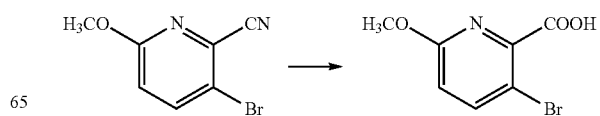

To a solution of 3-bromo-6-methoxypicolinonitrile (1 eq) in EtOH was added NaOH (3 eq). The reaction was warmed to 100° C. for 12 h, and then cooled and acidified with 2M HCl until the pH ~4-5. The reaction was concentrated to remove the EtOH, and then diluted with EtOAc and water. The layers were separated. The organic layer was washed with brine, dried (MgSO₄) and concentrated in vacuo to give the title compound which was used without further purification.

ESI-MS (m/z): 231.99 [M+1]⁺.

Step 4: 6-methoxy-3-(2H-1,2,3-triazol-2-yl)picolinic acid

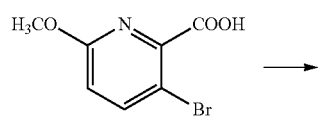

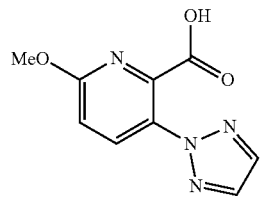 [SMILES: COc1ccc(-n2nccn2)c(C(=O)O)n1]

A mixture of 3-bromo-6-methoxypicolinic acid (1 eq), 1,2,3-triazole (2 eq), (1S,2S)—N1,N2-dimethylcyclohexane-1,2-diamine (0.2 eq), Cs₂CO₃ (2 eq) and CuI (0.5 mol %) in dioxane/H₂O (200/1) was degassed and heated at 100° C. for 4 h. The reaction was cooled to RT, diluted with MeOH, and acidified with AcOH to pH ~4-5. The solvent was removed in vacuo to obtain the crude which was purified by silica gel chromatography (0~100% DCM/EtOAc) to obtain the title compound. ESI-MS (m/z): 221.1, [M+1]⁺.

Compound cm: 3-(2H-1,2,3-triazol-2-yl)-6-(trifluoromethyl)picolinic acid

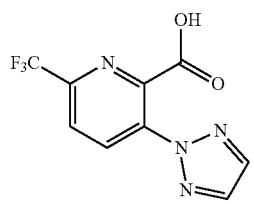 [SMILES: O=C(O)c1nc(C(F)(F)F)ccc1-n1nccn1]

The title compound was made following the same general protocol as described for Compound c1 starting with 5-bromo-2-(trifluoromethyl)pyridine. ESI-MS (m/z): 259.1 [M+1]⁺.

Compound cn: 6-methyl-3-(2-methyl-2H-tetrazol-5-yl)picolinic acid

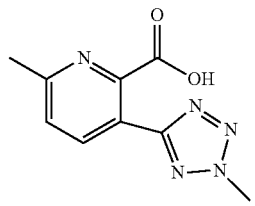

The acid was prepared following the same general protocol as described for 5-chloro-2-(2-methyl-2H-tetrazol-5-yl)benzoic acid in Compound bq using methyl methyl 3-cyano-6-methylpicolinate. ESI-MS (m/z): 220.23 [M+1]⁺.

Compound co: 1-methyl-4-(6-(trifluoromethyl)pyridin-2-yl)-1H-pyrazole-3-carboxylic acid

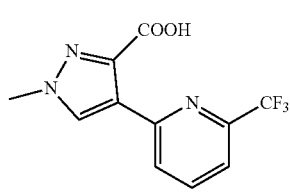 [SMILES: Cn1cc(-c2cccc(C(F)(F)F)n2)c(C(=O)O)n1]

The title compound was synthesized following the same general protocol as described for 4-(5-chloropyrimidin-2-yl)-1-methyl-1H-pyrazole-3-carboxylic acid using (3-(methoxycarbonyl)-1-methyl-1H-pyrazol-4-yl)boronic acid and 2-bromo-6-(trifluoromethyl)pyridine. ESI-MS (m/z): 272.05 [M+1]⁺.

Compound cp: 1-methyl-4-(pyrimidin-5-yl)-1H-pyrazole-3-carboxylic acid

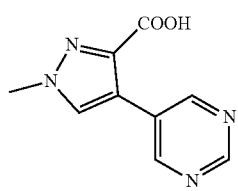

The title compound was synthesized following the same general protocol as described for 4-(5-chloropyrimidin-2-yl)-1-methyl-1H-pyrazole-3-carboxylic acid using (3-(methoxycarbonyl)-1-methyl-1H-pyrazol-4-yl)boronic acid and 5-bromopyrimidine. ESI-MS (m/z): 205.03 [M+1]⁺.

155

Compound cq: 1-methyl-4-(pyrazin-2-yl)-1H-pyrazole-3-carboxylic acid

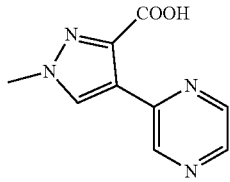

The title compound was synthesized following the same general protocol as described for 4-(5-chloropyrimidin-2-yl)-1-methyl-1H-pyrazole-3-carboxylic acid using (3-(methoxycarbonyl)-1-methyl-1H-pyrazol-4-yl)boronic acid and 2-bromopyrazine. ESI-MS (m/z): 205.11 [M+1]⁺.

Compound cr: 1-methyl-4-(pyrimidin-4-yl)-1H-pyrazole-3-carboxylic acid

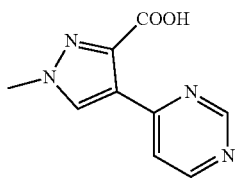

Step 1: 1-methyl-4-(4,4,5,5-tetramethyl-1,3,2-dioxaborolan-2-yl)-1H-pyrazole-3-carboxylic acid

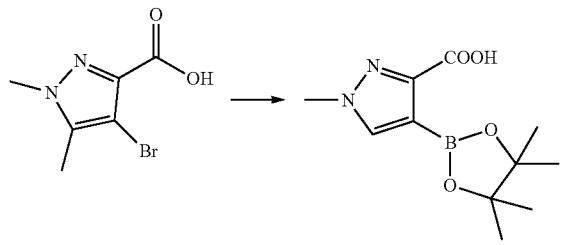

A mixture of methyl 4-bromo-1-methyl-1H-pyrazole-3-carboxylic acid (1 eq), 4,4,4',4',5,5,5',5'-octamethyl-2,2'-bi(1,3,2-dioxaborolane) (1 eq), KOAc (2 eq) and Pd(dppf)Cl₂ (5 mol %) in 1,4-dioxane (10 mL) was stirred at 100° C. overnight. The precipitate was removed by filtration and the filtrate was used for next step without further purification. ESI-MS (m/z): 267.20 [M+1]⁺.

Step 2: 1-methyl-4-(pyrimidin-4-yl)-1H-pyrazole-3-carboxylic acid

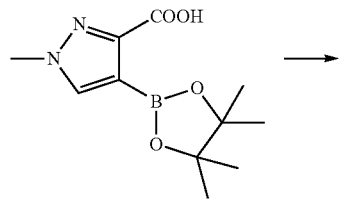

156

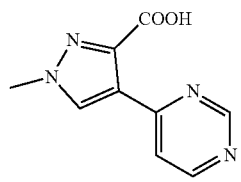

To the solution of crude 1-methyl-4-(4,4,5,5-tetramethyl-1,3,2-dioxaborolan-2-yl)-1H-pyrazole-3-carboxylic acid from Step 1 were added 4-chloropyrimidine (1.1 eq), Na₂CO₃ (2 eq), Pd(PPh₃)₄ (10 mol %), 1,4-dioxane (20 mL) and H₂O (5 mL). The mixture was stirred at 100° C. overnight. After removal of solvents under reduced pressure, the residue was purified by prep-HPLC to afford the title compound as a colorless solid. ESI-MS (m/z): 205.17 [M+1]⁺.

Compound cs: 5,6'-dimethyl-[2,3'-bipyridine]-2'-carboxylic acid

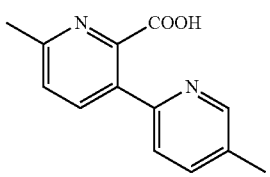

Step 1: 5,6'-dimethyl-[2,3'-bipyridine]-2'-carbonitrile

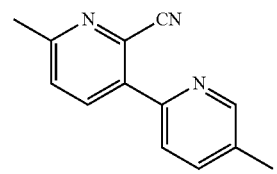

To a mixture of 3-bromo-6-methylpicolinonitrile (1.0 eq), (5-methylpyridin-2-yl)boronic acid (1.3 eq) and K₂CO₃ (3.0 eq) in dioxane/H₂O (4:1) was added Pd(PPh₃)₄ (0 mol %). The mixture was degassed and then heated for 30 min at 120° C. in a microwave reactor. The completion of the reaction was monitored by analytical HPLC. When complete, the reaction mixture was cooled to RT and diluted with EtOAc and washed with H₂O and the layers were separated. The aqueous layer was extracted with EtOAc (2×). The combined organic layers were concentrated to provide the crude which was purified by column chromatography on silica gel to obtain the desired product. ESI-MS (m/z): 210.09 [M+1]⁺.

157

Step 2: 5,6'-dimethyl-[2,3'-bipyridine]-2'-carboxylic acid

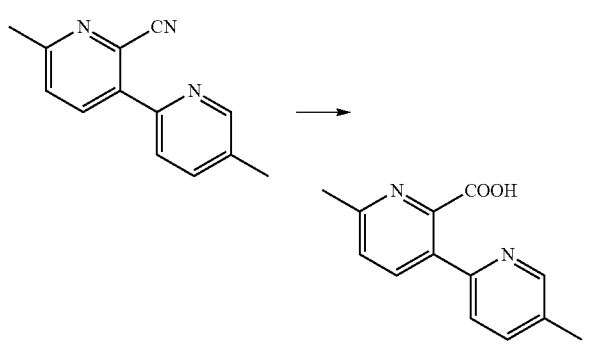

A mixture of 5,6'-dimethyl-[2,3'-bipyridine]-2'-carbonitrile (1.0 eq) and NaOH (5 eq) in MeOH/H$_2$O (1/1) was warmed to reflux overnight. After 12 h, the reaction was concentrated to remove the MeOH. EtOAc was added, and 2M HCl was added until pH ~6. The layers were separated. The aqueous layer was extracted with EtOAc (2×). The combined organics were washed with brine, dried (MgSO$_4$) and concentrated to afford the title acid as a near colorless solid which was used without further purification. ESI-MS (m/z): 229.26 [M+1]$^+$.

Compound ct: 4-(5-fluoropyrimidin-2-yl)-1,5-dimethyl-1H-pyrazole-3-carboxylic acid

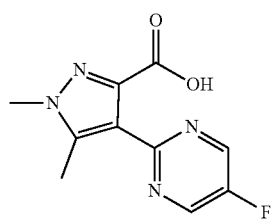 [SMILES: Cc1c(-c2ncc(F)cn2)c(C(=O)O)nn1C]

The title compound was prepared following the same general procedure as described for Compound aa using tert-butyl 4-bromo-1,5-dimethyl-1H-pyrazole-3-carboxylate and 2-chloro-5-(trifluoromethyl)pyrimidine. ESI-MS (m/z): 236.80 [M+1]$^+$.

Compound cu: 6-methyl-3-(1-methyl-1H-pyrazol-4-yl)picolinic acid

158

Step 1: methyl 6-methyl-3-(1-methyl-1H-pyrazol-4-yl)picolinate

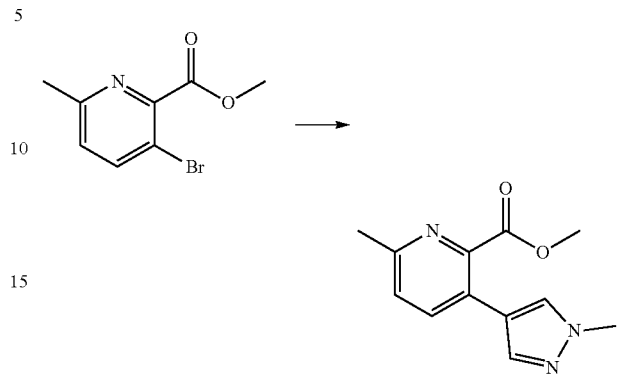

To a solution of methyl 3-bromo-6-methylpicolinate (1 eq) and (1-methyl-1H-pyrazol-4-yl)boronic acid (1.5 eq) in DMF/H$_2$O (5:1) was added K$_2$CO$_3$ (1.5 eq) and Pd(PPh$_3$)$_4$ (2.5 mol %). The mixture was degassed and then heated overnight in an 80° C. oil bath under argon. When the reaction was complete as judged by analytical HPLC, the reaction mixture was cooled to RT, and filtered through a celite pad to remove K$_2$CO$_3$ and Pd. The filter cake was washed with toluene. The filtrate was diluted with toluene was washed with H$_2$O and the layers were separated. The aqueous layer was extracted with toluene (2×). The combined organic layers were dried (Na$_2$SO$_4$) and concentrated to provide the title compound which was purified by chromatography on SiO$_2$ (EtOAc/hex). ESI-MS (m/z): 213.95 [M+1]$^+$.

Step 2: 6-methyl-3-(1-methyl-1H-pyrazol-4-yl)picolinic acid

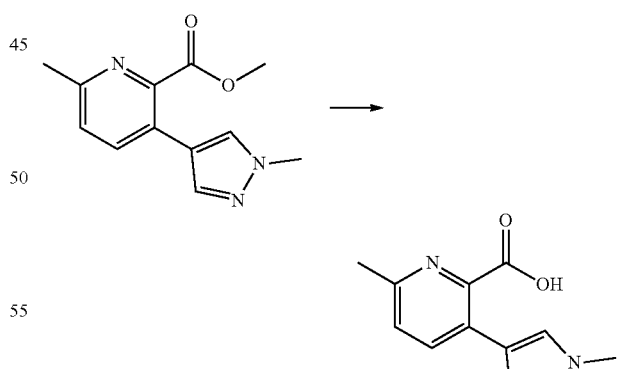

Methyl 6-methyl-3-(1-methyl-1H-pyrazol-4-yl)picolinate was stirred in THF/1M LiOH (1/1 v:v) until starting material was consumed as judged by analytical HPLC. When complete, the reaction was diluted with EtOAc, and 1M HCl was added to adjust the pH ~5-6. The layers were separated, and the aqueous layer was extracted with EtOAc (2×). The combined organic layers were washed with brine, dried (MgSO$_4$) and concentrated to afford the title compound as a solid that was used without further purification. ESI-MS (m/z): 217.97[M+1]$^+$.

Compound cv: 6-chloro-1,2-dimethyl-1H-benzo[d]imidazole-4-carboxylic acid

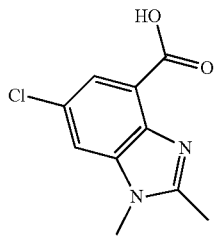

To a solution of methyl 2,3-diamino-5-chlorobenzoate (1 eq) and 1,1,1-trimethoxyethane (5 eq) in MeOH was added NH$_2$SO$_3$H. The reaction was stirred at room temperature for 12 h, and then concentrated in vacuo. The crude was taken up in EtOAc, and washed with sat. aq. NaHCO$_3$, brine, dried (MgSO$_4$) and concentrated in vacuo. Purification by chromatography on SiO$_2$ (EtOAc/hex afforded the benzimidazole.

To a solution of the benzimidazole in THF was added NaH (1.4 eq). After 30 min, MeI (2 eq) was added. When the starting material was consumed as judged by analytical HPLC, the reaction was quenched with 0.5 M HCl, and diluted with EtOAc. The layers were separated, and the organic layer was washed with brine, dried (MgSO$_4$) and concentrated in vacuo. The crude N-methyl benzimidazole was purified by chromatography on SiO$_2$ (EtOAc/hex).

To a solution of the crude N-methyl benzimidazole in MeOH/H$_2$O was added 1M KOH. The reaction was warmed to 50° C. until starting material was consumed as judged by T.L.C. analysis. The reaction was cooled to room temperature, acidified with 2 M HCl until the pH was ~5-6, and concentrated in vacuo. The crude was taken up in EtOAc and water, and the layers were separated. The organic layer was washed with brine, dried (MgSO$_4$) and concentrated to give the title compound as a light yellow solid. ESI-MS (m/z): 225.1 [M+1]$^+$.

Synthesis of Compounds 1 and 2

Compound 1: ((2S,3R)-5,5-difluoro-3-methyl-2-(((5-(trifluoromethyl)pyrimidin-2-yl)amino)methyl)piperidin-1-yl)(5-fluoro-2-(2H-1,2,3-triazol-2-yl)phenyl)methanone

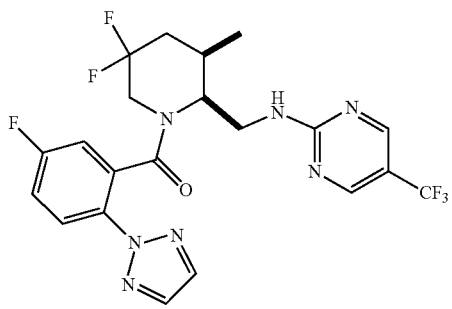 [SMILES: C[C@@H]1CC(F)(F)CN(C(=O)c2cc(F)ccc2-n2nccn2)[C@@H]1CNc1ncc(C(F)(F)F)cn1]

Step 1: (2S,3R)-benzyl 5,5-difluoro-3-methyl-2-(((5-(trifluoromethyl)pyrimidin-2-yl)amino)methyl)piperidine-1-carboxylate

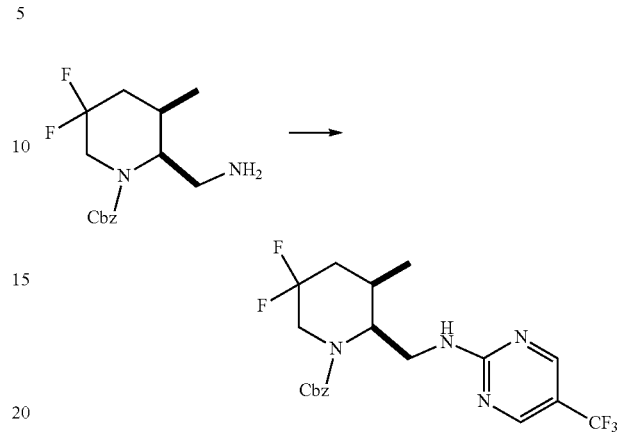

To a mixture of (2S,3R)-Benzyl 2-(aminomethyl)-5,5-difluoro-3-methylpiperidine-1-carboxylate (1 eq) and K$_2$CO$_3$ (2 eq) in DMF (20 mL) was added 2-chloro-5-(trifluoromethyl)pyrimidine (2 eq). The reaction was warmed to 80° C. for 2 h wherein the starting material was judged consumed as indicated by reverse-phase analytical HPLC. The reaction was cooled, and diluted with EtOAc, and water. The layers were separated, and the organic phase was washed with water (3×), brine, dried (MgSO$_4$) and concentrated. The crude residue was purified by chromatography on SiO$_2$ (EtOAc/hex) to give the title compound as a near colorless oil which solidified. ESI-MS (m/z): 445.4 [M+1]$^+$.

Step 2: N-(((2S,3R)-5,5-difluoro-3-methylpiperidin-2-yl)methyl)-5-(trifluoromethyl)pyrimidin-2-amine hydrobromide

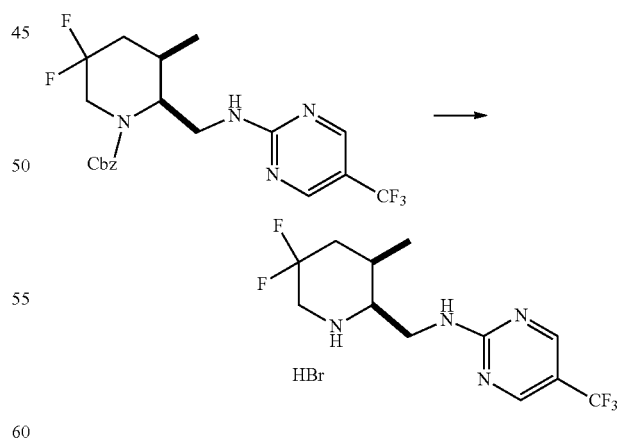

To the carbamate from the previous step was added to 30% HBr in HOAc. The reaction was stirred at rt (1-2 h) until sm was consumed as judged by HPLC analysis. The reaction was concentrated in vacuo to give the title compound as a pale yellow foam which was used without further purification. ESI-MS (m/z): 311.3 [M+1]$^+$.

Step 3: ((2S,3R)-5,5-difluoro-3-methyl-2-(((5-(trifluoromethyl)pyrimidin-2-yl)amino)methyl)piperidin-1-yl)(5-fluoro-2-(2H-1,2,3-triazol-2-yl)phenyl)methanone

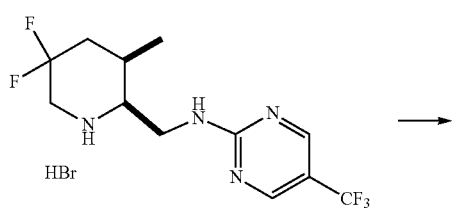

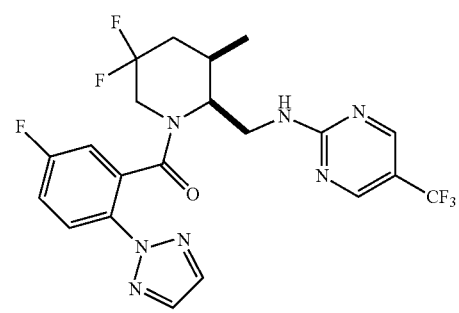

To a solution of N-(((2S,3R)-5,5-difluoro-3-methylpiperidin-2-yl)methyl)-5-(trifluoromethyl)pyrimidin-2-amine hydrobromide (10 mg) in DMF (0.5 mL) was added DIEA (3 eq) followed by 5-fluoro-2-(2H-1,2,3-triazol-2-yl)benzoic acid (6 mg) and HATU (8 mg). The reaction was allowed to stir at room temperature for 15 h, and was then diluted with EtOAc and washed with 1 M HCl, sat aq. NaHCO$_3$, brine, dried (MgSO$_4$), and concentrated. The crude residue was purified by chromatography on silica gel (EtOAc/hex) to give the title compound as a colorless oil which solidified. ESI-MS (m/z): 500.09 [M+1]$^+$.

Compound 2: ((2S,3R)-2-(((5-chloropyrimidin-2-yl)amino)methyl)-5,5-difluoro-3-methylpiperidin-1-yl)(5-fluoro-2-(2H-1,2,3-triazol-2-yl)phenyl)methanone

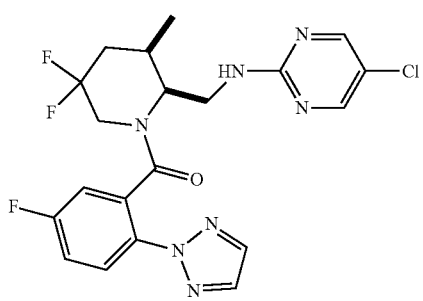 [SMILES: C[C@@H]1CC(F)(F)CN(C(=O)c2cc(F)ccc2-n2nccn2)[C@@H]1CNc1ncc(Cl)cn1]

Step 1: (2S,3R)-benzyl 2-(((5-chloropyrimidin-2-yl)amino)methyl)-5,5-difluoro-3-methylpiperidine-1-carboxylate

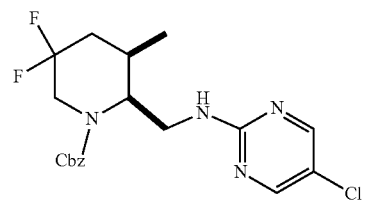 [SMILES: C[C@@H]1CC(F)(F)CN(C(=O)OCc2ccccc2)[C@@H]1CNc1ncc(Cl)cn1]

The title compound was prepared following the same general procedure as described in Compound 1 using 2,5-dichloropyrimidine in Step 1. ESI-MS (m/z): 411.2 [M+1]$^+$.

Step 2: 5-chloro-N-(((2S,3R)-5,5-difluoro-3-methylpiperidin-2-yl)methyl)pyrimidin-2-amine

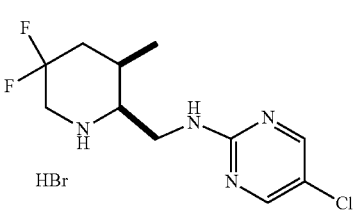 [SMILES: C[C@@H]1CC(F)(F)CN[C@@H]1CNc1ncc(Cl)cn1 ; Br]

The title compound was prepared following the same general protocol as described in Compound 1, Step 2. ESI-MS (m/z): 277.1 [M+1]$^+$.

Step 3: ((2S,3R)-2-(((5-chloropyrimidin-2-yl)amino)methyl)-5,5-difluoro-3-methylpiperidin-1-yl)(5-fluoro-2-(2H-1,2,3-triazol-2-yl)phenyl)methanone

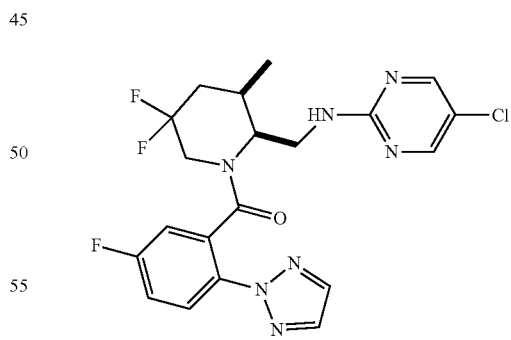

The title compound was prepared following the same general procedure as described in Compound 1, Step 3, using 5-fluoro-2-(2H-1,2,3-triazol-2-yl)benzoic acid. ESI-MS (m/z): 466.19 [M+1]$^+$.

Compounds 3-15, 19-53, 58-98, 100-101, 103-119, 121-161, 163-203, 210-211, 217-219, 221, 224-227, 229-233, 237-242, 249-250, 252-253, and 254 were prepared in a manner analogous to that shown above for Compound 1.

Compound 68: ((2S,3R)-5,5-difluoro-3-methyl-2-(((5-(trifluoromethyl)pyrimidin-2-yl)amino)methyl)piperidin-1-yl)(5-(4-fluorophenyl)-2-methylthiazol-4-yl)methanone

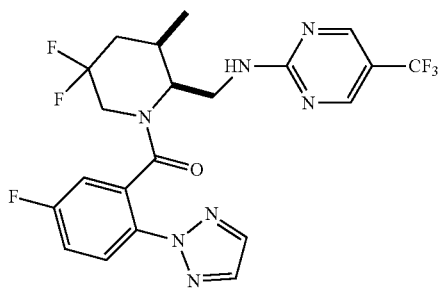 [SMILES: C[C@@H]1CC(F)(F)CN(C(=O)c2cc(F)ccc2-n2nccn2)[C@@H]1CNc1ncc(C(F)(F)F)cn1]

$^1$H NMR (MeOD, 400 MHz) δ 8.42 (s, 2H), 7.44-7.39 (m, 2H), 7.18-7.13 (m, 2H), 4.9-4.77 (m, 1H), 4.20 (br s, 1H), 3.82-3.60 (m, 1H), 3.47 (m, 2H), 3.4-3.25 (m, 1H), 2.45 (s, 3H), 2.0-1.75 (m, 2H), 1.35-1.1 (m, 2H), 0.87 (d, 3H); ESI-MS (m/z): 530.12 [M+1]$^+$.

Compound 97: ((2S,3R)-5,5-difluoro-3-methyl-2-(((5-(trifluoromethyl)pyrimidin-2-yl)amino)methyl)piperidin-1-yl)(1-methyl-4-(pyrimidin-2-yl)-1H-pyrazol-3-yl)methanone

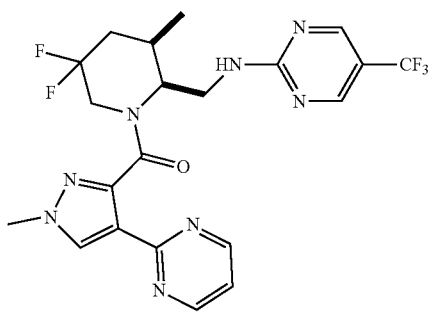 [SMILES: C[C@@H]1CC(F)(F)CN(C(=O)c2nn(C)cc2-c2ncccn2)[C@@H]1CNc1ncc(C(F)(F)F)cn1]

$^1$H NMR (CDCl$_3$, 400 MHz) δ 8.80-8.79 (m, 2H), 8.54 (s, 0.6H), 8.45-8.42 (m, 1.4H), 8.20 (s, 0.6H), 8.10 (s, 0.4H), 7.25-7.20 (m, 0.4H), 7.13-7.09 (m, 1H), 7.02-7.0 (m, 0.6H), 5.29-5.26 (m, 0.6H), 5.20-5.05 (t, 0.4H), 4.25-4.16 (m, 0.6H), 4.10-4.05 (m, 0.4H), 3.99 (s, 1.9H), 3.97 (s, 1.1H), 3.9-3.7 (m, 1H), 3.55-3.45 (m, 1H), 3.40-3.25 (m, 0.6H), 3.10-3.0 (m, 0.4H), 2.6-2.45 (m, 1H), 2.4-2.1 (m, 1H), 2.05-1.75 (m, 1H), 1.20 (d, 1.9H), 0.99 (d, 1.1H); ESI-MS (m/z): 497.38 [M+1]$^+$.

Compound 98: ((2S,3R)-2-(((5-chloropyrimidin-2-yl)amino)methyl)-5,5-difluoro-3-methylpiperidin-1-yl)(1-methyl-4-(pyrimidin-2-yl)-1H-pyrazol-3-yl)methanone

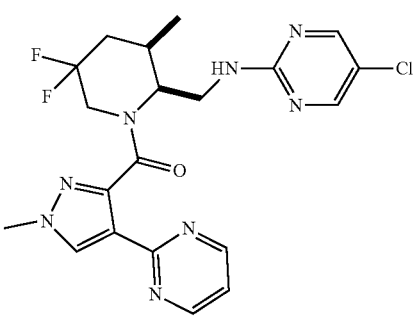 [SMILES: C[C@@H]1CC(F)(F)CN(C(=O)c2nn(C)cc2-c2ncccn2)[C@@H]1CNc1ncc(Cl)cn1]

$^1$H NMR (DMSO-d$_6$, 400 MHz) δ 8.79-8.78 (d, 0.6H), 8.63-8.62 (d, 1.4H), 8.48 (s, 0.3H), 8.4-8.3 (br s, 0.5H), 8.26 (s, 0.7H), 8.2-8.1 (m, 1.5H), 7.32-7.28 (m, 1H), 7.23-7.21 (m, 0.7H), 7.05-7.0 (m, 0.3H), 5.0-4.95 (m, 0.3H), 4.85-4.75 (m, 0.7H), 4.0-3.95 (m, 0.7H), 3.91 (s, 1H), 3.85-3.8 (m, 0.3H), 3.67 (s, 2H), 3.7-3.3 (m, 3H), 2.10-1.95 (m, 3H), 1.10 (d, 1H), 0.80 (d, 2H); ESI-MS (m/z): 463.2 [M+1]$^+$.

Compound 159: ((2S,3R)-5,5-difluoro-3-methyl-2-(((5-(trifluoromethyl)pyrazin-2-yl)amino)methyl)piperidin-1-yl)(1-methyl-4-(pyrimidin-2-yl)-1H-pyrazol-3-yl)methanone

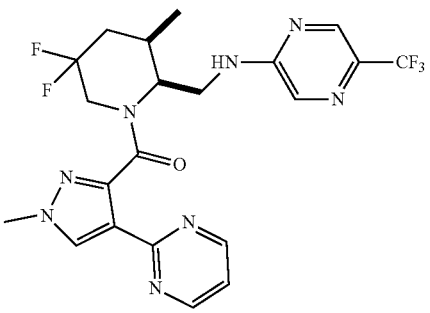 [SMILES: C[C@@H]1CC(F)(F)CN(C(=O)c2nn(C)cc2-c2ncccn2)[C@@H]1CNc1cnc(C(F)(F)F)cn1]

$^1$H NMR (DMSO-d$_6$, 400 MHz) δ 8.71-8.69 (d, 0.4H), 8.62-8.60 (d, 1.6H), 8.43 (s, 0.4H), 8.18 (s, 1.6H), 7.95 (br s, 1H), 7.88 (s, 1H), 7.27-7.21 (m, 1H), 5.0-4.79 (m, 1H), 3.85 (s, 0.5H), 4.0-3.75 (m, 1H), 3.55 (s, 2.5H), 3.6-3.50 (m, 2H), 3.40-3.30 (m, 1H), 2.15-1.95 (m, 3H), 1.11 (d, 0.5H), 0.82 (d, 2.5H); ESI-MS (m/z): 497.24 [M+1]$^+$.

Compound 200: ((2S,3R)-5,5-difluoro-3-methyl-2-(((5-(trifluoromethyl)pyridin-2-yl)amino)methyl)piperidin-1-yl)(1-methyl-4-(pyrimidin-2-yl)-1H-pyrazol-3-yl)methanone

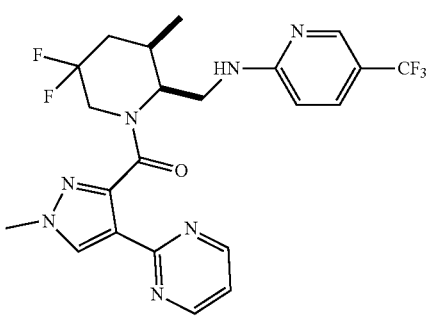 [SMILES: C[C@@H]1CC(F)(F)CN(C(=O)c2nn(C)cc2-c2ncccn2)[C@@H]1CNc1ccc(C(F)(F)F)cn1]

¹H NMR (DMSO-d₆, 400 MHz) δ 8.73 (d, 0.6H), 8.64 (d, 1.4H), 8.5 (s, 0.3H), 8.45 (br s, 0.3H), 8.20 (s, 0.7H), 8.15 (s, 0.7H), 7.7-7.6 (m, 0.3H), 7.55-7.5 (m, 0.7H), 7.30-7.25 (m, 0.3H), 7.25-7.15 (m, 1.7H), 6.60-6.50 (m, 0.3H), 6.45-6.35 (m, 0.7H), 5.0-4.9 (br s, 0.2H), 4.85-4.75 (m, 0.7H), 3.90 (s, 0.7H), 3.95-3.9 (m, 0.5H), 3.59 (s, 2.3H), 3.65-3.45 (m, 2.5H), 3.40-3.30 (m, 1H), 2.20-1.95 (m, 3H), 1.15 (d, 0.7H), 0.83 (d, 2.3H); ESI-MS (m/z): 496.15 [M+1]⁺.

Compound 202: ((2S,3R)-5,5-difluoro-3-methyl-2-(((5-(trifluoromethyl)pyridin-2-yl)amino)methyl)piperidin-1-yl)(6-methoxy-3-(2H-1,2,3-triazol-2-yl)pyridin-2-yl)methanone

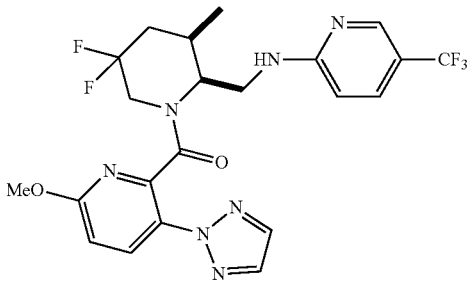 [SMILES: COc1ccc(-n2nccn2)c(C(=O)N2CC(F)(F)C[C@@H](C)[C@H]2CNc2ccc(C(F)(F)F)cn2)n1]

¹H NMR (CDCl₃, 400 MHz) δ 8.38-8.14 (m, 2H), 7.89 (s, 1H), 7.74 (s, 1H), 7.6-7.55 (m, 0.5H), 7.55-7.45 (m, 0.5H), 6.95-6.92 (m, 1H), 6.6-6.35 (m, 2H), 5.2-5.05 (m, 0.5H), 5.0-4.9 (m, 0.5H), 4.25-4.15 (m, 0.5H), 3.98 (s, 1.6H), 3.92 (s, 1.4H), 3.9-3.6 (m, 2.5H), 3.5-3.35 (m, 0.5H), 3.1-2.95 (m, 0.5H), 2.8-2.7 (m, 0.5H), 2.5-2.4 (m, 0.5H), 2.3-2.0 (m, 2H), 1.4 (d, 1.6H), 1.08 (d, 1.4H); ESI-MS (m/z): 512.5 [M+1]⁺.

Compound 203: (3-(2H-1,2,3-triazol-2-yl)-6-(trifluoromethyl)pyridin-2-yl)((2S,3R)-5,5-difluoro-3-methyl-2-(((5-(trifluoromethyl)pyridin-2-yl)amino)methyl)piperidin-1-yl)methanone

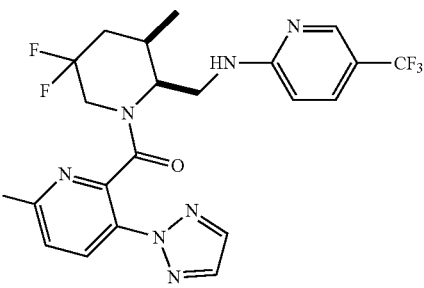

¹H NMR (CDCl₃, 400 MHz) δ 8.66-8.60 (m, 1H), 8.37-8.33 (m, 1H), 7.95-7.84 (m, 3H), 7.58-7.54 (m, 1H), 6.6-6.4 (m, 2H), 5.2-5.1 (m, 0.2H), 4.99-4.92 (t, 0.8H), 4.20-4.00 (m, 1.5H), 4.0-3.7 (m, 0.5H), 3.5-3.3 (m, 1H), 3.15-3.0 (dd, 1H), 2.70 (br s, 0.8H), 2.5 (br s, 0.2H), 2.3-2.2 (m, 1H), 2.1-1.95 (m, 1H), 1.2 (d, 0.6H), 1.02 (d, 2.4H); ESI-MS (m/z): 550.2 [M+1]⁺.

Compound 217: ((2S,3R)-5,5-difluoro-3-methyl-2-(((5-(trifluoromethyl)pyrimidin-2-yl)amino)methyl)piperidin-1-yl)(4-(5-fluoropyrimidin-2-yl)-1-methyl-1H-pyrazol-3-yl)methanone

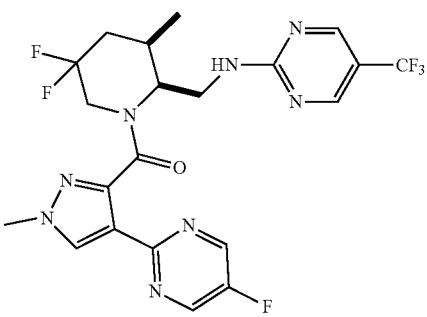 [SMILES: C[C@@H]1CC(F)(F)CN(C(=O)c2nn(C)cc2-c2ncc(F)cn2)[C@@H]1CNc1ncc(C(F)(F)F)cn1]

¹H NMR (CDCl₃, 400 MHz) δ 8.8 (s, 1.2H), 8.7 (s, 0.8H), 8.6-8.45 (m, 2H), 8.15 (s, 0.6H), 8.0 (s, 0.4H), 7.1 (br s, 0.6H), 6.8 (m, 0.4H), 5.35-5.25 (m, 0.6H), 5.2-5.1 (m, 0.4H), 4.2-4.1 (m, 1H), 3.98 (s, 1.6H), 3.97 (s, 1.4H), 3.9-3.75 (m, 1H), 3.6-3.55 (m, 0.6H), 3.5-3.4 (m, 0.4H), 3.35-3.2 (m, 0.6H), 3.2-3.0 (m, 0.4H), 2.6-2.35 (m, 1H), 2.3-2.1 (m, 1H), 2-1.8 (m, 1H), 1.2 (d, 1.8H), 1.0 (d, 1.2H); ESI-MS (m/z): 515.3 [M+1]⁺.

Compound 218: (4-(5-chloropyrimidin-2-yl)-1-methyl-1H-pyrazol-3-yl)((2S,3R)-5,5-difluoro-3-methyl-2-(((5-(trifluoromethyl)pyrimidin-2-yl)amino)methyl)piperidin-1-yl)methanone

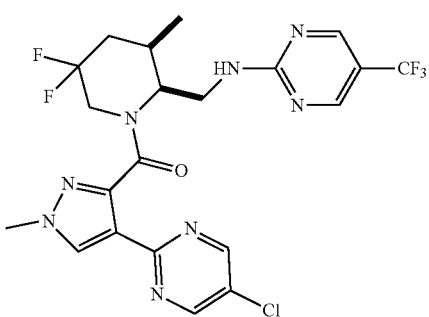 [SMILES: C[C@@H]1CC(F)(F)CN(C(=O)c2nn(C)cc2-c2ncc(Cl)cn2)[C@@H]1CNc1ncc(C(F)(F)F)cn1]

¹H NMR (CDCl₃, 400 MHz) δ 8.85 (s, 1.2H), 8.75 (s, 0.8H), 8.6-8.4 (m, 2H), 8.2 (s, 0.6H), 8.05 (s, 0.4H), 7.0 (br s, 0.6H), 6.68 (m, 0.4H), 5.35-5.25 (m, 0.6H), 5.2-5.1 (m, 0.4H), 4.15-4.05 (m, 1H), 4.07 (s, 1.6H), 4.06 (s, 1.4H), 3.9-3.75 (m, 1H), 3.6-3.5 (m, 0.6H), 3.5-3.4 (m, 0.4H), 3.35-3.2 (m, 0.6H), 3.2-3.0 (m, 0.4H), 2.6-2.4 (m, 1H), 2.3-2.15 (m, 1H), 2.05-1.8 (m, 1H), 1.2 (d, 1.8H), 1.0 (d, 1.2H); ESI-MS (m/z): 531.3 [M+1]⁺.

Compound 219: ((2S,3R)-5,5-difluoro-3-methyl-2-(((5-(trifluoromethyl)pyrimidin-2-yl)amino)methyl)piperidin-1-yl)(1-methyl-4-(5-methylpyrimidin-2-yl)-1H-pyrazol-3-yl)methanone

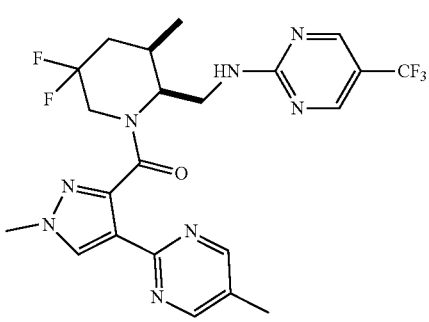 [SMILES: Cc1cnc(-c2cn(C)nc2C(=O)N2CC(F)(F)C[C@@H](C)[C@H]2CNc2ncc(C(F)(F)F)cn2)nc1]

¹H NMR (DMSO-d₆, 400 MHz) δ 8.75-8.65 (m, 0.5H), 8.65-8.6 (m, 1.0H), 8.55-8.5 (m, 0.5H), 8.5-8.4 (m, 1.5H), 8.25-8.15 (m, 0.5H), 7.95-7.85 (m, 0.5H), 7.75-7.2 (m, 0.5H), 6.95-6.65 (m, 0.5H), 5.35-5.3 (m, 0.5H), 4.85-4.75 (m, 0.5H), 4.5-4.45 (m, 0.5H), 4.05-3.90 (m, 1.0H), 3.89 (s, 1.0H), 3.8-3.65 (m, 1.0H), 3.61 (s, 2.0H), 2.25 (s, 1.0H), 2.23 (2.0H), 2.05-1.9 (m, 3.0H), 1.5-1.4 (m, 1.0H) 1.11 (d, 1.0H), 0.86 (d, 2.0H) ppm; ESI-MS (m/z): 511.3 [M+1]⁺.

Compound 221: (4-(5-chloropyridin-2-yl)-1-methyl-1H-pyrazol-3-yl)((2S,3R)-5,5-difluoro-3-methyl-2-(((5-(trifluoromethyl)pyrimidin-2-yl)amino)methyl)piperidin-1-yl)methanone

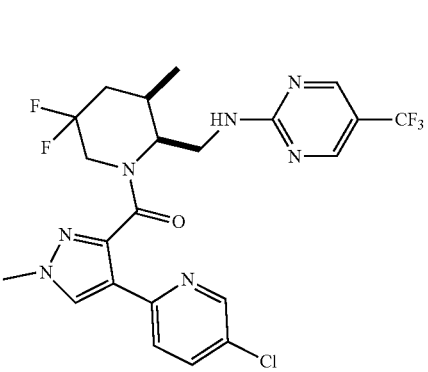 [SMILES: C[C@@H]1CC(F)(F)CN(C(=O)c2nn(C)cc2-c2ccc(Cl)cn2)[C@@H]1CNc1ncc(C(F)(F)F)cn1]

¹H NMR (d₆-DMSO, 400 MHz) δ 8.7-8.5 (m, 1H), 8.4 (m, 1.3H), 8.35 (s, 0.3H), 8.3 (m, 0.7H), 8.2 (s, 0.7H), 8.0 (m, 0.7H), 7.9 (dd, 0.3H), 7.8 (m, 0.3H), 7.8 (dd, 0.7H), 7.5 (d, 0.3H), 7.35 (d, 0.7H), 5.1 (m, 0.3H), 4.8 (m, 0.7H), 3.9 (s, 0.8H), 3.7 (s, 2.2H), 3.6-3.3 (m, 3H), 2.2-1.9 (m, 3H), 1.1 (d, 0.6H), 0.9 (d, 2.4H); ESI-MS (m/z): 529.9 [M+1]⁺.

Compound 224: ((2S,3R)-5,5-difluoro-3-methyl-2-(((5-(trifluoromethyl)pyrimidin-2-yl)amino)methyl)piperidin-1-yl)(1-methyl-4-(pyrazin-2-yl)-1H-pyrazol-3-yl)methanone

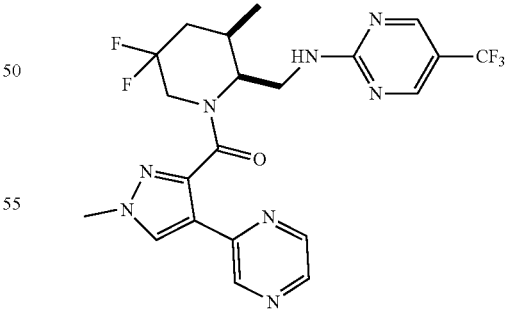

¹H NMR (CDCl₃, 400 MHz) δ 8.8 (d, 1H), 8.55 (d, 1H), 8.5-8.3 (m, 3H), 7.8 (d, 1H), 7.3 (m, 0.6H), 6.35 (m, 0.4H), 5.3-5.0 (m, 3H), 4.3 (m, 0.5H), 4.0 (s, 1.5H), 3.9 (s, 1.5H), 3.9-2.7 (m, 0.5H), 3.5-3.3 (m, 0.5H), 3.1-3.0 (m, 0.5H), 2.4-2.3 (m, 1H), 2.2-1.9 (m, 2H), 1.2 (d, 1.5H), 1.0 (d, 1.5H); ESI-MS (m/z): 497.32 [M+1]⁺.

Compound 225: ((2S,3R)-5,5-difluoro-3-methyl-2-(((5-(trifluoromethyl)pyrimidin-2-yl)amino)methyl)piperidin-1-yl)(1-methyl-4-(4-methylpyrimidin-2-yl)-1H-pyrazol-3-yl)methanone

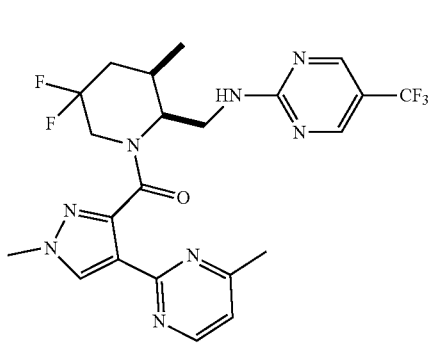 [SMILES: Cc1ccnc(-c2cn(C)nc2C(=O)N2CC(F)(F)C[C@@H](C)[C@H]2CNc2ncc(C(F)(F)F)cn2)n1]

$^1$H NMR (CDCl$_3$, 400 MHz) δ 8.7 (d, 1.2H), 8.65 (d, 0.8H), 8.6-8.4 (m, 2H), 8.2 (s, 0.6H), 8.1 (s, 0.4H), 7.4 (br s, 0.6H), 7.2 (m, 0.4H), 5.3-5.2 (m, 0.6H), 5.2-5.1 (m, 0.4H), 4.25-4.15 (m, 0.6H), 4.1-4.0 (m, 0.4H), 3.97 (s, 3H), 3.9-3.75 (m, 1H), 3.6-3.45 (m, 1H), 3.4-3.35 (m, 0.6H), 3.15-3.0 (m, 0.4H), 2.5 (s, 1.8), 2.49 (s, 1.2H), 2.45-1.7 (m, 3H), 1.2 (d, 1.8H), 1.0 (d, 1.2H); ESI-MS (m/z): 511.4 [M+1]$^+$.

Compound 226: ((2S,3R)-5,5-difluoro-3-methyl-2-(((5-(trifluoromethyl)pyrimidin-2-yl)amino)methyl)piperidin-1-yl)(1-methyl-4-(5-(trifluoromethyl)pyrimidin-2-yl)-1H-pyrazol-3-yl)methanone

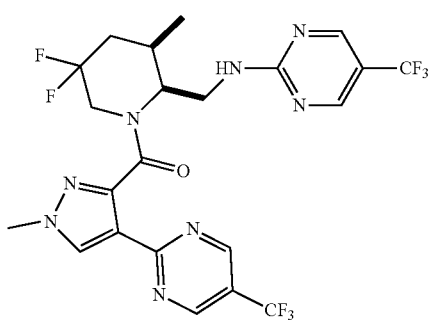 [SMILES: C[C@@H]1CC(F)(F)CN(C(=O)c2nn(C)cc2-c2ncc(C(F)(F)F)cn2)[C@@H]1CNc1ncc(C(F)(F)F)cn1]

$^1$H NMR (d$_6$-DMSO, 400 MHz) δ 9.2 (s, 0.6H), 9.0 (s, 1.4H), 8.75 (m, 0.5H), 8.6 (m, 0.5H), 8.42 (br s, 1.4H), 8.3 (br s, 0.6H), 7.8 (m, 0.7H), 7.6 (m, 0.3H), 5.2 (m, 0.3H), 4.85 (m, 0.7H), 4.05 (m, 1H), 3.95 (s, 0.8H), 3.8 (s, 2.2H), 3.8-3.4 (m, 3H), 2.2-1.9 (m, 3H), 1.2 (d, 0.8H), 0.85 (d, 2.2H); ESI-MS (m/z): 565.3 [M+1]$^+$.

Compound 227: (4-(4-chloropyridin-2-yl)-1-methyl-1H-pyrazol-3-yl)((2S,3R)-5,5-difluoro-3-methyl-2-(((5-(trifluoromethyl)pyrimidin-2-yl)amino)methyl)piperidin-1-yl)methanone

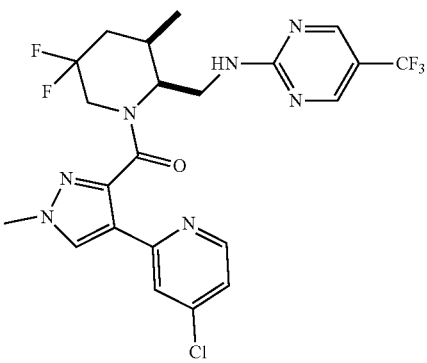 [SMILES: C[C@@H]1CC(F)(F)CN(C(=O)c2nn(C)cc2-c2cc(Cl)ccn2)[C@@H]1CNc1ncc(C(F)(F)F)cn1]

$^1$H NMR (d$_6$-DMSO, 400 MHz) δ 8.55-8.35 (m, 3H), 8.2 (s, 1H), 8.0 (m, 0.8H), 7.8 (m, 0.2H), 7.6 (d, 0.2H), 7.45 (d, 0.8H), 7.4 (dd, 0.2H), 7.3 (dd, 0.8H), 5.1 (m, 0.2H), 4.8 (m, 0.8H), 4.3 (m, 1H), 3.7 (s, 0.8H), 3.4 (s, 2.2H), 3.6-3.3 (m, 3H), 2.2-2.0 (m, 3H), 1.15 (d, 0.6H), 0.9 (d, 2.4H); ESI-MS (m/z): 530.3 [M+1]$^+$.

Compound 229: ((2S,3R)-5,5-difluoro-3-methyl-2-(((5-(trifluoromethyl)pyrimidin-2-yl)amino)methyl)piperidin-1-yl)(1-methyl-4-(6-(trifluoromethyl)pyridin-2-yl)-1H-pyrazol-3-yl)methanone

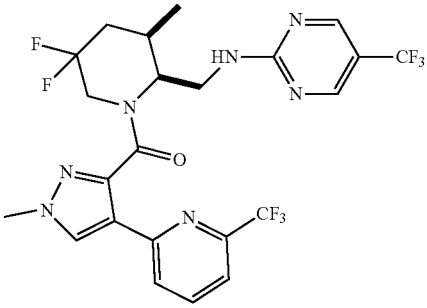 [SMILES: C[C@@H]1CC(F)(F)CN(C(=O)c2nn(C)cc2-c2cccc(C(F)(F)F)n2)[C@@H]1CNc1ncc(C(F)(F)F)cn1]

$^1$H NMR (CDCl$_3$, 400 MHz) δ 8.6-8.4 (m, 2H), 8.1 (s, 0.7H), 8.05 (s, 0.3H), 7.93 (s, 1H), 7.9-7.7 (m, 1H), 7.6-7.5 (m, 1H), 7.4 (br s, 0.7H), 5.9 (br s, 0.3H), 5.3-5.1 (m, 1H), 4.4-4.3 (m, 0.7H), 4.2-3.9 (m, 1.2H), 4.05 (s, 2H), 3.92 (s, 1H), 3.7-3.4 (m, 1.4H), 3.2-3.0 (m, 0.7H), 2.5-2.1 (m, 2H), 2.1-1.7 (m, 1H), 1.2 (d, 1H), 1.0 (d, 2H); ESI-MS (m/z): 563.7 [M+1]$^+$.

Compound 230: ((2S,3R)-5,5-difluoro-3-methyl-2-(((5-(trifluoromethyl)pyrimidin-2-yl)amino)methyl)piperidin-1-yl)(1-methyl-4-(pyrimidin-5-yl)-1H-pyrazol-3-yl)methanone

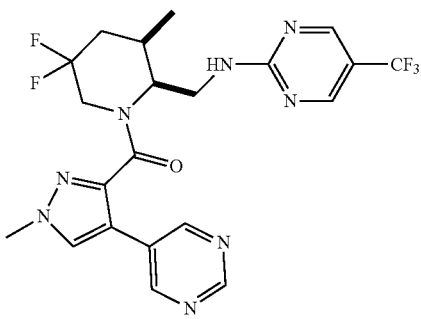

$^1$H NMR (CDCl$_3$, 400 MHz) δ 9.1 (br d, 1H), 8.9-8.7 (m, 2H), 8.6-8.4 (m, 2H), 7.65 (s, 1H), 7.6 (s, 1H), 7.25 (br s, 0.5H), 5.9 (br s, 0.5H), 5.2-5.1 (m, 0.5H), 5.1-5.0 (m, 0.5H), 4.7-4.6 (m, 0.5H), 4.5-4.4 (m, 0.5H), 4.2-3.9 (m, 1H), 4.05 (s, 1.5H), 3.9 (s, 1.5H), 3.9-2.7 (m, 0.5H), 3.7-3.5 (m, 1.5H), 3.2-3.0 (m, 0.5H), 2.4-1.8 (m, 3H), 1.2 (d, 1.6H), 1.0 (d, 1.4H); ESI-MS (m/z): 496.8 [M+1]$^+$.

Compound 231: ((2S,3R)-5,5-difluoro-3-methyl-2-(((5-(trifluoromethyl)pyrimidin-2-yl)amino)methyl)piperidin-1-yl)(5,6'-dimethyl-[2,3'-bipyridin]-2'-yl)methanone

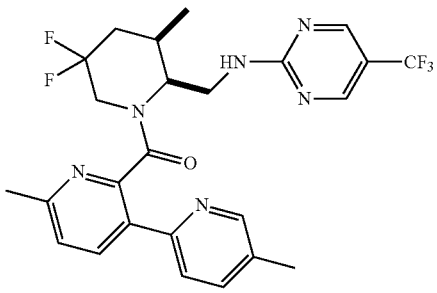

$^1$H NMR (CDCl$_3$, 400 MHz) δ 8.8 (br s, 1H), 8.5 (s, 3H), 7.95 (d, 1H), 7.6-7.5 (m, 2H), 7.3 (m, 1H), 5.1-5.0 (m, 1H), 4.25-4.15 (m, 1H), 3.9-3.8 (m, 1H), 3.45-3.4 (m, 1H), 3.1-2.9 (m, 1H), 2.9-2.8 (m, 1H), 2.7 (s, 3H), 2.4 (s, 3H), 2.1-2.0 (m, 2H), 1.0 (d, 3H); ESI-MS (m/z): 521.3 [M+1]$^+$.

Compound 232: ((2S,3R)-5,5-difluoro-3-methyl-2-(((5-(trifluoromethyl)pyrimidin-2-yl)amino)methyl)piperidin-1-yl)(1-ethyl-4-(pyrimidin-2-yl)-1H-pyrazol-3-yl)methanone

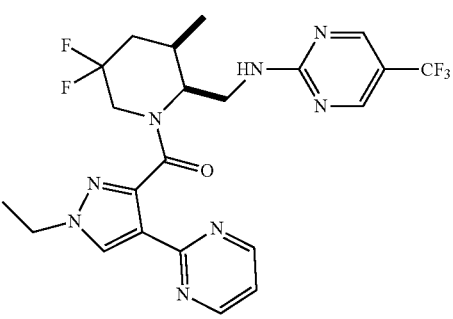

$^1$H NMR (CDCl$_3$, 400 MHz) δ 8.9 (s, 2H), 8.6-8.3 (m, 3H), 7.4-7.0 (m, 2H), 5.4-5.3 (m, 0.5H), 5.2-5.1 (0.5H), 4.4-4.3 (m, 2H), 4.3-4.1 (m, 1H), 4.0-3.8 (m, 1H), 3.6-3.1 (m, 2H), 2.5-2.0 (m, 3H), 1.7-1.6 (m, 3H), 1.2 (d, 1.6H), 1.0 (d, 1.4H); ESI-MS (m/z): 511.0 [M+1]$^+$.

Compound 233: ((2S,3R)-5,5-difluoro-3-methyl-2-(((5-(trifluoromethyl)pyrimidin-2-yl)amino)methyl)piperidin-1-yl)(1,5-dimethyl-4-(pyrimidin-2-yl)-1H-pyrazol-3-yl)methanone

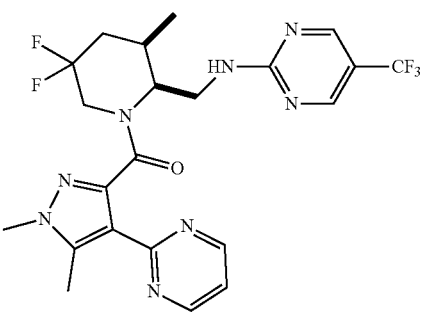

$^1$H NMR (CDCl$_3$, 400 MHz) δ 8.9-8.8 (m, 2H), 8.6-8.45 (m, 2H), 7.6 (br s, 0.6H), 7.15-7.05 (m, 1H), 6.85-6.8 (m, 0.4H), 5.35-5.3 (m, 0.4H), 5.2-5.1 (m, 0.6H), 4.2-4.1 (m, 1H), 4.0-3.8 (m, 1H), 3.9 (s, 3H), 3.6-3.55 (m, 0.4H), 3.5-3.4 (m, 0.6H), 3.3-3.2 (m, 0.4H), 3.1-3.0 (m, 0.6H), 2.8 (s, 1.3H), 2.7 (s, 1.7H), 2.6-2.5 (m, 0.6H), 2.5-2.4 (m, 0.4H), 2.3-2.15 (m, 1H), 2.1-1.8 (m, 1H), 1.2 (d, 1.3H), 1.05 (d, 1.7H); ESI-MS (m/z): 511.1 [M+1]$^+$.

Compound 237: ((2S,3R)-5,5-difluoro-3-methyl-2-(((5-(trifluoromethyl)pyrimidin-2-yl)amino)methyl)piperidin-1-yl)(1-isopropyl-4-(pyrimidin-2-yl)-1H-pyrazol-3-yl)methanone

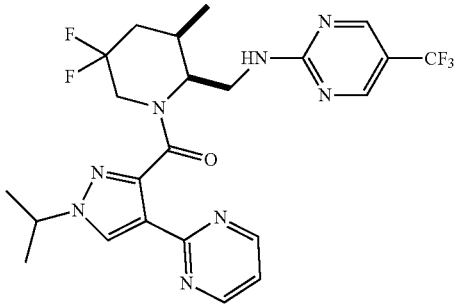

$^1$H NMR (CDCl$_3$, 400 MHz) δ 8.80-8.78 (m, 2H), 8.54-8.42 (m, 2H), 8.25-8.14 (m, 1H), 7.12-7.08 (m, 1H), 5.3-5.2 (m, 0.5H), 5.15-5.05 (m, 0.5H), 4.60-4.54 (m, 1H), 4.2-4.1 (m, 0.5H), 4.1-4.0 (m, 0.5H), 3.85-3.75 (m, 1H), 3.55-3.35 (m, 1H), 3.35-2.95 (m, 1H), 2.6-2.35 (m, 1H), 2.3-2.05 (m, 1H), 1.57 (d, 6H), 1.19 (d, 1.7H), 0.98 (m, 1.3H) ppm; ESI-MS (m/z): 525.40 [M+1]$^+$.

Compound 238: ((2S,3R)-5,5-difluoro-3-methyl-2-(((5-(trifluoromethyl)pyrimidin-2-yl)amino)methyl)piperidin-1-yl)(4-(pyrimidin-2-yl)-1-(2,2,2-trifluoroethyl)-1H-pyrazol-3-yl)methanone

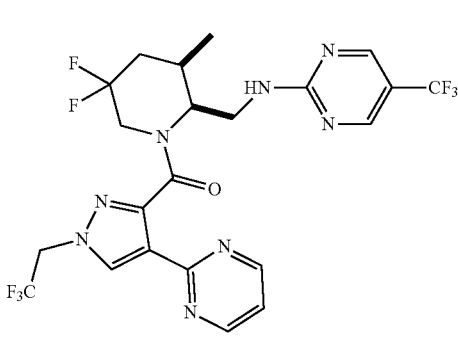

$^1$H NMR (CDCl$_3$, 400 MHz) δ 8.86-8.83 (m, 2H), 8.54-8.38 (m, 2H), 8.35 (s, 0.5H), 8.22 (s, 0.5H), 7.19-7.13 (m, 1H), 7.1-7.0 (m, 0.5H), 6.85-6.75 (m, 0.5H), 5.3-5.2 (m, 0.5H), 5.15-5.05 (m, 0.5H), 4.84-4.72 (m, 2H), 4.15-4.0 (m, 0.5H), 4.0-3.95 (m, 0.5H), 3.8-3.7 (m, 1H), 3.6-3.5 (m, 0.5H), 3.5-3.4 (m, 0.5H), 3.4-3.35 (m, 0.5H), 3.15-3.0 (m, 0.5H), 2.6-2.5 (m, 0.5H), 2.4-2.3 (m, 0.5H), 2.25-2.1 (m, 1H), 1.20 (d, 1.5H), 0.98 (d, 1.5H) ppm; ESI-MS (m/z): 565.70 [M+1]$^+$.

Compound 239: ((2S,3R)-2-(((5-ethylpyrimidin-2-yl)amino)methyl)-5,5-difluoro-3-methylpiperidin-1-yl)(5-(4-fluorophenyl)-2-methylthiazol-4-yl)methanone

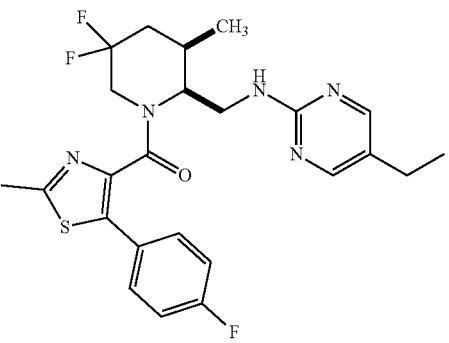 [SMILES: CCc1cnc(NC[C@@H]2[C@H](C)CC(F)(F)CN2C(=O)c2nc(C)sc2-c2ccc(F)cc2)nc1]

$^1$H NMR (MeOD, 400 MHz) δ 8.03 (s, 2.0H), 7.40-7.36 (m, 2.0H), 7.16-7.08 (m, 2.0H), 4.85-4.75 (m, 1.0H), 4.3-4.2 (m, 1.0H), 4.45-4.4 (m, 2.0H), 3.30 (s, 2.0H), 2.5-2.4 (m, 5.0H), 1.9-1.8 (m, 2.0H), 1.18 (t, 3.0H), 0.88 (d, 3.0H) ppm; ESI-MS (m/z): 490.43 [M+1]$^+$.

Compound 240: ((2S,3R)-5,5-difluoro-3-methyl-2-(((5-(trifluoromethyl)pyrimidin-2-yl)amino)methyl)piperidin-1-yl)(6-methyl-3-(2-methyl-2H-tetrazol-5-yl)pyridin-2-yl)methanone

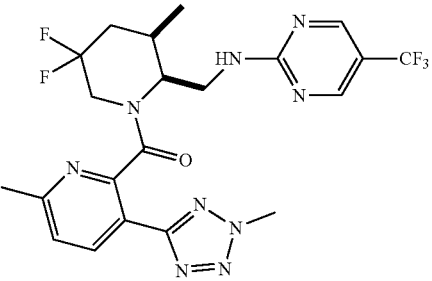

The title compound was prepared following the same general procedure as described in Compound 1 using 6-methyl-3-(2-methyl-2H-tetrazol-5-yl)picolinic acid in Step 3. $^1$H NMR (CDCl$_3$, 400 MHz) δ 8.43 (s, 2.0H), 8.31 (d, 1.0H), 7.31 (d, 1.0H), 5.35-5.25 (m, 1.0H), 5.05-4.95 (m, 1.0H), 4.31 (s, 3.0H), 3.95-3.85 (m, 1.0H), 3.85-3.75 (m, 1.0H), 3.4-3.3 (m, 1.0H), 3.1-2.95 (m, 1.0H), 2.69 (s, 3.0H), 1.6-1.5 (m, 1.0H), 0.93 (d, 3.0H) ppm; ESI-MS (m/z): 512.4 [M+1]$^+$.

Compound 241: ((2S,3R)-5,5-difluoro-3-methyl-2-(((5-(trifluoromethyl)pyrimidin-2-yl)amino)methyl)piperidin-1-yl)(1-methyl-4-(pyrimidin-4-yl)-1H-pyrazol-3-yl)methanone

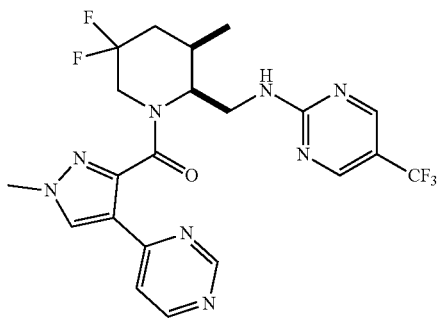 [SMILES: C[C@@H]1CC(F)(F)CN(C(=O)c2nn(C)cc2-c2ccncn2)[C@@H]1CNc1ncc(C(F)(F)F)cn1]

¹H NMR (CDCl₃, 400 MHz) δ 9.20 (s, 1H), 8.65-8.62 (m, 1H), 8.55-8.4 (m, 2H), 8.10 (s, 0.6H), 8.03 (s, 0.4H), 7.52-7.50 (m, 0.6H), 7.44-7.42 (m, 0.4H), 6.4-6.3 (m, 0.4H), 5.3-5.2 (m, 0.4H), 5.15-5.05 (m, 0.6H), 4.3-4.2 (m, 0.6H), 4.01 (s, 1.6H), 3.95 (s, 1.4H), 3.92-3.8 (m, 2H), 3.55-3.4 (m, 1.3H), 3.15-3.0 (m, 0.7H), 2.5-2.35 (m, 0.4H), 2.35-2.25 (m, 0.6H), 2.2-2.1 (m, 1.3H), 1.21 (d, 1.4H), 1.01 (d, 1.6H) ppm; ESI-MS (m/z): 497.3 [M+1]⁺.

Compound 242: ((2S,3R)-5,5-difluoro-2-(((3-fluoro-5-(trifluoromethyl)pyridin-2-yl)amino)methyl)-3-methylpiperidin-1-yl)(4-(5-fluoropyrimidin-2-yl)-1-methyl-1H-pyrazol-3-yl)methanone

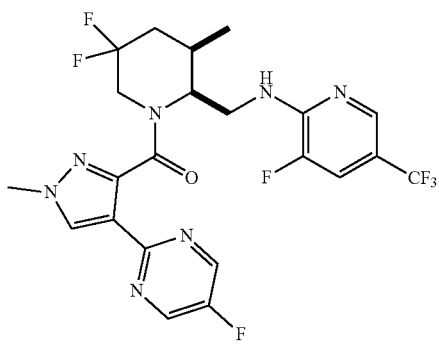 [SMILES: C[C@@H]1CC(F)(F)CN(C(=O)c2nn(C)cc2-c2ncc(F)cn2)[C@@H]1CNc1ncc(C(F)(F)F)cc1F]

¹H NMR (CDCl₃, 400 MHz) δ 8.50 (s, 0.9H), 8.41 (s, 0.6H), 8.20 (s, 0.4H), 8.13 (s, 0.5H), 8.09 (s, 0.3H), 8.02 (s, 0.4H), 7.31-7.27 (m, 1.0H), 6.57 (br s, 0.5H), 6.25 (br s, 0.3H), 5.25-5.05 (m, 0.9H), 4.15-4.05 (m, 1.0H), 3.97 (d, 3.0H), 3.8-3.65 (m, 1.0H), 3.45-3.3 (m, 1.0H), 3.2-3.0 (m, 0.8H), 2.4-2.35 (m, 1.0H), 2.25-2.2 (m, 0.7H), 2.2-2.1 (m, 1.0H), 2.05-1.95 (m, 1.0H), 1.22 (d, 1.3H), 0.98 (d, 1.7H) ppm; ESI-MS (m/z): 532.3 [M+1]⁺.

Compound 252: ((2S,3R)-5,5-difluoro-3-methyl-2-(((5-(trifluoromethyl)pyrimidin-2-yl)amino)methyl)piperidin-1-yl)(5-fluoro-2-(2-methyl-2H-tetrazol-5-yl)phenyl)methanone

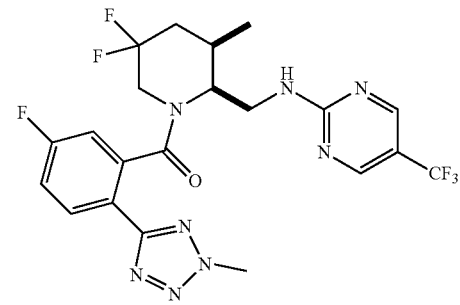 [SMILES: C[C@@H]1CC(F)(F)CN(C(=O)c2cc(F)ccc2-c2nnn(C)n2)[C@@H]1CNc1ncc(C(F)(F)F)cn1]

¹H NMR CDCl₃, 400 MHz) δ 8.5-8.4 (m, 1.8H), 8.4-8.3 (m, 0.2H), 8.2-8.1 (m, 0.6H), 8.1-8.0 (m, 0.4H), 7.2-7.1 (m, 0.4H), 7.1-7.0 (m, 0.6H), 7.0-6.9 (m, 1H), 5.4-5.25 (m, 0.8H), 5.1-5.0 (m, 0.8H), 4.37 (s, 2.0H), 4.28 (s, 1.0H), 4.2-4.1 (m, 0.8H), 3.7-3.6 (m, 1H), 3.5-3.4 (m, 1.8H), 2.35-2.2 (m, 1H), 2.2-2.05 (m, 1H), 2.0-1.9 (m, 2H), 1.85-1.7 (m, 2.0H), 1.6-1.5 (m, 2H), 1.10 (d, 2.0H), 1.02 (d, 1.0H) ppm: ESI-MS (m/z): 515.00 [M+1]⁺.

Compound 16: ((2S,3R)-5,5-difluoro-3-methyl-2-(((5-(trifluoromethyl)pyrimidin-2-yl)amino)methyl)piperidin-1-yl)(6'-methyl-[2,3'-bipyridin]-2'-yl)methanone

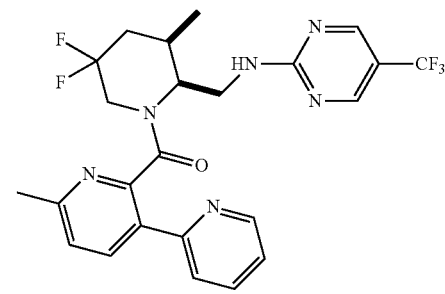

Step 1: (3-bromo-6-methylpyridin-2-yl)((2S,3R)-5,5-difluoro-3-methyl-2-(((5-(trifluoromethyl)pyrimidin-2-yl)amino)methyl)piperidin-1-yl)methanone

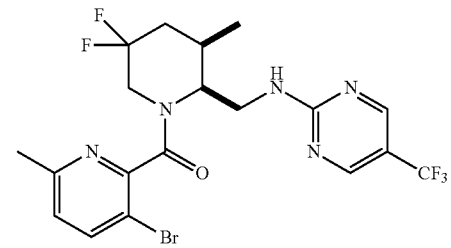 [SMILES: Cc1ccc(Br)c(C(=O)N2CC(F)(F)C[C@@H](C)[C@H]2CNc2ncc(C(F)(F)F)cn2)n1]

The title compound was prepared following the same general procedure as described in Compound 1 using 3-bromo-6-methylpicolinic acid in Step 3. ESI-MS (m/z): 508.06/510.08 [M+1]$^+$.

Step 2: ((2S,3R)-5,5-difluoro-3-methyl-2-(((5-(trifluoromethyl)pyrimidin-2-yl)amino)methyl)piperidin-1-yl)(6'-methyl-[2,3'-bipyridin]-2'-yl)methanone To a solution of (3-bromo-6-methylpyridin-2-yl)((2S,3R)-5,5-difluoro-3-methyl-2-(((5-(trifluoromethyl)pyrimidin-2-yl)amino)methyl)piperidin-1-yl)methanone (1 eq) and 2-(tributylstannyl)pyridine (1.2 eq) in DMF was added Pd(PPh$_3$)$_4$ (10 mol %). The reaction mixture was heated to 120° C. for 2 h in a microwave reactor and then the mixture was cooled and concentrated. The crude was dissolved with EtOAc and washed with sat'd NaHCO$_3$, brine, dried (MgSO$_4$) and concentrated. The crude was purified by chromatography on SiO2 (EtOAc/hex) to obtain the title compound. ESI-MS (m/z): 507.2 [M+1]$^+$.

Compounds 17, 54, and 99 were prepared in a manner analogous to that for Compound 16.

Compound 17: ((2S,3R)-5,5-difluoro-3-methyl-2-(((5-(trifluoromethyl)pyrimidin-2-yl)amino)methyl)piperidin-1-yl)(6-methyl-3-(pyrimidin-2-yl)pyridin-2-yl)methanone

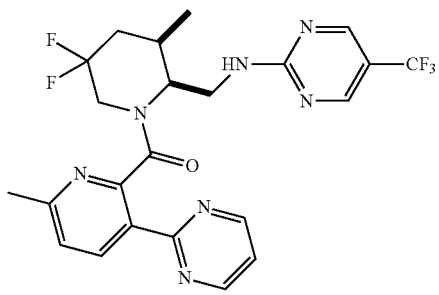

$^1$H NMR (CDC$_3$, 400 MHz) δ 8.81-8.79 (m, 2H), 8.6 (br s, 1H), 8.55-8.50 (m, 2H), 7.37-7.35 (m, 1H), 7.25-7.22 (m, 1H), 5.15-5.05 (m, 1H), 4.15-4.05 (m, 1H), 3.9-3.8 (m, 1H), 3.4-3.35 (m, 1H), 3.15-2.95 (m, 1H), 2.85-2.8 (m, 1H), 2.76 (s, 3H), 2.25-2.2 (m, 1H), 2.05-2.0 (m, 1H), 1.00 (d, 3H) ppm; ESI-MS (m/z): 508.03 [M+1]$^+$.

Compound 18: ((2S,3R)-2-(((5-chloropyrimidin-2-yl)amino)methyl)-5,5-difluoro-3-methylpiperidin-1-yl)(6-methyl-3-(pyrimidin-2-yl)pyridin-2-yl)methanone

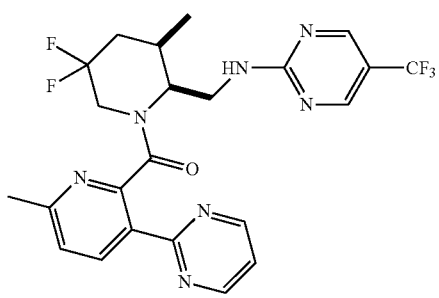

Step 1: (3-bromo-6-methylpyridin-2-yl)((2S,3R)-2-(((5-chloropyrimidin-2-yl)amino)methyl)-5,5-difluoro-3-methylpiperidin-1-yl)methanone

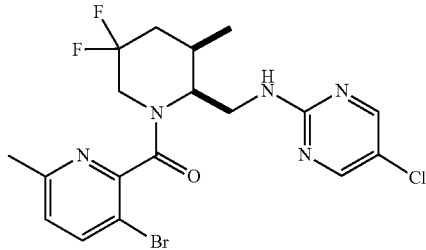 [SMILES: Cc1ccc(Br)c(C(=O)N2CC(F)(F)C[C@@H](C)[C@H]2CNc2ncc(Cl)cn2)n1]

The title compound was prepared following the same general procedure as described in Compound 1 using 2,5-dichloropyrimidine in Step 1 and 3-bromo-6-methylpicolinic acid in Step 3. ESI-MS (m/z): 473.93/475.81 [M+1]$^+$.

Step 2: ((2S,3R)-2-(((5-chloropyrimidin-2-yl)amino)methyl)-5,5-difluoro-3-methylpiperidin-1-yl)(6-methyl-3-(pyrimidin-2-yl)pyridin-2-yl)methanone The title compound was prepared following the same general procedure as described in Compound 16 using 2-(tributylstannyl)pyrimidine in Step 2. ESI-MS (m/z): 474.05 [M+1]$^+$.

Compound 55: ((2S,3R)-5,5-difluoro-3-methyl-2-(((5-(trifluoromethyl)pyrimidin-2-yl)amino)methyl)piperidin-1-yl)(5-methyl-2-(pyrimidin-2-yl)phenyl)methanone

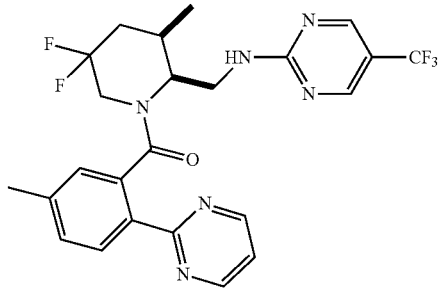 [SMILES: Cc1ccc(-c2ncccn2)c(C(=O)N2CC(F)(F)C[C@@H](C)[C@H]2CNc2ncc(C(F)(F)F)cn2)c1]

Step 1: (2-bromo-5-methylphenyl)((2S,3R)-5,5-difluoro-3-methyl-2-(((5-(trifluoromethyl)pyrimidin-2-yl)amino)methyl)piperidin-1-yl)methanone

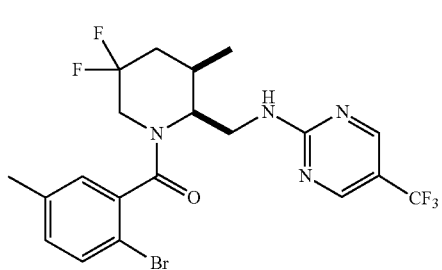 [SMILES: Cc1ccc(Br)c(C(=O)N2CC(F)(F)C[C@@H](C)[C@H]2CNc2ncc(C(F)(F)F)cn2)c1]

The title compound was prepared following the same general procedure as described in Compound 1 using 2-bromo-5-methylbenzoic acid in Step 3. ESI-MS (m/z): 507.0/509.0 [M+1]+.

Step 2: ((2S,3R)-5,5-difluoro-3-methyl-2-(((5-(trifluoromethyl)pyrimidin-2-yl)amino)methyl)piperidin-1-yl)(5-methyl-2-(pyrimidin-2-yl)phenyl)methanone The title compound was prepared following the same general procedure as described in Compound 16 using 2-(tributylstannyl)pyrimidine in Step 2. ESI-MS (m/z): 506.94 [M+1]+.

Compound 56: (5-chloro-2-(pyrimidin-2-yl)phenyl)((2S,3R)-5,5-difluoro-3-methyl-2-(((5-(trifluoromethyl)pyrimidin-2-yl)amino)methyl)piperidin-1-yl)methanone

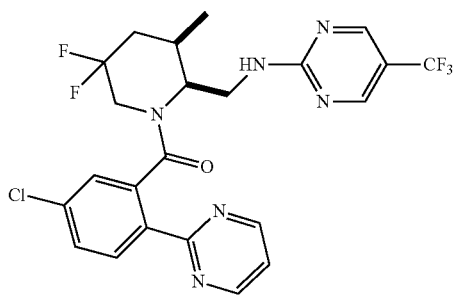 [SMILES: C[C@@H]1CC(F)(F)CN(C(=O)c2cc(Cl)ccc2-c2ncccn2)[C@@H]1CNc1ncc(C(F)(F)F)cn1]

Step 1: (5-chloro-2-iodophenyl)((2S,3R)-5,5-difluoro-3-methyl-2-(((5-(trifluoromethyl)pyrimidin-2-yl)amino)methyl)piperidin-1-yl)methanone

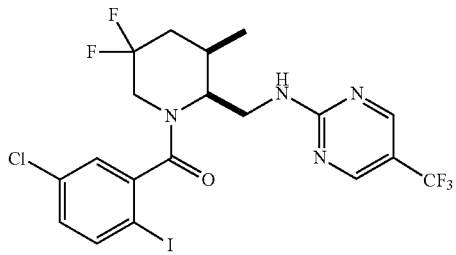 [SMILES: C[C@@H]1CC(F)(F)CN(C(=O)c2cc(Cl)ccc2I)[C@@H]1CNc1ncc(C(F)(F)F)cn1]

The title compound was prepared following the same general procedure as described in Compound 1 using 2-bromo-5-chlorobenzoic acid in Step 3. ESI-MS (m/z): 575.0 [M+1]+.

Step 2: (5-chloro-2-(pyrimidin-2-yl)phenyl)((2S,3R)-5,5-difluoro-3-methyl-2-(((5-(trifluoromethyl)pyrimidin-2-yl)amino)methyl)piperidin-1-yl)methanone The title compound was prepared following the same general procedure as described in Compound 16 using 2-(tributylstannyl)pyrimidine in Step 2. ESI-MS (m/z): 526.92 [M+1]+.

Compound 57: (5-chloro-2-(pyrimidin-2-yl)phenyl)((2S,3R)-2-(((5-chloropyrimidin-2-yl)amino)methyl)-5,5-difluoro-3-methylpiperidin-1-yl)methanone

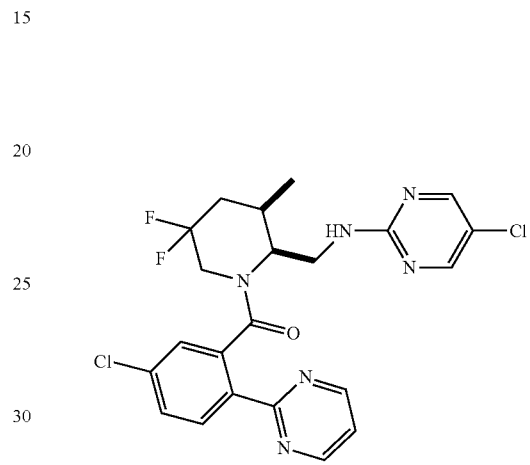

Step 1: (5-chloro-2-iodophenyl)((2S,3R)-2-(((5-chloropyrimidin-2-yl)amino)methyl)-5,5-difluoro-3-methylpiperidin-1-yl)methanone

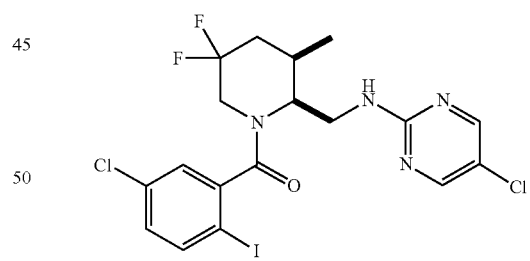

The title compound was prepared following the same general procedure as described in Compound 1 using 2,5-dichloropyrimidine in Step 1 and 2-bromo-5-chlorobenzoic in Step 3. ESI-MS (m/z): 540.93 [M+1]+.

Step 2: (5-chloro-2-(pyrimidin-2-yl)phenyl)((2S,3R)-2-(((5-chloropyrimidin-2-yl)amino)methyl)-5,5-difluoro-3-methylpiperidin-1-yl)methanone The title compound was prepared following the same general procedure as described in Compound 16 using 2-(tributylstannyl)pyrimidine in Step 2. ESI-MS (m/z): 493.3 [M+1]+.

Compound 102: ((2S,3R)-5,5-difluoro-2-(((4-methoxy-5-(trifluoromethyl)pyrimidin-2-yl)amino)methyl)-3-methylpiperidin-1-yl)(1-methyl-4-(pyridin-2-yl)-1H-pyrazol-3-yl)methanone

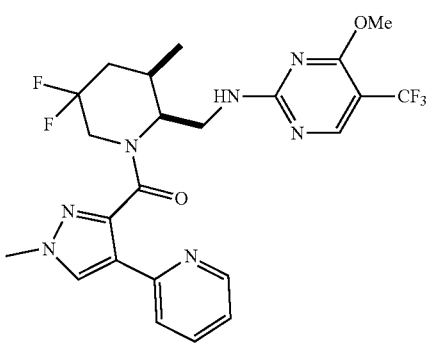 [SMILES: COc1nc(NC[C@@H]2[C@H](C)CC(F)(F)CN2C(=O)c2nn(C)cc2-c2ccccn2)ncc1C(F)(F)F]

Step 1: (2S,3R)-benzyl 5,5-difluoro-2-(((4-methoxy-5-(trifluoromethyl)pyrimidin-2-yl)amino)methyl)-3-methylpiperidine-1-carboxylate

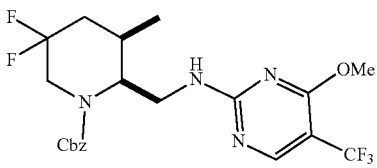 [SMILES: COc1nc(NC[C@@H]2[C@H](C)CC(F)(F)CN2C(=O)OCc2ccccc2)ncc1C(F)(F)F]

The title compound was prepared following the same general procedure as described in Compound 1 using 2-chloro-4-methoxy-5-(trifluoromethyl)pyrimidine in Step 1. ESI-MS (m/z): 475.22 [M+1]$^+$.

Step 2: N-(((2S,3R)-5,5-difluoro-3-methylpiperidin-2-yl)methyl)-4-methoxy-5-(trifluoromethyl)pyrimidin-2-amine

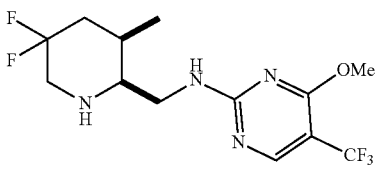 [SMILES: COc1nc(NC[C@H]2NCC(F)(F)C[C@H]2C)ncc1C(F)(F)F]

A mixture of (2S,3R)-benzyl 5,5-difluoro-2-(((4-methoxy-5-(trifluoromethyl)pyrimidin-2-yl)amino)methyl)-3-methylpiperidine-1-carboxylate and 10% Pd/C and EtOAc was stirred under a balloon of hydrogen. When starting material was consumed as judged by T.L.C. analysis, the reaction mixture was filtered through a pad of celite and washed with EtOAc. The organics were concentrated in vacuo to afford the title compound which was used without further purification. ESI-MS (m/z): 341.06 [M+1]$^+$.

Step 3: ((2S,3R)-2-(((5-chloropyrimidin-2-yl)amino)methyl)-5,5-difluoro-3-methylpiperidin-1-yl)(5-fluoro-2-(2H-1,2,3-triazol-2-yl)phenyl)methanone The title compound was prepared following the same general procedure as described in Compound 1, Step 3, using 1-methyl-4-(pyridin-2-yl)-1H-pyrazole-carboxylic acid. ESI-MS (m/z): 526.2 [M+1]$^+$.

Compound 120: ((2S,3R)-5,5-difluoro-3-methyl-2-(((5-(trifluoromethyl)pyrazin-2-yl)amino)methyl)piperidin-1-yl)(1-methyl-4-phenyl-1H-pyrazol-3-yl)methanone

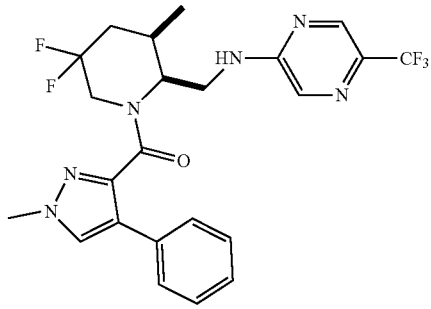 [SMILES: C[C@@H]1CC(F)(F)CN(C(=O)c2nn(C)cc2-c2ccccc2)[C@@H]1CNc1cnc(C(F)(F)F)cn1]

Step 1: (2S,3R)-benzyl 5,5-difluoro-3-methyl-2-(((5-(trifluoromethyl)pyrazin-2-yl)amino)methyl)piperidine-1-carboxylate

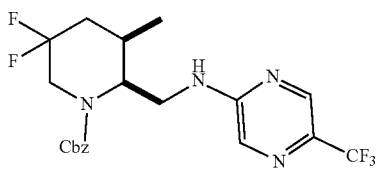 [SMILES: C[C@@H]1CC(F)(F)CN(C(=O)OCc2ccccc2)[C@@H]1CNc1cnc(C(F)(F)F)cn1]

The title compound was prepared following the same general procedure as described in Compound 1 using 2-chloro-5-(trifluoromethyl)pyrazine in Step 1. ESI-MS (m/z): 445.4 [M+1]$^+$.

Step 2: N-(((2S,3R)-5,5-difluoro-3-methylpiperidin-2-yl)methyl)-5-(trifluoromethyl)pyrazin-2-amine hydrobromide

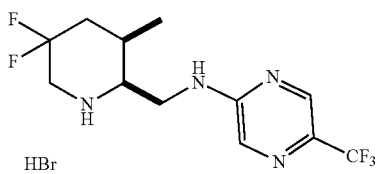 [SMILES: C[C@@H]1CC(F)(F)CN[C@@H]1CNc1cnc(C(F)(F)F)cn1 ; Br]

The title compound was prepared following the same general procedure as described in Compound 1, Step 2. ESI-MS (m/z): 311.3 [M+1]$^+$.

183

Step 3: ((2S,3R)-5,5-difluoro-3-methyl-2-(((5-(trifluoromethyl)pyrazin-2-yl)amino)methyl)piperidin-1-yl)(1-methyl-4-phenyl-1H-pyrazol-3-yl)methanone

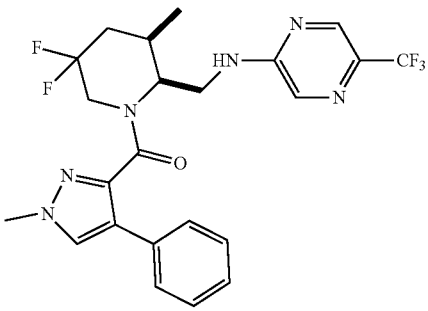 [SMILES: C[C@@H]1CC(F)(F)CN(C(=O)c2nn(C)cc2-c2ccccc2)[C@@H]1CNc1cnc(C(F)(F)F)cn1]

The title compound was prepared following the same general procedure as described in Compound 1, Step 3, using 1-methyl-4-phenyl-1H-pyrazole-3-carboxylic acid. $^1$H NMR (CDCl$_3$, 400 MHz) δ 8.15 (s, 0.25H), 8.05 (s, 0.75H), 7.8 (s, 0.75H), 7.7 (s, 0.25H), 7.2-7.1 (m, 6H), 6.4 (m, 0.8H), 5.1 (m, 0.2H), 5.0 (m, 0.26H), 4.75 (m, 0.75H), 3.7-3.8 (m, 1H), 3.65 (s, 0.8H), 3.60 (s, 2.2H), 3.4-3.3 (m, 2H), 2.75-2.9 (m, 1H), 1.8 (m, 1H), 1.3-1.5 (m, 2H), 1.0 (d, 0.85H), 0.70 (d, 2.15H); ESI-MS (m/z): 495.07 [M+1]$^+$.

Compound 162: ((2S,3R)-5,5-difluoro-3-methyl-2-(((5-(trifluoromethyl)pyridin-2-yl)amino)methyl)piperidin-1-yl)(1-methyl-4-(4-methylpyridin-2-yl)-1H-pyrazol-3-yl)methanone

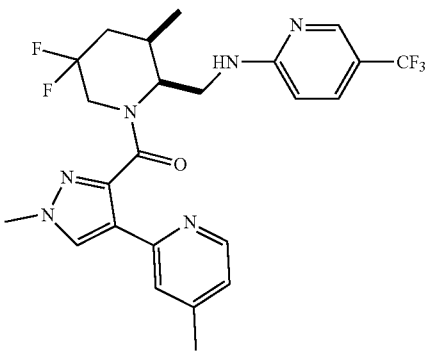 [SMILES: Cc1ccnc(-c2cn(C)nc2C(=O)N2CC(F)(F)C[C@@H](C)[C@H]2CNc2ccc(C(F)(F)F)cn2)c1]

Step 1: (2S,3R)-benzyl 5,5-difluoro-3-methyl-2-(((5-(trifluoromethyl)pyridin-2-yl)amino)methyl)piperidine-1-carboxylate

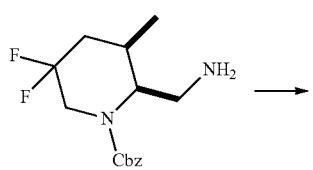

184

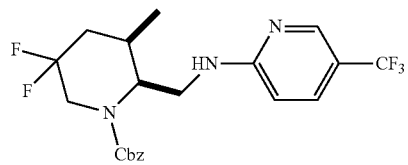

To a mixture of (2S,3R)-benzyl 2-(aminomethyl)-5,5-difluoro-3-methylpiperidine-1-carboxylate (1 eq) and K$_2$CO$_3$ (2 eq) in DMF (20 mL) was added 2-fluoro-5-(trifluoromethyl)pyridine (3 eq). The reaction was warmed to 80° C. for 2 h wherein the starting material was judged consumed as indicated by reverse-phase analytical HPLC. The reaction was cooled, and diluted with EtOAc, and water. The layers were separated, and the organic phase was washed with water (3×), brine, dried (MgSO$_4$) and concentrated. The crude residue was purified by chromatography on SiO$_2$ (EtOAc/hex) to give the title compound as a near colorless oil which solidified. ESI-MS (m/z): 444.4 [M+1]$^+$.

Step 2: N-(((2S,3R)-5,5-difluoro-3-methylpiperidin-2-yl)methyl)-5-(trifluoromethyl)pyridin-2-amine hydrobromide

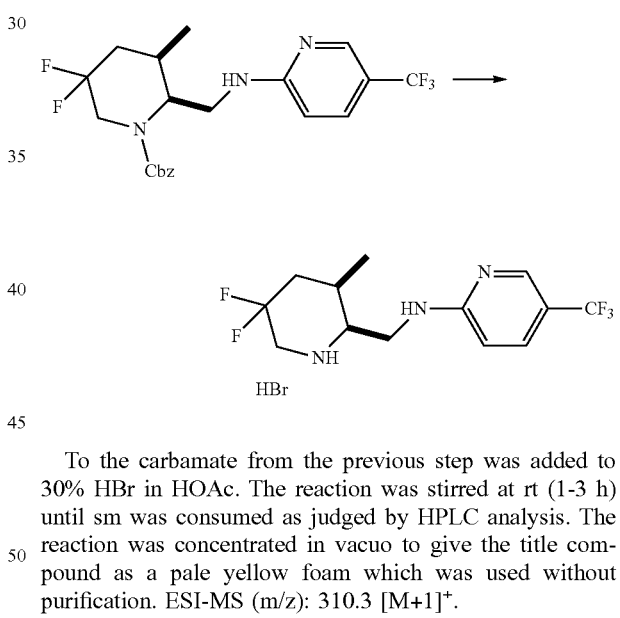

To the carbamate from the previous step was added to 30% HBr in HOAc. The reaction was stirred at rt (1-3 h) until sm was consumed as judged by HPLC analysis. The reaction was concentrated in vacuo to give the title compound as a pale yellow foam which was used without purification. ESI-MS (m/z): 310.3 [M+1]$^+$.

Step 3: ((2S,3R)-5,5-difluoro-3-methyl-2-(((5-(trifluoromethyl)pyridin-2-yl)amino)methyl)piperidin-1-yl)(1-methyl-4-(4-methylpyridin-2-yl)-1H-pyrazol-3-yl)methanone

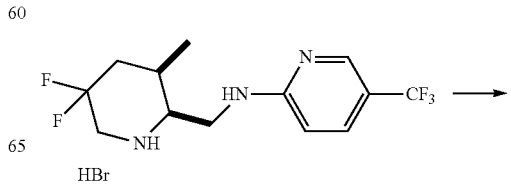

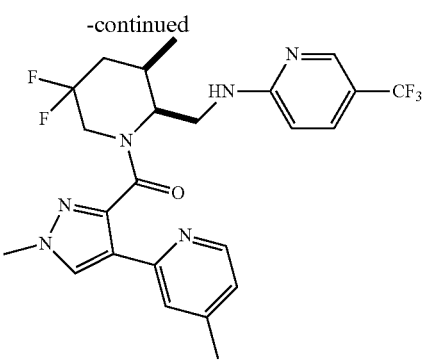

The title compound was prepared following the same general procedure as described in Compound 1 using 1-methyl-4-(4-methylpyridin-2-yl)-1H-pyrazole-3-carboxylic acid in Step 3. ESI-MS (m/z): 509.22 [M+1]+.

Compound 183: ((2S,3R)-5,5-difluoro-3-methyl-2-(((5-(trifluoromethyl)pyridin-2-yl)amino)methyl)piperidin-1-yl)(6-methyl-3-(pyrimidin-2-yl)pyridin-2-yl)methanone

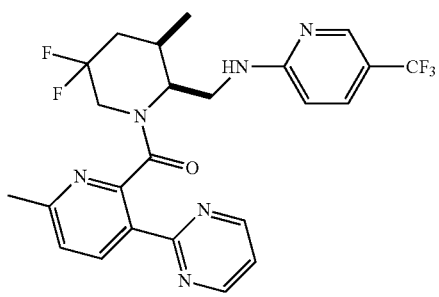 [SMILES: Cc1ccc(-c2ncccn2)c(C(=O)N2CC(F)(F)C[C@@H](C)[C@H]2CNc2ccc(C(F)(F)F)cn2)n1]

Step 1: (3-bromo-6-methylpyridin-2-yl)((2S,3R)-5,5-difluoro-3-methyl-2-(((5-(trifluoromethyl)pyridin-2-yl)amino)methyl)piperidin-1-yl)methanone

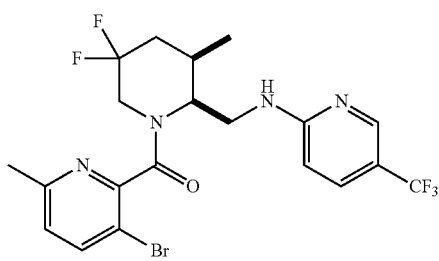 [SMILES: Cc1ccc(Br)c(C(=O)N2CC(F)(F)C[C@@H](C)[C@H]2CNc2ccc(C(F)(F)F)cn2)n1]

The title compound was prepared following the same general procedure as described in Compound 1 using 2-chloro-5-(trifluoromethyl)pyridine in Step 1 and 3-bromo-6-methylpicolinic acid in Step 3. ESI-MS (m/z): 507.12/509.1 [M+1]+.

Step 4: ((2S,3R)-5,5-difluoro-3-methyl-2-(((5-(trifluoromethyl)pyridin-2-yl)amino)methyl)piperidin-1-yl)(6-methyl-3-(pyrimidin-2-yl)pyridin-2-yl)methanone The title compound was synthesized following the same general protocol as described for Compound 16 using (3-bromo-6-methylpyridin-2-yl)((2S,3R)-5,5-difluoro-3-methyl-2-(((5-(trifluoromethyl)pyridin-2-yl)amino)methyl)piperidin-1-yl)methanone and 2-(tributylstannyl)pyrimidine. ESI-MS (m/z): 507.16 [M+1]+.

Compound 204: ((2S,3R)-5,5-difluoro-3-methyl-2-(((5-(trifluoromethyl)pyridin-2-yl)oxy)methyl)piperidin-1-yl)(6-methyl-3-(2H-1,2,3-triazol-2-yl)pyridin-2-yl)methanone

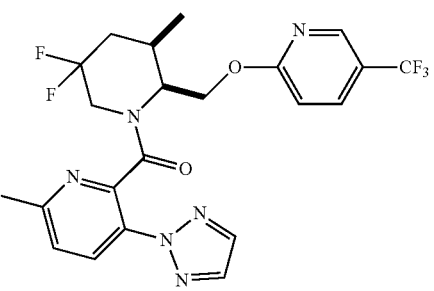 [SMILES: Cc1ccc(-n2nccn2)c(C(=O)N2CC(F)(F)C[C@@H](C)[C@H]2COc2ccc(C(F)(F)F)cn2)n1]

Step 1: ((2S,3R)-5,5-difluoro-3-methylpiperidin-2-yl)methanol

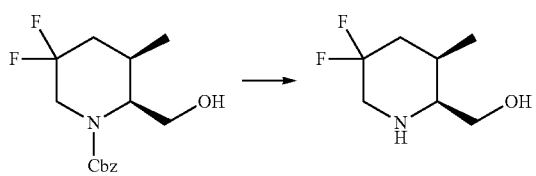 [SMILES: C[C@@H]1CC(F)(F)CN(C(=O)OCc2ccccc2)[C@@H]1CO ; C[C@@H]1CC(F)(F)CN[C@@H]1CO]

A mixture of (2S,3R)-benzyl 5,5-difluoro-2-(hydroxymethyl)-3-methylpiperidine-1-carboxylate and 10% Pd/C and EtOAc were stirred under a balloon of $H_2$ until T.L.C. analysis indicated starting material had been consumed. The reaction was filtered through a celite pad washing with EtOAc. The organics were concentrated in vacuo to give the title compound which was used without further purification. $^1$H NMR (CD$_3$OD, 400 MHz) δ 3.5-3.65 (m, 2H), 3.05-3.15 (m, 1H), 2.8-2.95 (m, 2H), 2.15-2.25 (m, 1H), 1.85-2.1 (m, 2H), 0.97-1.01 (dm, 3H).

Step 2: ((2S,3R)-5,5-difluoro-2-(hydroxymethyl)-3-methylpiperidin-1-yl)(6-methyl-3-(2H-1,2,3-triazol-2-yl)pyridin-2-yl)methanone

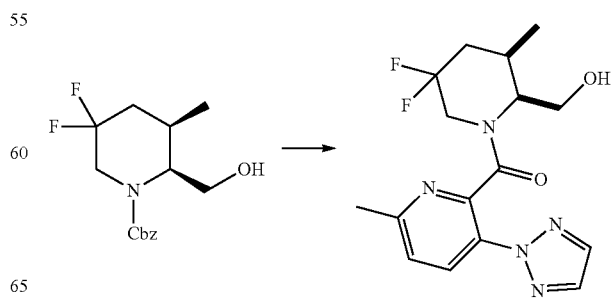

To a solution of ((2S,3R)-5,5-difluoro-3-methylpiperidin-2-yl)methanol (1 eq) and DIEA (4 eq) in DMF was added 6-methyl-3-(2H-1,2,3-triazol-2-yl)picolinic acid (1.5 eq) followed by HATU (1.2 eq). The reaction was stirred at room temperature for 2 h, and then diluted with 1M HCl and EtOAc. The layers were separated, and the organic layer was washed with 1M HCl (2×), sat. aq. NaHCO$_3$ (2×), brine (1×), dried (MgSO$_4$) and concentrated in vacuo. The crude residue was purified by chromatography on silica gel to give the title compound as a colorless solid. ESI-MS (m/z): 351.99 [M+1]$^+$.

Step 3: ((2S,3R)-5,5-difluoro-3-methyl-2-(((5-(trifluoromethyl)pyridin-2-yl)oxy)methyl)piperidin-1-yl)(6-methyl-3-(2H-1,2,3-triazol-2-yl)pyridin-2-yl)methanone

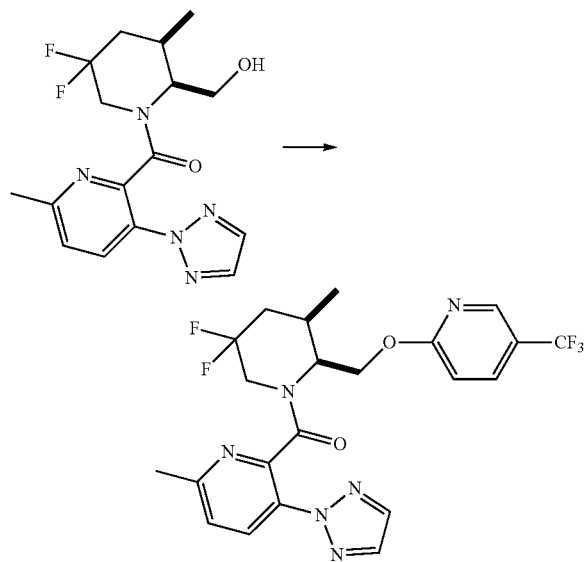

To a solution of ((2S,3R)-5,5-difluoro-2-(hydroxymethyl)-3-methylpiperidin-1-yl)(6-methyl-3-(2H-1,2,3-triazol-2-yl)pyridin-2-yl)methanone (1 eq) and 2-fluoro-5-(trifluoromethyl)pyridine (4 eq) in DMF was added NaH (1.5 eq). After 20 min, one drop of 1M HCl was added to quench the reaction, and the crude mixture was purified by reverse-phase preparative HPLC to afford the title compound as a colorless solid. ESI-MS (m/z): 496.9 [M+1]$^+$.

Compound 205: ((2S,3R)-5,5-difluoro-3-methyl-2-(((5-(trifluoromethyl)pyridin-2-yl)oxy)methyl)piperidin-1-yl)(4-(4-fluorophenyl)-1-methyl-1H-pyrazol-3-yl)methanone

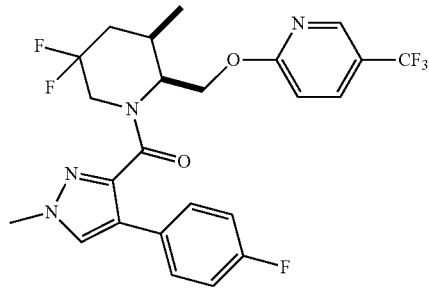 [SMILES: C[C@@H]1CC(F)(F)CN(C(=O)c2nn(C)cc2-c2ccc(F)cc2)[C@@H]1COc1ccc(C(F)(F)F)cn1]

Step 1: ((2S,3R)-5,5-difluoro-2-(hydroxymethyl)-3-methylpiperidin-1-yl)(4-(4-fluorophenyl)-1-methyl-1H-pyrazol-3-yl)methanone

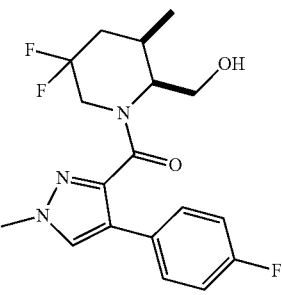 [SMILES: C[C@@H]1CC(F)(F)CN(C(=O)c2nn(C)cc2-c2ccc(F)cc2)[C@@H]1CO]

The title compound was synthesized following the same general protocol as described for Compound 204 using ((2S,3R)-5,5-difluoro-3-methylpiperidin-2-yl)methanol and 4-(4-fluorophenyl)-1-methyl-1H-pyrazole-3-carboxylic acid. ESI-MS (m/z): 368.09 [M+1]$^+$.

Step 2: ((2S,3R)-5,5-difluoro-3-methyl-2-(((5-(trifluoromethyl)pyridin-2-yl)oxy)methyl)piperidin-1-yl)(4-(4-fluorophenyl)-1-methyl-1H-pyrazol-3-yl)methanone The title compound was synthesized following the same general protocol as described for Compound 204 using ((2S,3R)-5,5-difluoro-2-(hydroxymethyl)-3-methylpiperidin-1-yl)(4-(4-fluorophenyl)-1-methyl-1H-pyrazol-3-yl)methanone and 2-fluoro-5-(trifluoromethyl)pyridine. ESI-MS (m/z): 512.73 [M+1]$^+$.

Compound 206: ((2S,3R)-5,5-difluoro-3-methyl-2-(((5-(trifluoromethyl)pyridin-2-yl)oxy)methyl)piperidin-1-yl)(1-methyl-4-(5-methylpyridin-2-yl)-1H-pyrazol-3-yl)methanone

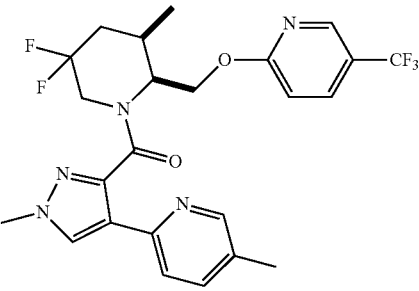 [SMILES: Cc1ccc(-c2cn(C)nc2C(=O)N2CC(F)(F)C[C@@H](C)[C@H]2COc2ccc(C(F)(F)F)cn2)nc1]

Step 1: ((2S,3R)-5,5-difluoro-2-(hydroxymethyl)-3-methylpiperidin-1-yl)(1-methyl-4-(5-methylpyridin-2-yl)-1H-pyrazol-3-yl)methanone

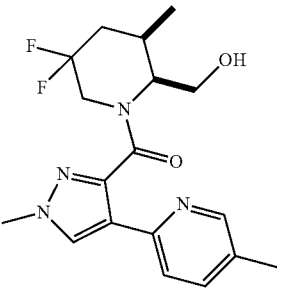

The title compound was synthesized following the same general protocol as described for Compound 204 using ((2S,3R)-5,5-difluoro-3-methylpiperidin-2-yl)methanol and 1-methyl-4-(5-methylpyridin-2-yl)-1H-pyrazole-3-carboxylic acid. ESI-MS (m/z): 365.11 [M+1]$^+$.

Step 2: (2S,3R)-5,5-difluoro-3-methyl-2-(((5-(trifluoromethyl)pyridin-2-yl)oxy)methyl)piperidin-1-yl)(1-methyl-4-(5-methylpyridin-2-yl)-1H-pyrazol-3-yl)methanone The title compound was synthesized following the same general protocol as described for Compound 204 using ((2S,3R)-5,5-difluoro-2-(hydroxymethyl)-3-methylpiperidin-1-yl)(1-methyl-4-(5-methylpyridin-2-yl)-1H-pyrazol-3-yl)methanone and 2-fluoro-5-(trifluoromethyl)pyridine. ESI-MS (m/z): 510.14 [M+1]$^+$.

Compounds 207, 222-223, and 244-248 were prepared in a manner analogous to that for Compound 204.

Compound 207: ((2S,3R)-5,5-difluoro-3-methyl-2-(((5-(trifluoromethyl)pyridin-2-yl)oxy)methyl)piperidin-1-yl)(5-(4-fluorophenyl)-2-methylthiazol-4-yl)methanone

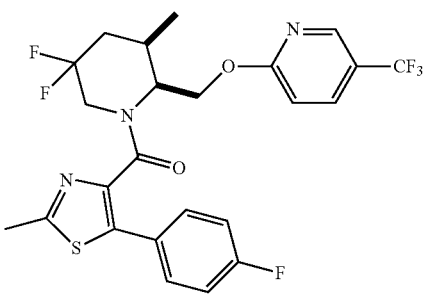 [SMILES: Cc1nc(C(=O)N2CC(F)(F)C[C@@H](C)[C@H]2COc2ccc(C(F)(F)F)cn2)c(-c2ccc(F)cc2)s1]

$^1$H NMR (CDCl$_3$, 400 MHz) δ 8.45 (s, 0.4H), 8.30 (s, 0.6H), 7.77-7.72 (m, 1H), 7.46-7.40 (m, 2H), 7.11-7.07 (m, 1H), 6.97-6.92 (m, 1H), 6.76-6.72 (m, 1H), 5.2 (br s, 0.4H), 5.0-4.9 (m, 0.6H), 4.75-4.7 (m, 0.5H), 4.6-4.5 (m, 0.5H), 4.40-4.37 (m, 0.6H), 4.10 (br s, 0.5H), 3.85-3.75 (m, 0.5H), 3.50-3.35 (m, 0.5H), 3.15-3.05 (m, 0.5H), 2.69 (s, 1.3H), 2.59 (s, 1.7H), 2.30-2.20 (m, 0.7H), 2.15-1.90 (m, 2H), 1.85-1.6 (m, 1H), 1.15 (d, 1.3H), 0.86 (d, 1.7H) ppm; ESI-MS (m/z): 530.25 [M+1]$^+$.

Compound 222: ((2S,3R)-5,5-difluoro-3-methyl-2-(((5-(trifluoromethyl)pyrimidin-2-yl)oxy)methyl)piperidin-1-yl)(1-methyl-4-(pyrimidin-2-yl)-1H-pyrazol-3-yl)methanone

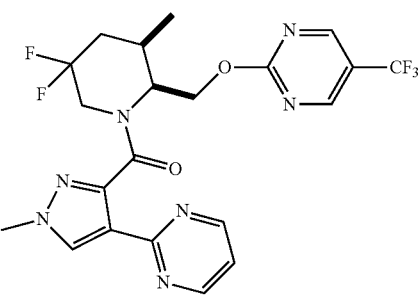 [SMILES: C[C@@H]1CC(F)(F)CN(C(=O)c2nn(C)cc2-c2ncccn2)[C@@H]1COc1ncc(C(F)(F)F)cn1]

$^1$H NMR (CDCl$_3$, 400 MHz) δ 8.80 (s, 1.3H), 8.70 (s, 0.7H), 8.59-8.57 (m, 0.7H), 8.48-8.46 (m, 1.3H), 8.11 (s, 0.7H), 8.06 (s, 0.3H), 7.05-6.95 (m, 0.4H), 6.96-6.93 (m, 0.6H), 5.35-5.15 (m, 1H), 4.95-4.88 (m, 1.4H), 4.68-4.65 (m, 0.6H), 3.98 (s, 2.1H), 3.88 (s, 0.9H), 3.85-3.75 (m, 1H), 3.7-3.55 (m, 1H), 2.5-2.4 (m, 1H), 2.2-2.05 (m, 2H), 1.20 (s, 2.1H), 0.96 (d, 0.9H) ppm; ESI-MS (m/z): 498.3 [M+1]$^+$.

Compound 223: ((2S,3R)-5,5-difluoro-3-methyl-2-(((5-(trifluoromethyl)pyrazin-2-yl)oxy)methyl)piperidin-1-yl)(1-methyl-4-(pyrimidin-2-yl)-1H-pyrazol-3-yl)methanone

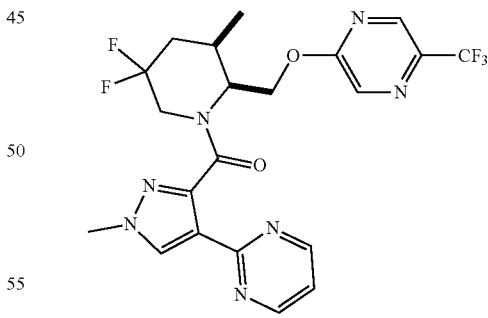

$^1$H NMR (CDCl$_3$, 400 MHz) δ 8.6-8.58 (m, 1H), 8.56-8.49 (m, 0.6H), 8.48-8.46 (m, 1H), 8.35-8.31 (m, 0.4H), 8.29-8.28 (m, 1H), 8.11 (s, 0.6H), 7.99 (s, 0.4H), 7.05-7.02 (m, 0.5H), 6.98-6.95 (m, 0.5H), 5.4-5.15 (m, 1H), 4.90-4.87 (m, 1H), 4.7-4.55 (m, 1H), 4.2-4.1 (m, 0.4H), 3.96 (s, 1.7H), 3.9-3.8 (m, 0.6H), 3.76 (s, 1.3H), 3.55-3.4 (m, 0.6H), 3.3-3.2 (m, 0.4H), 2.5-2.35 (m, 1H), 2.25-2.15 (m, 1H), 2.10-1.85 (m, 1H), 1.20 (d, 1.7H), 0.96 (d, 1.3H) ppm; ESI-MS (m/z): 498.2 [M+1]$^+$.

Compound 208: (4-(4-chlorophenyl)-1-methyl-1H-pyrazol-3-yl)((2S,3R)-5,5-difluoro-3-methyl-2-(((5-(trifluoromethyl)pyridin-2-yl)oxy)methyl)piperidin-1-yl)methanone

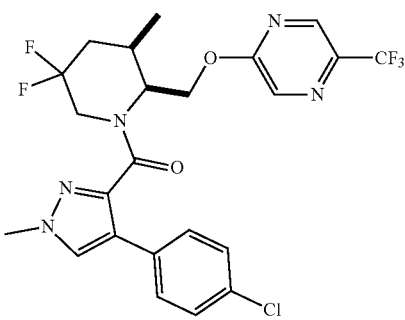 [SMILES: C[C@@H]1CC(F)(F)CN(C(=O)c2nn(C)cc2-c2ccc(Cl)cc2)[C@@H]1COc1cnc(C(F)(F)F)cn1]

Step 1: (2S,3R)-benzyl 5,5-difluoro-3-methyl-2-(((5-(trifluoromethyl)pyridin-2-yl)oxy)methyl)piperidine-1-carboxylate

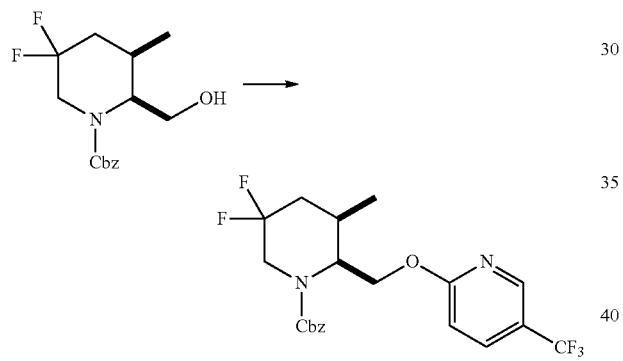

To a mixture of (2S,3R)-benzyl 5,5-difluoro-2-(hydroxymethyl)-3-methylpiperidine-1-carboxylate (1 eq) and Cs$_2$CO$_3$ (2 eq) in DMF was added 2-fluoro-5-(trifluoromethyl)pyridine (5 eq). The reaction mixture was stirred at room temperature for 12 h, and then diluted with EtOAc and water. The layers were separated, and the organic layer was washed with 1M HCl (2×), sat. aq. NaHCO$_3$ (2×), brine (1×), dried (MgSO$_4$) and concentrated in vacuo. Chromatography on SiO$_2$ (EtOAc/hex) afforded the title compound.

Step 2: 2-(((2S,3R)-5,5-difluoro-3-methylpiperidin-2-yl)methoxy)-5-(trifluoromethyl)pyridine

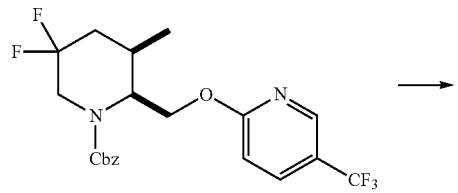

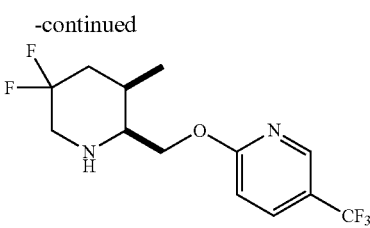

To the carbamate from the previous step was added to 30% HBr in HOAc. The reaction was stirred at rt (1-3 h) until sm was consumed as judged by HPLC analysis. The reaction was concentrated in vacuo to give the title compound as a pale yellow foam which was used without purification. ESI-MS (m/z): 311.3 [M+1]$^+$.

Step 3: (4-(4-chlorophenyl)-1-methyl-1H-pyrazol-3-yl)((2S,3R)-5,5-difluoro-3-methyl-2-(((5-(trifluoromethyl)pyridin-2-yl)oxy)methyl)piperidin-1-yl)methanone

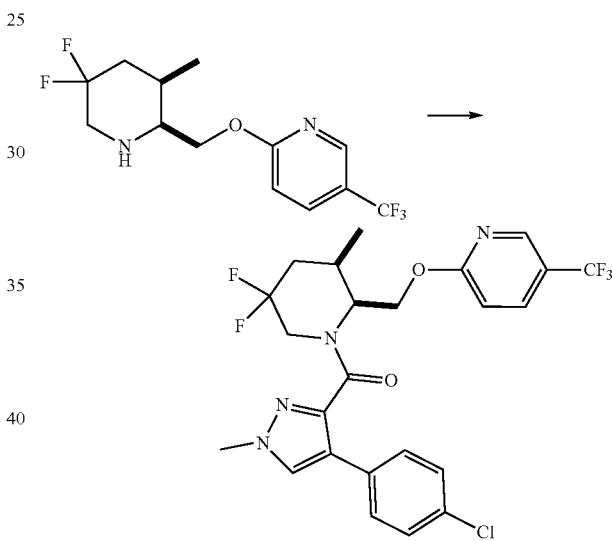

To a solution of 2-(((2S,3R)-5,5-difluoro-3-methylpiperidin-2-yl)methoxy)-5-(trifluoromethyl)pyridine (1 eq) and DIEA (4 eq) in DMF was added 4-(4-chlorophenyl)-1-methyl-1H-pyrazole-3-carboxylic acid (1.5 eq) followed by HATU (1.2 eq). The reaction was stirred at room temperature for 2 h, and then diluted with 1M HCl and EtOAc. The layers were separated, and the organic layer was washed with 1M HCl (2×), sat. aq. NaHCO$_3$ (2×), brine (1×), dried (MgSO$_4$) and concentrated in vacuo. The crude residue was purified by chromatography on silica gel to give the title compound as a colorless solid. H NMR (CDC$_3$, 400 MHz) δ 8.46 (s, 0.5H), 8.30 (s, 0.5H), 8.80-8.75 (m, 0.5H), 8.70-8.65 (m, 0.5H), 7.49 (s, 0.5H), 7.42 (s, 0.5H), 7.36-7.26 (m, 3H), 7.17-7.15 (m, 1H), 6.75-6.72 (m, 0.5H), 6.55-6.50 (m, 0.5H), 5.30 (br s, 0.5H), 5.05-4.95 (m, 0.5H), 4.8-4.7 (m, 0.5H), 4.63-4.6 (m, 0.5H), 4.5-4.35 (m, 1H), 4.3 (br s, 0.5H), 4.1-4.0 (m, 0.5H), 3.93 (s, 1.5H), 3.84 (s, 1.5H), 3.45-3.3 (m, 0.5H), 3.2-3.05 (m, 0.5H), 2.4-2.25 (m, 0.5H), 2.23-2.2 (m, 0.5H), 2.05-1.95 (m, 2H), 1.7-1.6 (m, 1H), 1.16 (d, 1.5H), 0.89 (d, 1.5H) ppm; ESI-MS (m/z): 529.3 [M+1]$^+$.

Compounds 212-214, 216, 220, and 243 were prepared in a manner analogous to that for Compound 208.

Compound 212: ((2S,3R)-5,5-difluoro-3-methyl-2-(((5-(trifluoromethyl)pyridin-2-yl)oxy)methyl)piperidin-1-yl)(1-methyl-4-(pyrimidin-2-yl)-1H-pyrazol-3-yl)methanone

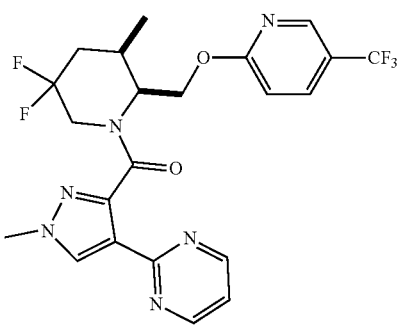 [SMILES: C[C@@H]1CC(F)(F)CN(C(=O)c2nn(C)cc2-c2ncccn2)[C@@H]1COc1ccc(C(F)(F)F)cn1]

¹H NMR (CDCl₃, 400 MHz) δ 8.60 (d, 0.7H), 8.51 (s, 0.7H), 8.42 (d, 1.3H), 8.35 (s, 0.3H), 8.15-8.10 (m, 1H), 7.81-7.78 (m, 1H), 7.05-7.0 (m, 0.4H), 6.95-6.92 (m, 0.6H), 6.84-6.80 (m, 1H), 5.30-5.15 (m, 1.2H), 4.86 (m, 1.3H), 4.56 (m, 0.8H), 4.2-4.05 (m, 0.6H), 3.97 (s, 2H), 3.84 (s, 1H), 3.82-3.7 (m, 1H), 3.65-3.5 (m, 0.6H), 3.35-3.2 (m, 0.4H), 2.5-2.3 (m, 1.4H), 2.25-2.05 (m, 1.6H), 1.19 (d, 2H), 0.95 (d, 1H) ppm; ESI-MS (m/z): 497.3 [M+1]⁺.

Compound 213: ((2S,3R)-5,5-difluoro-3-methyl-2-(((5-(trifluoromethyl)pyridin-2-yl)oxy)methyl)piperidin-1-yl)(2-methyl-5-(pyrimidin-2-yl)thiazol-4-yl)methanone

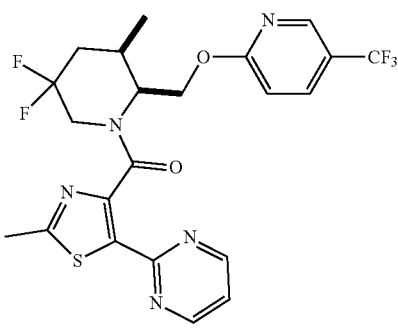

¹H NMR (CDCl₃, 400 MHz) δ 8.64-8.63 (m, 0.7H), 8.51-8.48 (m, 2H), 8.33 (s, 0.3H), 7.82-7.78 (m, 1H), 7.09-7.05 (m, 0.4H), 7.01-6.96 (m, 0.6H), 6.83-6.8 (m, 1H), 5.25-5.15 (br m, 1.3H), 4.90-4.87 (m, 1.3H), 4.57-4.54 (m, 0.7H), 3.95 (br s, 0.4H), 3.75-3.55 (m, 1.4H), 3.4-3.25 (m, 0.4H), 2.76 (s, 2H), 2.64 (s, 1H), 2.5-2.3 (m, 1H), 2.25-2.1 (m, 2H), 2.05-1.95 (m, 1.4H), 1.9-1.7 (m, 1.8H), 1.7-1.6 (m, 0.6H), 1.19 (d, 2H), 0.96 (d, 1H) ppm; ESI-MS (m/z): 514.08 [M+1]⁺.

Compound 214: ((2S,3R)-5,5-difluoro-3-methyl-2-(((5-(trifluoromethyl)pyridin-2-yl)oxy)methyl)piperidin-1-yl)(2-methyl-5-(pyridin-2-yl)thiazol-4-yl)methanone

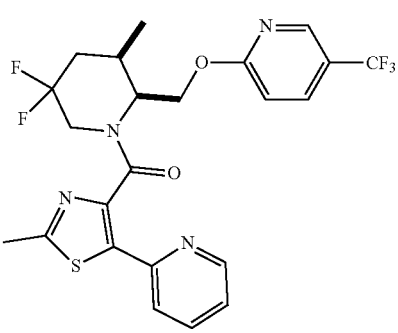 [SMILES: Cc1nc(C(=O)N2CC(F)(F)C[C@@H](C)[C@H]2COc2ccc(C(F)(F)F)cn2)c(-c2ccccn2)s1]

¹H NMR (CDCl₃, 300 MHz) δ 8.77-8.73 (m, 1H), 8.46-8.41 (m, 2H), 7.90-7.82 (m, 1H), 7.48-7.45 (m, 1H), 7.34-7.28 (m, 1H), 7.0-6.9 (m, 0.6H), 5.35-5.30 (m, 0.7H), 5.05-4.95 (m, 0.8H), 4.85-4.70 (m, 3H), 4.5-4.3 (m, 1H), 3.8-3.6 (m, 0.9H), 3.5-3.3 (m, 1H), 2.98 (s, 1.5H), 2.90 (s, 1.5H), 2.5-2.3 (m, 1H), 2.25-2.1 (m, 2H), 2.05-1.95 (m, 2H), 1.80-1.70 (m, 3H), 1.20 (d, 2H), 0.88 (d, 1H) ppm; ESI-MS (m/z): 513.3 [M+1]⁺.

Compound 216: (5-chloro-2-(2-methyl-2H-tetrazol-5-yl)phenyl)((2S,3R)-5,5-difluoro-3-methyl-2-(((5-(trifluoromethyl)pyridin-2-yl)oxy)methyl)piperidin-1-yl)methanone

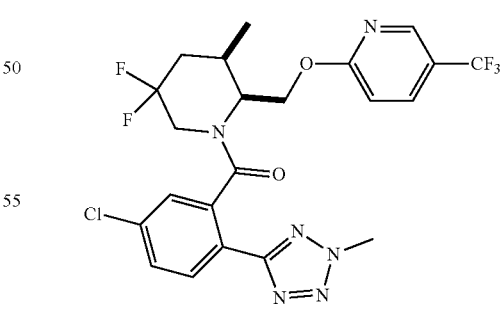

¹H NMR (CDCl₃, 400 MHz) δ 8.50-8.36 (m, 1.0H), 8.15-8.05 (m, 1.0H), 7.92-7.75 (m, 1.0H), 7.55-7.35 (m, 3.0H), 7.0-6.8 (m, 1.0H), 5.4-5.3 (m, 2.0H), 5.15-4.95 (m, 1.0H), 4.85-4.65 (m, 1.0H), 4.36 (s, 2.0H), 4.15 (s, 1.0H), 3.90-3.8 (m, 0.4H), 3.7-3.4 (m, 1.2H), 3.25-3.05 (m, 0.3H), 2.25-2.15 (m, 2.0H), 1.21 (d, 2.0H), 0.90 (d, 1.0H) ppm; ESI-MS (m/z): 553.2 [M+Na]⁺.

Compound 220: ((2S,3R)-5,5-difluoro-3-methyl-2-(((5-(trifluoromethyl)pyridin-2-yl)oxy)methyl)piperidin-1-yl)(1-methyl-4-(pyridin-2-yl)-1H-pyrazol-3-yl)methanone

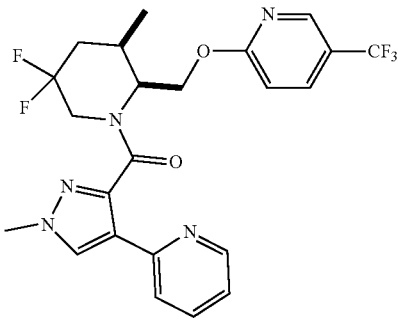 [SMILES: C[C@@H]1CC(F)(F)CN(C(=O)c2nn(C)cc2-c2ccccn2)[C@@H]1COc1ccc(C(F)(F)F)cn1]

$^1$H NMR (CDCl$_3$, 400 MHz) δ 8.6 (br s, 0.5H), 8.5 (br s, 0.5H), 8.4 (br s, 0.5H), 8.3 (br s, 0.5H), 7.9-7.8 (m, 1H), 7.8-7.5 (m, 3H), 7.2 (m, 0.5H), 7.05 (m, 0.5H), 6.8 (d, 0.5H), 6.6 (d, 0.5H), 5.4 (m, 0.5H), 5.1 (m, 0.5H), 4.9-4.7 (m, 1H), 4.6-4.4 (m, 1H), 4.35 (m, 0.5H), 4.0 (m, 0.5H), 3.95 (s, 1.5H), 3.8 (s, 1.5H), 3.6-3.5 (m, 0.5H), 3.3-3.2 (m, 0.5H), 2.4-1.7 (m, 3H), 1.2 (d, 1.5H), 0.95 (d, 1.5H); ESI-MS (m/z): 496.0 [M+1]$^+$.

Compound 243: ((2S,3R)-5,5-difluoro-3-methyl-2-(((5-(trifluoromethyl)pyridin-2-yl)oxy)methyl)piperidin-1-yl)(1-methyl-4-phenyl-1H-pyrazol-3-yl)methanone

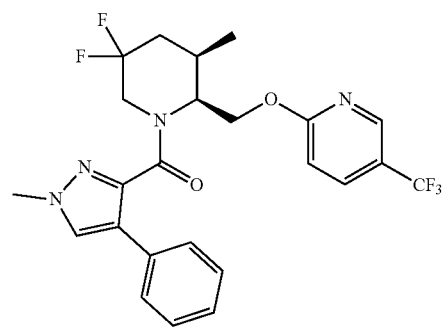 [SMILES: C[C@@H]1CC(F)(F)CN(C(=O)c2nn(C)cc2-c2ccccc2)[C@@H]1COc1ccc(C(F)(F)F)cn1]

$^1$H NMR (CDCl$_3$, 400 MHz) δ 8.6-8.47 (m, 1.0H), 8.4-8.31 (m, 1.0H), 7.94-7.89 (m, 1.0H), 7.85-7.75 (m, 0.5H), 7.7-7.6 (m, 1.5H), 7.6-7.45 (m, 2.0H), 7.2-7.1 (m, 0.5H), 7.1-7.0 (m, 0.5H), 6.85-6.75 (m, 0.5H), 6.55-6.5 (m, 0.5H), 5.4-5.35 (m, 0.5H), 5.1-5.0 (m, 0.5H), 4.85-4.7 (m, 1.0H), 4.55-4.4 (m, 1.0H), 4.4-4.3 (m, 0.5H), 4.1-4.0 (m, 0.5H), 3.94 (s, 1.5H), 3.85 (s, 1.5H), 3.6-3.55 (m, 0.5H), 3.3-3.15 (m, 0.5H), 2.4-2.3 (m, 0.5H), 2.25-2.2 (m, 0.5H), 2.1-2.05 (m, 1.0H), 1.7-1.6 (m, 1.0H), 1.19 (d, 1.5H), 0.93 (d, 1.5H) ppm; ESI-MS (m/z): 495.97 [M+1]$^+$.

Compound 215: ((2S,3R)-5,5-difluoro-3-methyl-2-(((5-(trifluoromethyl)pyridin-2-yl)oxy)methyl)piperidin-1-yl)(6-methyl-3-(pyrimidin-2-yl)pyridin-2-yl)methanone

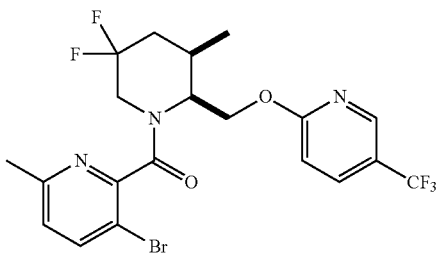 [SMILES: Cc1ccc(Br)c(C(=O)N2CC(F)(F)C[C@@H](C)[C@H]2COc2ccc(C(F)(F)F)cn2)n1]

Step 1: (3-bromo-6-methylpyridin-2-yl)((2S,3R)-5,5-difluoro-3-methyl-2-(((5-(trifluoromethyl)pyridin-2-yl)oxy)methyl)piperidin-1-yl)methanone The title compound was synthesized following the same general protocol as described for Compound 208 using 2-(((2S,3R)-5,5-difluoro-3-methylpiperidin-2-yl)methoxy)-5-(trifluoromethyl)pyridine and 3-bromo-6-methylpicolinic acid.

Step 2: ((2S,3R)-5,5-difluoro-3-methyl-2-(((5-(trifluoromethyl)pyridin-2-yl)oxy)methyl)piperidin-1-yl)(6-methyl-3-(pyrimidin-2-yl)pyridin-2-yl)methanone To a solution of (3-bromo-6-methylpyridin-2-yl)((2S,3R)-5,5-difluoro-3-methyl-2-(((5-(trifluoromethyl)pyridin-2-yl)oxy)methyl)piperidin-1-yl)methanone (1 eq) and 2-(tributylstannyl)pyrimidine (1.2 eq) in DMF was added Pd(PPh$_3$)$_4$ (10 mol %). The reaction mixture was heated to 120° C. for 2 h in a microwave reactor and then the mixture was cooled and concentrated. The crude was dissolved with EtOAc and washed with sat'd NaHCO$_3$, brine, dried (MgSO$_4$) and concentrated. The crude was purified by chromatography on SiO2 (EtOAc/hex) to obtain the title compound. H NMR (CDCl$_3$, 400 MHz) δ 8.69-8.67 (m, 1.0H), 8.58-8.54 (m, 1.6H), 8.47-8.45 (m, 1.0H), 8.45-8.4 (m, 0.4H), 7.74-7.72 (m, 1.0H), 7.3-7.27 (m, 1.0H), 7.2-7.15 (m, 0.4H), 7.05-7.0 (m, 0.6H), 6.8-6.75 (m, 1.0H), 5.15-5.05 (m, 1.0H), 4.85-4.8 (m, 1.0H), 4.7-4.6 (m, 1.0H), 3.8-3.75 (m, 0.5H), 3.4-3.25 (m, 0.5H), 2.57 (s, 1.6H), 2.50 (s, 1.4H), 2.45-2.4 (m, 0.4H), 2.4-2.3 (m, 0.6H), 2.2-2.0 (m, 2.0H), 1.12 (d, 1.6H), 0.86 (d, 1.4H) ppm; ESI-MS (m/z): 508.4 [M+1]$^+$.

Compound 228: ((2S,3R)-5,5-difluoro-2-(((3-fluoro-5-(trifluoromethyl)pyridin-2-yl)amino)methyl)-3-methylpiperidin-1-yl)(1-methyl-4-(pyrimidin-2-yl)-1H-pyrazol-3-yl)methanone

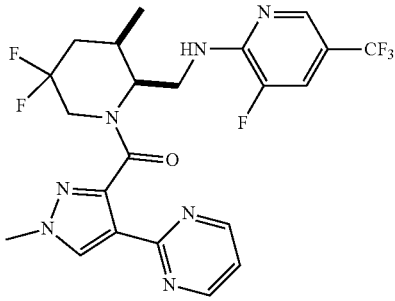 [SMILES: C[C@@H]1CC(F)(F)CN(C(=O)c2nn(C)cc2-c2ncccn2)[C@@H]1CNc1ncc(C(F)(F)F)cc1F]

Step 1: (2S,3R)-benzyl 5,5-difluoro-2-(((3-fluoro-5-(trifluoromethyl)pyridin-2-yl)amino)methyl)-3-methylpiperidine-1-carboxylate

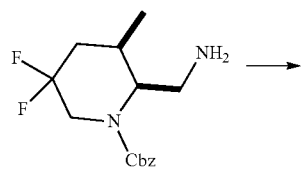

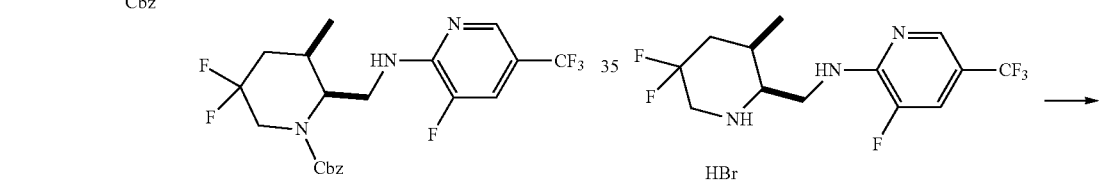

To a mixture of (2S,3R)-benzyl 2-(aminomethyl)-5,5-difluoro-3-methylpiperidine-1-carboxylate (1 eq) and Cs$_2$CO$_3$ (2 eq) in DMF (20 mL) was added 2,3-difluoro-5-(trifluoromethyl)pyridine (3 eq). The reaction was stirred at room temperature for 2 h wherein the starting material was judged consumed as indicated by reverse-phase analytical HPLC. The reaction was cooled, and diluted with EtOAc, and water. The layers were separated, and the organic phase was washed with water (3×), brine, dried (MgSO$_4$) and concentrated. The crude residue was purified by chromatography on SiO$_2$ (EtOAc/hex) to give the title compound as a near colorless oil which solidified. ESI-MS (m/z): 462.2 [M+1]$^+$.

Step 2: N-(((2S,3R)-5,5-difluoro-3-methylpiperidin-2-yl)methyl)-3-fluoro-5-(trifluoromethyl)pyridin-2-amine hydrobromide

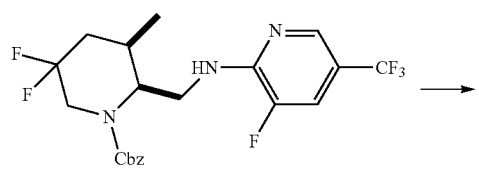

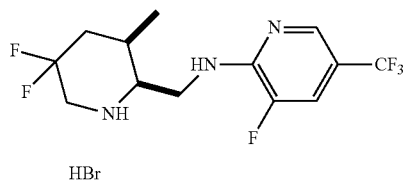

To the carbamate from the previous step was added to 30% HBr in HOAc. The reaction was stirred at rt (1-3 h) until sm was consumed as judged by HPLC analysis. The reaction was concentrated in vacuo to give the title compound as a pale yellow foam which was used without purification. ESI-MS (m/z): 328.3 [M+1]$^+$.

Step 3: ((2S,3R)-5,5-difluoro-3-methyl-2-(((5-(trifluoromethyl)pyridin-2-yl)amino)methyl)piperidin-1-yl)(1-methyl-4-(4-methylpyridin-2-yl)-1H-pyrazol-3-yl)methanone

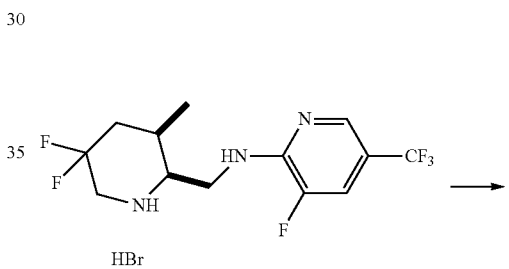

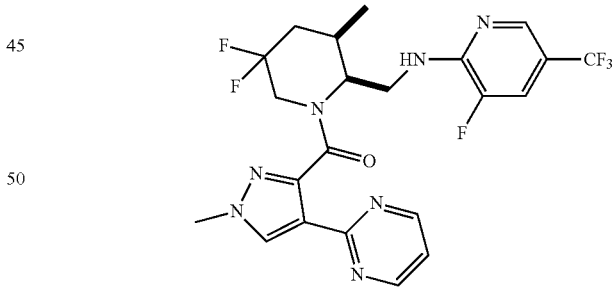

The title compound was prepared following the same general procedure as described in Compound 1 using 1-methyl-4-(pyrimidin-2-yl)-1H-pyrazole-3-carboxylic acid in Step 3. $^1$H NMR (CDC$_3$, 400 MHz) δ 8.65 (d, 1H), 8.6 (d, 1H), 8.25 (s, 0.5H), 8.2 (s, 0.5H), 8.15 (s, 0.5H), 8.1 (s, 0.5H), 7.35-7.2 (m, 1H), 7.1 (m, 1H), 6.7-6.6 (m, 1H), 5.35-5.2 (m, 1H), 4.35-4.25 (m, 0.5H), 4.15-4.05 (m, 0.5H), 4.0 (s, 1.5H), 3.95 (s, 1.5H), 3.9-3.8 (m, 0.5H), 3.6-3.5 (m, 0.5H), 3.5-3.3 (m, 1.5H), 3.2-3.05 (m, 0.5H), 2.5-2.4 (m, 1H), 2.2-2.1 (m, 1H), 2-1.6 (m, 1H), 1.25 (d, 1.5H), 1.0 (d, 1.5H); ESI-MS (m/z): 513.7 [M+1]$^+$.

Compound 234: (3-(cyclopropylethynyl)-6-methylpyridin-2-yl)((2S,3R)-5,5-difluoro-3-methyl-2-(((5-(trifluoromethyl)pyrimidin-2-yl)amino)methyl)piperidin-1-yl)methanone

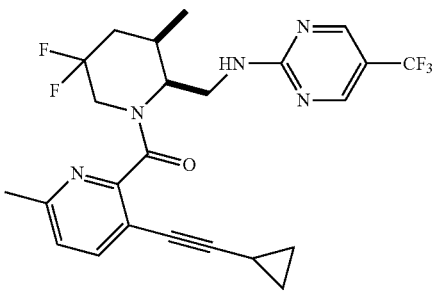 [SMILES: Cc1ccc(C#CC2CC2)c(C(=O)N2CC(F)(F)C[C@@H](C)[C@H]2CNc2ncc(C(F)(F)F)cn2)n1]

To a solution of (3-bromo-6-methylpyridin-2-yl)((2S,3R)-5,5-difluoro-3-methyl-2-(((5-(trifluoromethyl)pyrimidin-2-yl)amino)methyl)piperidin-1-yl)methanone (1 eq) and ethynylcyclopropane (1.2 eq) in diisopropylamine was added CuI (0.1 eq), and Pd(Ph$_3$P)$_2$Cl$_2$ (5 mol %). The reaction was warmed to 85° C. for 14 h, and then cooled and concentrated. The crude was taken up in EtOAc and washed with sat. aq. NaHCO$_3$, brine, dried (Na$_2$SO$_4$) and concentrated in vacuo. The crude was purified by chromatography on SiO$_2$ (EtOAc/hex) to afford the title compound. H NMR (MeOD, 400 MHz) δ 8.65-8.45 (m, 1.0H), 8.3-8.25 (s, 0.7H), 7.75-7.55 (m, 1.0H), 7.4-7.3 (s, 0.3H), 7.25-7.05 (m, 1.0H), 5.4-5.3 (m, 0.7H), 4.05-3.95 (m, 1.0H), 3.7-3.6 (m, 1.0H), 2.86 (s, 0.5H), 2.66 (s, 2.5H), 2.1-2.0 (m, 4.0H), 1.65-1.55 (m, 1.0H), 1.45-1.4 (m, 1.0H), 1.23 (d, 0.5H), 1.07 (d, 2.5H), 0.9-0.8 (m, 4.0H) ppm; ESI-MS (m/z): 494.4 [M+1]$^+$.

Compound 235: ((2S,3R)-5,5-difluoro-3-methyl-2-(((5-(trifluoromethyl)pyrimidin-2-yl)amino)methyl)piperidin-1-yl)(6-methyl-3-(prop-1-yn-1-yl)pyridin-2-yl)methanone

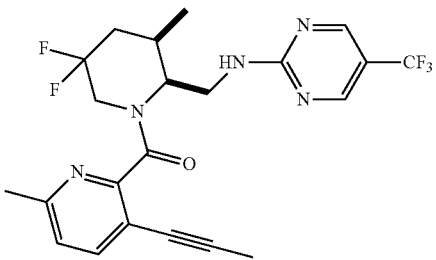 [SMILES: CC#Cc1ccc(C)nc1C(=O)N1CC(F)(F)C[C@@H](C)[C@H]1CNc1ncc(C(F)(F)F)cn1]

To a solution of (3-bromo-6-methylpyridin-2-yl)((2S,3R)-5,5-difluoro-3-methyl-2-(((5-(trifluoromethyl)pyrimidin-2-yl)amino)methyl)piperidin-1-yl)methanone (1 eq) and tributyl(prop-1-yn-1-yl)stannane (1.2 eq) in DMF was added CsF (2 eq), CuI (0.1 eq), and Pd(Ph$_3$P)$_4$ (5 mol %). The reaction was warmed to 80° C. for 12 h, and then cooled and concentrated. The crude was taken up in EtOAc and washed with sat. aq. NaHCO$_3$, brine, dried (Na$_2$SO$_4$) and concentrated in vacuo. The crude was purified by chromatography on SiO$_2$ (EtOAc/hex) to afford the title compound. $^1$H NMR (MeOD, 400 MHz) δ 8.50 (s, 1.0H), 8.27 (s, 1.0H), 8.57-8.54 (m, 1.0H), 7.12-7.09 (m, 1.0H), 5.4-5.3 (m, 1.0H), 4.15-3.95 (m, 1.0H), 3.7-3.6 (m, 1.0H), 3.6-3.4 (m, 2.0H), 2.65-2.55 (m, 1.0H), 2.5-2.4 (m, 1.0H), 2.34 (s, 3.0H), 2.2-2.1 (m, 4.0H), 1.06 (d, 3.0H) ppm; ESI-MS (m/z): 468.32 [M+1]$^+$.

Compound 236: ((2S,3R)-5,5-difluoro-3-methyl-2-(((5-(trifluoromethyl)pyrimidin-2-yl)amino)methyl)piperidin-1-yl)(3-ethynyl-6-methylpyridin-2-yl)methanone

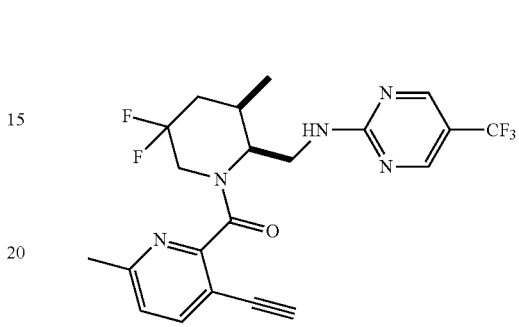

The title compound was prepared following the same general protocol as described for Compound 235 using tributyl(ethynyl)stannane. $^1$H NMR (CDCl$_3$, 400 MHz) δ 8.51-8.47 (m, 2.0H), 7.95-7.85 (s, 0.7H), 7.81-7.71 (m, 1.0H), 7.22-7.14 (m, 1.0H), 6.05-6.0 (m, 0.3H), 5.3-5.2 (m, 0.3H), 5.15-5.05 (m, 0.7H), 3.90-3.7 (m, 2.0H), 3.55-3.45 (m, 0.5H), 3.4-3.3 (m, 1.5H), 3.1-2.95 (m, 1.0H), 2.67 (s, 2.1H), 2.52 (s, 0.9H), 2.45-2.35 (m, 1.0H), 2.25-2.15 (m, 1.0H), 1.95-1.80 (m, 1.0H), 1.20 (d, 0.9H), 1.01 (d, 2.1H) ppm; ESI-MS (m/z): 454.27 [M+1]$^+$.

Compound 251: ((2S,3R)-5,5-difluoro-3-methyl-2-(((5-(trifluoromethyl)pyrimidin-2-yl)amino)methyl)piperidin-1-yl)(2-fluoro-3-methyl-6-(2H-1,2,3-triazol-2-yl)phenyl)methanone

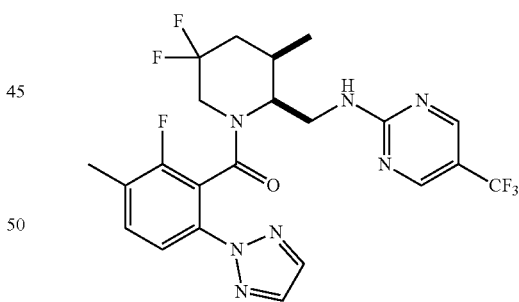

To 2-fluoro-3-methyl-6-(2H-1,2,3-triazol-2-yl)benzoic acid in CH$_2$Cl$_2$ was added SOCl$_2$. The reaction was warmed to 50° C. for 3 h, and then concentrated in vacuo. A solution of this acid chloride in CH$_2$Cl$_2$ was added to a solution of N-(((2S,3R)-5,5-difluoro-3-methylpiperidin-2-yl)methyl)-5-(trifluoromethyl)pyrimidin-2-amine hydrobromide and DIEA (4 eq) in CH$_2$Cl$_2$. The reaction was stirred at room temperature until starting piperidine was consumed by HPLC analysis. The reaction was concentrated in vacuo, and then taken up in EtOAc and washed with 1M HCl, sat. aq. NaHCO$_3$, brine, dried (MgSO$_4$) and concentrated. Purification by chromatography on SiO$_2$ (EtOAc/hex) provided the title compound as a solid. ESI-MS (m/z): 514.1 [M+1]$^+$.

Synthesis of Compound 185 and Compound 129

Compound 185: ((2S,3R)-5,5-difluoro-3-methyl-2-(((5-(trifluoromethyl)pyridin-2-yl)amino)methyl)piperidin-1-yl)(5-(4-fluorophenyl)-2-methylthiazol-4-yl)methanone

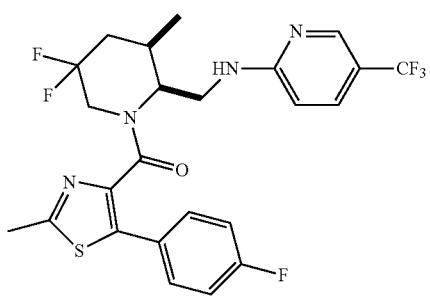

Step 1: (2S,3R)-benzyl 5,5-difluoro-3-methyl-2-(((5-(trifluoromethyl)pyridin-2-yl)amino)methyl)piperidine-1-carboxylate To a mixture of the crude amine compound r (1 eq) and $K_2CO_3$ (2 eq) in DMF (20 mL) was added 2-fluoro-5-(trifluoromethyl)pyridine (3 eq). The reaction was warmed to 80° C. for 2 h wherein the starting material was judged consumed as indicated by reverse-phase analytical HPLC. The reaction was cooled, and diluted with EtOAc, and water. The layers were separated, and the organic phase was washed with water (3×), brine, dried ($MgSO_4$) and concentrated. The crude residue was purified by chromatography on $SiO_2$ (EtOAc/hex) to give the title compound as a near colorless oil which solidified. ESI-MS (m/z): 444.4 [M+1]$^+$.

Step 2: N-(((2S,3R)-5,5-difluoro-3-methylpiperidin-2-yl)methyl)-5-(trifluoromethyl)pyridin-2-amine hydrobromide To the carbamate from the previous step was added to 30% HBr in HOAc.
The reaction was stirred at rt (1-3 h) until sm consumed as judged by HPLC analysis. The reaction was concentrated in vacuo to give the title compound as a pale yellow foam which was used without purification. ESI-MS (m/z): 310.3 [M+1]$^+$.

Step 3: ((2S,3R)-5,5-difluoro-3-methyl-2-(((5-(trifluoromethyl)pyridin-2-yl)amino)methyl)piperidin-1-yl)(5-(4-fluorophenyl)-2-methylthiazol-4-yl)methanone To a solution of N-(((2S,3R)-5,5-difluoro-3-methylpiperidin-2-yl)methyl)-5-(trifluoromethyl)pyridin-2-amine hydrobromide (10 mg) in DMF (0.5 mL) was added DIEA (3 eq) followed by 5-(4-fluorophenyl)-2-methylthiazole-4-carboxylic acid (6 mg) and HATU (8 mg). The reaction was allowed to stir at room temperature for 15 h, and was then diluted with EtOAc and washed with 1M HCl, sat aq. $NaHCO_3$, brine, dried ($MgSO_4$), and concentrated. The crude residue was purified by chromatography on silica gel (EtOAc/hex) to give the title compound as a colorless oil which solidified. ESI-MS (m/z): 529.5 [M+1]$^+$.

Compound 129: (4-(4-chlorophenyl)-1-methyl-1H-pyrazol-3-yl)((2S,3R)-5,5-difluoro-3-methyl-2-(((5-(trifluoromethyl)pyrazin-2-yl)amino)methyl)piperidin-1-yl)methanone

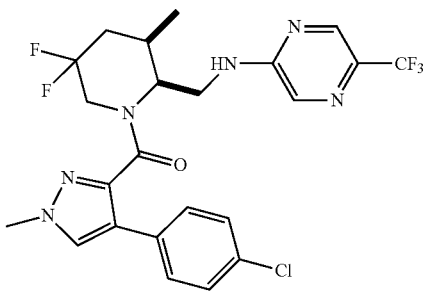 [SMILES: C[C@@H]1CC(F)(F)CN(C(=O)c2nn(C)cc2-c2ccc(Cl)cc2)[C@@H]1CNc1cnc(C(F)(F)F)cn1]

Step 1: (2S,3R)-benzyl 5,5-difluoro-3-methyl-2-(((5-(trifluoromethyl)pyrazin-2-yl)amino)methyl)piperidine-1-carboxylate To a mixture of the crude amine compound r (1 eq) and $K_2CO_3$ (2 eq) in DMF (20 mL) was added 2-chloro-5-(trifluoromethyl)pyrazine (1.5 eq). The reaction was warmed to 80° C. for 2 h wherein the starting material was judged consumed as indicated by reverse-phase analytical HPLC. The reaction was cooled, and diluted with EtOAc, and water. The layers were separated, and the organic phase was washed with water (3×), brine, dried ($MgSO_4$) and concentrated. The crude residue was purified by chromatography on $SiO_2$ (EtOAc/hex) to give the title compound as a pale yellow solid. ESI-MS (m/z): 445.4 [M+1]$^+$.

Step 2: N-(((2S,3R)-5,5-difluoro-3-methylpiperidin-2-yl)methyl)-5-(trifluoromethyl)pyrazin-2-amine hydrobromide To the carbamate from the previous step was added to 30% HBr in HOAc. The reaction was stirred at rt (1-3 h) until sm was consumed as judged by HPLC analysis. The reaction was concentrated in vacuo to give the title compound as a pale yellow foam which was used without purification. ESI-MS (m/z): 311.3 [M+1]$^+$.

Step 3: (4-(4-chlorophenyl)-1-methyl-1H-pyrazol-3-yl)((2S,3R)-5,5-difluoro-3-methyl-2-(((5-(trifluoromethyl)pyrazin-2-yl)amino)methyl)piperidin-1-yl)methanone The title compound was prepared following the same general procedure as that described for Compound 1, Step 3 using N-(((2S,3R)-5,5-difluoro-3-methylpiperidin-2-yl)methyl)-5-(trifluoromethyl)pyrazin-2-amine hydrobromide and 4-(4-chlorophenyl)-1-methyl-H-pyrazole-3-carboxylic acid. Purification of the crude residue by chromatography on silica gel (EtOAc/hex) to give the title compound as a light yellow oil which solidified. ESI-MS (m/z): 529.9 [M+1]$^+$.

Compounds 207, 208, 212, 213, 214, 215, 216, 220, 222, 223, and 228, were prepared in a manner analogous to that shown above for Compounds 185 and 129.

Compound 207: ((2S,3R)-5,5-difluoro-3-methyl-2-(((5-(trifluoromethyl)pyridin-2-yl)oxy)methyl)piperidin-1-yl)(5-(4-fluorophenyl)-2-methylthiazol-4-yl)methanone

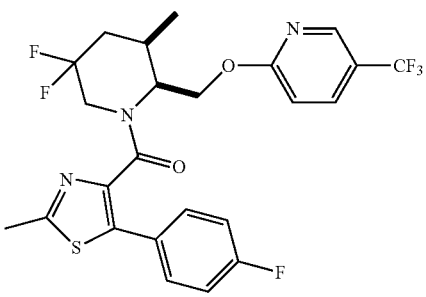 [SMILES: Cc1nc(C(=O)N2CC(F)(F)C[C@@H](C)[C@H]2COc2ccc(C(F)(F)F)cn2)c(-c2ccc(F)cc2)s1]

$^1$H NMR (CDC$_3$, 400 MHz) δ 8.45 (s, 0.4H), 8.30 (s, 0.6H), 7.77-7.72 (m, 1H), 7.46-7.40 (m, 2H), 7.11-7.07 (t, 1H), 6.97-6.92 (t, 1H), 6.76-6.72 (t, 1H), 5.2 (br s, 0.4H), 5.0-4.9 (m, 0.6H), 4.75-4.7 (m, 1H), 4.6-4.5 (m, 0.5H), 4.40-4.37 (m, 1H), 4.10 (br s, 0.5H), 3.85-3.75 (m, 1H), 3.50-3.35 (m, 0.5H), 3.15-3.05 (m, 0.5H), 2.69 (s, 1.3H), 2.59 (s, 1.7H), 2.30-1.8 (m, 2H), 1.15 (d, 1.2H), 0.86 (d, 1.8H); ESI-MS (m/z): 530.3 [M+1]$^+$.

Compound 208: (4-(4-chlorophenyl)-1-methyl-1H-pyrazol-3-yl)((2S,3R)-5,5-difluoro-3-methyl-2-(((5-(trifluoromethyl)pyridin-2-yl)oxy)methyl)piperidin-1-yl)methanone

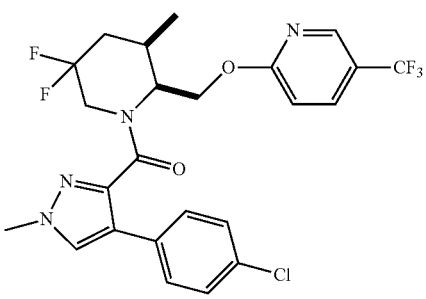

$^1$H NMR (CDCl$_3$, 400 MHz) δ 8.46 (s, 0.5H), 8.30 (s, 0.5H), 7.80-7.75 (dd, 0.5H), 7.70-7.65 (dd, 0.5H), 7.49 (s, 0.5H), 7.42 (s, 0.5H), 7.36-7.26 (m, 3H), 7.2 (d, 1H), 6.75 (d, 0.5H), 6.55 (d, 0.5H), 5.30 (br s, 0.5H), 5.05-4.95 (m, 0.5H), 4.8-4.7 (m, 0.5H), 4.63-4.6 (m, 0.5H), 4.5-4.4 (m, 1H), 4.3 (br s, 0.5H), 4.1-4.0 (m, 0.5H), 3.93 (s, 1.5H), 3.84 (s, 1.5H), 3.45-3.3 (m, 0.5H), 3.2-3.05 (m, 0.5H), 2.3-2.25 (m, 0.5H), 2.23-2.2 (m, 0.5H), 2.05-1.7 (m, 2H), 1.16 (d, 1.5H), 0.89 (d, 1.5H); ESI-MS (m/z): 529.3 [M+1]$^+$.

Compound 212: ((2S,3R)-5,5-difluoro-3-methyl-2-(((5-(trifluoromethyl)pyridin-2-yl)oxy)methyl)piperidin-1-yl)(1-methyl-4-(pyrimidin-2-yl)-1H-pyrazol-3-yl)methanone

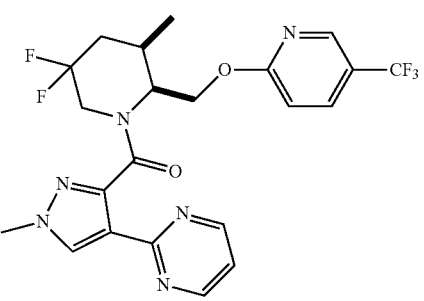

$^1$H NMR (CDCl$_3$, 400 MHz) δ 8.60 (d, 0.7H), 8.51 (s, 0.7H), 8.42 (d, 1.3H), 8.35 (s, 0.3H), 8.15-8.10 (m, 1H), 7.81-7.78 (m, 1H), 7.05-7.0 (m, 0.4H), 6.95-6.92 (m, 0.6H), 6.84-6.80 (m, 1H), 5.30-5.15 (m, 1H), 4.86 (m, 1H), 4.56 (m, 1H), 4.2-4.05 (m, 0.3H), 3.97 (s, 2H), 3.84 (s, 1H), 3.82-3.7 (m, 0.7H), 3.65-3.5 (m, 0.6H), 3.35-3.2 (m, 0.4H), 2.5-2.3 (m, 1H), 2.25-2.05 (m, 2H), 1.19 (d, 2H), 0.95 (d, 1H); ESI-MS (m/z): 497.3 [M+1]$^+$.

Compound 213: ((2S,3R)-5,5-difluoro-3-methyl-2-(((5-(trifluoromethyl)pyridin-2-yl)oxy)methyl)piperidin-1-yl)(2-methyl-5-(pyrimidin-2-yl)thiazol-4-yl)methanone

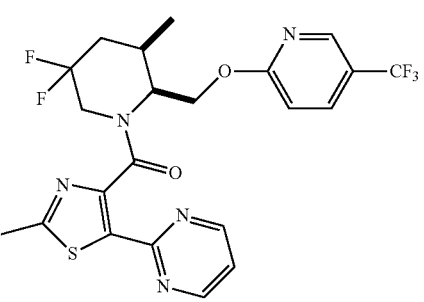 [SMILES: Cc1nc(C(=O)N2CC(F)(F)C[C@@H](C)[C@H]2COc2ccc(C(F)(F)F)cn2)c(-c2ncccn2)s1]

$^1$H NMR (CDCl$_3$, 400 MHz) δ 8.64-8.63 (d, 0.7H), 6.62 (br s, 0.7H), 8.5 (d, 1.3H), 8.33 (s, 0.3H), 7.82-7.78 (m, 1H), 7.09-7.05 (t, 0.4H), 7.01-6.95 (t, 0.6H), 6.83-6.8 (m, 1H), 5.25-5.15 (m, 1H), 4.90-4.87 (m, 1.3H), 4.57-4.54 (m, 0.7H), 3.95 (m, 0.4H), 3.75-3.55 (m, 1.2H), 3.4-3.25 (m, 0.4H), 2.76 (s, 2H), 2.64 (s, 1H), 2.5-2.3 (m, 1H), 2.4-1.8 (m, 2H), 1.19 (d, 2H), 0.96 (d, 1H); ESI-MS (m/z): 514.08 [M+1]$^+$.

Compound 214: ((2S,3R)-5,5-difluoro-3-methyl-2-(((5-(trifluoromethyl)pyridin-2-yl)oxy)methyl)piperidin-1-yl)(2-methyl-5-(pyridin-2-yl)thiazol-4-yl)methanone

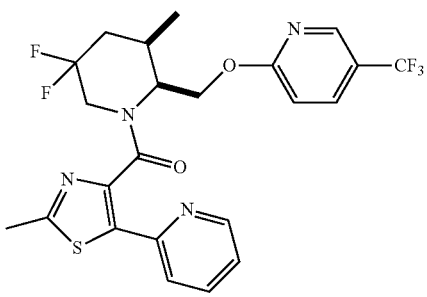 [SMILES: Cc1nc(C(=O)N2CC(F)(F)C[C@@H](C)[C@H]2COc2ccc(C(F)(F)F)cn2)c(-c2ccccn2)s1]

$^1$H NMR (CDCl$_3$, 300 MHz) δ 8.77-8.73 (m, 1H), 8.46-8.41 (m, 2H), 7.90-7.82 (m, 1H), 7.48-7.45 (m, 1H), 7.34-7.28 (m, 1H), 7.0-6.9 (m, 0.6H), 5.35-5.30 (m, 0.5H), 5.05-4.95 (m, 0.5H), 4.85-4.70 (m, 2.5H), 4.5-4.3 (m, 0.5H), 3.8-3.6 (m, 0.5H), 3.5-3.3 (m, 0.5H), 2.98 (s, 1.5H), 2.9 (s, 1.5H), 2.8-2.6 (s, 1H), 2.4-2.3 (m, 1H), 2.25-1.8 (m, 1H), 1.2 (d, 2H), 0.9 (d, 1H); ESI-MS (m/z): 513.3 [M+1]$^+$.

Compound 215: ((2S,3R)-5,5-difluoro-3-methyl-2-(((5-(trifluoromethyl)pyridin-2-yl)oxy)methyl)piperidin-1-yl)(6-methyl-3-(pyrimidin-2-yl)pyridin-2-yl)methanone

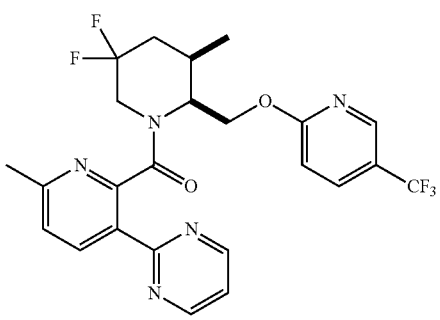 [SMILES: Cc1ccc(-c2ncccn2)c(C(=O)N2CC(F)(F)C[C@@H](C)[C@H]2COc2ccc(C(F)(F)F)cn2)n1]

$^1$H NMR (CDCl$_3$, 400 MHz) δ 8.67 (d, 1H), 8.63-8.55 (m, 1.6H), 8.5 (s, 1H), 8.35 (br s, 0.4H), 7.8-7.7 (m, 1H), 7.35-7.25 (m, 1H), 7.25 (t, 0.5H), 7.05 (t, 0.5H), 6.8 (t, 1H), 5.2-5.1 (m, 1H), 4.9-4.85 (m, 1H), 4.7-4.6 (m, 1H), 3.8 (br s, 0.5H), 3.65-3.45 (m, 1H), 3.4-3.25 (m, 0.5H), 2.6 (s, 1.6H), 2.5 (s, 1.4H), 2.5-2.3 (m, 1H), 2.2-1.9 (m, 2H), 1.2 (d, 1.5H), 0.9 (d, 1.5H); ESI-MS (m/z): 508.4 [M+1]$^+$.

Compound 216: (5-chloro-2-(2-methyl-2H-tetrazol-5-yl)phenyl)((2S,3R)-5,5-difluoro-3-methyl-2-(((5-(trifluoromethyl)pyridin-2-yl)oxy)methyl)piperidin-1-yl)methanone

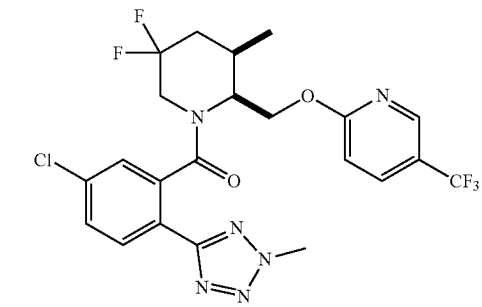 [SMILES: C[C@@H]1CC(F)(F)CN(C(=O)c2cc(Cl)ccc2-c2nnn(C)n2)[C@@H]1COc1ccc(C(F)(F)F)cn1]

ESI-MS (m/z): 531.3 [M+1]$^+$.

Compound 220: ((2S,3R)-5,5-difluoro-3-methyl-2-(((5-(trifluoromethyl)pyridin-2-yl)oxy)methyl)piperidin-1-yl)(1-methyl-4-(pyridin-2-yl)-1H-pyrazol-3-yl)methanone

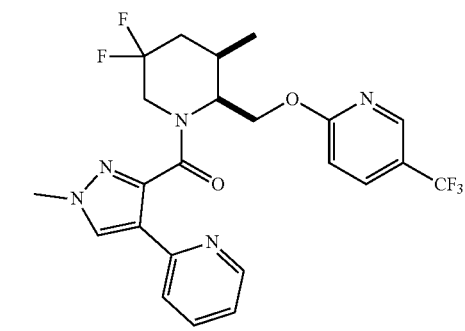

$^1$H NMR (CDCl$_3$, 400 MHz) δ 8.6 (br s, 0.5H), 8.5 (br s, 0.5H), 8.4 (br s, 0.5H), 8.3 (br s, 0.5H), 7.9-7.8 (m, 1H), 7.8-7.5 (m, 3H), 7.2 (m, 0.5H), 7.05 (m, 0.5H), 6.8 (d, 0.5H), 6.6 (d, 0.5H), 5.4 (m, 0.5H), 5.1 (m, 0.5H), 4.9-4.7 (m, 1H), 4.6-4.4 (m, 1H), 4.35 (m, 0.5H), 4.0 (m, 0.5H), 3.95 (s, 1.5H), 3.8 (s, 1.5H), 3.6-3.5 (m, 0.5H), 3.3-3.2 (m, 0.5H), 2.4-1.7 (m, 3H), 1.2 (d, 1.5H), 0.95 (d, 1.5H); ESI-MS (m/z): 496.0 [M+1]$^+$.

Compound 222: ((2S,3R)-5,5-difluoro-3-methyl-2-(((5-(trifluoromethyl)pyrimidin-2-yl)oxy)methyl)piperidin-1-yl)(1-methyl-4-(pyrimidin-2-yl)-1H-pyrazol-3-yl)methanone

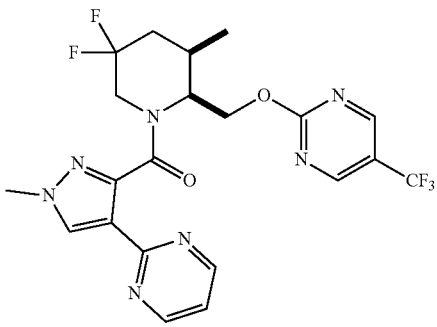 [SMILES: C[C@@H]1CC(F)(F)CN(C(=O)c2nn(C)cc2-c2ncccn2)[C@@H]1COc1ncc(C(F)(F)F)cn1]

¹H NMR (CDCl₃, 400 MHz) δ 8.8 (s, 1.4H), 8.7 (s, 0.6H), 8.6 (d, 0.6H), 8.5 (d, 1.4H), 8.15 (s, 0.7H), 8.1 (s, 0.3H), 7.2 (m, 0.5H), 7.0 (t, 0.3H), 6.9 (t, 0.7H), 5.4-5.2 (m, 1H), 5.0-4.9 (m, 2H), 4.2-4.1 (m, 0.3H), 4.0 (s, 2H), 3.9 (s, 1H), 3.9-3.8 (m, 0.7H), 3.75-3.6 (m, 0.7H), 3.4 (m, 0.3H), 2.5-2.4 (m, 1H), 2.4-2.0 (m, 2H), 1.2 (d, 2H), 1.0 (d, 1H); ESI-MS (m/z): 498.3 [M+1]⁺.

Compound 223: ((2S,3R)-5,5-difluoro-3-methyl-2-(((5-(trifluoromethyl)pyrazin-2-yl)oxy)methyl)piperidin-1-yl)(1-methyl-4-(pyrimidin-2-yl)-1H-pyrazol-3-yl)methanone

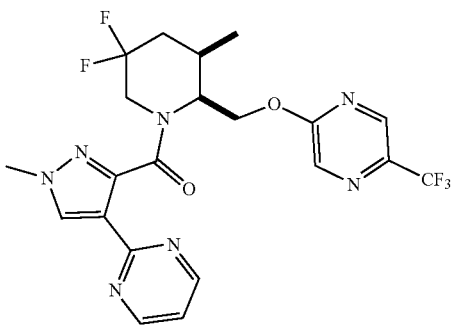 [SMILES: C[C@@H]1CC(F)(F)CN(C(=O)c2nn(C)cc2-c2ncccn2)[C@@H]1COc1cnc(C(F)(F)F)cn1]

¹H NMR (CDCl₃, 400 MHz) δ 8.65 (d, 1H), 8.6 (s, 0.5H), 8.5 (d, 1.5H), 8.4 (s, 0.5H), 8.3 (s, 0.5H), 8.15 (s, 0.55H), 8.0 (s, 0.45H), 7.05 (t, 0.4H), 7.0 (m, 0.6H), 5.4-5.35 (m, 0.5H), 5.3 (t, 0.5H), 4.9 (dd, 1H), 4.7-4.6 (m, 1H), 4.25-4.15 (m, 0.5H), 4.0 (s, 1.6H), 3.9-3.8 (m, 0.5H), 3.8 (s, 1.4H), 3.6-3.5 (m, 0.5H), 3.45-3.35 (m, 0.5H), 2.5-2.4 (m, 1H), 2.3-1.9 (m, 2H), 1.2 (d, 1.6H), 1.0 (d, 1.4H); ESI-MS (m/z): 498.2 [M+1]⁺.

Compound 228: ((2S,3R)-5,5-difluoro-2-(((3-fluoro-5-(trifluoromethyl)pyridin-2-yl)amino)methyl)-3-methylpiperidin-1-yl)(1-methyl-4-(pyrimidin-2-yl)-1H-pyrazol-3-yl)methanone

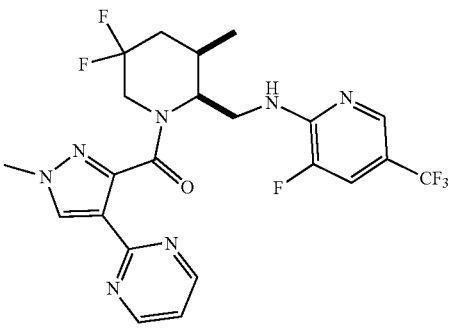 [SMILES: C[C@@H]1CC(F)(F)CN(C(=O)c2nn(C)cc2-c2ncccn2)[C@@H]1CNc1ncc(C(F)(F)F)cc1F]

¹H NMR (CDCl₃, 400 MHz) δ 8.65 (d, 1H), 8.6 (d, 1H), 8.25 (s, 0.5H), 8.2 (s, 0.5H), 8.15 (s, 0.5H), 8.1 (s, 0.5H), 7.35-7.2 (m, 1H), 7.1 (m, 1H), 6.7-6.6 (m, 1H), 5.35-5.2 (m, 1H), 4.35-4.25 (m, 0.5H), 4.15-4.05 (m, 0.5H), 4.0 (s, 1.5H), 3.95 (s, 1.5H), 3.9-3.8 (m, 0.5H), 3.6-3.5 (m, 0.5H), 3.5-3.3 (m, 1.5H), 3.2-3.05 (m, 0.5H), 2.5-2.4 (m, 1H), 2.2-2.1 (m, 1H), 2-1.6 (m, 1H), 1.25 (d, 1.5H), 1.0 (d, 1.5H); ESI-MS (m/z): 513.7 [M+1]⁺.

Compound 264: ((2S,3R)-5,5-difluoro-3-methyl-2-(((5-(trifluoromethyl)pyrimidin-2-yl)amino)methyl)piperidin-1-yl)(4-(5-fluoropyrimidin-2-yl)-1,5-dimethyl-1H-pyrazol-3-yl)methanone

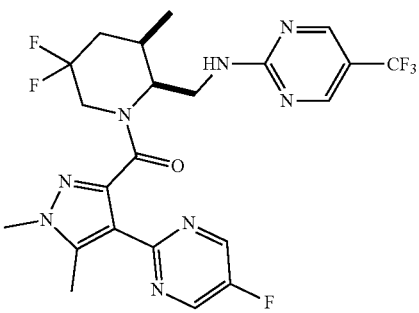 [SMILES: Cc1c(-c2ncc(F)cn2)c(C(=O)N2CC(F)(F)C[C@@H](C)[C@H]2CNc2ncc(C(F)(F)F)cn2)nn1C]

ESI-MS (m/z): 529.1 [M+1]⁺.

TABLE 2

| MS Characterization of Exemplary Compounds | |
|---|---|
| Compound # | MS (m/z) |
| 1 | 500.2 |
| 2 | 466.19 |
| 3 | 501.2 |
| 4 | 517.1 |
| 5 | 496.2 |
| 6 | 462.2 |
| 7 | 510.2 |
| 8 | 511.2 |
| 9 | 477.2 |
| 10 | 516.2 |
| 11 | 482.2 |
| 12 | 497.1 |

TABLE 2-continued

MS Characterization of Exemplary Compounds

| Compound # | MS (m/z) |
|---|---|
| 13 | 463.25 |
| 14 | 507.2 |
| 15 | 473.2 |
| 16 | 507.2 |
| 17 | 508.2 |
| 18 | 474.05 |
| 19 | 531.2 |
| 20 | 455.2 |
| 21 | 495.16 |
| 22 | 461.15 |
| 23 | 513.2 |
| 24 | 509.15 |
| 25 | 513.11 |
| 26 | 509.15 |
| 27 | 529.18 |
| 28 | 495.15 |
| 29 | 525.09 |
| 30 | 513.13 |
| 31 | 479.16 |
| 32 | 509.18 |
| 33 | 529.1 |
| 34 | 495.19 |
| 35 | 525.14 |
| 36 | 496.08 |
| 37 | 462.2 |
| 38 | 514.15 |
| 39 | 510.21 |
| 40 | 510.21 |
| 41 | 474.22 |
| 42 | 514.1 |
| 43 | 480.1 |
| 44 | 510.2 |
| 45 | 526.26 |
| 46 | 510.16 |
| 47 | 526.22 |
| 48 | 512.2 |
| 49 | 514.09 |
| 50 | 480.06 |
| 51 | 506.2 |
| 52 | 472.05 |
| 53 | 500.05 |
| 54 | 511.2 |
| 55 | 506.94 |
| 56 | 526.92 |
| 57 | 493.3 |
| 58 | 531.19 |
| 59 | 497.18 |
| 60 | 526.14 |
| 61 | 542.08 |
| 62 | 542.05 |
| 63 | 526.11 |
| 64 | 526.09 |
| 65 | 512.2 |
| 66 | 530.13 |
| 67 | 530.12 |
| 68 | 530.12 |
| 69 | 496.15 |
| 70 | 513.13 |
| 71 | 479.15 |
| 72 | 531.16 |
| 73 | 497.17 |
| 74 | 527.19 |
| 75 | 527.13 |
| 76 | 527.08 |
| 77 | 527.2 |
| 78 | 543.08 |
| 79 | 531.17 |
| 80 | 543.13 |
| 81 | 514.15 |
| 82 | 496.2 |
| 83 | 497.16 |
| 84 | 514.14 |
| 85 | 496.07 |
| 86 | 462.17 |
| 87 | 497.2 |
| 88 | 463.15 |
| 89 | 510.2 |
| 90 | 496.2 |
| 91 | 512.13 |
| 92 | 478.12 |
| 93 | 496.06 |
| 94 | 462.06 |
| 95 | 496.06 |
| 96 | 462.15 |
| 97 | 497.38 |
| 98 | 463.2 |
| 99 | 517.2 |
| 100 | 488.1 |
| 101 | 517.2 |
| 102 | 526.2 |
| 103 | 543.09 |
| 104 | 543.16 |
| 105 | 543.15 |
| 106 | 543.16 |
| 107 | 539.19 |
| 108 | 539.26 |
| 109 | 555.23 |
| 110 | 555.23 |
| 111 | 542.17 |
| 112 | 560.17 |
| 113 | 560.2 |
| 114 | 560.19 |
| 115 | 556.2 |
| 116 | 556.19 |
| 117 | 556.2 |
| 118 | 572.23 |
| 119 | 572.19 |
| 120 | 495.07 |
| 121 | 513.05 |
| 122 | 509.16 |
| 123 | 509.15 |
| 124 | 525.16 |
| 125 | 525.07 |
| 126 | 513.14 |
| 127 | 513.18 |
| 128 | 529.09 |
| 129 | 529.13 |
| 130 | 496.23 |
| 131 | 514.13 |
| 132 | 510.22 |
| 133 | 510.28 |
| 134 | 510.19 |
| 135 | 526.24 |
| 136 | 526.2 |
| 137 | 530.15 |
| 138 | 526.13 |
| 139 | 526.13 |
| 140 | 512.12 |
| 141 | 542.1 |
| 142 | 542.14 |
| 143 | 530.07 |
| 144 | 530.07 |
| 145 | 526.08 |
| 146 | 531.1 |
| 147 | 527.2 |
| 148 | 527.14 |
| 149 | 527.2 |
| 150 | 531.06 |
| 151 | 543.17 |
| 152 | 527.19 |
| 153 | 497.1 |
| 154 | 516.1 |
| 155 | 496.16 |
| 156 | 497.15 |
| 157 | 496.1 |
| 158 | 496.06 |
| 159 | 497.24 |
| 160 | 512.04 |
| 161 | 531.15 |
| 162 | 509.22 |
| 163 | 509.14 |
| 164 | 509.2 |

TABLE 2-continued

MS Characterization of Exemplary Compounds

| Compound # | MS (m/z) |
|---|---|
| 165 | 525.1 |
| 166 | 525.23 |
| 167 | 495.2 |
| 168 | 511.17 |
| 169 | 512.13 |
| 170 | 494.15 |
| 171 | 512.11 |
| 172 | 512.1 |
| 173 | 508.09 |
| 174 | 496.17 |
| 175 | 508.2 |
| 176 | 524.14 |
| 177 | 524.19 |
| 178 | 528.24 |
| 179 | 528.18 |
| 180 | 515.2 |
| 181 | 510.21 |
| 182 | 530.16 |
| 183 | 507.16 |
| 184 | 513.06 |
| 185 | 529.14 |
| 186 | 525.11 |
| 187 | 525.17 |
| 188 | 541.16 |
| 189 | 541.16 |
| 190 | 511.18 |
| 191 | 529.16 |
| 192 | 529.16 |
| 193 | 525.14 |
| 194 | 526.14 |
| 195 | 512.1 |
| 196 | 526.17 |
| 197 | 526.05 |
| 198 | 526.18 |
| 199 | 542.17 |
| 200 | 496.15 |
| 201 | 509.23 |
| 202 | 512.5 |
| 203 | 550.2 |
| 204 | 496.9 |
| 205 | 512.73 |
| 206 | 510.14 |
| 207 | 530.25 |
| 208 | 529.3 |
| 210 | 494.95 |
| 211 | 513.2 |
| 212 | 497.3 |
| 213 | 514.08 |
| 214 | 513.3 |
| 215 | 508.4 |
| 216 | 553.2 |
| 217 | 515.3 |
| 218 | 531.3 |
| 219 | 511.3 |
| 220 | 496.0 |
| 221 | 529.9 |
| 222 | 498.3 |
| 223 | 498.2 |
| 224 | 497.32 |
| 225 | 511.4 |
| 226 | 565.3 |
| 227 | 530.3 |
| 228 | 513.7 |
| 229 | 563.7 |
| 230 | 496.8 |
| 231 | 521.3 |
| 232 | 511.0 |
| 233 | 511.1 |
| 234 | 494.4 |
| 235 | 468.32 |
| 236 | 454.27 |
| 237 | 525.40 |
| 238 | 565.70 |
| 239 | 490.43 |
| 240 | 512.4 |
| 241 | 497.3 |
| 242 | 532.3 |
| 243 | 495.97 |
| 244 | 515.86 |
| 245 | 532.87 |
| 246 | 515.86 |
| 247 | 514.79 |
| 248 | 514.79 |
| 249 | 531.35 |
| 250 | 500.19 |
| 253 | 511.2 |
| 254 | 461.06 |
| 264 | 529.1 |

Example 2: Orexin Receptor Cell-Based Functional Assay

Measurement of $[Ca^{2+}]i$ using a FLIPR: CHO—$OX_1$ or CHO—$OX_2$ cells were seeded into black-walled clear-base 384-well plates (Corning, catalog #3712) at a density of 20,000 cells per well in F12-K medium supplemented with 10% FBS and then incubated in a 5% $CO_2$, 37° C. incubator overnight to reach 90% confluency. The cells were incubated with equal volume of calcium6 loading buffer (Molecular Devices, Inc.) containing 2.5 mM probenecid at 37° C. for 2 h, followed by test compounds (dose-range 0.1 nM-10 μM) for another 30 min. The plates were then placed into a FLIPR (Molecular Devices, Inc.) to monitor fluorescence (λ excitation 488 nm, λ emission 540 nm) before and after the addition of $EC_{90}$ of [OX]. Results for exemplary compounds of Formulae (I), (Ia), (Ib), (II), (IIa), (III), (IIIa), (IV), (IVa), (V), or (Va) are shown in Table 3.

TABLE 3

$IC_{50}$ Bioactivity of Exemplary Compounds of the Application with Respect to $OX_1$ and $OX_2$

| Compound # | OX2, IC50 (nM) | OX1, IC50 (nM) |
|---|---|---|
| 200 | >5000 | 4 |
| 210 | >5000 | 250 |
| 203 | 3700 | >5000 |
| 202 | >5000 | 150 |
| 97 | >5000 | 12 |
| 13 | >5000 | 15 |
| 129 | 3500 | 4 |
| 33 | 4700 | 4 |
| 206 | NT | 22 |
| 205 | >5000 | 52 |
| 187 | 3000 | 7 |
| 186 | >5000 | 6 |
| 177 | 170 | 6 |
| 197 | >5000 | 3 |
| 175 | 4136 | 4 |
| 174 | >5000 | 4 |
| 204 | >5000 | 40 |
| 147 | >5000 | 5 |
| 148 | >5000 | 6 |
| 45 | >5000 | 47 |
| 48 | >5000 | 607 |
| 29 | >5000 | 4 |
| 135 | >5000 | 19 |
| 136 | >5000 | 40 |
| 124 | 1000 | 4 |
| 125 | >5000 | 4 |
| 139 | >5000 | 10 |
| 125 | >5000 | 2 |
| 138 | >5000 | 6 |
| 137 | NT | 5 |

TABLE 3-continued

IC$_{50}$ Bioactivity of Exemplary Compounds of the Application with Respect to OX$_1$ and OX$_2$

| Compound # | OX2, IC50 (nM) | OX1, IC50 (nM) |
|---|---|---|
| 132 | >5000 | 7 |
| 63 | >5000 | 3 |
| 134 | >5000 | 4 |
| 123 | >5000 | 2 |
| 133 | >5000 | 11 |
| 64 | >5000 | 4 |
| 122 | >5000 | 5 |
| 76 | >5000 | 10 |
| 75 | >5000 | 12 |
| 74 | >5000 | 6 |
| 44 | >5000 | 10 |
| 24 | >5000 | 385 |
| 26 | >5000 | 4 |
| 32 | >5000 | 12 |
| 39 | >5000 | 1160 |
| 32 | >5000 | 6 |
| 46 | >5000 | 7 |
| 38 | >5000 | 150 |
| 23 | >5000 | 3 |
| 25 | >5000 | 4 |
| 121 | >5000 | 5 |
| 161 | >5000 | 9 |
| 182 | NT | 17 |
| 85 | >5000 | 12 |
| 183 | >5000 | 12 |
| 167 | >5000 | 5 |
| 142 | >5000 | 4 |
| 141 | NT | 6 |
| 151 | >5000 | 11 |
| 150 | >5000 | 3 |
| 77 | >5000 | 4 |
| 78 | >5000 | 2 |
| 210 | >5000 | 122 |
| 209 | >5000 | 280 |
| 95 | >5000 | >1000 |
| 93 | >5000 | 156 |
| 96 | >5000 | >1000 |
| 158 | >5000 | 62 |
| 157 | >5000 | 186 |
| 86 | >5000 | 1388 |
| 85 | >5000 | 30 |
| 156 | >5000 | >1000 |
| 87 | >5000 | >1000 |
| 155 | >5000 | 38 |
| 154 | >5000 | 12 |
| 92 | >5000 | 24 |
| 90 | >5000 | 206 |
| 153 | >5000 | 27 |
| 20 | >5000 | 87 |
| 83 | >5000 | 56 |
| 72 | >5000 | 237 |
| 84 | >5000 | 130 |
| 41 | >5000 | >5000 |
| 82 | >5000 | 45 |
| 81 | >5000 | 102 |
| 42 | >5000 | >1000 |
| 22 | >5000 | 7 |
| 211 | >5000 | 2 |
| 130 | >5000 | 6 |
| 120 | >5000 | 2 |
| 21 | >5000 | 2 |
| 89 | >5000 | 23 |
| 91 | >5000 | 7 |
| 19 | >5000 | 10 |
| 15 | >5000 | 46 |
| 14 | >5000 | 52 |
| 17 | >5000 | 8 |
| 70 | >5000 | 5 |
| 31 | >5000 | 4 |
| 30 | >5000 | 3 |
| 101 | 1603 | 38 |
| 185 | >5000 | 2 |
| 57 | >5000 | 24 |
| 169 | >5000 | 2 |
| 36 | >5000 | 19 |
| 100 | >5000 | 9 |
| 18 | >5000 | 18 |
| 52 | >5000 | 9 |
| 53 | >5000 | 29 |
| 4 | >5000 | 81 |
| 12 | >5000 | 15 |
| 16 | >5000 | 60 |
| 51 | >5000 | 4 |
| 55 | >5000 | 30 |
| 56 | >5000 | 7 |
| 50 | >5000 | 20 |
| 9 | >5000 | 6 |
| 6 | >5000 | 8 |
| 8 | >5000 | 8 |
| 11 | >5000 | 8 |
| 7 | >5000 | 7 |
| 10 | >5000 | 7 |
| 5 | >5000 | 10 |
| 1 | >5000 | 192 |
| 54 | >5000 | 43 |
| 49 | >5000 | 6 |
| 67 | 1113 | 5 |
| 66 | 2076 | 1 |
| 65 | >5000 | 2 |
| 69 | >5000 | 9 |
| 68 | >5000 | 8 |
| 215 | >5000 | 5 |
| 216 | >5000 | 4 |
| 217 | >5000 | 4 |
| 218 | >5000 | 7 |
| 219 | >5000 | 120 |
| 225 | >5000 | 17 |
| 226 | >5000 | 350 |
| 227 | >5000 | 14 |
| 228 | >5000 | 14 |
| 229 | >5000 | 7 |
| 220 | >5000 | 8 |
| 221 | >5000 | 2 |
| 222 | >5000 | 26 |
| 223 | >5000 | 52 |
| 224 | >5000 | 62 |
| 230 | >5000 | 74 |
| 231 | >5000 | 14 |
| 232 | >5000 | 82 |
| 233 | >5000 | 1 |
| 234 | >5000 | 29 |
| 235 | >5000 | 250 |
| 237 | >5000 | 1700 |
| 238 | >5000 | >2000 |
| 239 | >5000 | 29 |
| 240 | >5000 | 29 |
| 241 | >5000 | >1000 |
| 242 | >5000 | 5 |
| 243 | >5000 | 8 |
| 244 | >5000 | 1000 |
| 245 | >5000 | 1000 |
| 246 | >5000 | 4816 |
| 247 | >5000 | 437 |
| 248 | >5000 | 50 |
| 249 | >5000 | 8 |
| 252 | >5000 | 8 |
| 254 | >5000 | 70 |
| 263 | >5000 | 57 |
| 264 | >5000 | 3 |

Example 3: Nicotine Self-Administration Assay

For all experiments, rats weighing 250-300 g were housed in groups of 1-23 per cage, in a temperature-controlled vivarium under a reversed 12-h light/dark cycle (lights off at 8 am). Food and water were provided ad libitum until behavioral training commences. During training, rats were food-restricted to maintain ~85-90% of their free-feeding body weight. Behavioral testing occurred during the dark portion of the light/dark cycle between the hours of 9 am-1 pm, during the early portion of the dark phase of the cycle. All procedures were conducted in strict adherence with the National Institutes of Health Guide for the Care and Use of Laboratory Animals and were approved by the Institutional Animal Care and Use Committee of The Scripps Research Institute. Rats were anesthetized by inhalation of 1-3% isoflurane in oxygen and silastic catheters were inserted into the jugular veins. Briefly, the catheters consist of a 14 cm length of silastic tubing fitted to a guide cannula (Plastics One, Wallingford, Conn.), bent at a curved right angle and encased in dental acrylic. The catheter tubing was passed subcutaneously from each animal's back to the right jugular vein, and 1 cm length of the catheter tip is inserted into the vein. After surgery, catheters are flushed daily with 0.1 mL of a heparinized (30 USP units/ml) sterile saline solution. Following 7 d of surgical recovery, rats were mildly food restricted to 85-90% of their free-feeding body weight and trained to press a lever in an operant chamber (Med Associates, St. Albans, Vt.) for food pellets (20 mg; TestDiet, Richmond, Ind.) under a fixed-ratio 5, time out 20 s (FR5TO20 s) schedule of reinforcement prior to catheter implantation. Once stable responding was achieved (>25 pellets per session), rats were permitted to acquire IV nicotine self-administration by autoshaping during 1-h daily sessions, 7 days per week. Nicotine was delivered through the tubing into the IV catheter by a Razel syringe pump (Med Associates). Each nicotine self-administration session was performed using two retractable levers (1 active; 1 inactive). Completion of the response criteria on the active lever resulted in the delivery of an IV nicotine infusion (0.03 mg/kg/infusion). After 1 week, the nicotine dose was increased to 0.1 mg/kg/inf for the remainder of the experiment, including subsequent training and test sessions. Delivery of all nicotine infusions coincided with the initiation of a 20-s time-out (TO) period, signaled by a light cue located above the lever. During the TO period, responding on the lever was recorded but without scheduled consequence. Catheter integrity was tested with the ultrashort-acting barbiturate Brevital (methohexital sodium; Eli Lilly) at the end of the experiment.

Example 4: Metabolic Stability and Intrinsic Clearances in Rat Hepatocytes

Stock solutions of compounds and control compounds were prepared in 10 mM in appropriate solvent, such as DMSO. L-15 medium was placed in a 37° C. water bath and allowed to warm for at least 15 minutes prior to use. A quenching plate was prepared by adding 80 μL of acetonitrile to each well of a 96-well plate. In a new 96-well plate, the 10 mM stock solution of test compounds and control compounds were diluted to 100 μM by combining 198 μL of acetonitrile and 2 μL of the 10 mM stock. A vial of cryopreserved rat hepatocytes were removed from storage and maintained at cryogenic temperatures until thawing. The cells were thawed as quickly as possible, in a 37° C. water bath under gentle shaking. The vials were kept in the water bath until all ice crystals have dissolved and are no longer visible. After the thawing was completed, the vials were sprayed with 70% ethanol and transferred to a biosafety cabinet. The contents of the vial were transferred into a 50 mL conical tube containing L-15 medium. The conical tube was then centrifuged at 50 g for 3 minutes at room temperature and a pellet was formed at the bottom of the tube. After aspiration, the pellet was resuspended with a small volume of buffer (~200 μL) first and then diluted to 50 mL in buffer for centrifugation. Upon completion of spin and aspiration, the pellet of hepatocytes was resuspended in enough incubation medium to yield ~1.5×10$^6$ cells/mL.

Cells were then counted with Cellometer® Vision. Cells with poor viability (<80% viability) were not acceptable for use. Counted cells were then diluted with incubation medium to a working cell density of 1.0×10$^6$ viable cells/ mL. 247.5 μL of hepatocytes were transferred into each wells of a 96-well cell culture plate and the plate was placed on an Eppendorf Thermomixer Comfort plate shaker to allow the hepatocytes to warm for 10 minutes. 2.5 μL of 100 μM test compound or control compounds were added into an incubation well containing cells and the mixture was mixed to achieve a homogenous suspension at 0.5 min, which when achieved, were defined as the 0.5 min time point. At the 0.5 min time point, 20 μL incubated mixture was transferred to wells in a "Quenching plate" followed by vortexing. The quenching plate was incubated at 37° C. at 900 rpm on an Eppendorf Thermomixer Comfort plate shaker. At 5, 15, 30, 45, 60, 80, 100 and 120 min, the incubation system was mixed and aliquots of samples (20 μL) were transferred and incubated at each time point to wells in a separated "Quenching plate" followed by vortexing. The quenching plates were centrifuged for 20 minutes at 4,000 rpm. Four different compounds were pooled into one cassette and used for LC/MS/MS analysis. All incubations were performed in singlicate.

All calculations were carried out using Microsoft Excel. Peak areas were determined from extracted ion chromatograms. in vitro half-life (t½) of parent compound was determined by regression analysis of the Ln percent parent disappearance vs. time curve. The in vitro intrinsic clearance (in vitro Clint, in L/min/10$^6$ cells) was determined from the slope value using the following equation: in vitro Clint=kV/ N: V=incubation volume (0.25 mL); N=number of hepatocytes per well (0.25×10$^6$ cells).

TABLE 4

Metabolic Stability and Intrinsic Clearances in Rat Hepatocytes

| Compound # | rHeps CLint (ug/min/10^6 cells) |
|---|---|
| 185 | 107 |
| 129 | 3.8 |

Example 5: Metabolic Stability and Intrinsic Clearances in Human Liver Microsomes Human Liver Microsomes (HLM) were obtained from BD Gentest UltraPool 150 donor (Lot no. 38289) at a concentration of 20 mg/mL protein. HLMs are stored in a −80° C. freezer. Prior to use, the pooled HLM were removed from the freezer and allowed to thaw in a 37° C. water bath and then stored on wet ice. 100 μmol/L test compound solution and positive control (PC) solutions (phenacetin, verapamil, diclofenac, imiprimine, benzydamine and metoprolol) were prepared by adding 2 μL of 10 mmol/L stock solution in DMSO to 198 μL of acetonitrile. HML mixtures were prepared by adding 1325 μL of 20 mg/mL HLM to 22260 μL of phosphate buffer to obtain the HLM mixture at 1.1236 mg/mL. Prior to testing the compounds, 222.5 μL of 1.1236 mg/mL HLM mixtures and 25 μL of the 10 mM NADPH were mixed in the incubation plates on a whirly mixer for 10 seconds. The incubation plates were pre-warmed at 37° C. for 8 min. The reaction was initiated with the addition of 2.5 μL of the 100 μM test compound solutions or PC solutions to the incubation plate and the reaction solutions were mixed on a whirly mixer for 10 seconds and incubated at 37° C. 20 μL of reaction mixture was transferred at 0.5, 5, 10, 15, 20, and 30 minutes into the quenching plate containing 100 μL of cold acetonitrile. The quenching plates were then centrifuged at 4000 rpm for 20 minutes and were placed at 4° C. for 30 minutes, then re-centrifuged at 4000 rpm for 20 minutes to precipitate protein. 40 μL of supernatant of each compound was transferred into a 96-well analysis plate. 4 compounds were pooled together into one cassette and 160 μL of pure water was added into each well. All incubations were performed in singlicate.

Quantitative LC-MS analysis were carried out with an API 4000 (AB sciex, USA) Ultra mass spectrometer at MRM mode (MS/MS). Peak areas were determined from extracted ion chromatograms. Percent parent remaining was calculated from peak area of test compound or PC. The slope value, k, was determined by linear regression of the natural logarithm of percent parent remaining vs. incubation time curve. All calculations were carried out using Microsoft Excel.

The in vitro half-life (in vitro $t_{1/2}$) was determined from the slope value: in vitro $t\frac{1}{2}=-(0.693/k)$. Conversion of the in vitro $t_{1/2}$ (in min) into the in vitro intrinsic clearance (in vitro CLint, in μL/min/mg proteins) is done using the following equation:

$$\text{in vitro } CL_{int} = \left(\frac{0.693}{(t_{1/2})}\right) * \left(\frac{\text{volume of incubation } (\mu L)}{\text{amount of proteins (mg)}}\right).$$

TABLE 5

Metabolic Stability and Intrinsic Clearances in Human Liver Microsomes

| Compound # | hMics CLint (ug/min/mg protein) |
|---|---|
| 185 | 29 |
| 129 | <3 |

The compounds described in this patent application show favorable rat and human in vitro metabolic stabilities (as measured in human liver microsomes and rat hepatocytes) as well as good in vivo pharmacokinetic properties in rodents.

Example 6: Pharmacokinetic Evaluation Via Intravenous Cassette Administration in Harlan RCC Strain of Wistar Rats Two male Wistar rats (strain: Harlan RCC) of 10-12 weeks old on the day of dosing were recruited and assigned as one study group. Each rat weighed 250-300 g on the day of dosing and was not fasted prior to dosing. Rats were housed in a controlled environment (set up to maintain 20-25° C. and 40-70% relative humidity). A 12-hour light/12-hour dark cycle was maintained except when interrupted by study-related events. The rats were dosed via IV bolus to tail vein over approximately 5 seconds. Individual dosing values were calculated based on the rats' most recently recorded body weight. The dosing level was 0.5 mg/kg body weight (1 mL/kg with a concentration of 0.5 mg/mL). Rats were evaluated during in-life phase. The single dose formulation samples were collected from the middle of formulation and stored at 5±3° C. for potential analysis. Samples (0.2 mL sample size) were collected from blood via a cannulated tube in foot dorsal vein at 2 min, 5 min, 10 min, 30 min, 1 h, 2 h, 4 h, 8 h, and 24 h post dosing. EDTA was used as an anticoagulant.

The blood samples were then centrifuged at 5 minutes at 4° C. to obtain plasma. Plasma samples were stored in polypropylene tubes, quickly frozen in ice box and kept at −80° C. Then the plasma samples were deproteinated by solvent precipitation. Concentrations of test articles in plasma and tissue samples were analyzed using a LC-MS/MS method with 8-10 standards, 2× dilutions, with 10 ng/mL LOQ and 75% of standards within 25% of nominal; high, medium and low duplicate QCs were 5/6<25% error. WinNonlin version 6.2 was used for pharmacokinetic parameters calculations. PK parameters including $C_0$, $C_{max}$, $T_{max}$, CL, $V_{ss}$, Vz, $T_{1/2}$, $T_{last}$, $AUC_{0-t}$, $AUC_{0-infinity}$, AUC Extrap (%), and MRT using non-compartmental model.

To determine terminal $T_{1/2}$, the latest three time points with quantifiable concentration were used. $T_{1/2}$ was reported as not calculated, if the correlative coefficient (Rsq adjusted) was <0.85 at the terminal phase. AUC were calculated using log trapezoidal method.

Example 7: Pharmacokinetics and Brain/Plasma Distribution in Male Sprague-Dawley Rats after Cassette Intravenous (Bolus) and Oral Administration Male SD (Sprague-Dawley) rats, 250-300 g and 7-9 weeks old, were recruited and assigned into two dose groups: Group #1 for intravenous administration (IV) study and Group #2 for oral administration (PO, per os). In Group #1, rats were dosed at 0.5 mg/kg, (0.5 mg/kg for each analyte) with a dosing concentration of 0.5 mg/mL (of each analyte). The formulation for IV dosing comprises: 5:95 DMSO:SBE-β-CD (30% w/v) in water. pH value was adjusted with 1M HCl (SBE is same as Captisol). The formulation was administered via IV bolus at a dose volume of 1 mL/kg for each single dose. Brains were harvested from rats at 15 min after second dose on Day 2 of the study. In Group #2, rats were dosed at 1.0 mg/kg (1 mg/kg for each analyte) with a dosing concentration of 0.2 mg/mL (of each analyte). The formulation for PO dosing comprises: 0.5% HPMC, 0.1% Tween80 and were administrated via oral gavage at a level of 5 mL/kg for each single dose. 150 μL of blood sample was collected per each time point in both groups at 5, 10, 15, 30, 60, 120, 240, 360, 480, 720 and 1440 min.

In a second arm study, plasma samples from each rat in both groups were collected for PK study. Brain and plasma samples from Group #1 administered an IV dose (0.5 mg/kg of each analyte as a cassette dose) were collected at 15 min post dose. Group #1 rats were dosed on second day, after the last time point (24 h) has been collected from the initial dose. Brain samples were weighed into appropriate size tubes so they can be homogenized in the same vessel. Dose solutions and plasma/brain samples were stored at −80° C. until being analyzed.

Aliquots of dose formulation were diluted with appropriate solvent and analyzed by LC/MS to obtain the concentrations of the analyte in the dosing solutions. The plasma samples from PK study were analyzed by a LC/MS/MS method developed by Frontage Laboratories according to Frontage Bioanalytical Tier 2 criteria. The brain samples were homogenized in 0.1 M phosphate buffer, pH 7.4 (1:3 volumes, brain:buffer) and an aliquot from each homogenate were further diluted 2-4 fold with control rat plasma before extracted by protein precipitation for analyses by LC/MS/MS. An aliquot of the brain homogenates (prepared in 0.1M phosphate buffer only) were also subjected to equilibrium dialysis in RED device (6 h) and free brain concentrations were determined. At the same time, LC/Ms/MS analyses of brain homogenates, plasma and samples from the RED study (all from the IV dosed animals sacrificed at 15 min post dose) were carried out. The concentrations of analytes present in plasma and brain were used to obtain brain/plasma ratio for each compound. The measured plasma concentrations of each analyte were used to obtain the PK parameters using Phoenix® WinNonlin® software (version 6.5.1).

INCORPORATION BY REFERENCE

All references cited in this application, and their references, are incorporated by reference herein in their entirety where appropriate for teachings of additional or alternative details, features, and/or technical background.

The invention claimed is:

1. A method of treating a disease or disorder regulated by orexin receptor $OX_1$ activity in a patient in need thereof, comprising administering a compound of formula (I),

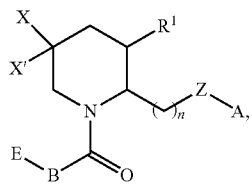

or a pharmaceutically acceptable salt thereof, wherein:
X is halogen;
X' is H or halogen;
Z is $NR^2$ or O;
A is aryl, aroyl, heteroaryl, or heteroaroyl, wherein A is optionally substituted with one or more substituents independently selected from the group consisting of alkyl, cycloalkyl, halo, —OH, alkoxy, —$CHF_2$, —$CF_3$, —CN, —$NR^aR^b$, —$N(R^a)C(O)$ alkyl, —$N(R^a)CO_2$alkyl, —$N(R^a)SO_2$alkyl, —$C(O)$alkyl, —$CO_2H$, —$CO_2$alkyl, —$CONR^aR^b$, —$SO_2$alkyl, and —$SO_2NR^aR^b$; wherein $R^a$ and $R^b$ are independently for each occurrence H or alkyl;
B is aryl or heteroaryl, wherein B is optionally substituted with one or more substituents independently selected from the group consisting of alkyl, cycloalkyl, halo, —OH, alkoxy, $CH_2CF_3$, —$CHF_2$, —$CF_3$, —CN, —$NR^cR^d$, —$N(R^c)C(O)$ alkyl, —$N(R^c)CO_2$alkyl, —$N(R^c)SO_2$alkyl, —$C(O)$alkyl, —$CO_2H$, —$CO_2$alkyl, —$CONR^cR^d$, —$SO_2$alkyl, and —$SO_2NR^cR^d$; wherein $R^c$ and $R^d$ are independently for each occurrence H or alkyl;
E is aryl or heteroaryl, wherein E is optionally substituted with one or more substituents independently selected from the group consisting of alkyl, cycloalkyl, halo, —OH, alkoxy, —$CHF_2$, —$CF_3$, —CN, —$NR^eR^f$, —$N(R^e)C(O)$ alkyl, —$N(R^e)CO_2$alkyl, —$N(R^e)$ $SO_2$alkyl, —$C(O)$alkyl, —$CO_2H$, —$CO_2$alkyl, —$CONR^eR^f$, —$SO_2$alkyl, and —$SO_2NR^eR^f$; wherein $R^e$ and $R^f$ are independently for each occurrence H or alkyl;

n=1, 2, or 3;
$R^1$ is alkyl; and
$R^2$ is H or alkyl;
wherein the disease or disorder is selected from the group consisting of drug abuse or addiction, obesity and an eating disorder.

2. The method of claim 1, wherein A is optionally substituted aryl or optionally substituted heteroaryl.

3. The method of claim 1, wherein the compound has the structure of formula (Ia):

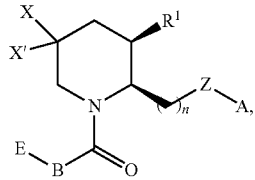

or a pharmaceutically acceptable salt thereof.

4. The method of claim 1, wherein Z is $NR^2$.
5. The method of claim 1, wherein $R^2$ is hydrogen.
6. The method of claim 1, wherein X is —F.
7. The method of claim 1, wherein X' is —F.
8. The method of claim 1, wherein $R^1$ is methyl.
9. The method of claim 1, wherein A is selected from the list consisting of pyridinyl, pyrimidinyl, pyrazinyl, pyridazinyl, and benzoxazolyl, all of which may be optionally substituted.
10. The method of claim 1, wherein A is optionally substituted with one or more substituents independently selected from the list consisting of —F, —Br, —Cl, —$CHF_2$, —$CF_3$, methyl, ethyl, and methoxy.
11. The method of claim 1, wherein A is substituted with —$CHF_2$ or —$CF_3$.
12. The method of claim 1, wherein B is an optionally substituted aryl.
13. The method of claim 1, wherein B is selected from the list consisting of pyridinyl, thiophenyl, oxazolyl, thiazolyl, pyrazolyl, triazolyl, and benzoimidazolyl, all of which may be optionally substituted.
14. The method of claim 1, wherein B is optionally substituted with one or more substituents independently selected from the group consisting of —F, —Cl, —Br, —CN, methyl, ethyl, isopropyl, —$CF_3$, —$CH_2CF_3$, isopropoxy, and methoxy.
15. The method of claim 14, wherein B is substituted with one or more methyl.
16. The method of claim 1, wherein E is an optionally substituted phenyl.
17. The method of claim 1, wherein E is selected from the group consisting of triazolyl, tetrazolyl, pyrazolyl, pyridinyl, oxadiazolyl, pyrazinyl, and pyrimidinyl, all of which may be optionally substituted.
18. The method of claim 1, wherein E is optionally substituted with one or more substituents independently selected from the group consisting of —F, —Cl, —Br, methoxy, methyl, ethyl, —$CHF_2$ or —$CF_3$.
19. The method of claim 1, wherein E is optionally substituted with one or more methyl or —F.
20. The method of claim 1, wherein Z is O.
21. The method of claim 1, wherein n=1.
22. The method of claim 1, wherein the compound has a structure of formula (II):

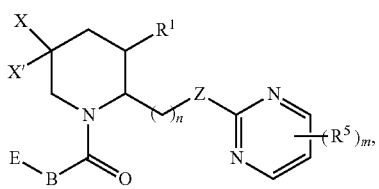

(II)

or a pharmaceutically acceptable salt thereof; wherein:
m is 1, 2, or 3;
$R^5$ represents alkyl, cycloalkyl, halo, —OH, alkoxy, —CN, —$NR^jR^k$, —$N(R^j)C(O)$ alkyl, —$N(R^j)CO_2$alkyl, —$N(R^j)SO_2$alkyl, —C(O)alkyl, —$CO_2H$, —$CO_2$alkyl, —$CONR^jR^k$, —$SO_2$alkyl, or —$SO_2NR^jR^k$; wherein $R^j$ and $R^k$ are independently for each occurrence H or alkyl; and
X, X', Z, B, E, n, $R^1$ and $R^2$ are as defined in claim 1.

23. The method of claim 1, wherein the compound has a structure of formula (III):

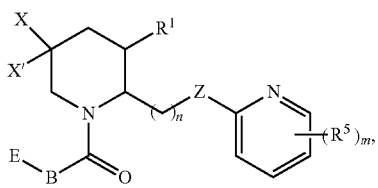

(III)

or a pharmaceutically acceptable salt thereof; wherein:
m is 1, 2, 3 or 4;
$R^5$ represents alkyl, cycloalkyl, halo, —OH, alkoxy, —CN, —$NR^jR^k$, —$N(R^j)C(O)$ alkyl, —$N(R^j)CO_2$alkyl, —$N(R^j)SO_2$alkyl, —C(O)alkyl, —$CO_2H$, —$CO_2$alkyl, —$CONR^jR^k$, —$SO_2$alkyl, or —$SO_2NR^jR^k$; wherein $R^j$ and $R^k$ are independently for each occurrence H or alkyl; and
X, X', Z, B, E, n, $R^1$ and $R^2$ are as defined in claim 1.

24. The method of claim 1, wherein the compound has a structure of formula (IV):

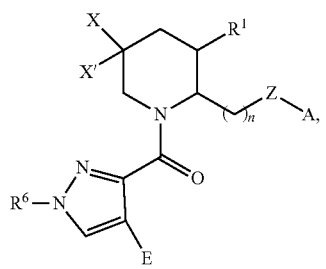

(IV)

or a pharmaceutically acceptable salt thereof; wherein:
$R^6$ represents alkyl, cycloalkyl, halo, —OH, alkoxy, —CN, —$NR^oR^p$), —$N(R^o)C(O)$ alkyl, —$N(R^p)CO_2$alkyl, —$N(R^o)SO_2$alkyl, —C(O)alkyl, —$CO_2H$, —$CO_2$alkyl, —$CONR^oR^p$, —$SO_2$alkyl, or —$SO_2NR^oR^p$; wherein $R^o$ and $R^p$ are independently for each occurrence H or alkyl; and
X, X', Z, A, E, n, $R^1$ and $R^2$ are as defined in claim 1.

25. The method of claim 1, wherein the compound has a structure of formula (V):

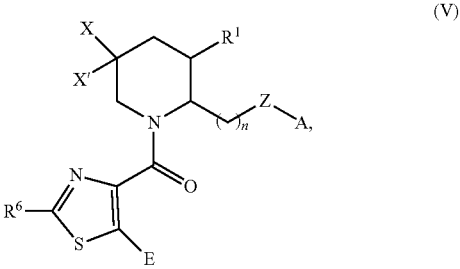

(V)

or a pharmaceutically acceptable salt thereof, wherein:
$R^6$ represents alkyl, cycloalkyl, halo, —OH, alkoxy, —CN, —$NR^oR^p$, —$N(R^o)C(O)$ alkyl, —$N(R^p)CO_2$alkyl, —$N(R^o)SO_2$alkyl, —C(O)alkyl, —$CO_2H$, —$CO_2$alkyl, —$CONR^oR^p$, —$SO_2$alkyl, or —$SO_2NR^oR^p$; wherein $R^o$ and $R^p$ are independently for each occurrence H or alkyl; and
X, X', Z, A, E, n, $R^1$ and $R^2$ are as defined in claim 1.

26. The method of claim 1, wherein the compound is compound 217,

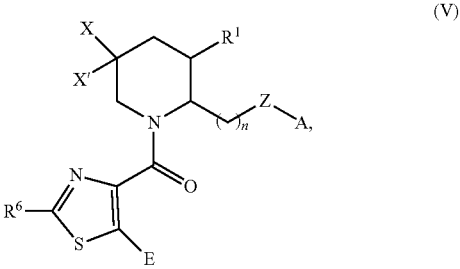

or a pharmaceutically acceptable salt thereof.

27. The method of claim 1, wherein the compound is Compound 12,

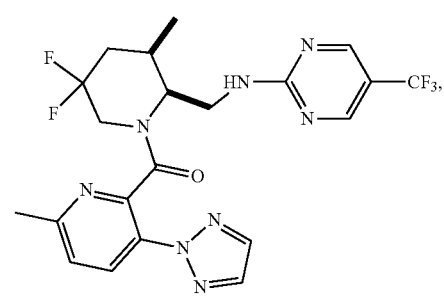 [SMILES: Cc1ccc(-n2nccn2)c(C(=O)N2CC(F)(F)C[C@@H](C)[C@H]2CNc2ncc(C(F)(F)F)cn2)n1]

or a pharmaceutically acceptable salt thereof.

28. The method of claim 1, wherein the compound is Compound 17,

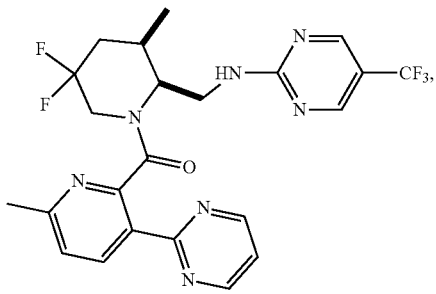 [SMILES: Cc1ccc(-c2ncccn2)c(C(=O)N2CC(F)(F)C[C@@H](C)[C@H]2CNc2ncc(C(F)(F)F)cn2)n1]

or a pharmaceutically acceptable salt thereof.

29. The method of claim 1, wherein the compound is Compound 56,

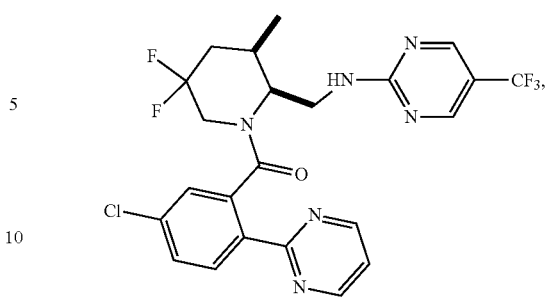

or a pharmaceutically acceptable salt thereof.

30. The method of claim 1, wherein the disease or disorder is drug abuse or addiction selected from abuse of or addiction to cocaine, opiates, amphetamines, ethanol or nicotine.

31. The method of claim 1, wherein the disease or disorder is obesity.

32. The method of claim 1, wherein the disease or disorder is an eating disorder.

* * * * *